(12) United States Patent
Poth et al.

(10) Patent No.: US 9,796,764 B2
(45) Date of Patent: Oct. 24, 2017

(54) CYCLOTIDE GENES IN THE FABACEAE PLANT FAMILY

(75) Inventors: Aaron G. Poth, St. Lucia (AU);
Michelle Colgrave, Campbell (AU);
Russell Lyons, Campbell (AU); David Craik, St. Lucia (AU)

(73) Assignees: The University of Queensland, St. Lucia (AU); Commonwealth Scientific and Industrial Research Organisation, Campbell (AU)

( * ) Notice: Subject to any disclaimer, the term of this patent is extended or adjusted under 35 U.S.C. 154(b) by 803 days.

(21) Appl. No.: 13/428,860

(22) Filed: Mar. 23, 2012

(65) Prior Publication Data
US 2012/0244575 A1 Sep. 27, 2012

Related U.S. Application Data

(60) Provisional application No. 61/466,888, filed on Mar. 23, 2011.

(51) Int. Cl.
*C07K 14/415* (2006.01)

(52) U.S. Cl.
CPC .................................. *C07K 14/415* (2013.01)

(58) Field of Classification Search
None
See application file for complete search history.

(56) References Cited

U.S. PATENT DOCUMENTS

| | | | |
|---|---|---|---|
| 5,990,385 A * | 11/1999 | Vezina et al. | 800/278 |
| 7,960,340 B2 * | 6/2011 | Craik | C07K 14/001 514/17.4 |
| 2003/0158096 A1 | 8/2003 | Craik | |
| 2006/0035819 A1 * | 2/2006 | Craik et al. | 514/9 |
| 2006/0156439 A1 * | 7/2006 | Diehn et al. | 800/287 |

FOREIGN PATENT DOCUMENTS

| | | |
|---|---|---|
| WO | 01/27147 | 4/2001 |
| WO | 01/34829 | 5/2007 |

OTHER PUBLICATIONS

Daly et al (Advanced Drug Delivery Reviews, 61, pp. 918-930, 2009).*
Gillon et al (Plant Journal, 53, pp. 505-515, 2008).*
Stoger et al (Current Opinion in Biotechnology, 16(2), pp. 167-173, 2005).*
GenEmbl AJ276882 (Published Mar. 2000).*
Austin et al (ChemBioChem, 2009, 10: 2663-2670).*
Simonsen et al (J. Bio. Chem., 2008, 283: 9805-9813; cited on IDS).*
Gunasekera et al (J. Med. Chem., 2008, 51: 7697-7704; cited on IDS).*
Abe et al. "Asparaginyl endopeptidase of jack bean seeds. Purification, characterization, and high utility in protein sequence analysis," J Biol Chem, 268: 3525-3529, 1993.
Barbeta et al. "Plant cyclotides disrupt epithelial cells in the midgut of lepidopteran larvae," PNAS, 105: 1221-1225, 2008.
Bendsten et al. "Improved prediction of signal peptides: SignalP 3.0," J Mol Biol, 340: 783-795, 2004.
Boscariol et al. "The use of the PMI/mannose selection system to recover transgenic sweet orange plants (*Citrus sinensis* L. Osbeck)," Plant Cell Rep, 22: 122-128, 2003.
Brunger et al. "Version 1.2 of the Crystallography and NMR system," Nat Protoc, 2: 2728-2733, 2007.
Camarero et al. "Biosynthesis of a fully functional cyclotide inside living bacterial cells," Chem Biochem, 8: 1363-1366, 2007.
Carrington et al. "Polypeptide ligation occurs during post-translational modification of concanavalin A.," Nature, 313: 64-67, 1985.
Chiche et al. "Squash inhibitors: from structural motifs to macrocyclic knottins," Curr Protein Pept Sci, 5: 341-349, 2004.
Chowrira et al. "Transgenic grain legumes obtained by in planta electroporation-mediated gene transfe," Mol Biotechnol, 5: 85-96, 1996.
Colgrave et al. "A new "era" for cyclotide sequencing," Biopolymers, 94: 592-601, 2010.
Colgrave et al. "Anthelmintic activity of cyclotides: In vitro studies with canine and human hookworms," Acta Trop, 109: 163-166, 2009.
Colgrave et al. "Cyclotide interactions with the nematode external surface," Antimicrob Agents Chemother, 54: 2160-2166, 2010.
Colgrave et al. "Cyclotides: natural, circular plant peptides that possess significant activity against gastrointestinal nematode parasites of sheep," Biochemistry, 47: 5581-5589, 2008.
Colgrave et al. "The anthelmintic activity of the cyclotides: natural variants with enhanced activity," Chem BioChem, 9: 1939-1945, 2008.
Colgrave et al. "Thermal, chemical, and enzymatic stability of the cyclotide kalata B1: the importance of the cyclic cystine knot," Biochemistry, 43: 5965-5975, 2004.
Collinge et al. "Engineering pathogen resistance in crop plants: current trends and future prospects," Ann Rev Phytopathol, 48: 269-291, 2010.
Cortese et al. "Identification of biologically active peptides using random libraries displayed on phage," Curr Opin Biotech, 6: 73-80, 1995.
Craik et al. "Chemistry. Seamless proteins tie up their loose ends," Science, 311: 1563-1564, 2006.
Craik et al. "Plant cyclotides: A unique family of cyclic and knotted proteins that defines the cyclic cystine knot structural motif," J Mol Biol, 294, 1327-1336, 1999.
Craik et al. "The cystine knot motif in toxins and implications for drug design," Toxicon, 39: 43-60, 2001.
Crooks et al. "WebLogo: a sequence logo generator," Genome Res, 14: 1188-1190, 2004.

(Continued)

*Primary Examiner* — Elizabeth McElwain
*Assistant Examiner* — Stephen Uyeno
(74) *Attorney, Agent, or Firm* — Casimir Jones, S.C.

(57) ABSTRACT

The present invention relates to cyclotides and cyclotide-encoding genes from the Fabaceae plant family, and to the expression of cyclotides in Fabaceae. The present invention further relates to isolated nucleic acids configured to express cyclotides comprising heterologous peptide grafts in plants of the Fabaceae family.

11 Claims, 37 Drawing Sheets

(56) References Cited

OTHER PUBLICATIONS

Da Silva et al. "Molecular requirements for the insecticidal activity of the plant peptide pea albumin 1 subunit b (PA1b)," J Biol Chem, 285: 32689-32694, 2010.
Daly et al. "Chemical synthesis and folding pathways of large cyclic polypeptides: studies of the cystine knot polypeptide kalata B1," Biochemistry, 38: 10606-10614, 1999.
Defreitas et al. "Structural characterization and promoter activity analysis of the gamma-kafirin gene from sorghum," Mol Gen Genet, 245: 177-186, 1994.
Dunwell et al. "Transgenic approaches to crop improvement," J Exp Bot, 57: 487-496, 2000.
Dutton et al. "Conserved structural and sequence elements implicated in the processing of gene-encoded circular proteins," J Biol Chem, 279: 46858-46867, 2004.
Ealing et al. "Expression of the pea albumin 1 gene in transgenic white clover and tobacco," Transgenic Res, 3: 344-354, 1994.
Eapen et al. "Cultivar dependence of transformation rates in moth bean after co-cultivation of protoplasts with Agrobacterium tumefaciens," TAG: Theor Appl Genet, 75: 207-210, 1987.
Eapen, "Advances in development of transgenic pulse crops," Biotechnol Adv, 26: 162-168, 2008.
Emanuelsson et al. "Locating proteins in the cell using TargetP, SignalP and related tools," Nature Protocols, 2: 953-971, 2007.
Fantz et al. "Ethnobotany of Clitoria (Leguminosae)," Econ Bot, 45: 511-520, 1991.
Gao et al. "Synthesis and disulfide bond connectivity-activity studies of a kalata B1-inspired cyclopeptide against dengue NS2B-NS3 protease," Bioorg Med Chem, 18: 1331-1336, 2010.
Gillon et al. "Biosynthesis of circular proteins in plants," Plant J, 53: 505-515, 2008.
Gran et al. "1. Gran L: An oxytocic principle found in Oldenlandia affinis DC.," Medd Nor Farm Selsk, 12: 173-180, 1970.
Gran et al. "Oxytocic principles of Oldenlandia affinis," Lloydia the Journal of Natural Products, 36: 174-178, 1973.
Gruber et al. "Distribution and evolution of circular miniproteins in flowering plants," Plant Cell, 20: 2471-2483, 2008.
Gunasekera et al. "Engineering stabilized vascular endothelial growth factor-A antagonists: synthesis, structural characterization, and bioactivity of grafted analogues of cyclotides," J Med Chem, 51: 7697-7704, 2008.
Guntert, "Automated NMR structure calculation with CYANA," Methods Mol Biol, 278: 353-378, 2004.
Gustafson et al. "Circulins A and B. Novel human immunodeficiency virus (HIV)-inhibitory macrocyclic peptides from the tropical tree Chassalia parvifolia.," J Am Chem Soc, 116: 9337-9338, 1994.
Gustafson et al. "New circulin macrocyclic polypeptides from Chassalia parvifolia," J Nat Prod, 63: 176-178, 2000.
Hajdukiewicz et al. "The small, versatile pPZP family of Agrobacterium binary vectors for plant transformation," Plant Mol Biol, 25: 989-994, 1994.
Halfon et al. "Autocatalytic activation of human legumain at aspartic acid residues," FEBS Lett, 438, 114-118, 1998.
Hernandez et al. "Squash trypsin inhibitors from Momordica cochinchinensis exhibit an atypical macrocyclic structure," Biochemistry, 39: 5722-5730, 2000.
Hernandez-Garcia et al. "A soybean (Glycine max) polyubiquitin promoter gives strong constitutive expression in transgenic soybean," Plant Cell Rep, 28: 837-849, 2009.
Huang et al. "Lysine-scanning mutagenesis reveals an amendable face of the cyclotide kalata B1 for the optimization of nematocidal activity," J Biol Chem, 285(14):10797-10805, 2010.
Huang et al. "The biological activity of the prototypic cyclotide kalata b1 is modulated by the formation of multimeric pores," J Biol Chem, 284: 20699-20707, 2009.
Hutchinson et al. "PROMOTIF—a program to identify and analyze structural motifs in proteins," Protein Sci, 5: 212-220, 1996.

Indurker et al. "Genetic transformation of chickpea (Cicer arietinum L.) with insecticidal crystal protein gene using particle gun bombardment," Plant Cell Rep, 26: 755-763, 2007.
Ireland et al. "A novel suite of cyclotides from Viola odorata: sequence variation and the implications for structure, function and stability," Biochem J, 400: 1-12, 2006.
Jennings et al. "Biosynthesis and insecticidal properties of plant cyclotides: the cyclic knotted proteins from Oldenlandia affinis," PNAS, 98: 10614-10619, 2001.
Kaas et al. "Analysis and classification of circular proteins in CyBase," Peptide Sci, 94: 584-591, 2010.
Kaas et al. "Conopeptide characterization and classifications: An analysis using ConoServer," Toxicon, 55: 2010 1491-1509, 2010.
Kamble et al. "A protocol for efficient biolistic transformation of mothbean Vigna aconitifolia L. Jacq. Marechal," Plant Mol Biol Reporter, 21: 457a-j, 2003.
Koenning et al. "Survey of crop losses in response to phytoparasitic nematodes in the United States for 1994," J Nematol, 31: 587-618, 1999.
Kohler et al. "Stable transformation of moth bean Vigna aconitifolia via direct gene transfer," Plant Cell Rep, 6: 1987 313-317, 1987.
Kohler et al. "Influence of plant cultivar and plasmid-DNA on transformation rates in tobacco and moth bean," Plant Sci, 53: 87-91, 1987.
Komari et al. "Binary vectors and super-binary vectors," Methods Mol Biol, 343: 15-42, 2006.
Koradi et al. "MOLMOL: a program for display and analysis of macromolecular structures," J Mol Graph, 14: 29-32, 1996.
Krishnamurthy et al. "Agrobacterium mediated transformation of chickpea ( Cicer arietinum L.) embryo axes," Plant Cell Rep, 19: 235-240, 2000.
Laskowski et al. "Aqua and Procheck-NMR: programs for checking the quality of protein structures solved by NMR.," J Biomol NMR, 8: 477-486, 1996.
Min et al. "In vitro splicing of concanavalin A is catalyzed by asparaginyl endopeptidase," Nat Struct Biol, 1: 502-504, 1994.
Mukherjee et al. "The Ayurvedic medicine Clitoria ternatea—from traditional use to scientific assessment.," J Ethnopharmacol, 120: 291-301, 2008.
Mulvenna et al. "Discovery, structural determination, and putative processing of the precursor protein that produces the cyclic trypsin inhibitor sunflower trypsin inhibitor 1," J Biol Chem, 280: 32245-32253, 2005.
Nguyen et al. "Discovery and characterization of novel cyclotides originated from chimeric precursors consisting of albumin-1 chain a and cyclotide domains in the Fabaceae family," J Biol Chem, 286(27): 24275-24287, 2011.
Opperman et al. "Sequence and genetic map of Meloidogyne hapla: A compact nematode genome for plant parasitism," PNAS, 105: 14802-14807, 2008.
Pallaghy et al. "A common structural motif incorporating a cystine knot and a triple-stranded beta-sheet in toxic and inhibitory polypeptides," Protein Sci, 3: 1833-1839, 1994.
Poth et al. "Discovery of cyclotides in the fabaceae plant family provides new insights into the cyclization, evolution, and distribution of circular proteins," ACS Chem Biol, 6: 345-355, 2011.
Qin et al. "Identification of candidates for cyclotide biosynthesis and cyclisation by expressed sequence tag analysis of Oldenlandia affinis," BMC Genomics, 11: 111, 2010.
Rogers et al. "[15] Improved vectors for plant transformation: Expression cassette vectors and new selectable markers," Methods Enzymol, 153: 253-277, 1987.
Rosengran et al. "Twists, knots, and rings in proteins. Structural definition of the cyclotide framework," J Biol Chem, 278: 8606-8616, 2003.
Saether et al. "Elucidation of the primary and three-dimensional structure of the uterotonic polypeptide kalata B1," Biochemistry, 34: 4147-4158, 1995.
Saska et al. "An asparaginyl endopeptidase mediates in vivo protein backbone cyclization," J Biol Chem, 282:29721-29728, 2007.
Saska et al. "Quantitative analysis of backbone-cyclised peptides in plants," J Chromatogr B, 872: 107-114, 2008.

(56) References Cited

OTHER PUBLICATIONS

Sharma et al. "Agrobacterium-mediated production of transgenic pigeonpea (*Cajanus cajan* L. Millsp.) expressing the synthetic Bt cry1Ab gene," In Vitro Cell Dev Biol Plant, 42: 165-173, 2006.

Simonsen et al. "Alanine scanning mutagenesis of the prototypic cyclotide reveals a cluster of residues essential for bioactivity," J Biol Chem, 283: 9805-9813, 2008.

Suto et al. "Crystal structures of novel vascular endothelial growth factors (VEGF) from snake venoms: insight into selective VEGF binding to kinase insert domain-containing receptor but not to fms-like tyrosine kinase-1," J Biol Chem, 290: 2126-2131, 2005.

Svangard et al. "Mechanism of action of cytotoxic cyclotides: cycloviolacin O2 disrupts lipid membranes," J Nat Prod, 70: 643-647, 2007.

Tam et al. "An unusual structural motif of antimicrobial peptides containing end-to-end macrocycle and cystine-knot disulfides," PNAS, 96: 8913-8918, 1999.

Tang et al. "A cyclic antimicrobial peptide produced in primate leukocytes by the ligation of two truncated alpha-defensins," Science, 286, 498-502, 1999.

Thongyoo et al. "Chemical and biomimetic total syntheses of natural and engineered MCoTI cyclotides," Org Biomol Chem, 6: 1462-1470, 2008.

Thongyoo et al. "Potent inhibitors of beta-tryptase and human leukocyte elastase based on the MCoTI-II scaffold," J Med Chem, 52: 6197-6200, 2009.

Trabi et al. "Tissue-specific expression of head-to-tail cyclized miniproteins in Violaceae and structure determination of the root cyclotide Viola hederacea root cyclotide1," Plant Cell, 16: 2204-2216, 2004.

Valvekens et al. "Agrobacterium tumefaciens-mediated transformation of Arabidopsis thaliana root explants by using kanamycin selection," PNAS, 85: 5536-5540, 1988.

Wright et al. "Nonenzymatic deamidation of asparaginyl and glutaminyl residues in proteins," Crit Rev Biochem Mol Biol, 26: 1-52, 1991.

\* cited by examiner

FIG. 9

```
CLUSTAL 2.1 multiple sequence alignment

CterB           G-VPCAESCVWIPCTVTALLGCSCKDKVCYLN 31 (SEQ ID NO:8)
CterC           G-VPCAESCVWIPCTVTALLGCSCKDKVCYLD 31 (SEQ ID NO:9)
CterE           G-IPCAESCVWIPCTVTALLGCSCKDKVCYLD 31 (SEQ ID NO:10)
CterD           G-IPCAESCVWIPCTVTALLGCSCKDKVCYLN 31 (SEQ ID NO:11)
CterR           G-IPCGESCVFIPCTVTALLGCSCKDKVCYKN 31 (SEQ ID NO:12)
CterA           GVIPCGESCVFIPC-ISTVIGCSCKNKVCYPN 31 (SEQ ID NO:7)
CterQ           G-IPCGESCVFIPC-ISTVIGCSCKNKVCYPN 30 (SEQ ID NO:14)
CterG           G-LPCGESCVFIPC-ITTVVGCSCKNKVCYNN 30 (SEQ ID NO:15)
CterH           G-LPCGESCVFIPC-ITTVVGCSCKNKVCYND 30 (SEQ ID NO:16)
CterK           H-EPCGESCVFIPC-ITTVVGCSCKNKVCYN- 29 (SEQ ID NO:17)
CterL           H-EPCGESCVFIPC-ITTVVGCSCKNKVCYD- 29 (SEQ ID NO:18)
CterF           G-IPCGESCVFIPC-ISSVVGCSCKSKVCYLD 30 (SEQ ID NO:19)
CterP           G-IPCGESCVFIPC-ITAAIGCSCKSKVCYPN 30 (SEQ ID NO:20)
PsyleF          GVIPCGESCVFIPC-ITAAVGCSCKNKVCYPD 31 (SEQ ID NO:21)
CterI           GTVPCGESCVFIPC-ITGIAGCSCKNKVCYIN 31 (SEQ ID NO:22)
CterJ           GTVPCGESCVFIPC-ITGIAGCSCKNKVCYID 31 (SEQ ID NO:23)
CterO           G-IPCGESCVFIPC-ITGIAGCSCKSKVCYRN 30 (SEQ ID NO:24)
CterM           GLPTCGETCTLGTC---YVPDCSCSWPICHKN 29 (SEQ ID NO:25)
CterN           GSAFCGETCVLGTC---YTPDCSCTALVCLKN 29 (SEQ ID NO:26)
                  *.*:*.  .*      .***.  :*
```

FIG. 10

```
     (SEQ ID NO:27)
  1  ACAGCAAAAGAGTAATTCCTTATTTTCATCAACTATGGCTTACGTTAGACTTACTTCTCT  60
                                   (SEQ ID NO:28) M  A  Y  V  R  L  T  S  L
 61  TGCCGTTCTCTTCTTCCTTGCTGCTTCCGTTATGAAGACAGAAGGAGGACTTcctacatg 120
      A  V  L  F  F  L  A  A  S  V  M  K  T  E  G  G  L  P  T  C
121  cggagaaacttgTACCCTGGGGACATGTTATGTGCCAGATTGTTCATGTTCATGGCCAAT 180
      G  E  T  C  L  G  T  C  Y  V  P  D  C  S  C  S  W  P  I
181  TTGCATGAAAAATCATATCATTGCAGCTAATGCAAAAACAGTGAATGAACATCGTCTCTT 240
      C  M  K  N  H  I  I  A  A  N  A  K  T  V  N  E  H  R  L  L
241  ATGTACATCTCATGAAGACTGTTTTAAGAAAGGCACTGGAAACTATTGTGCTTCTTTTCC 300
      C  T  S  H  E  D  C  F  K  K  G  T  G  N  Y  C  A  S  F  P
301  CGATTCTAACATCCATTTTGGTTGGTGTTTCCATGCTGAATCTGAAGGATATTTGTTGAA 360
      D  S  N  I  H  F  G  W  C  F  H  A  E  S  E  G  Y  L  L  K
361  AGACTTTATGAATATGTCAAAGGATGACTTAAAGATGCCTTTGGAAAGTACCAACTAAAA 420
      D  F  M  N  M  S  K  D  D  L  K  M  P  L  E  S  T  N  .
421  GTGATCATGTATGATACATCTATAAATTTAAATAAATGCTATGAAGCATATCTACTATTT 480
481  TAAATAAAAAAAAAAAAAAAAAAAAAAAAAAAAAA 514
```

FIG. 11 kB1 = SEQ ID NO: 29
kB3 & kB6 = SEQ ID NO: 30
kB2 = SEQ ID NO: 31
Q39837 Glycine max albumin-1 = SEQ ID NO: 32
P62929 Pisum sativum albumin-1 = SEQ ID NO: 33
Cter M = SEQ ID NO: 28

FIG. 13

Alignment of Precursor Polypeptides

A: Cter M (SEQ ID NO: 28)
B: Ct_Novel_Cyclotide3 (SEQ ID NO: 34)
C: Ct_Novel_Cyclotide1 (SEQ ID NO: 35)
D: Ct_Novel_Cyclotide2 (SEQ ID NO: 36)

```
A:  MAYVRLTSLAVLFFLAASVMKTEGGLFTCGETCTLGTCYVPDCSCSWPICMKNHIIAANAKTVNEHRLLCTSHEDCFFKGTGNYCASFPDSNIHFGWCFRAESEGYLLKOFMNMSKDLKMPLESTN  127
B:  ------------------------------VQGECTFGCSCDWPICKKNHIIATNAKTVNQHRLLCESHEDCFKKGTGNYCAFFPDSDVHFGWCFYAESDGVLSKDFPYMSKDNLKMPMTIIN----  94
C:  ------------------------------ITAAIGCSCKSKVCYRNHVIAAEAKTMDDHRLLCQSHEDCITKGTGNFCAPFPDQDIKYGWCFRAESEGFLLKDHLKMS------------ITN----  82
D:  ------------------------------ITGAIGCSCKSKVCYRNHVIAAEAKTMDDRHLLCQSHEDCITKGTGNFCAPFPDQDIKYGWCFRAESEGFMLKDHLKMS------------ITN----  82
                                  .  **.  .:  *  :*****:::****:.*****  ***:*:::****:******:.  ***  ****:*:  **;:**
```

FIG. 17
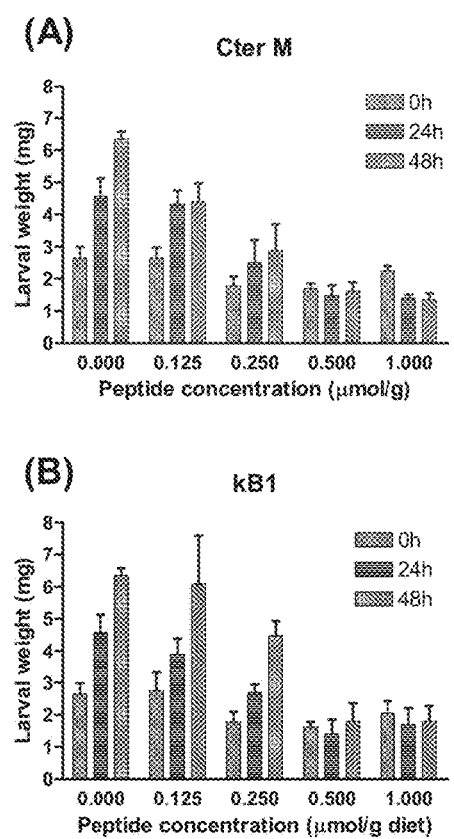
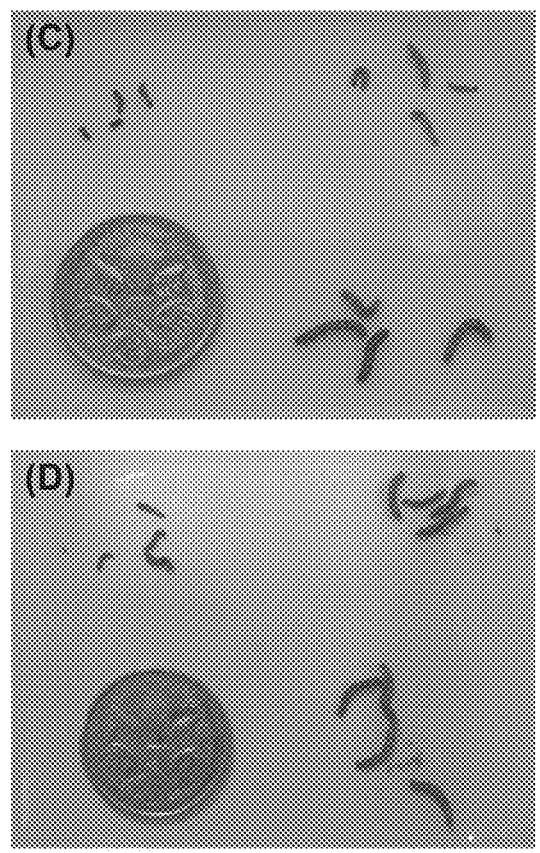

*Oldenlandia affinis* kalata B1 SignalP analysis

*Pisum sativum* Albumin-1 SignalP Analysis.

*Medicago truncatula* Albumin-1 SignalP analysis.

*Phaseolus vulgaris* Albumin-1 SignalP analysis.

*Glycine max* Albumin-1 SignalP analysis.

FIG. 21
(A)
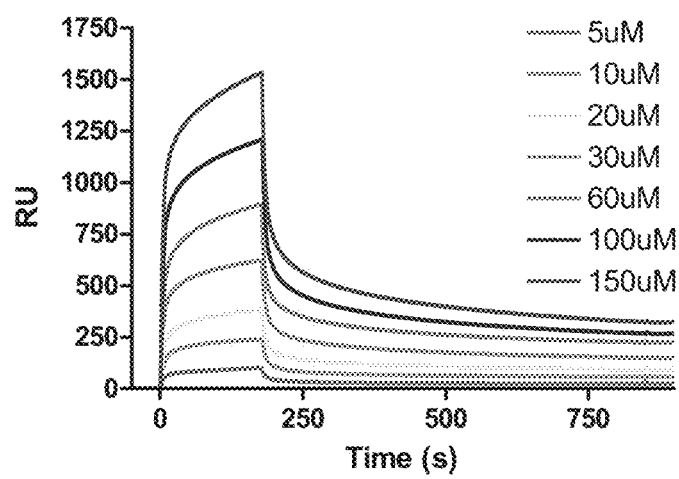
(B)
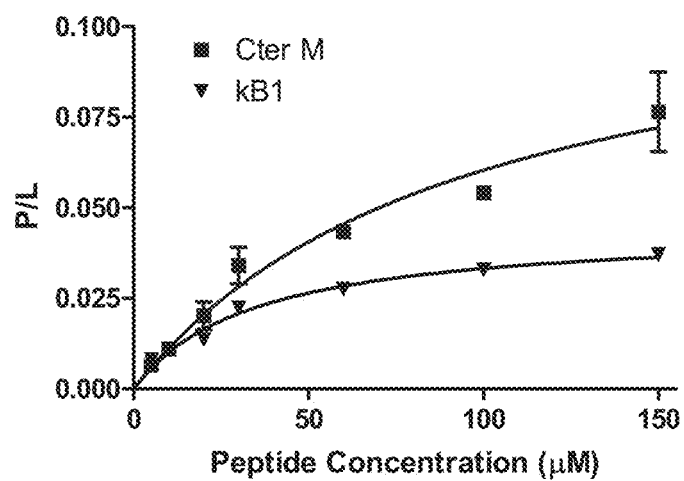

CYCLOTIDE GENES IN THE FABACEAE PLANT FAMILY

This application claims priority to U.S. Provisional Application Ser. No. 61/466,888, filed Mar. 23, 2011, which is incorporated herein by reference in its entirety.

FIELD OF THE INVENTION

The present invention relates to cyclotides and cyclotide genes from the Fabaceae plant family, and to the expression of cyclotides in Fabaceae. The present invention further relates to isolated nucleic acids configured to express cyclotides comprising heterologous peptide grafts in plants of the Fabaceae family.

BACKGROUND OF THE INVENTION

Cyclotides are a topologically unique family of plant proteins that are exceptionally stable (Craik, D. J., et al., (1999) *J. Mol. Biol.* 294, 1327-1336). They comprise ~30 amino acids arranged in a head-to-tail cyclized peptide backbone that additionally is restrained by a cystine knot motif associated with six conserved cysteine residues. The cystine knot (Pallaghy, P. K., Nielsen, K. J., Craik, D. J. & Norton, R. S. (1994) *Protein Sci.* 3, 1833-1839) is built from two disulfide bonds and their connecting backbone segments forming an internal ring in the structure that is threaded by the third disulfide bond to form an interlocking and cross braced structure (FIG. 1). Superimposed on this cystine knot core motif are a well-defined β-sheet and a series of turns displaying short surface-exposed loops.

Cyclotides express a diversity of peptide sequences within their backbone loops and have a broad range of biological activities, including uterotonic (Gran, L. (1970) *Medd. Nor. Farm. Selsk.* 12, 173-180), anti-HIV (Gustafson, K. R., Sowder, R. C. I., Henderson, L. E., Parsons, I. C., Kashman, Y., Cardellina, J. H. I., McMahon, J. B., Buckheit, R. W. J., Pannell, L. K. & Boyd, M. R. (1994) *J. Am. Chem. Soc.* 116, 9337-9338), antimicrobial (Tam, J. P., Lu, Y. A., Yang, J. L. & Chiu, K. W. (1999) *Proceedings of the National Academy of Sciences of the United States of America* 96, 8913-8918), and anticancer activities (Svångard, E., Burman, R., Gunasekera, S., Lovborg, H., Gullbo, J. & Göransson, U. (2007) *J Nat Prod* 70, 643-7). They are thus of great interest for pharmaceutical applications. Some plants from which they are derived are used in indigenous medicines, including kalata-kalata, a tea from the plant *Oldenlandia affinis* that is used for accelerating childbirth in Africa that contains the prototypic cyclotide kalata B1 (Gran, L. (1973) *Lloydia* 36, 174-178). This ethnobotanical use and more recent biophysical studies (Colgrave, M. L. & Craik, D. J. (2004) *Biochemistry* 43, 5965-5975) illustrate the remarkable stability of cyclotides, i.e., they survive boiling and ingestion, observations unprecedented for conventional peptides. Their exceptional stability means that they have attracted attention as potential templates in peptide-based drug design applications (Craik, D. J. (2006) *Science* 311, 1563-1564). In particular, the grafting of bioactive peptide sequences into a cyclotide framework offers the promise of a new approach to stabilize peptide-based therapeutics, thereby overcoming one of the major limitations on the use of peptides as drugs. Chemical (Daly, N. L., Love, S., Alewood, P. F. & Craik, D. J. (1999) *Biochemistry* 38, 10606-14; Tam, J. P. & Lu, Y.-A. (1998) *Protein Sci.* 7, 1583-1592), chemo-enzymatic (Thongyoo, P., Roque-Rosell, N., Leatherbarrow, R. J. & Tate, E. W. (2008) *Org Biomol Chem* 6, 1462-1470), and recombinant (Camarero, J. A., Kimura, R. H., Woo, Y.-H., Shekhtman, A. & Cantor, J. (2007) *ChemBioChem* 8, 1363-1366) approaches to the synthesis of cyclotides have been developed, thus facilitating these pharmaceutical applications. See also WO 01/27147 to Craik, et al, and WO 01/34829 to Craik, et al., each incorporated herein by reference.

One issue with expressing cyclotides in different host plants is ensuring that the host plant has the necessary cellular machinery to process the expressed polypeptides to produce mature cyclic molecules. One approach is to identify host plant families that produce naturally occurring cyclotides, and to adapt the natural genes to facilitate the expression of foreign or engineered cyclotides (e.g., cyclotides from other plant families, or cyclotides engineered to contain one or more grafted peptide sequences). Until recently cyclotides had been found only in the Rubiaceae (coffee) and Violaceae (violet) plant families (Kaas, Q., Westermann, J. C. & Craik, D. J. (2010) *Toxicon* 55, 1491-509), apart from two atypical members in the Cucurbitaceae (cucurbit) family (Chiche, L., Heitz, A., Gelly, J. C., Gracy, J., Chau, P. T., Ha, P. T., Hernandez, J. F. & Le-Nguyen, D. (2004) *Curr Protein Pept Sci* 5, 341-349). Cyclotides from the Rubiaceae and Violaceae are biosynthesized via processing from dedicated precursor proteins encoded by multi-domain genes which contain one, two or three cyclotide domains (Dutton, J. L., Renda, R. F., Waine, C., Clark, R. J., Daly, N. L., Jennings, C. V., Anderson, M. A. & Craik, D. J. (2004) *J. Biol. Chem.* 279, 46858-46867).

There remains a need for expression systems configured to express foreign and modified cyclotides in additional plant families.

SUMMARY OF THE INVENTION

The present invention provides systems and methods for producing cyclotides in plants of the Fabaceae family. In some embodiments, the present invention provides isolated genes encoding cyclotides of the Fabaceae family, while in some embodiments, the present invention provides expression systems making use of Fabaceae cyclotide genetic framework for the expression of foreign or modified cyclotides in plants of the Fabaceae family.

In some embodiments, the present invention provides an isolated nucleic acid molecule comprising a sequence of nucleotides encoding a precursor form of a cystine knot polypeptide (e.g., a linear polypeptide), wherein the amino acid sequence of the precursor form comprises a signal peptide, a cystine knot polypeptide, and a non-cystine knot polypeptide, wherein the cystine knot polypeptide in its mature form comprises the structure:

$$C_1(X_1 \ldots X_a)C_2(X^I_1 \ldots X^I_b)C_3(X^{II}_1 \ldots X^{II}_c)C_4(X^{III}_1 \ldots X^{III}_d)C_5(X^{IV}_1 \ldots X^{IV}_e)C_6(X^V_1 \ldots X^V_f);$$

loop 1 loop 2 loop 3 loop 4 loop 5 loop 6 wherein $C_1$ to $C_6$ are cysteine residues;
wherein each of $C_1$ and $C_4$, $C_2$ and $C_5$, and $C_3$ and $C_6$ are connected by a disulfide bond to form a cystine knot;
wherein each X represents an amino acid residue in a loop, wherein the amino acid residues may be the same or different;
wherein d is about 1-2;
wherein for a, b, c, e, and f, and
i) a may be any number from 3-10, and
ii) b, c, e, and f may be any number from 1 to 20.

In certain embodiments, in the isolated nucleic acid molecule described above, a is from about 3 to 6, b is from about 3 to about 5, c is from about 2 to about 7, e is from about 3 to about 6 and f is from about 4 to about 9. In some embodiments, a is about 3, b is about 4, c is from about 4 to about 7, d is about 1, e is about 4 or 5 and f is from about 4 to about 7.

In some embodiments, in the precursor form of a cystine knot polypeptide, the sequence of at least one cystine knot polypeptide comprises on at least one end an amino acid triplet selected from the group consisting of GLP, GIP, and SLP. In certain preferred embodiments, in the cyclic form of the cystine knot polypeptide, loop 6 of the encoded polypeptide has an amino acid sequence selected from the group consisting of YRNGVIP (SEQ ID NO:110), YLNGVIP (SEQ ID NO:111), YLDGVP (SEQ ID NO:112), YLNGIP (SEQ ID NO:113), YLDGIP (SEQ ID NO:114), YLNGLP (SEQ ID NO:115), YNNGLP (SEQ ID NO:116), YNDGLP (SEQ ID NO:117), YINGTVP (SEQ ID NO:118), YIDGTVP (SEQ ID NO:119), YNHEP (SEQ ID NO:120), YDHEP (SEQ ID NO:121), LKNGSAF (SEQ ID NO:122), MKNGLP (SEQ ID NO:123), YRNGIP (SEQ ID NO:124), YKNGIP (SEQ ID NO:125, and YRDGVIP (SEQ ID NO:126).

In some embodiments, the cystine knot polypeptide portion of said linear precursor comprises the structure:

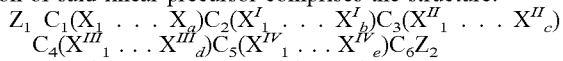

wherein $C_1$ to $C_6$ are cysteine residues;
wherein each of $C_1$ and $C_4$, $C_2$ and $C_5$, and $C_3$ and $C_6$ are connected by a disulfide bond to form a cystine knot,
wherein each X represents an amino acid residue in a loop, wherein said amino acid residues may be the same or different;
wherein d is about 1-2;
wherein for a, b, c, and e, and
i) a may be any number from 3-10, and
ii) b, c, and e may be any number from 1 to 20 and
wherein $Z_1$ is GVP, GIP, GVIP, GLP, HEP, GTVP, or GSA, and $Z_2$ is YLN, YLD, YKN, YRN, YNN, YND, TN, TD, YRD, YIN, MKN, or LKN.

In some embodiments of the encoded precursor form of the cystine knot polypeptide, a linker peptide comprising two or more amino acids connects the non-cystine knot polypeptide with the C-terminal amino acid of the sequence that forms the mature form of the cystine knot polypeptide. The non-cystine knot polypeptide may comprise a protein associated with a different function in an organism (e.g., a protein such as albumin, known to have functions that are not typically associated with or requiring the presence of a cyclic cystine knot peptide). In certain preferred embodiments, the non-cystine knot polypeptide comprises an albumin or albumin-like polypeptide, and the CCK portion replaces a portion of a typical albumin polypeptide sequence. In some particularly preferred embodiment, the albumin polypeptide comprises an albumin-1 a-chain and the CCK portion replaces some or, all of the b-chain portion of the albumin-1 polypeptide.

As used herein, the "signal" peptide generally refers to an endoplasmic reticulum (ER) signal sequence, typically of about 24 amino acids. (Emanuelsson, O., Brunak, S., von Heijne, G., Nielsen H. (2007) *Nature Protocols*, 2, 953-971) In certain embodiments, in the isolated nucleic acid molecule described above, in the amino acid sequence of the precursor form the signal peptide is contiguous with the N-terminal amino acid of the sequence that makes up the mature form of the cystine knot polypeptide. In particularly preferred embodiments, the isolated nucleic acid molecule comprising a sequence encoding a precursor form of a cystine knot polypeptide is from a plant belong to the family Fabaceae. In certain particularly preferred embodiments, the nucleic acid sequence encoding the precursor form of a cystine knot polypeptide is from *Clitoria ternatea*. In some embodiments, the signal peptide is encoded by a nucleotide sequence comprising ATGGCTTACGTTAGACTTACT-TCTCTTGCCGTTCTCTTCTTCCTTGCTGCTTCCGTT ATGAAGACAGAAGGA (JF501210) (SEQ ID NO:127), while in some embodiments, the signal peptide is encoded by a nucleic acid sequence selected from SEQ ID NOS:150, 152, 154, 156, 158, and 160. In some embodiments, the isolated nucleic acid encodes a signal peptide comprising the amino acid sequence MAYVRLTSLAVLFFLAASVMK-TEG (JF501210) (SEQ ID NO:128), while in some embodiments, the isolated nucleic acid encodes a signal peptide having an amino acid sequence selected from SEQ ID NOS:151, 153, 155, 157, 159 and 161.

In some embodiments, the present invention provides an isolated nucleic acid molecule encoding a proteinaceous molecule having a cyclic cystine knot backbone and a defined biological activity, comprising a sequence of nucleotides encoding a precursor form of a cystine knot polypeptide operably linked to a promoter, wherein the amino acid sequence of the precursor form comprises a signal peptide, a cystine knot polypeptide and a non-cystine knot polypeptide, wherein the cystine knot polypeptide in its mature form comprises the structure:

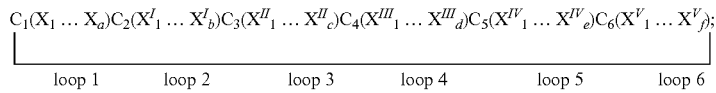

wherein $C_1$ to $C_6$ are cysteine residues and each of $C_1$ and $C_4$, $C_2$ and $C_5$, and $C_3$ and $C_6$ are connected by a disulfide bond to form a cystine knot, and wherein each X represents an amino acid residue in a loop, which may be the same or different. In certain preferred embodiments, d is about 1-2 and one or more of loops 1, 2, 3, 5 or 6 have an amino acid sequence comprising the sequence of a heterologous peptide comprising a plurality of contiguous amino acids and having a defined biological activity, the peptide being generally about 2 to 30 amino acid residues, such that any loop comprising the sequence of the peptide comprises 2 to about 30 amino acids, and such that for any of loops 1, 2, 3, 5, or 6 that do not contain the sequence of the peptide, a, b, c, e, and f, may be the same or different, and a may be any number from 3-10, and b, c, e, and f may be any number from 1 to 20.

In some embodiments of the isolated nucleic acid described above, the amino acid sequence of the heterologous peptide comprises a portion of an amino acid sequence of a larger protein, wherein the heterologous peptide confers the defined biological activity on the larger protein.

In some embodiments of the isolated nucleic acid described above, for any of loops 1, 2, 3, 4, 5, or 6 that do not contain the sequence of the heterologous peptide, a is from about 3 to 6, b is from about 3 to about 5, c is from about 2 to about 7, d is about 1 to 2, e is from about 3 to about 6 and f is from about 4 to about 9. In some preferred embodiments, a is about 3 and d is about 1, and for any of loops 2, 3, 5, or 6 that do not contain the sequence of the heterologous peptide, b is about 4, c is from about 4 to about 7, e is about 4 or 5 and f is from about 4 to about 7. In certain particularly preferred embodiments, a is about 6 and d is about 1, and for any of loops 2, 3, 5, or 6 that do not contain the sequence of the heterologous peptide, b is about 5, c is about 3, e is from about 5 and f is from about 8.

In some embodiments, any loop comprising the sequence of the heterologous peptide comprises 2 to about 20 amino acids, more preferably 2 to about 10 amino acids.

In certain embodiments of the isolated nucleic acid described above, when the encoded cystine knot polypeptide is processed into a cyclic form, loop 6 comprises an amino acid sequence selected from the group consisting of YRNGVIP (SEQ ID NO:110), YLNGVIP (SEQ ID NO:111), YLDGVP (SEQ ID NO:112), YLNGIP (SEQ ID NO:113), YLDGIP (SEQ ID NO:114), YLNGLP (SEQ ID NO:115), YNNGLP (SEQ ID NO:116), YNDGLP (SEQ ID NO:117), YINGTVP (SEQ ID NO:118), YIDGTVP (SEQ ID NO:119), YNHEP (SEQ ID NO:120), YDHEP (SEQ ID NO:121), LKNGSAF (SEQ ID NO:122), MKNGLP (SEQ ID NO:123), YRNGIP (SEQ ID NO:124), YKNGIP (SEQ ID NO:125), and YRDGVIP (SEQ ID NO:126).

In some embodiments of the isolated nucleic acid molecule the non-cystine knot polypeptide comprises an albumin-1 polypeptide and in certain preferred embodiments, the albumin polypeptide comprises an albumin-1 a-chain.

In some embodiments of the isolated nucleic acid molecule, in the encoded amino acid sequence of the precursor form, the signal peptide is adjacent to the N-terminal amino acid of the mature form of the cystine knot polypeptide.

In some embodiments the present invention provides a composition comprising a host cell comprising a heterologous nucleic acid comprising an isolated nucleic acid as described above. In some embodiments, the host cell is a plant cell, and in certain preferred embodiments, the plant cell is from the plant family Fabaceae. In particularly preferred embodiments, the host cell carries an enzyme for processing a precursor form of the cystine knot polypeptide expressed from the nucleic acid to produce a cyclic cystine knot polypeptide.

In some embodiments, the present invention provides a method for producing a cystine knot polypeptide comprising transforming a host cell with a vector comprising a nucleic acid molecule as described above and the precursor form of the cystine knot polypeptide is expressed in the host cell.

In some embodiments the present invention provides methods for producing a cyclic cystine knot polypeptide, comprising: transforming a host cell with a vector comprising a nucleic acid molecule as described above; expressing a linear precursor form of a cyclic cystine knot polypeptide; and processing the linear precursor form to form a mature cyclic cystine knot polypeptide having the structure:

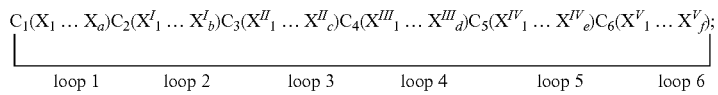

$$C_1(X_1 \ldots X_a)C_2(X^I_1 \ldots X^I_b)C_3(X^{II}_1 \ldots X^{II}_c)C_4(X^{III}_1 \ldots X^{III}_d)C_5(X^{IV}_1 \ldots X^{IV}_e)C_6(X^V_1 \ldots X^V_f);$$

loop 1    loop 2    loop 3    loop 4    loop 5    loop 6

In some embodiments, when the cystine knot polypeptide is processed into a cyclic form, loop 6 comprises an amino acid sequence selected from the group consisting of YRNGVIP (SEQ ID NO:110), YLNGVIP (SEQ ID NO:111), YLDGVP (SEQ ID NO:112), YLNGIP (SEQ ID NO:113), YLDGIP (SEQ ID NO:114), YLNGLP (SEQ ID NO:115), YNNGLP (SEQ ID NO:116), YNDGLP (SEQ ID NO:117), YINGTVP (SEQ ID NO:118), YIDGTVP (SEQ ID NO:119), YNHEP (SEQ ID NO:120), YDHEP (SEQ ID NO:121), LKNGSAF (SEQ ID NO:122), MKNGLP (SEQ ID NO:123), YRNGIP (SEQ ID NO:124), YKNGIP (SEQ ID NO:125), and YRDGVIP (SEQ ID NO:126).

In some embodiments, the host cell is a plant cell, and in certain preferred embodiments, the plant cell is from the plant family Fabaceae. In particularly preferred embodiments, the host cell carries an enzyme for processing the precursor form of the cystine knot polypeptide to produce a cyclic cystine knot polypeptide. In some embodiments, a linear form of the cystine knot polypeptide is cyclized in vitro using, e.g., enzymatic and/or chemical treatment.

BRIEF DESCRIPTION OF THE DRAWINGS

FIG. 9 provides a CLUSTAL 2.1 multiple sequence alignment of nineteen cyclotides from seeds, leaves and flowers of *C. ternatea*. Identical amino acids are indicated by "*", strongly similar amino acids are indicated by ":" and similar amino acids are indicated by ".".

FIG. 10 provides a schematic representation of the complete cDNA sequence (SEQ ID NO:27) and putative translated protein sequence (SEQ ID NO:28) for the Cter M isolate from leaf tissue of butterfly pea (*Clitoria ternatea*). The site of initial degenerate primer Ct-For1A is shown in lower case letters, and gene-specific primers used for 5' RACE are italicized. The mature cyclotide peptide is double underlined and the putative albumin-1 a-chain domain is single-underlined.

FIG. 11A provides a comparison of several genes encoding kalata cyclotides in the Rubiaceae plant *Oldenlandia affinis*.

FIG. 11B provides a comparison of the gene structures for two Fabaceae family albumin genes [*Glycine max* (soybean) albumin-1 and *Pisum savitum* (green pea) albumin-1] with the gene encoding the Cter M cyclotide isolate from *C. ternatea*.

FIG. 13 provides an alignment of several complete and partial precursor cyclotide polypeptides from *C. ternatea*.

FIG. 17 illustrates the effect of Cter M and kB1 on the growth of *Helicoverpa armigera*. The weight of larvae at 0, 24 and 48 h is plotted versus peptide concentration for Cter M (A) and kB1 (B) and the size of control larvae (bottom, right) alongside larvae fed at medium (0.25 μmol/g diet) (top, right) and high (1.0 μmol/g diet)(top, left) peptide concentrations at 48 h is depicted for Cter M (C) and kB1 (D).

FIG. 21 provides a sensorgram for Cter M binding to POPC vesicles (A) immobilized on the chip surface. The peptide samples were injected from 0 to 180 s otherwise buffer was flowing. The sensorgrams were referenced using a blank flow cell with no peptide. Equilibrium binding curves for Cter M and kB1 binding to immobilized lipid vesicles (B). Fit to the single site binding model is shown as a solid line.

DEFINITIONS

Figure 1:
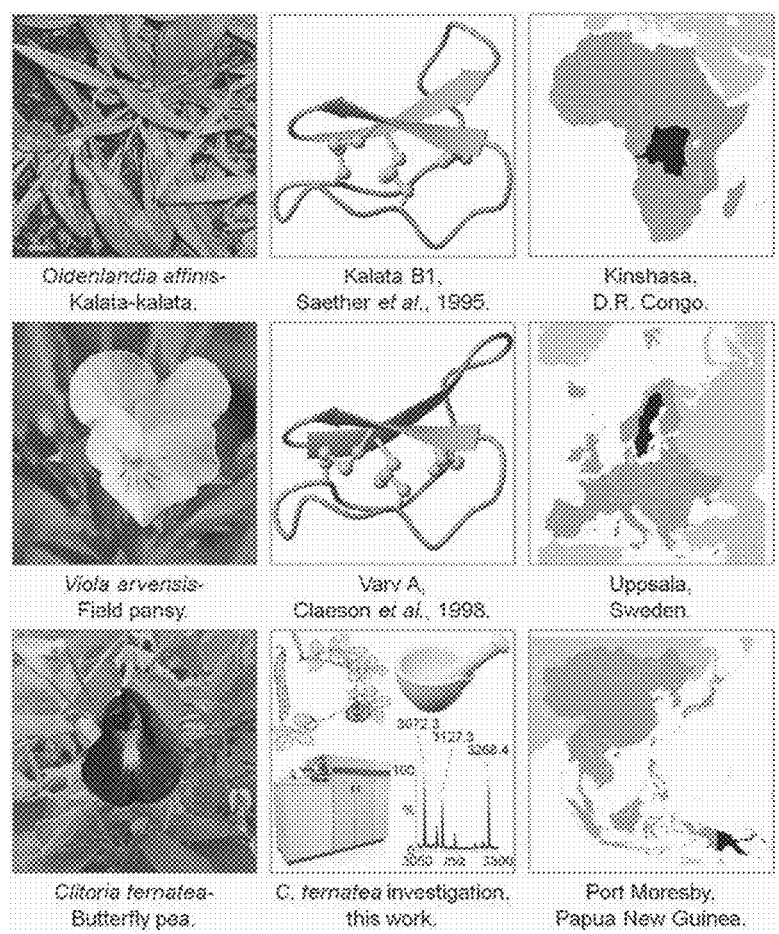
FIG. 1 provides a diagram illustrating the botanical and geographical origins of the first cyclotides described from Rubiaceae, Violaceae and Fabaceae plant families.

As used herein, the term "molecular framework" refers to a proteinaceous molecule having a defined three-dimensional structure. This defined three-dimensional structure comprises loops of amino acid residues and other elements of molecular structure held in defined orientation with respect to each other. The molecular framework itself may exhibit a particularly useful property such as having anti-pathogen activities against viruses, microorganisms, fungi, yeast, arachnids and insects or it may confer useful therapeutic properties in plants or animals. Furthermore, it may provide the framework for inserting one or more amino acids or amino acid sequences capable of conferring a desired biological effect. Insertion of one or more amino acid residues or sequences may occur on a beta-turn or within a loop. The molecular framework may also be presented in a linear form as a substrate for cyclization. Alternatively, a cyclic molecule may be derivatized into a linear form which itself may have useful properties or it may act as an agonist or antagonist of such properties.

The sequence of amino acids forming the backbone of the molecular framework may be naturally occurring amino acid residues or chemical analogues thereof. Chemical analogues of amino acid residues include non-naturally occurring amino acids. Examples of non-naturally occurring amino acids are shown in Table 3.

By way of example, when a molecular framework in the form of a cyclic polypeptide is isolated and purified from a biological source, such as a plant, the molecule generally comprises naturally occurring amino acid residues. However, the present invention extends to derivatives of such a molecular framework resulting from the insertion or substitution of non-naturally occurring amino acid residues or chemical analogues of amino acid residues. Alternatively, a single and/or a heterologous sequence of naturally occurring amino acid residues may be inserted or substituted into the molecular framework to confer desired properties on the molecule.

As used herein, the term "cyclic backbone" refers to a molecule comprising a sequence of amino acid residues or analogues thereof without free amino and carboxy termini. Preferably, the linkage between all amino acids in the cyclic backbone is via amide (peptide) bonds, but other chemical linkers are also possible. The cyclic backbone of the molecular framework of the present invention comprises sufficient disulfide bonds, or chemical equivalents thereof, to confer a knotted topology on the three-dimensional structure of the cyclic backbone.

In some embodiments, a cyclic backbone comprises a structure referred to herein as a "cystine knot". A cystine knot occurs when a disulfide bond passes through a closed cyclic loop formed by two other disulfide bonds and the amino acids in the backbone. Such a cystine knot is referred to herein as a "cyclic cystine knot" or "CCK". However, reference herein to a "cyclic cystine knot" or a "CCK" includes reference to structural equivalents thereof which provide similar constraints to the three-dimensional structure of the cyclic backbone. For example, appropriate turns and loops in the cyclic backbone may also be achieved by engineering suitable covalent bonds or other forms of molecular associations. All such modifications to the cyclic backbone which result in retention of the three-dimensional knotted topology conferred by the cyclic cystine knot are encompassed by the present invention. Furthermore, although a cyclic cystine knot is characterized by a knot formed by three disulfide bonds, the present invention extends to molecules comprising only two disulfide bonds. In such a case, the molecular framework may need to be further stabilized using other means or the molecular framework may retain suitable activity despite a change in three-dimensional structure caused by the absence of a third disulfide bond.

Cyclic backbones may comprise more than three disulfide bonds such as those occurring in a double or multiple cystine knot arrangement or in a single cystine knot arrangement supplemented by one or two additional disulfide bonds.

The term "cyclic cystine knot" and "CCK" and "cyclotide" are used interchangeably and encompass natural cystine knot peptides, as well as cystine knot peptides comprising modified amino acids, substituted loop sequences, grafted peptides, and other modifications. The terms "knot" and "cystine knot" are not to be limited by any mathematical or geometrical definition of the term "knot". The knots contemplated by the present invention are referred to as such due to their similarity to a mathematical knot and/or by virtue of the intertwined features of the folded molecule.

The present invention provides, therefore, genes and expression systems encoding a molecular framework comprising a sequence of amino acids or analogues thereof forming a cyclic backbone and wherein said cyclic backbone comprises a cystine knot or its chemical or structural equivalent which confers a knotted topology on the three-dimensional structure of said cyclic backbone.

Accordingly, one aspect of the present invention contemplates an isolated nucleic acid molecule encoding a molecular framework comprising a sequence of amino acids forming a cyclic backbone wherein the cyclic backbone comprises sufficient disulfide bonds or chemical equivalents hereof to confer knotted topology on the molecular framework or part thereof wherein said cyclic backbone comprises the structure:—

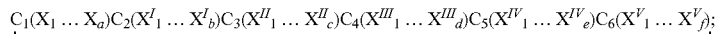

wherein C is cysteine; each of $(X_1 \ldots X_a)$, $(X^I_1 \ldots X^I_b)$, $(X^{II}_1 \ldots X^{II}_c)$, $(X^{III}_1 \ldots X^{III}_d)$, $(X^{IV}_1 \ldots X^{IV}_e)$, $(X^V_1 \ldots X^V_f)$ represents one or more amino acid residues, wherein each one or more amino acid residues within or between the cysteine residues may be the same or different; and wherein a, b, c, d, e and f represent the number of amino acid residues in each respective sequence. In some embodiments, a, b, c, d, e and f may range from 1 to about 10, 11, 12, 13, 14, 15, 16, 17, 18, 19, or 20.

In certain preferred embodiments, the cyclic backbone of the present invention comprises the structure:

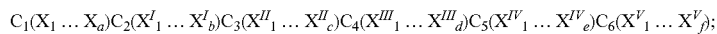

wherein a is about 6, b is about 5, c is about 3, d is about 1 or 2, e is about 5 and f is about 8; or an analogue of said sequence.

The molecular framework of the present invention is also referred to herein as a "cyclotide". A cyclotide is regarded as being equivalent to a molecular framework as herein described and, in its most preferred embodiment, comprises a cyclic cystine knot motif defined by a cyclic backbone, at least two but preferably at least three disulfide bonds and associated beta strands in a particular knotted topology. The knotted topology involves an embedded ring formed by at least two disulfide bonds and their connecting backbone segments being threaded by a third disulfide bond. As stated above, however, a disulfide bond may be replaced or substituted by another form of bonding such as a covalent bond.

Each amino acid has a carboxyl group and an amine group, and amino acids link to one another to form a chain by joining the amine group of one amino acid to the carboxyl group of the next. Thus, linear polypeptide chains generally have an end with an unbound carboxyl group, the C-terminus, and an end with an amine group, the N-terminus. The convention for writing polypeptide sequences is to put the N-terminus on the left and write the sequence from N- to C-terminus. Sequences with longer or non-linear (e.g., cyclized) polypeptide that do not have unbound termini can nonetheless be directionally oriented by reference to the direction of the N and C groups on internal amino acid residues. For example, the amino acid in an internal region that would have a carboxyl group if on a terminus may be referred to as the C-terminal end of the internal sequence. The N and C designations also are used to indicate directionality on a polypeptide strand. For example, a first region of a polypeptide sequence that is attached by its C-terminal residue to the N-terminal residue of a second region of the same polypeptide may be referred to as being in the N or N-terminal direction from the second region. Conversely, the second region is in the C or C-terminal direction from the first region.

As used herein, the term "adjacent" as used in reference to amino acids or peptide regions refers to residues or regions that are contiguous or are immediately next to each other, e.g., in a polypeptide chain, with no intervening residues.

The terms "peptide" and "polypeptide" are used interchangeably herein to refer to a chain comprising a plurality amino acid residues connected by peptide bond(s). "Residue" as used in reference to an amino acid refers to an individual amino acid in a polypeptide chain.

As used herein, the term "graft" or "grafted" as used in reference to a peptide sequence used to modify a framework molecule, refers to the integration of a heterologous sequence of amino acids (a "heterologous peptide") into the polypeptide strand at one or more positions on a framework molecule. For example, one or more loops of a CCK molecule may be made to comprise a heterologous sequence of amino acids in addition to, or as a full or partial replacement for a normal or native loop sequence. Grafting of a peptide into a CCK framework molecule need not be done after the proteinaceous framework molecule has been produced. In certain preferred embodiments, a peptide sequence, e.g., a bioactive peptide, is grafted into a framework proteinaceous molecule by creation of a nucleic acid molecule comprising a nucleotide sequence that encodes the framework CCK molecule along with the grafted peptide amino acid sequence.

In addition to the grafts described above, the present invention encompasses a range of amino acid substitutions, additions and/or insertions to the amino acid sequence of the molecular framework. Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example, Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some nonconventional amino acids may also be suitable replacements for the naturally occurring amino acids. For example, ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (e.g. substituting a charged or hydrophobic amino acid with alanine), or alternatively, in which a naturally-occurring amino acid is substituted with a nonconventional amino acid.

Amino acid substitutions are typically of single residues, but may be of multiple residues, either clustered or dispersed. Amino acids of the cyclic peptide backbone are preferably conservative in order to maintain the three-dimensional structure in a form functionally similar to the cyclic peptide before derivatization. Substitutions of amino acid residues in the cyclic peptide to introduce or otherwise graft heterologous sequences onto the backbone need not be conservative.

Additions encompass the addition of one or more naturally occurring or non-conventional amino acid residues. Deletion encompasses the deletion of one or more amino acid residues.

The present invention also includes molecules in which one or more of the amino acids has undergone side chain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulfhydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues preferably does not affect the ability of the peptide to form the necessary disulfide bonds. It is also possible to replace the sulfhydryl groups of cysteine with selenium or tellurium equivalents such that the peptide forms a diselenide or ditelluride bond in place of one or more of the disulfide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Proline residues may be modified by, for example, hydroxylation in the 4-position. Other modifications include succinimide derivatives of aspartic acid.

A list of some amino acids having modified side chains and other unnatural amino acids is shown in Table 3, below.

TABLE 3

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| α-aspartic acid | Aaa |  |  |
| β-aspartic acid | Baa |  |  |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |

TABLE 3-continued

| Non-conventional amino acid | Code | Non-conventional amino acid | Code |
|---|---|---|---|
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethy)glycine | Nthr |
| D-N-methylhistidine | Dnmhis | N-(hydroxyethy))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

As used herein, the terms "isolated" or "substantially isolated" as used in reference to molecules, e.g., either nucleic or amino acid, refers to molecules that are removed from their natural environment, purified or separated, and are at least partially free, preferably 50% free, more preferably 75% free, and most preferably 90% free from other components with which they are naturally associated. An "isolated" molecule that is separated from components with which it is associated in nature need not be isolated from other materials, and may be, for example, combined with other components e.g., heterologous host cell components, reaction components and the like.

DETAILED DESCRIPTION OF THE INVENTION

The present invention provides cyclotides isolated from plants in the Fabaceae family of plants. In some embodiments, the present invention further provides isolated nucleic acids configured for expression in plants of the Fabaceae family and encoding a molecular framework comprising a sequence of amino acids or analogues thereof forming a cyclic backbone, wherein said cyclic backbone comprises sufficient disulfide bonds, or chemical equivalents thereof, to confer a knotted topology on the three-dimensional structure of said cyclic backbone. In still other embodiments, the present invention provides isolated nucleic acids configured for expression in plants of the Fabaceae family and encoding a molecular framework as described above and containing a heterologous grafted peptide. In preferred embodiments, the grafted peptide confers a bioactivity on said molecular framework molecule.

The Fabaceae (legume) plant family is the third largest family of plants on earth comprising 18,000 species, many of which, e.g., peas and beans, are centrally involved in human nutrition. The discovery of cyclotides in the Fabaceae family broadens interest in this family of molecules because it facilitates the possibility of expressing genetically modified cyclotide sequences in crop plants from the Fabaceae. In addition to their importance as crop plants, multiple members of the Fabaceae family of plants are amenable to transfection. Modification of these plants to express foreign or engineered cyclotides finds a number of applications, including conferring insect resistance traits on the host plants themselves. In some embodiments, the host plants may be used to manufacture cyclotides having, for example, pharmaceutical attributes. It is envisioned that expressed cyclotides may be purified from the host plants or, in some embodiments, plant materials having beneficial pharmaceutical attributes may be used directly, e.g., in foods or food supplements or in the preparation of topical treatments, etc.

The present invention provides a genetic system for the expression of cyclotides in the Fabaceae plant family. We provide herein nucleic acid sequences encoding cyclotides from the Fabaceae plant family and show that the corresponding peptide is ultra-stable and insecticidal like other cyclotides, but has an unexpected biosynthetic origin in that it is embedded within an albumin precursor sequence.

In some embodiments, the present invention comprises isolated nucleic acids configured to encode Fabaceae-derived cyclotides comprising grafted heterologous peptides. The heterologous amino acids inserted or substituted in the molecular framework have the capacity to confer a range of activities and biological properties to the molecule including modulating calcium channel-binding, which is useful in the treatment of pain or a stroke, C5a binding, useful as an anti-inflammatory agent, proteinase inhibitor activity in plants or animals, antibiotic activity, anti-HIV activity, antimicrobial activity, anti-fungal activity, anti-viral activity, anthelmintic activity, cytokine binding ability and blood clot inhibition and plant pathogen activity (e.g., insecticidal activity) amongst other properties. The molecule may be a modulator in the sense that it may facilitate the activity or inhibit the activity. Accordingly, the molecule may act as an agonist or antagonist. Furthermore, the heterologous amino acids may form a sequence which may be readily cleaved to form a linear molecule, or to activate a peptide that requires cleavage by a proteinase for activation.

Peptides having defined biological activity, including peptides containing about 30 or fewer amino acid residues, particularly suitable for grafting, are well known. At this time, tens of thousands of peptides of this kind have been described in the scientific literature and have been recorded in peptide databases. See, e.g., Peptide Atlas published on the worldwide web at peptideatlas.org, at or PepBank, maintained online by Massachusetts General Hospital, Harvard University, Cambridge, Mass., each incorporated by reference herein. In addition, screening of peptides of unknown sequence to identify peptides having defined biological activities, including random combinatorial libraries containing millions of peptides, is conventional in the art and requires no knowledge of what amino acid sequence or peptide structure would predictably result in the desired activity. See, for example, Cortese, et al., (1995) Curr. Opin. Biotech. 6:73-80, incorporated by reference herein, which discusses of the phage display method of screening random combinatorial peptide libraries. In some embodiments, the present invention comprises selecting an amino acid sequence of a peptide having a defined biological activity, preparing protein molecules having cyclic cystine knot backbones in which one or more of the loops contains the amino acid sequence of the peptide, and screening the prepared proteins using an assay for the defined biological activity so as to identify a CCK protein having the defined biological activity. In some embodiments, the peptide has a sequence of about 30 or fewer amino acids. In certain embodiments, peptides are grafted into one or more of loops 1, 2, 3, 4, 5, and/or 6. In certain preferred embodiments, peptides are grafted into one or more of loops 1, 2, 3, 5, and/or 6.

While some embodiments of CCK molecules contain loops comprising 1 to about 7 amino acids, it is known that cystine knot structures comprising six cysteines and three disulfide bonds can be formed with larger polypeptides. Larger polypeptides of this configuration have loop sizes from 1 up to 30 or more amino acid residues.

The molecular frameworks of the Fabaceae CCK molecules permit modifications to be made to the molecule while retaining the stable structural scaffold. Such modifications include, for example, different amino acid residues inserted or substituted anywhere in the molecule but preferably in one or more beta-turns and/or within a loop. The newly exposed amino acids, for example, may provide functional epitopes or activities not present in the molecular framework prior to modification. Alternatively, the newly exposed amino acids may enhance an activity already possessed by the molecular framework. A substitution or insertion may occur at a single location or at multiple locations. Furthermore, the molecular framework may be specifically selected to more readily facilitate substitution and/or insertion of amino acid sequences. Such modified forms of the molecular framework are proposed to have a range of useful properties including as therapeutic agents for animals and mammals (including humans) and plants. Therapeutic agents for plants include pest control agents. As stated above, the molecular framework has advantages in terms of increased stability relative to, for example, conventional peptide drugs. The increased stability includes resistance or less susceptibility to protease cleavage. Furthermore, the molecules may have a hydrophobic face which may benefit their interaction with membranes while still being highly water soluble.

Accordingly, another aspect of the present invention is directed to a Fabaceae molecular framework comprising a sequence of amino acids or analogues thereof forming a cyclic backbone and wherein said cyclic backbone comprises sufficient disulfide bonds or chemical equivalents thereof, to confer a knotted topology on the three-dimensional structure of said cyclic backbone and wherein at least one exposed amino acid residue such as on one or more beta turns and/or within one or more loops, is inserted or substituted relative to the naturally occurring amino acid sequence.

Even more particularly, the present invention contemplates a Fabaceae molecular framework comprising a sequence of amino acids or analogues thereof forming a cyclic backbone and wherein said cyclic backbone comprises a cystine knot or its chemical or structural equivalent which confers a knotted topology on the three-dimensional structure of said cyclic backbone and wherein at least one exposed amino acid residue such as on one or more beta turns and/or within one or more loops is inserted or substituted relative to the naturally occurring amino acid sequence.

More particularly, the present invention is directed to a Fabaceae molecular framework comprising a sequence of amino acids or analogues thereof forming a cyclic cystine knot motif defined by a cyclic backbone, at least three disulfide bonds and associated beta stands in a defined knotted topology and wherein at least one exposed amino acid residue such as on one or more beta turns or within one or more loops is inserted or substituted relative to the naturally occurring amino acid sequence.

It is contemplated that in some embodiments, a cyclic cystine knot is formed by expression of a linear precursor molecule comprising the cystine knot motif in a host cell that comprises a system of one or more enzymes for processing a precursor form of a cystine knot polypeptide to produce a cyclic cystine knot polypeptide. In other embodiments, a cystine knot polypeptide is cyclized in vitro. In some embodiments, in vitro processing is carried out enzymatically, e.g., using an isolated enzymatic processing system e.g., from a cyclotide-forming plant species, while in some embodiments, in vitro cyclizing is done by chemical treatment, e.g. in ammonium bicarbonate with triscarboxyethyl-phosphine (TCEP), as described, e.g., by Craik, et al., US Patent Publication 2003/0158096, which is incorporated by reference herein it its entirety for all purposes.

Although the inserted or substituted amino acid is preferably an exposed amino acid on a beta turn, the present invention contemplates an inserted or substituted amino acid anywhere on the molecule.

The inserted or substituted amino acid residues may be a single residue or may be a linear sequence of from about two residues to about 60 residues, preferably from about two to about 30 residues, and even more preferably, from about 2 residues to about 10 residues. The insertion or substitution may occur at a single location or at multiple locations. The latter includes the insertion of non-contiguous amino acid sequences. Furthermore, different amino acid molecules may be inserted/substituted at different sites on the molecule. This is particularly useful in the preparation of multivalent or multifunctional molecules.

Figure 2:
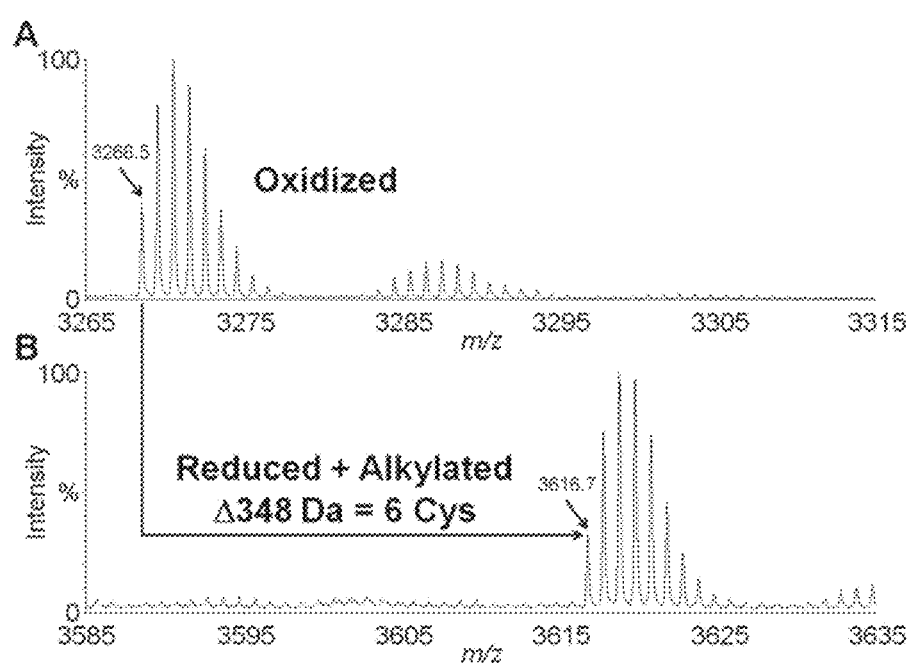
FIG. 2 provides MALDI-TOF spectra indicating the presence of cyclotides in C. ternatea seed extract. Offset-aligned MALDI-TOF spectra of 'native' (A) and 'reduced and carbamidomethylated' (B) putative cyclotide species, Cter A.

One example of a class of larger cystine knotted polypeptides is the Vascular Endothelial Growth Factors (VEGFs), described in the reference by K. Suto, et al., (2005) J. Biol. Chem. 290:2126. For example, VEGF-A$_{165}$ is composed of 165 residues (p 2126, col 2). Suto et al., provides a sequence comparison of two VEGF-related proteins called vammin (110 residues) and VR-1 (109 residues) to VEGF-A$_{165}$ and PlGF (Placental Growth Factor). As shown in FIG. 2 of Suto et al., each of these cystine knot polypeptides contains loops of up to 33 amino acid residues.

Inclusion of loops of 30 or more amino acids is not limited to the VEGF polypeptides. See, e.g., Table 2, which comprises about 1500 naturally occurring polypeptides containing cystine knot motifs. Each of the polypeptides listed has been reported to contain a cystine knot comprising six cysteine residues and at least five loops, while circular molecules have a sixth loop. The polypeptides are identified by database identifiers listed in column 1. The table provides the complete list of polypeptides reciting the sizes of each of loops in its cystine knot motif, and shows the amino acid sequences of each of the loops in its cystine knot motif. The table of cystine knot polypeptide sequences provided herewith shows that cystine knot structures can readily accommodate 30 or more amino acids in one or several loops.

Identification of Cyclotides in C. ternatea.

Clitoria ternatea, an ornamental perennial climber also known as the Butterfly pea, is a member of plant family Fabaceae, originally from Africa but now also distributed among equatorial Asiatic countries and the Americas. Preparations of C. ternatea are utilized in a variety of indigenous medicines throughout these regions, with anecdotal evidence of their use in the traditional medicines of the Philippines, Cuba and Indo-China to promote uterine contractions and expedite childbirth (Fantz, P. R. (1991) Econ. Bot. 45, 511-520; Mukherjee, P. K., et al. (2008) J. Ethnopharmacol. 120, 291-301).

Initial screening of crude seed extracts of C. ternatea revealed the presence of proteins with masses in the range 2500-4000 Da, consistent with those of known cyclotides. Following preparative RP-HPLC of the crude extract, the putative cyclotides were detected in late-eluting fractions via MALDI-TOF MS (FIG. 2A), and the masses of 12 of these putative cyclotides are reported in Table 1. In accordance with established diagnostic methodology for cyclotides (Gruber, supra), purified peptides were lyophilized, reduced and carbamidomethylated, and re-analyzed via MALDI-TOF MS. Mass increases of 348 Da, were observed following this process (FIG. 2B), indicating the presence of three intramolecular disulfide bonds in the corresponding proteins. Thus, the 12 peptides complied with all three diagnostic criteria previously identified for cyclotides (Gruber, supra), of mass profile, hydrophobicity profile, and disulfide content.

Seven cyclotide sequences were also identified from C. ternatea leaf and flower of which one, Cter A, was common to seed. Cter M was tested for insecticidal activity and was determined to have insecticidal activity against the cotton budworm Helicoverpa armigera and anthelmintic activity against Haemonchus contortus. Cter M also binds to PE membranes, suggesting its activity is modulated by membrane disruption. Sequences of the leaf and flower cyclotides, along with the seed cyclotides, are shown in FIG. 9.

Tandem MS Enables the Differentiation of Cyclotides from Linear Peptides.

Figure 3:
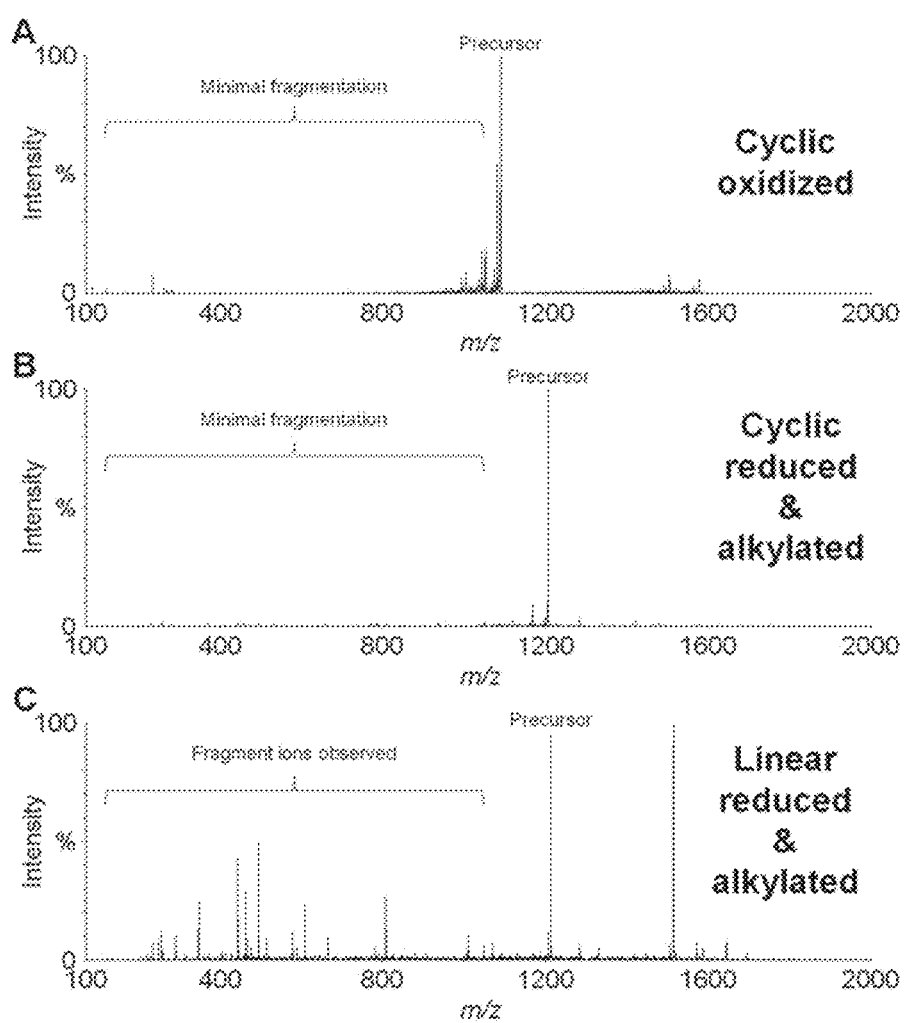
FIG. 3 provides nanospray tandem MS fragmentation patterns for 'native' vs. chemically modified Cter A at a collision energy setting of 50 V. (A) 'Native' (cyclic oxidized) cyclotide precursor m/z 1090.1, (B) cyclic reduced and alkylated precursor m/z 1206.1, (C) linear reduced and alkylated precursor m/z 1212.1. These apparent triply-charged fragment ions correspond to species of molecular masses 3267 Da, 3615 Da and 3633 Da, respectively.

There are several examples of linear proteins, including knottins and also some defensins, which are of similar size to cyclotides, possess three disulfide bonds, and display hydrophobic properties. Therefore, we sought to extend the diagnostic criteria for the detection of cyclotides by including an additional step to distinguish between peptides with cyclic or linear backbones. This additional step is illustrated for the putative cyclotide from C. ternatea seed extract, Cter A, with a 'native' mass of 3267.3 Da that increases by 348 Da after reduction and carbamidomethylation and a further 18 Da after enzymatic digestion of the peptide backbone with endoproteinase Glu-C (FIG. 3). The determination of peptide sequence via tandem MS relies in part upon the ability of the N- and C-termini to retain charge. The absence of termini in cyclotides, brought about by their macrocyclic peptide backbone, therefore prevents their efficient fragmentation in tandem MS analyses, either as fully folded CCK-containing 'native' proteins or as reduced and alkylated cyclic proteins, as illustrated for Cter A in panels A and B of FIG. 3, respectively. Only after enzymatic cleavage of reduced (or reduced and alkylated) C. ternatea peptides into their linear forms were the various fragment ions detected during tandem MS analyses (FIG. 3C). Hence, we propose that the characteristic lack of fragmentation observed in tandem MS analyses of reduced and/or reduced and alkylated cyclotides is a suitable determinant of their cyclic nature, and should be added to previously proposed criteria (Gruber, supra) as an indicator for the presence of cyclotides in a given plant.

In combination, the newly defined criteria proposed here for the positive identification of cyclotides are late-eluting properties via RP-HPLC, a mass of 2500 to 4000 Da, an increase in mass of 348 Da following reduction and alkylation with iodoacetamide, and inefficient fragmentation in MS/MS analyses of 'native' or reduced and alkylated forms. Although yet to be described from plants, cyclic peptides with three intramolecular disulfide bonds not forming a cystine knot arrangement, similar to rhesus θ-defensin-1 (Tang, Y.-Q., et al., (1999) Science 286, 498-502), could also meet these criteria. However, judging from the size and hydrophobicity of described O-defensins, false positives are unlikely.

De Novo Sequencing of Cyclotides.

Figure 4:
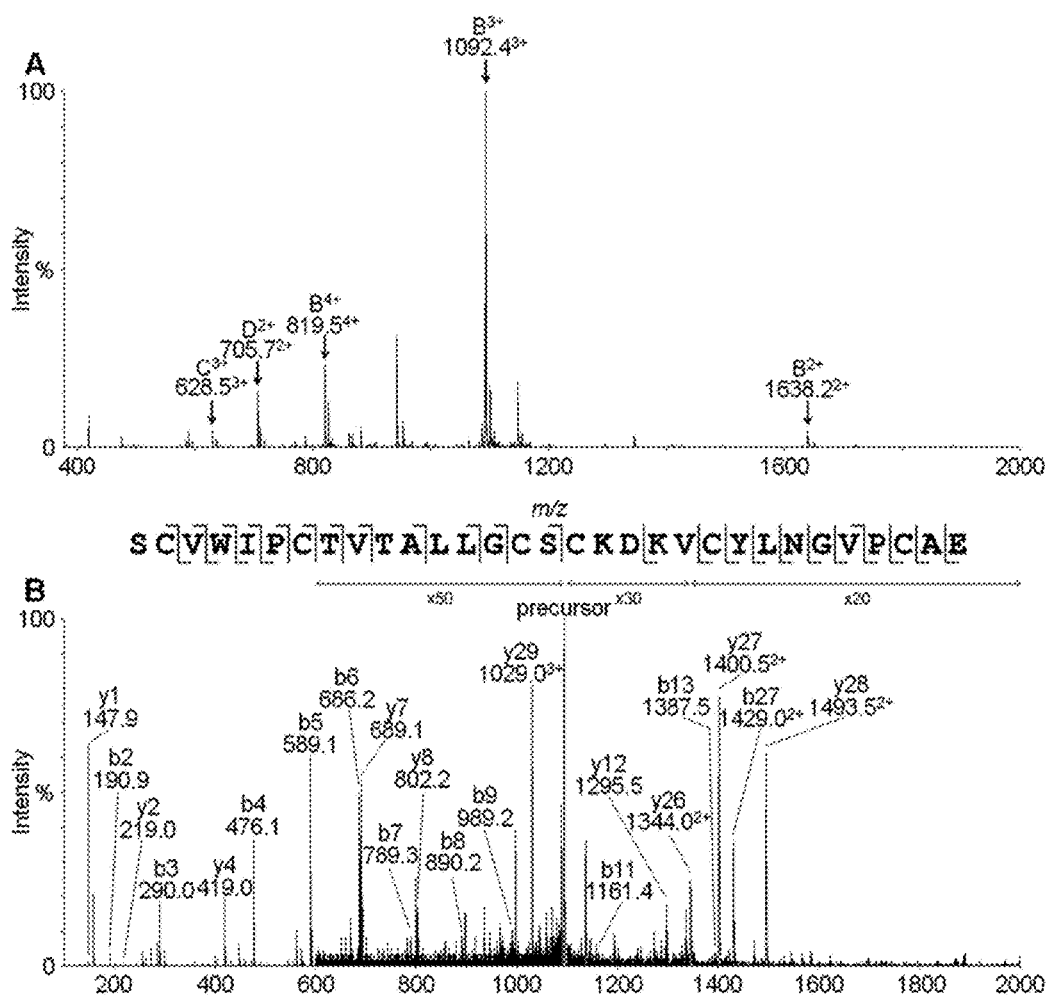
FIGS. 4A-E provide nanospray sequencing of Cter B. (A) TOF-MS spectrum of combined trypsin and endoproteinase Glu-C digest. The peaks are labelled according to their charge state, where $B^{2+}$, $B^{3+}$ and $B^{4+}$ correspond to the full-length linearized Cter B, and $C^{3+}$ and $D^{2+}$ signify smaller fragments produced through cleavage of the cyclic precursor at two points along the peptide backbone. (B) MS/MS of precursor $1092.4^{3+}$ (3274.2 Da) (SEQ ID NO:1). (C) MS/MS of precursor $628.5^{3+}$ (1882.6 Da) (SEQ ID NO:2). (D) MS/MS of precursor 705.7$^{2+}$ (1409.4 Da) (SEQ ID NO:3). (E) Digestion scheme and mass of proteolytic fragments.
Figure 4:
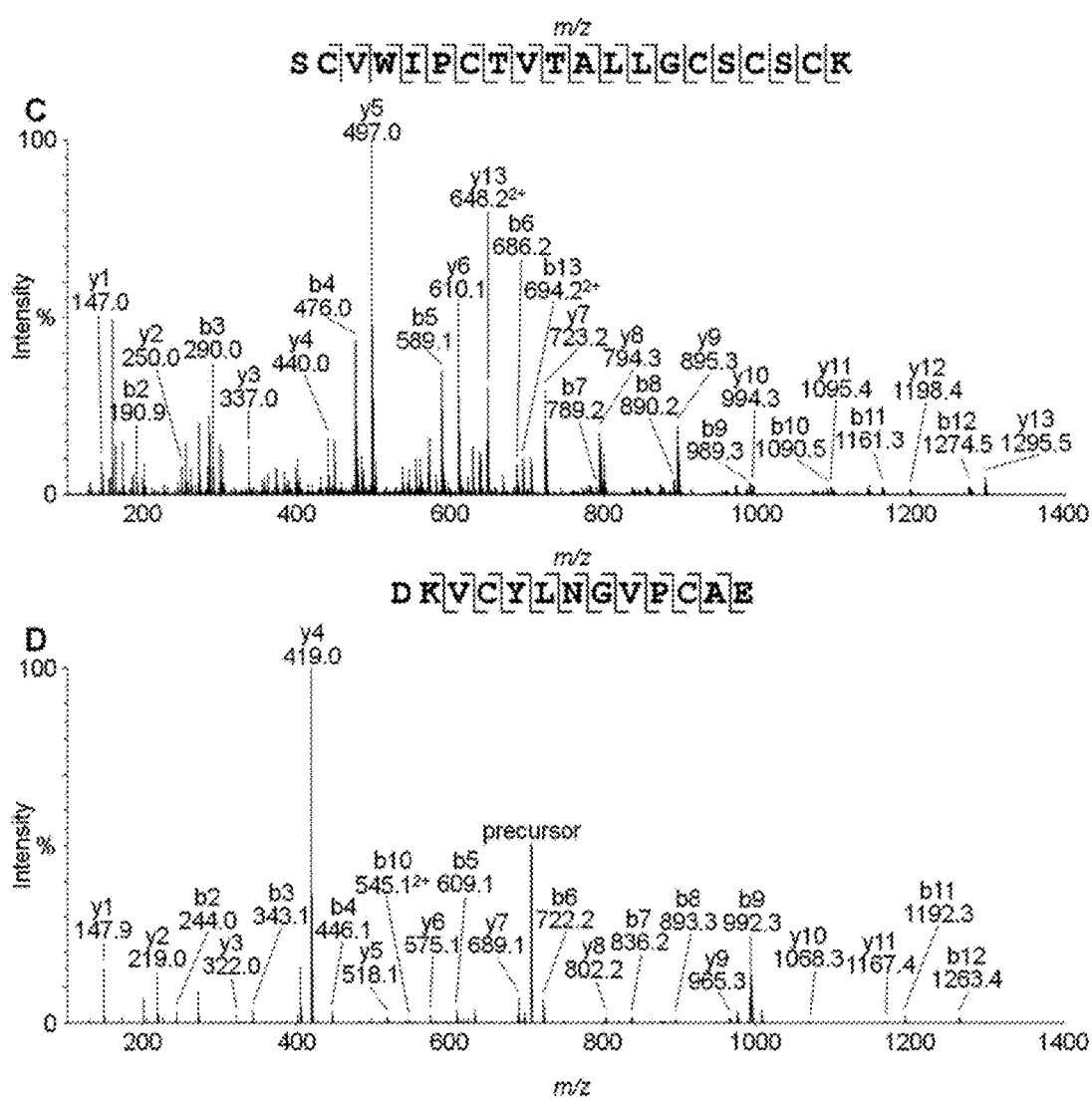
Figure 4:
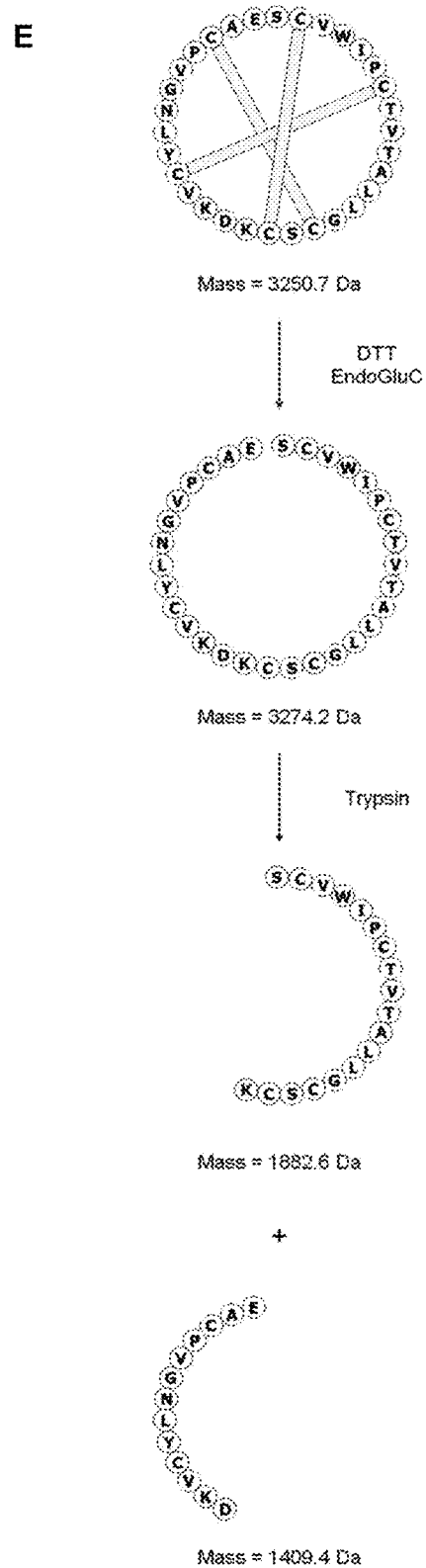

To illustrate the sequencing of the new cyclotides the step-by-step MS/MS analysis of Cter B is shown in FIG. 4. The linearized peptide resulting from endoproteinase Glu-C digestion of the reduced form of Cter B was analyzed via nanospray MS/MS. De novo sequencing yielded a tentative identification of SCVWIPCTVTALLGCSCKDKV-CYLNGVPCAE (SEQ ID NO:1). As indicated in FIG. 4B, sequence ion coverage permitted definitive assignment of the sequence near the termini of the peptide, but presented incomplete evidence for sequence close to the middle of the peptide, a feature observed in the analyses of many full-length linearized cyclotides. Combined trypsin and endoproteinase Glu-C digestion of reduced Cter B produced peptide fragments with complementary molecular weights of 1882.6 Da and 1409.4 Da. Complete sequence coverage for both precursors was attained in tandem MS analyses (FIGS. 4C and 4D), verifying the initial sequence assignment for the full-length linearized cyclotide. Using this approach, 12 novel cyclotides from *C. ternatea* were sequenced (see Table 1 in Example 1). Amino acid analyses were conducted to confirm the MS/MS determined sequences and to discriminate between Ile and Leu for a representative set of cyclotides, including Cter A, Cter B and C, Cter D and E, Cter F, and Cter G and Cter H.

Cyclotides are classified mainly into two subfamilies, Möbius or bracelet, based upon the presence or absence of a cis-Pro amide bond in loop 5. Cyclotides belonging to the bracelet subfamily are the most widely represented in the literature, at approximately three-fold greater incidence than cyclotides belonging to the Möbius subfamily. Consistent with this prominence, the sequences discovered in the current study, all belong to the bracelet subfamily. However, several of them have unusual residues at key processing sites, making them of interest for understanding processing mechanisms of cyclotides.

Figure 5:
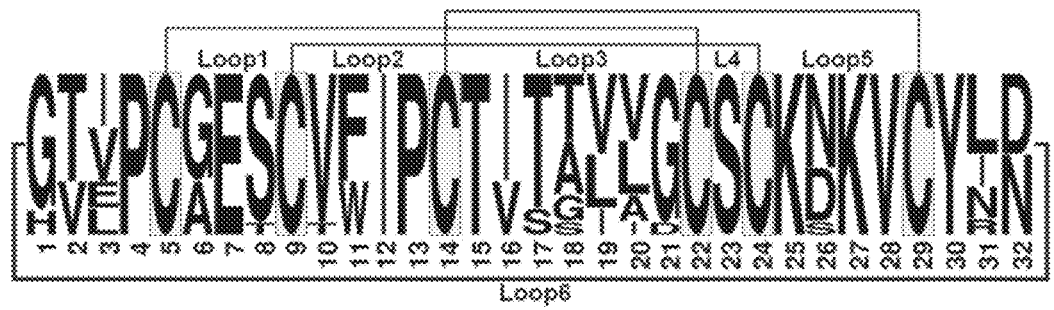
FIG. 5 provides a "sequence logo" relative frequency plot of the amino acids in the first 12 *C. ternatea* cyclotides listed in Table 1. Conserved residues among sequences include Pro4, CysS, Glu7, Cys9, Ile12, Pro13, Cys14, Thr15, Cys22, Ser23, Cys24, Lys25, Lys27, Val28, Cys29 and Tyr30.

An efficient way in which to describe and compare the features of cyclotides is by referring to the inter-cysteine loops, illustrated in FIG. 5 as an amino acid incidence plot for the 12 new sequences in sequence logo format (Crooks, G. E., et al., (2004), *Genome Res.* 14, 1188-1190). Most of the new cyclotides comprised combinations of known loops from previously characterized cyclotides, or novel loops with conservative amino acid substitutions. As a result, the majority of sequences displayed significant homology to known cyclotides. According to the sequence logo plot, the greatest variation in loop size and/or composition are in loops 3 and 6, consistent with data for all published cyclotide sequences as assessed using the 'cyclotide loop view' tool within Cybase (Kaas, Q., and Craik, D. J. (2010), *Peptide Sci.* 94, 584-591).

Biochemical Properties, of Novel Cyclotides.

Since the initial discovery of the insecticidal activity of cyclotides (Jennings, C., et al., (2001) *Proc. Natl. Acad. Sci. USA* 98, 10614-10619), several studies have demonstrated that this and other bioactivities are mediated through interactions with membranes (Barbeta, B. L., et al., (2008), *Proc. Natl. Acad. Sci. USA* 105:1221-1225). An important physicochemical feature of cyclotides, with regard to membrane interaction, is a surface-exposed patch of hydrophobic residues. This surface-exposure presumably results from the exclusion of hydrophobic amino acids from the core of cyclotides owing to the presence of the CCK motif. In addition to the importance of defined hydrophobic moieties in potentiating cyclotide-membrane interactions, clusters of charged residues have been demonstrated as determinants of hemolytic, insecticidal and anthelmintic activity. In particular, the hemolytic and anthelmintic properties of cyclotide variants correlate with these important structural features (Colgrave, M. L., et al., (2008) *ChemBioChem* 9, 1939-1945), with the most bioactive bracelet cyclotides displaying hydrophobic residues in loops 2 and 3, and positively charged residues in loops 5 and 6.

Among the novel Cter cyclotides identified here, Cter A has the largest net positive charge (2+) with basic residues clustered in loops 5 and 6, similar to the cycloviolacin peptides derived from *Viola odorata* that have been shown to possess potent anthelmintic activity (Colgrave, M. L., et al., (2008) *ChemBioChem* 9, 1939-1945; and Colgrave, M. L., et al., (2009), *Acta Trop.* 109, 163-166). The remaining peptides are clustered into groups with net positive 1+ (Cter G and Cter I), neutral (Cter B, Cter F, Cter H, Cter J and Cter K) and those with net negative charge –1 (Cter C, Cter E and Cter L). The bioactivities of cyclotides are further influenced by the manner in which they self-associate in membranes, which in turn is reliant upon the display of hydrophilic moieties on a 'bioactive face' spatially distinct from the hydrophobic patches (Huang, Y. H., et al., (2009) *J. Biol. Chem.* 284, 20699-20707, Huang, et al., (2010) *J. Biol. Chem.*; DOI: 10.1074/jbc.M109.089854). The proposed 'bioactive face' is centred around a glutamic acid residue, an absolutely conserved feature among previously reported cyclotides. Consistent with previous findings, this glutamic acid is conserved among all novel cyclotides described in this study.

Detection of N and D Peptide Isomers.

Figure 6:
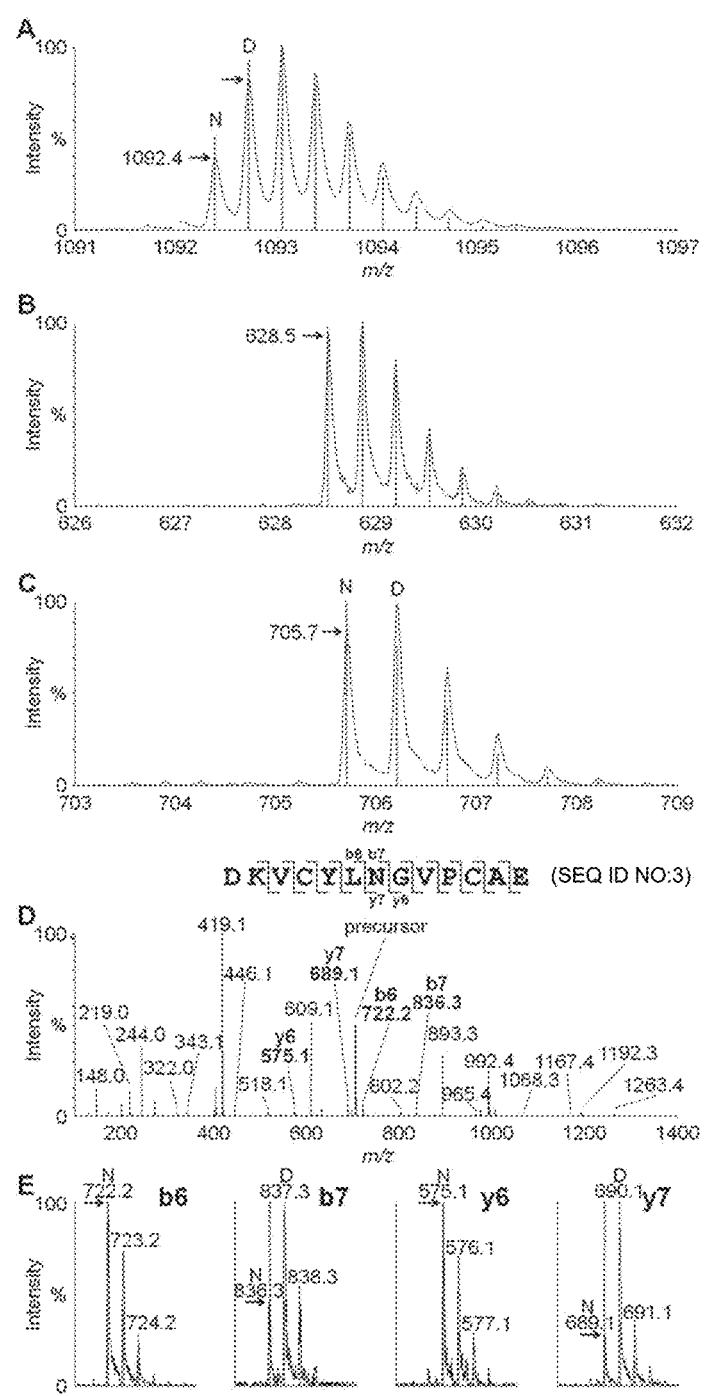
FIG. 6 shows isotopic distribution delineating isoform-specific sequence ions. Nanospray spectra for reduced and digested (trypsin and endoproteinase Glu-C) Cter B. (A) TOF-MS spectrum of full-length linearized Cter B-precursor 3274.2 Da. (B) TOF-MS spectrum of Cter B digest product with precursor 628.5$^{3+}$ (1882.6 Da). (C) TOF-MS spectrum of Cter B digest product with precursor 705.7$^{2+}$ (1409.4 Da). (D) Full product ion spectrum of precursor m/z 705.7$^{2+}$ (1409.4 Da). Sequence ions shown in bold represent cleavage of the amide bonds either side of the amino acid at position 7. (E) Isotopic distributions of diagnostic fragment ions b6, b7, y6 and y7 indicate the presence of both Asn and Asp at position 7 and thus the heterogeneous nature of the selected precursor ion within the transmission window. Dotted lines illustrate the theoretical isotopic distributions for precursor and fragment ions, assuming that the residue at position 7 is an asparagine. Arrows indicate the observed intensities of labelled monoisotopic peaks.
Figure 7:
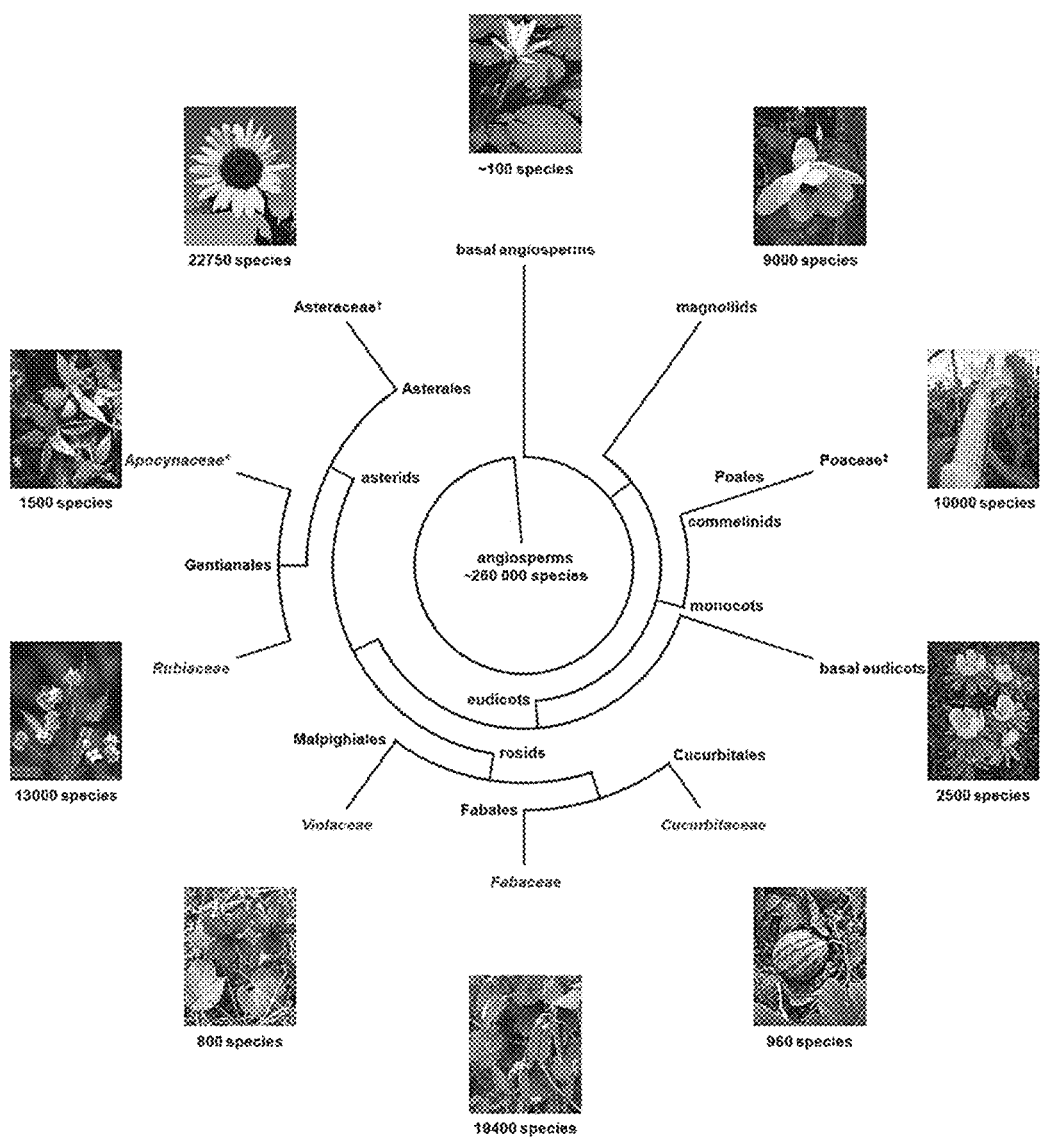
FIG. 7 illustrates distribution of ribosomally synthesized circular proteins within angiosperms. Cyclotide-containing plant families as reported in the literature appear in red italicized font. *A recent study reported evidence of cyclotides within the Apocynaceae family (Gruber, C. W., et al., (2008) Plant Cell 20, 2471-2483), but no cyclotide peptide or nucleic acid sequences have been published yet. ‡Gene sequences encoding putative linear cyclotide-like proteins have been identified in several species within the Poaceae family. (These sequences lack the C-terminal Asn or Asp considered crucial for in planta cyclization). †Backbone-cyclized circular peptides distinct from cyclotides have been characterized from species within the Asteraceae family.
Figure 8:
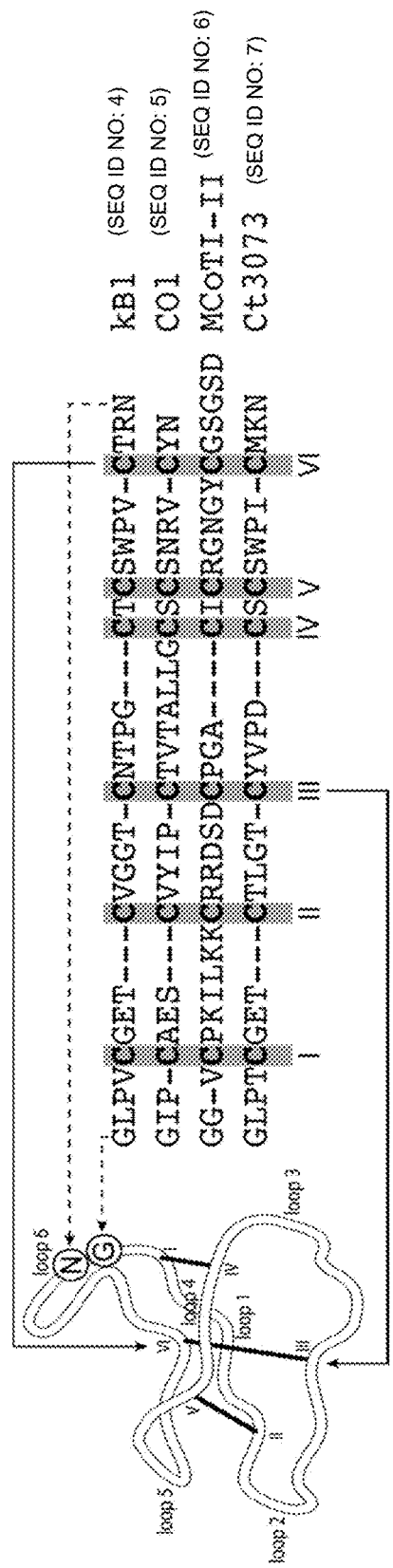
FIG. 8 provides a sequence alignment of the prototypical cyclotide kalata B1 (kB1) from the Rubiaceae plant *Oldenlandia affinis* with other selected cyclotide sequences. The six conserved cysteine residues are labeled with Roman numerals and various loops in the backbone between these cysteines are labeled loops 1-6. The cystine knot arrangement is indicated. The sequences of kalata B1 (SEQ ID NO:4, Saether, O., et al. (1995) *Biochemistry* 34:4147-4158), cycloviolacin O2 (SEQ ID NO:5, Craik, D. J., et al., (1999) *J Mol Biol* 294:1327-1336), MCoTI-II (SEQ ID NO:6, Hernandez J.-F., et al. (2000) *Biochemistry* 39:5722-5730) and Cter A (SEQ ID NO:7, Poth, A. G., et al., (2011) *ACS Chem. Biol.* 10.1021/cb100388j) represent examples of cyclotides isolated from the Rubiaceae, Violaceae, Cucurbitaceae and Fabaceae plant families. The conserved cysteines are boxed and their location on the structure is indicated by the dotted arrows. The putative processing points by which mature cyclotides are excised from their precursor proteins are indicated and correspond to an N terminal glycine residue and a C terminal Asn (N) or Asp (D) residue. PDB ID code for kalata B1 is 1NB1.
Figure 12:
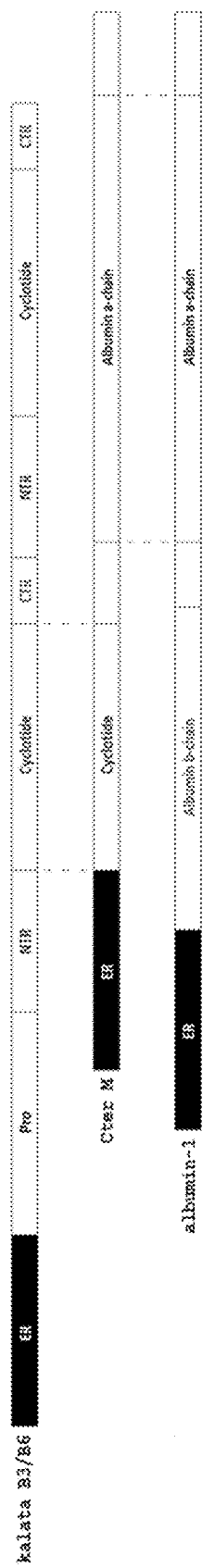
FIG. 12 compares the gene structures for an exemplary kalata cyclotide gene from *O. affinis* (encoding kB3/6), the gene encoding the Cter M cyclotide isolate from *C. ternatea*, and the *Pisum savitum* albumin-1 gene.

Mass spectrometric analyses of a majority of isolated *C. ternatea* cyclotides generated peptide ions with ambiguous isotope patterns. The isotopic distributions of full-length linearized Cter B, as well as fragment peptides produced from dual enzyme digests of Cter B are shown in FIG. 6. As illustrated in panel A, the measured intensity of the monoisotopic peak at m/z 1092.4 relative to the rest of the isotopic envelope for full-length linearized Cter B is less than the theoretical intensity (indicated by dashed lines). Panel B demonstrates that the experimental and calculated isotopic distributions for the triply charged precursor at m/z 628.5 corresponding to the sequence SCVWIPCTVTALLGCSCK (SEQ ID NO:2) match closely, whereas the experimental and calculated isotopic distributions for the doubly charged precursor at m/z 705.7 (panel C) corresponding to the sequence DKVCYLNGVPCAE (SEQ ID NO:3) are clearly different. These mass spectral data indicate that multiple full-length cyclotide precursors are present in the sample, and that the variable isotopic distributions observed among the precursor ions are associated with the cyclotide fragment corresponding to m/z 705.7.

Subsequent tandem MS analysis of the m/z 705.7 fragment was conducted to determine the point of variation in the peptide sequence. Panel D shows the tandem MS spectrum of the m/z 705.7 precursor, with diagnostic sequence ions indicated in bold. In panel E the b6 (DKVCYL (SEQ ID NO:132), m/z 722.2) and y6 (GVPCAE (SEQ ID NO:133), m/z 575.1) ions exhibit typical isotopic distributions for their size, with the monoisotopic peak appearing as the most intense and with isotopic patterns matching closely with the theoretical patterns. The distributions for b7 (DKVCYLN (SEQ ID NO:134), m/z 836.3) and y7 (NGVPCAE (SEQ ID NO:135), m/z 689.1) ions, however, are skewed such that the most intense peak within their respective isotopic envelopes is that which normally corresponds to the monoisotopic peak of an analyte bearing a single $^{13}C$ atom. The fact that the peptide fragments in question are too small for this to be the case, along with the abrupt deviations in isotopic distribution from adjacent sequence ions, suggests the co-existence of peptides with an Asn or Asp at position 7 within the m/z 705.7 fragment, i.e., DKVCYLNGVPCAE (SEQ ID NO:3) and DKVCYLDGVPCAE (SEQ ID NO:136), corresponding to position 31 in the sequence of Cter B shown in Table 1. Of the C. ternatea cyclotides listed in Table 1, five pairs of sequences appear to be related through dual-isotope patterns of this nature, i.e. Cter B and C; Cter D and E; Cter G and H; Cter I and J; and Cter K and L.

In the initial report detailing the discovery of cyclotides from Viola odorata (Craik, D. J., et al., (1999) J. Mol. Biol. 294, 1327-1336), the reported cyclotides, named cycloviolacins, all possessed an Asn in loop 6 corresponding to the C-terminus of linear precursor proteins. Subsequent examination of V. odorata using modified HPLC conditions (Ireland, D. C., et al., (2006) Biochem. J. 400, 1-12) uncovered a range of novel cyclotides. The novel peptides included cycloviolacin O19 and cycloviolacin O20, whose sequences are highly homologous to those of previously reported cyclotides cycloviolacin 08 and cycloviolacin O3, respectively. Cycloviolacin O19 and cycloviolacin O20 possess a loop 6 Asp, in the place of Asn, and were not reported in the earlier study (Craik, D. J., et al., (1999) J. Mol. Biol. 294, 1327-1336). The study by Ireland et al. therefore provided the first evidence for the existence of Asn and Asp C-terminal cyclotide isoforms in V. odorata, indicating that highly homologous cyclotides differing by a C-terminal Asn or Asp, or other single amino acid substitutions co-elute during standard HPLC separations. Given that most cyclotide separations reported in the literature have relied on these standard HPLC conditions, it is likely that in these studies, cyclotides with C-terminal Asn and Asp co-eluted, thus eluding analysis.

MS analysis demonstrates that Asn and Asp variants can be identified in a mixture through careful scrutiny of MS data. Furthermore, this study suggests that cyclotides with C-terminal Asp might be more common than previously reported, being missed in earlier MS analyses. The possibility also exists that cyclotides differing by 1 Da but whose sequences are homologous such as those that would result from the differential incorporation of Gln or Glu, or those that differ at a range of positions may co-elute.

N and D Peptide Isomers Exist Naturally in Planta.

Of the more than 150 cyclotides characterized previously, only four pairs share sequences otherwise identical to each other apart from Asn and Asp variation in loop 6, i.e., kalata B1 and B4, kalata B6 and B10, cycloviolacin O8 and O19, and cycloviolacin O3 and O20 (Kaas, Q., and Craik, D. J. (2010), Peptide Sci. 94, 584-591). Therefore, the high incidence of Asn and Asp variants warranted further examination to rule out deamidation as a possible cause of the synonymous sequences. Deamidation of Asn residues during sample workup is a commonly observed artefact in proteomic analyses, catalysed by exposure of the sample to elevated temperatures and basic pH (Wright, H. T. (1991), Crit. Rev. Biochem. Mol. Biol. 26, 1-52), typically during enzymatic cleavage, and occurring most frequently at Asn residues immediately N-terminal to Gly, as would be the case in these cyclic proteins. However, the isotopic distributions of 'native' cyclotides extracted from fresh plant material at low pH and not heated before MS analysis suggest that Asn and Asp cyclotide variants described, e.g., Cter B and C; Cter D and E; Cter G and H; Cter I and J; and Cter K and L, co-exist naturally. The existence of Cter A and Cter F, which do not display 'Asn or Asp variability' and which were isolated from the same starting material and processed in parallel supports the natural co-existence of Asn and Asp C-terminal cyclotide isoforms.

A recent study of ESTs from the cyclotide-producing plant O. affinis reports high relative expression of a protein with close homology to asparaginase, whose biological function is the conversion of asparagine to aspartic acid (Qin, Q., et al., (2010) BMC Genomics 11, DOI: 10.1186/1471-2164-11-111). With respect to pairs of cyclotides isolated from O. affinis differing only at the nascent C-terminus, the fact that only kalata B1 and kalata B6 (C-terminal Asn) genes have been found despite peptide evidence for kalata B1 and B4, and kalata B6 and B10 (each pair identical except for C-terminal Asn or Asp), led Qin et al. to suggest the alternative possibility that the 'Asp' peptides are a product of post-translational processing occurring in planta (Qin 2010, supra). A similar situation exists for related V. odorata peptides cycloviolacin O8 (C-terminal Asn) and cycloviolacin O19 (C-terminal Asp), with only the gene encoding the former cyclotide having been characterized (Dutton, J. L., et al., (2004) J. Biol. Chem. 279, 46858-46867). However, it remains to be determined whether the observed 'Asn or Asp' variable peptide pairs from O. affinis and V. odorata are a product of enzymatic post-translational processing, and further, whether a similar enzyme is involved in the biosynthesis of some metabolites with C-terminal Asp described from C. ternatea in this study.

Variable Residues in the Ligation Site Imply Catalytic Promiscuity.

Since the discovery of the first cyclotide-encoding gene, it has been evident that amino acids participating in cyclization are located in loop 6 of fully-formed cyclotides. Recent studies exploring the structural characteristics of cyclotide precursor sequences involved in their cyclization (Gillon, A. D., et al., (2008) Plant J. 53, 505-515; Saska, I., et al., (2007) J. Biol. Chem. 282, 29721-29728) emphasize the importance of tripeptide motifs (typically Gly-Leu-Pro or Ser-Leu-Pro or Ala-Leu-Pro) demarcating the cyclotide domain, and the positioning of an Asn or Asp residue immediately prior to the C-terminal tripeptide. In addition, these studies suggest that an as yet unidentified asparaginyl endopeptidase (AEP) is responsible for the ligation of cyclotide proto-termini as the final step of cyclotide biosynthesis.

Among the cyclotides encoded by the genes provided herein, Cter G and Cter H, and Cter K and Cter L contain novel amino acid sequences at their respective predicted sites of in planta cyclization. In the case of Cter G and Cter H, the loop 6 sequences 'YNNGLP' (SEQ ID NO:137) and 'YNDGLP' (SEQ ID NO:117) present the unique motifs Asn-Asn-Gly and Asn-Asp-Gly, which are noteworthy because they present two possible cyclization sites. The position of the peptide bond formed during cyclization of linear cyclotide precursors, as corroborated by gene sequencing efforts, is frequently observed at an Asn-Gly or the Asp-Gly junction. By itself, this information would suggest that the cyclization site in Cter H is Asp-Gly; however, the demonstrated cyclic nature of cycloviolacin O25 (Ireland, D. C., et al., (2006) *Biochem. J.* 400, 1-12), which presents a loop 6 sequence 'YFNDIF' (SEQ ID NO:138), tenders the alternative possibility that the cyclization reaction takes place between Asn-Asp. In the case of Cter K and Cter L, the loop 6 sequences are 'YNHEP' (SEQ ID NO:139) and 'YDHEP' (SEQ ID NO:140) with presumed novel cyclization sites Asn-His or Asp-His. Although there are other examples of cyclotides with a positively charged residue following Asp in the cyclization site (for example 'YHDKIP' (SEQ ID NO:141) in circulin D and circulin E) (Gustafson, K. R., et al., (2000) *J. Nat. Prod.* 63, 176-178), this is the first example with an acidic residue in place of the typically small hydrophobic residue (Ala, Ile, Leu or Val) at this position (second residue of mature cyclotide in presumed gene sequence). The existence of mature cyclic peptides with unusual residues within the N-terminal tripeptide motif (e.g. HEP in Cter K and Cter L) suggests greater flexibility in cyclotide processing mechanisms within *C. ternatea* than observed in other cyclotide-producing species. A recent study in which a modified cyclotide gene was expressed in transgenic non-cyclotide-containing plant species reported that mechanisms central to the processing of fully-formed cyclotides are sensitive to changes in N-terminal sequence. In particular, Ala mutations at $Gly_1$ or $Leu_2$ in kalata B1 genes were found to disrupt the formation of cyclic products (Gillon, A. D., et al., (2008) *Plant J.* 53, 505-515).

Legumain, an AEP with transpeptidation (peptide ligation) activity, first described in jack beans (Carrington, D. M., et al., (1985) *Nature* 313, 64-67, Min, W., and Jones, D. H. (1994) *Nat. Struct. Biol.* 1, 502-504), is of potential significance to the processing of cyclotides. In particular, the demonstrated flexibility of a Fabaceae legumain that cleaves at almost all Asn-Xaa bonds (Abe, Y., et al., (1993) *J. Biol. Chem.* 268, 3525-3529) and to a lesser extent Asp-Xaa bonds (Halfon, S., et al., (1998) *FEBS Lett.* 438, 114-118) may prove to be relevant in the biosynthesis of cyclotides from *C. ternatea*. Among the Fabaceae cyclotides investigated in the current study, those with non-typical sequence in loop 6 including 'YNHEP' (SEQ ID NO:139) or 'YDHEP' (SEQ ID NO:140) in Cter K and Cter L, and 'YNNGIP' (SEQ ID NO:141) or 'YNDGIP' (SEQ ID NO:142) in Cter G and Cter H were all observed as fully cyclized gene products.

Besides *C. ternatea* cyclotides possessing novel loop 6 sequences, there are a number of 'orphan' cyclotides whose loop 6 sequences appear incompatible with the typical activity of AEPs previously implicated in cyclotide bioprocessing. Apart from cycloviolacin O25, whose loop 6 sequence indicates the lack of typical putative N-terminal amino acids Gly, Ser or Ala in putative precursors, *Chassalia parvifolia* cyclotides circulin D and circulin E are distinct from other known cyclotides in that they have positively charged proto-N-termini, whereas circulin F does not have an Asn or Asp in loop 6. Cyclization by AEP is one of the proposed biosynthetic mechanisms proposed as being central to the cyclization of SFTI-1 (Mulvenna, J. P., et al., (2005) *J. Biol. Chem.* 280, 32245-32253) in *Helianthus annuus*, however the gene sequence corresponding to amino acids surrounding the expressed protein sequence does not indicate the involvement of Gly-Leu-Pro tripeptide motifs regarded as essential in cyclotide precursor proteins (Gillon, A. D., et al., (2008) *Plant J.* 53, 505-515; Saska, I., et al., (2007) *J. Biol. Chem.* 282, 29721-29728). In addition, sequence alignments of cyclic trypsin inhibitors MCoTI-1 and MCoTI-II from *Momordica cochinchinensis* with related linear trypsin inhibitors (Hernandez, J.-F., et al., (2000) *Biochemistry* 39, 5722-5730 suggest that they exhibit C-terminal Gly as unprocessed precursor proteins. Therefore, it is tempting to speculate that cyclization strategies utilized by organisms in the production of cyclotides and other cyclic proteins vary between species, based in part upon the capabilities of available processing enzymes.

The amino acid sequence of cyclotide Cter M (FIG. 9), while bearing the classic hallmark of other cyclotides, including the spacing of the six conserved Cys residues and a CCK fold, as determined by NMR, has some sequence differences that suggest a greater flexibility in cyclotide processing than has hitherto been reported. Its conserved Asn residue at the C-terminus of the mature cyclotide domain suggests processing by AEP like other cyclotides but the residue immediately following this Asn in the Cter M precursor, His, has not been seen in any other cyclotide genes, which exclusively contain a small amino acid (usually Gly or Ala at this position).

Fabaceae Cyclotide Gene Organization

All cyclotides reported to date from other plant families are biosynthesized from precursor proteins that are encoded by dedicated genes. In contrast, the cyclotides of *C. ternatea* are expressed from genes having a markedly different configuration.

The gene encoding the Cter M cyclotide is shown in FIG. 10. In contrast to the configuration seen other plant families, the gene in *C. ternatea* encodes a precursor that comprises the cyclotide amino acid sequence along with an albumin subunit sequence. While not limiting the present invention to any particular model, the cyclotide gene encoding Cter Mappears to have hijacked an albumin gene, encoding the cyclotide in place of subunit b of the albumin. Pea albumin 1 subunit b (PA1b) is a 37-amino acid protein isolated from pea seeds (*Pisum sativum*), that has been shown to act as a potent insecticidal agent (Da Silva, P., et al., (2010) *J Biol Chem* 285, 32689-32694). See also Nguyen, et al. *J. Biol. Chem.* 286(27):24275-87 (2011), incorporated herein by reference for all purposes. PA1b is characterized as a knottin owing to the three braced disulfide bonds. In an analogous fashion to the cyclotide kalata B1 (Simonsen, S. M., et al., (2008) *J Biol Chem* 283, 9805-9813), the three-dimensional structure of PA1b has been demonstrated to be extremely tolerant to modifications (Da Silva, supra). Furthermore, both receptor-binding and insecticidal activities of PA1b were dependent on a cluster of hydrophobic residues located on a single face of the molecule (Da Silva, supra). These data show striking parallels with recent studies highlighting the importance of the hydrophobic patch of kalata B1 in modulating insecticidal and membrane binding interactions (Simonsen, supra, Huang, Y. H., et al., (2009) *J Biol Chem* 284, 20699-20707).

The current study shows that fully folded cyclotides are produced naturally in a member of the Fabaceae plant family, demonstrating both the presence and capabilities of necessary post-translational modification infrastructure involved in their biosynthesis. Although the sequences of novel cyclotides described in this study are mostly conservative permutations of previously identified proteins, the sequence variability displayed at putative cyclization sites in a number of *C. ternatea* cyclotides suggests that alternative biosynthetic cyclization mechanisms may be responsible. In particular, cyclotides described in this study possessing novel putative N-termini are suggestive of significantly different, or additional specialized capabilities with respect to enzymes supporting their cyclization. Numerous species within the Fabaceae are known to possess legumain, an AEP which was initially discovered as the enzyme responsible for peptide ligation in the post-translational processing of the lectin concanavalin A from *Canavalia ensiformis* (Jackbean) seeds (Carrington, D. M., et al., (1985) Nature 313, 64-67) If a homologous enzyme exists in *C. ternatea*, its presence could explain the existence of cyclotides with unusual sequence at their putative cyclization sites characterized described in the current study, as legumain activity has been reported across a wide range of Asn-Xaa bonds (Abe, Y., et al., (1993) *J Biol Chem* 268, 3525-3529).

These considerations, coupled with the importance of Fabaceous crops to nutrition, industry and agriculture, give Fabaceae species special relevance in future cyclotide-focused transgenic studies. Cyclotides have been previously exploited as ultra-stable scaffolds for the presentation of bioactive epitopes (Gao, Y., et al., (2010) *Bioorg Med Chem* 18, 1331-1336; Gunasekera, S., et al., (2008) *J Med Chem* 51, 7697-7704; Thongyoo, P., et al., (2009) *J Med Chem* 52, 6197-6200). Fabaceae plants represent novel vectors for biotechnological production of a broader range of designer cyclic proteins than previously considered possible. The demonstrated capacity of *C. ternatea* to produce fully formed cyclotides suggests that cyclotides with optimized resistance traits and/or possessing other traits of pharmaceutical, economic or agricultural significance may be readily expressed in a functional form within Fabaceae species. Due to the previously demonstrated efficacy of naturally occurring cyclotides as insecticidal (Barbeta, B. L., et al. (2008) *Proc. Nat'l. Acad. Sci. USA* 105, 1221-1225, Jennings, C., et al., (2001) *Proc. Nat'l. Acad. Sci. USA* 98, 10614-10619) and nematocidal (Colgrave, M. L., et al., (2008) *Biochemistry* 47, 5581-5589, Colgrave, M. L., et al., (2008) *Chembiochem* 9, 1939-1945, Colgrave, M. L., et al., (2009) *Acta Trop* 109, 163-166, and Colgrave, M. L., et al., (2010) *Antimicrob Agents Chemother* 54, 2160-6) agents, it is believed that the natural role of cyclotides is as plant defence agents, making them excellent candidates for incorporation in transgenic crops to provide resistance against important pests.

Cyclotides are known to possess potent in vitro anthelmintic activity against human, canine and ovine nematode parasites. Root-knot nematodes, which are estimated to cause more than $100 billion of crop losses worldwide (Koenning, S. R., et al., (1999) *J Nematol* 31, 587-618, Opperman, C. H., et al., (2008) *Proc Natl Acad Sci USA* 105, 14802-14807) represent obvious targets in this regard, however the efficacy of cyclotides against them remains untested. Cyclotides are differentially expressed among plant tissues, presumably in order to counter the selective pressures specific to their respective microenvironments (Trabi, M. & Craik, D. J. (2004) Plant Cell 16, 2204-2216). Cyclotide Vhr-1 from *Viola hederacea* is expressed exclusively in the root tissue of *Viola hederaceae*.

The present invention contemplates linear molecules of from about 20 amino acids to about 100 amino acids and more preferably from about 25 amino acids to about 50 amino acids such as about 30 amino acids which are used as substrates for cyclization reactions. The resulting cyclized molecules having the same or functionally similar structure as the cyclic framework as herein described.

As stated above, the present invention extends to a range of derivatives, homologues and analogues of the molecular framework. A derivative includes parts, fragments, portions and linear forms. One particularly useful linear form is referred to herein as "uncycles" which are acyclic permutations of the cyclic molecular framework. Circular permutation involves the synthesis or expression of proteins having amino- and carboxy-termini permuted from their native locality. In relation to the naturally occurring cyclic molecular frameworks of the present invention, such molecules do not have native amino and carboxy termini. However, cyclic permutation permits a range of different linear molecules to be prepared with different amino and carboxy termini. An uncycle may have increased activity relative to its cyclic form or no activity or may exhibit antagonist activity. An uncycle exhibiting no activity may nevertheless be useful, for example, in the generation of antibodies.

By way of example only, particularly preferred CCK molecules comprise six cysteine residues and, hence, have six loops in the backbone which can be opened to form six possible topologically distinct acyclic permutants. Similarly, each of the 6 linear topologies may also be cyclized. This aspect of the present invention provides, therefore, for the cyclization of any linear topology into a CCK framework.

The uncycles of the present invention may be useful as antagonists of the cyclic molecular framework or may themselves exhibit useful activity.

Still another aspect of the present invention is directed to antibodies to the molecular framework of the present invention. Such antibodies may be monoclonal or polyclonal. Polyclonal antibodies are particularly preferred. Antibodies may be made using standard techniques.

The cyclic molecular frameworks according to the present invention are useful as therapeutic agents in animals and as anti-pathogenic agents in plants. Accordingly, the present invention provides a method for the treatment or prophylaxis of conditions or diseases in mammals, preferably humans, including the step of administering a molecular framework as hereinbefore described either without modification or having heterologous amino acids grafted thereon.

In particular, molecular frameworks may be selected or engineered for use in the treatment of neurological disorders such as acute and chronic pain, stroke, traumatic brain injury, migraine, epilepsy, Parkinson's disease, Alzheimer's disease, multiple sclerosis, schizophrenia and depression as well as cystic fibrosis and/or other respiratory diseases. The molecular framework may also be selected to treat plants against pathogen infestation and mammals including humans from viral or microbial infection.

The present invention also provides a composition comprising cyclic molecular framework molecules as hereinbefore described and a pharmaceutically acceptable carrier and/or diluent. Preferably the composition is in the form of a pharmaceutical composition.

There is also provided the use of a cyclic molecular framework in the manufacture of a medicament for the treatment or a prophylaxis of diseases or other conditions in mammals, preferably in humans.

In some embodiments, a transgenic plant is produced comprising cells transformed with at least one gene encoding the CterM or CterM-like gene described above, such that a cyclotide is expressed in at least one of its tissues of organs. The present invention encompasses transgenic plants produced in this way to express CterM or CterM-like peptides (without or without heterologous grafted peptides) in any of Fabaceae and/or non-Fabaceae plants of agricultural and biotechnological significance. These plants can be obtained by conventional techniques of plant transgenesis as are presently well known and which have been rigourously tested in these many plant species (see, e.g., Dunwell, J. M. (2000). *J. Exp. Biol.* 51, 487-496; and Eapen, S. (2008) *Biotechnol. Adv.* 26, 162-168).

Genetic elements typically or optionally included for expression of heterologous proteins in plants are known in the art. For example, binary vectors, for plant transformation are generally configured to allow propagation in multiple host cell types, may typically contain an origin of replication, a selectable marker gene cassette with appropriate promoter, multiple cloning sites in which the gene of interest and/or reporter gene can be inserted, and T-DNA borders (e.g., as reviewed by Komari, T., et al., (2006) Binary Vectors and super-binary vectors. pp. 15-42. In: *Agrobacterium* Protocols. Ed, Kan Wang. *Methods in Molecular Biology* Volume 343). The vector backbone may also include a bacterial selectable marker gene unit, plasmid mobilization functions and plasmid replication functions, as well other factors relevant to plasmid mobilization and replication in, e.g., *Agrobacterium*. Examples include pCAMBIA series (see, e.g., the cambia.org site on the world wide web) and pPZP series (Hajdukiewicz, et al., (1994) The small, versatile pPZP family of *Agrobacterium* binary vectors for plant transformation. *Plant Mol. Biol.* 25, 989-994.). In some embodiments, binary vectors are used in conjunction with helper plasmids that provide one or more functions, e.g., for replication.

Methods of transformation of plant cells are known in the art. Commonly used methods typically comprise *Agrobacterium*-mediated transformation. See e.g., Eapen S, et al., (1987) Cultivar dependence of transformation rates in mothbean after co-cultivation of protoplasts with *Agrobacterium tumefaciens. Theor Appl Genet.* 75: 207-10; Krishnamurthy K V, et al., (2000) *Agrobacterium* mediated transformation of chickpea (*Cicer arietinum* L.) embryo axes. *Plant Cell Rep* 19: 235-40; and Sharma K K, et al., (2006) *Agrobacterium*-mediated production of transgenic pigeonpea (*Cajanus cajan* L Millsp) expressing synthetic Bt cryIAb gene. *In vitro Cell Dev Biol Plant* 42: 165-73. In *Agrobacterium*-mediated transformation, embryonic axes and cotyledonary nodes are most commonly used as explants, although shoot apices, leaf, callus, seed, stem segments or other plant tissues are also used. Other transformation techniques that find use with the present invention include but are not limited to particle gun bombardment (e.g., Kamble S, et al., (2003) A protocol for efficient biolistic transformation of mothbean (*Vigna aconitifolia* L. Marechal). *Plant Mol Biol Report* 21: 457a-j; Indurker S, et al., (2007) *Plant Cell Rep* 26: 755-63), electroporation of intact axillary buds (Chowrira G M, et al., (1996) *Mol Biotechnol* 5:85-96) and electroporation-PEG mediated transformation using protoplasts (Kohler F, et al., (1987a) *Plant Cell Rep* 6: 313-7 and Kohler F, et al., (1987b) *Plant Sci Lett* 53: 87-91.). Techniques used may vary according to the transgenic plant species to be generated. Plant regeneration is generally by de novo organogenesis, although somatic embryogenesis or proliferation of shoot meristems from areas surrounding a shoot bud are also options.

Transformation of plants may be assessed by a number of different methods. For example, plant tissues may be assessed for the presence of the gene of interest, or an RNA or protein produced therefrom, by standard hybridization, antibody, or other functional tests that are standard in the art. Further, selectable markers may be used to confirm transformation. For example selectable markers may include neomycin phosphotransferase (nptII) gene (Valvekens et al., (1988) *Proc. Natl. Acad. Sci. USA* 85: 5536-5540) and/or Phosphomannose isomerase (Boscariol et al., (2003) *Plant Cell Rep* 22, 122-128), which confer resistance to antibiotics (kanamycin, paromomycin), and eliminate natural plant toxicity to mannose, respectively. The selection of a particular selectable marker for use is typically based upon plant species to be transformed and downstream applications for which the transformed cells or tissues will be used (e.g., toxicity studies).

Numerous diverse plant species have been genetically transformed with foreign DNA, using several different gene insertive techniques. In some embodiments edible plants may be selected for expression of cyclotides such that the cyclotide (e.g., a cyclotide having nutrient or therapeutic function or activity) may be delivered to a subject in an edible material. In such embodiments, the host plant selected for genetic transformation preferably has edible tissue in which the cyclotide is expressed, such as the fruit, leaves, stems, sees, or roots, such that the tissue may be consumed by a human or an animal for whom the cyclotide is intended. For example, the Fabaceae family of plants comprises soy plants (e.g., *Glycine max*), which contains edible seeds and tissues, and from which numerous edible materials may be produced. A cyclotide may also be produced in a non-edible plant and may be isolated and used or administered in standard fashion such as may be used for any agricultural, pharmaceutical or nutrient substance or chemical.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the framework is not destroyed in the process and that the framework is able to reach its site of action without being destroyed. In some circumstances it may be necessary to protect the framework by means known in the art, such as, for example, micro encapsulation. Similarly the route of administration chosen should be such that the peptide reaches its site of action. In view of the improved stability and/or bioavailability of the cyclic frameworks relative to their "linear" counterparts, a wider range of formulation types and routes of administration is available.

The pharmaceutical forms suitable for injectable use include sterile injectable solutions or dispersions, and sterile powders for the extemporaneous preparation of sterile injectable solutions. They should be stable under the conditions of manufacture and storage and may be preserved against the contaminating action of microorganisms such as bacteria or fungi. The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal injection or infusion.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated; with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example, topical application such as creams, lotions and gels, or compositions suitable for inhalation or intranasal delivery, for example solutions or dry powders.

Parenteral dosage forms are preferred, including those suitable for intravenous, intrathecal, or intracerebral delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 µg to about 2000 mg. Expressed in proportions, the active compound is generally present in from about 0.25 µg to about 2000 mg/mL of carrier. In the case of compositions containing supplementary active ingredients, the dosages are determined by reference to the usual dose and manner of administration of the said ingredients.

The cyclic molecular frameworks of the present invention may also have useful application as anti-pathogen agents in plants. Examples of pathogens include insects, spiders, viruses, fungi and other microorganisms causing deleterious effects. In particular, molecular frameworks may be engineered for use in conferring protection from pathogen (including insect) infestation of plants; for example, protection from insect attack in cotton. Such an activity may be engineered by the introduction of appropriate amino acid residues into the molecular framework, as described above, and their use in topical applications such as, e.g. in sprays.

Accordingly, the present invention provides a method for conferring pathogen protection to a plant, including the step of administering an engineered framework as hereinbefore described. Reference to administering includes reference to the topical application in liquid, aerosol, droplet, powdered or particulate form.

EXPERIMENTAL EXAMPLES

The following examples serve to illustrate certain preferred embodiments and aspects of the present invention and are not to be construed as limiting the scope thereof.

The abbreviations used are: kB1, kalata B1; RP-HPLC, reversed-phase high performance liquid chromatography; MALDI-TOF, matrix-assisted laser desorption ionization time-of-flight; CCK, cyclic cystine knot; SFTI-1, sunflower trypsin inhibitor-1; AEP, asparaginyl endopeptidase; SPE, solid phase extraction; CHCA, α-Cyano-4-hydroxycinnamic acid; CE, collision energy.

Example 1

Isolation and Characterization from C. ternatea Seeds

Seed Extraction.

Seed material (~0.20 g) from *C. ternatea* (Milgarra variety as supplied by Heritage Seeds, Rocklea, Australia) was ground in a mortar and pestle prior to solvent extraction with 100 mL of 50% (v/v) acetonitrile, 2% (v/v) formic acid. Crude extract was centrifuged for 4 min at 4,000×g, and the supernatant passed through a 0.45 micron syringe filter prior to lyophilization, yielding 430 mg material.

Solid Phase Extraction (SPE).

Crude plant extracts were redissolved in 1% (v/v) formic acid and underwent an SPE clean up step prior to further analysis. Waters C18 SPE cartridges of 100 mg to 10 g resin capacity were activated with 10 bed volumes of methanol and subsequently equilibrated with 10 bed volumes of 1% (v/v) formic acid. Following application of crude plant extracts, the cartridges were washed with a further 10 bed volumes of 1% (v/v) formic acid. Interfering substances were eluted from the cartridges in 10% (v/v) acetonitrile, and cyclotides collected in 20% to 80% (v/v) acetonitrile elution steps as separate fractions and lyophilized.

HPLC Purification.

Separation of cyclotides from crude *C. ternatea* extracts or SPE fractions was carried out using preparative or semi-preparative HPLC. For preparative HPLC, samples were reconstituted in 10% (v/v) acetonitrile, 1% (v/v) trifluoroacetic acid and introduced to a Phenomenex C18 RP-HPLC column (Torrance, Calif., USA) (250×21.2 mm, 15 µm, 300 Å). Using a Waters 600E HPLC unit (Milford, Mass., USA), a linear 1% min$^{-1}$ acetonitrile gradient was delivered to the column at a flow rate of 8 mL min$^{-1}$ and the eluent was monitored using a dual wavelength UV detector set to 214 and 280 nm, and fractions were collected. In semi-preparative HPLC separations, a Phenomenex C18 RP-HPLC column (250×10 mm, 10 µm, 300 Å) was utilized with a flow rate of 3 mL min$^{-1}$. Selected cyclotides were purified to >95% purity through repetitive RP-HPLC and duplicate samples submitted for amino acid analysis.

MALDI-TOF MS.

MALDI-TOF analyses were conducted using an Applied Biosystems 4700 TOF-TOF Proteomics Analyser (Foster City, Calif., USA). Samples were prepared through 1:1 dilution with matrix consisting of 5 mg mL$^{-1}$ CHCA in 50% (v/v) acetonitrile, 1% (v/v) formic acid prior to spotting on a stainless steel MALDI target. MALDI-TOF spectra were acquired in reflector positive operating mode with source voltage set at 20 kV and Gridl voltage at 12 kV, mass range 1000-5000 Da, focus mass 1500 Da, collecting 1500 shots using a random laser pattern and with a laser intensity of 3500. External calibration was performed by spotting CHCA matrix 1:1 with Applied Biosystems Sequazyme Peptide Mass Standards Kit calibration mixture diluted 1:400 as described previously (Saska, I., et al., (2008) *J. Chromatogr. B* 872, 107-114).

Enzymatic Digestion.

Prior to tandem MS analyses, cyclotides were cleaved to produce linearized fragments following reduction and alkylation to prevent re-oxidation. Lyophilized samples were reconstituted in 100 mM NH$_4$HCO$_3$ (pH 8) and a 10 µL portion was reduced by addition of 10 µL of 10 mM dithiothreitol and incubation at 60° C. for 30 min in a nitrogenous atmosphere. Incubation with a further 10 µL of 100 mM iodoacetamide followed for 30 min at RT. Samples were split into three ~7 µL fractions for digestion by endoproteinase Glu-C (Sigma P2922), TPCK-treated bovine trypsin (Sigma T1426) or a combination of both enzymes. In the case of the single-enzyme digests, a sample of ~7 µL received 5 µL of 40 ng µL$^{-1}$ enzyme and 5 µL of 100 mM NH$_4$HCO$_3$. For the double-enzyme digest, a sample of ~7 µL was mixed with 5 µL of 40 ng µL$^{-1}$ of each enzyme. All three digests were incubated at 37° C. for 3 h and then quenched with formic acid. All samples were retained at 4° C. until further analysis.

Nanospray on QSTAR Pulsar.

Reduced and enzymatically digested samples were processed using C18 ziptips (Millipore) to remove salts and elicit a solvent exchange from aqueous solution to 80% (v/v) acetonitrile, 1% (v/v) formic acid. Samples (3 µL) were introduced to nanospray tips (Proxeon ES380) and 900 V was applied to the tip to induce nanoelectrospray ionization on a QSTAR Pulsar I QqTOF mass spectrometer (Applied Biosystems). The collision energy (CE) was varied from 10 to 60 V. Both TOF and product ion mass spectra were acquired and manually assigned using Analyst QS 1.1 Software.

Cter cyclotide peptides from seeds are aligned in Table 1, below.

TABLE 1

| SEQ ID NO: | Peptide | Amino acid sequence[a] | Exp. m/z | Exp. mass (Da) | Theor. mass (Da) | Error Δ(ppm) | Subfamily |
|---|---|---|---|---|---|---|---|
| 13 | Cter A | GVIPCGESCVFIPC-ISTVIGCSCKNKVCYRN | 1090.07 | 3267.19 | 3267.49 | -91.8 | Bracelet |
| 8 | Cter B | G-VPCAESCVWIPCTVTALLGCSCKDKVCYLN | 1084.58 | 3250.75 | 3250.45 | 92.6 | Bracelet |
| 9 | Cter C | G-VPCAESCVWIPCTVTALLGCSCKDKVCYLD | 1084.93 | 3251.76 | 3251.43 | 99.2 | Bracelet |
| 11 | Cter D | G-IPCAESCVWIPCTVTALLGCSCKDKVCYLN | 1089.26 | 3264.76 | 3264.46 | 91.0 | Bracelet |
| 10 | Cter E | G-IPCAESCVWIPCTVTALLGCSCKDKVCYLD | 1089.61 | 3265.79 | 3265.45 | 105.2 | Bracelet |
| 19 | Cter F | G-IPCGESCVFIPC-ISSVVGCSCKSKVCYLD | 1536.48 | 3070.94 | 3071.34 | -132.7 | Bracelet |
| 15 | Cter G | G-LPCGESCVFIPC-ITTVVGCSCKNKVCYNN | 1043.15 | 3126.42 | 3126.36 | 19.0 | Bracelet |
| 16 | Cter H | G-LPCGESCVFIPC-ITTVVGCSCKNKVCYND | 1043.48 | 3127.43 | 3127.34 | 26.8 | Bracelet |
| 22 | Cter I | GTVPCGESCVFIPC-ITGIAGCSCKNKVCYIN | 1052.33 | 3153.96 | 3154.39 | -135.7 | Bracelet |

TABLE 1-continued

| SEQ ID NO: | Peptide | Amino acid sequence[a] | Exp. m/z | Exp. mass (Da) | Theor. mass (Da) | Error Δ(ppm) | Subfamily |
|---|---|---|---|---|---|---|---|
| 23 | Cter J | GTVPCGESCVFIPC-ITGIAGCSCKNKVCYID | 1052.67 | 3154.99 | 3155.58 | -122.2 | Bracelet |
| 17 | Cter K | H-EPCGESCVFIPC-ITTVVGCSCKNKVCY-N | 1037.14 | 3108.39 | 3108.31 | 24.4 | Bracelet |
| 18 | Cter L | H-EPCGESCVFIPC-ITTVVGCSCKNKVCY-D | 1037.47 | 3109.39 | 3109.30 | 31.3 | Bracelet |

[a]Ile and Leu were determined by amino acid analysis where sufficient material was available, or assigned based upon homology with published cyclotide sequences.

Example 2

Isolation, Characterization and Synthesis of Cyclotides from *C. ternatea* Leaves Leaf Extraction.

Leaf material (~3.5 g) from *C. ternatea* plants (grown in St Lucia, Brisbane, Australia) was ground in a mortar and pestle prior to solvent extraction with 20 mL of 50% (v/v) acetonitrile, 2% (v/v) formic acid. Crude extract was centrifuged for 4 min at 4,000×g, and the supernatant passed through a 0.45 micron syringe filter prior to lyophilization.

Mass Spectrometry.

As described for the seed extracts, above, the aqueous leaf extract of was treated by reduction to break disulfide bonds, alkylation to block reactive cysteine residues, and digestion with endoproteinase Glu-C to linearize any cyclic peptides present in the extract. MALDI-TOF analyses were conducted using an Applied Biosystems 4700 TOF-TOF Proteomics Analyser (Foster City, Calif., USA) and UltrafleXtreme TOF-TOF instrument (Bruker, Bremen, Germany) as previously described (Poth, A. G., et al., (2011) *ACS Chem Biol*.). Linearized cyclotide-containing crude leaf extract was analyzed on a QStar® Elite hybrid LC-MS/MS system (Applied Biosystems/MDS SCIEX, Foster City, USA) equipped with a nano-electrospray ionization source. The collection of MS/MS spectra were searched against a custom-built database of cyclotides using the ERA methodology (Colgrave, et al., (2010), *Biopolymers* 94:592-601) using ProteinPilot. All MS/MS data were manually verified.

LC-MS/MS analyses showed a dominant peak at 20.9 min of m/z 1147.53 corresponding to a mass of 3439.60 Da for a linearized alkylated peptide (mass of native peptide 3073.60 Da). Examination of the full product ion MS/MS spectrum (FIG. 2) revealed the sequence of the peptide to be TCTLGTCYVPDCSCSWPICMKNGLPTCGE (SEQ ID NO:143) where the methionine was oxidised. The sequence was database (BLAST) searched and deduced to be a novel cyclotide. We previously reported the identification of 12 cyclotides in seed extracts from *C. ternatea* (Poth, et al., 2011, supra), all of which belong to the Bracelet cyclotide sub-family. This is the first report of a cyclotide belonging to the Möbius sub-family from Fabaceous plants. Using similar methods an additional six peptide sequences (including Cter A previously identified in *C. ternatea* seeds) were deduced and their sequences are summarized along with the original 12 sequences in FIG. 9.

NMR Spectroscopy.

Spectra were recorded at 600 and 900 MHz (Bruker Avance NMR spectrometers) on a sample containing 1 mM Cter M in 10% $D_2O$/90% $H_2O$. The two-dimensional spectra including, TOCSY, COSY and NOESY, were recorded as previously described Rosengren, K. J., et al., (2003) *J. Biol. Chem.* 278, 8606-8616. Distance restraints were obtained from a NOESY spectrum recorded with a 200 ms mixing time at 290 K. A family of structures that are consistent with the experimental restraints was calculated using the programs CYANA (Guntert, P. (2004) *Methods Mol Biol* 278, 353-378) and CNS (Brunger, A. T. (2007) *Nat Protoc* 2, 2728-2733). A set of 50 structures was calculated and the 20 lowest energy structures selected for further analysis. Structures were analyzed using the programs PROCHECK_NMR (Laskowski, R. A., et al., (1996) *J. Biomol. NMR* 8, 477-486) and PROMOTIF (Hutchinson, E. G. & Thornton, J. M. (1996) *Protein Sci.* 5, 212-220. MolMol (Koradi, R., et al., (1996) *J. Mol. Graph.* 14, 29-32) and PyMol were used to display the structural ensembles and surfaces of the peptides, respectively.

Example 3

Gene Discovery and Verification

One of the difficulties encountered when de novo analysing peptide MS/MS spectra is the inability to distinguish the isobaric residues Ile and Leu. Amino acid analysis can yield the amino acid composition, but when both residues are present in a given sequence it is not possible to determine their location. With this constraint in mind and with the aim of exploring biosynthesis of cyclotides within the Fabaceae we proceeded with gene sequence determination.

Total RNA was extracted from 97 mg leaf tissue of *C. ternatea* using TRIzol® LS reagent (Invitrogen). RNA was DNAse-treated (Ambion), and complementary DNA was generated using random hexamers and Superscript III reverse transcriptase (Invitrogen). A degenerate primer (Ct-For1A, 5'-CCiACNTGYGGNGARACNTG-3' SEQ ID NO:144) and an oligo-dT primer (5'-GCCCGGG $T_{20}$-3' SEQ ID NO:145) were initially used to amplify products from cDNA. Resulting PCR products were cloned into pGEM-T Easy Vector System (Promega) and independently amplified clones were sequenced. Rapid amplification of cDNA ends (RACE) was performed using the FirstChoice® RLM-RACE kit (Applied Biosystems) according to manufacturer's instructions. First strand cDNA synthesis was performed on leaf-derived RNA. Sequence-specific primers (Cter M-RACE-Rev1,5'-GGAAACACCAACCAAAATG-GATGT-3' SEQ ID NO:146; Cter M-RACE-Rev2,5'-TCACTGTTTTTGCATTAGCTGCAA-3' SEQ ID NO:147) were used for first and second round PCR amplifications respectively. PCR products were cloned and sequenced. Primers (Cter M-SpecFor, 5'-TCCTTATTTTCATCAAC-TATGGCTTA-3' SEQ ID NO:148; Cter M-SpecRev, 5'-TCATACATGATCACTTTTAGTTGG-3' SEQ ID NO:149) were designed near the ends of the overlapping gene sequences, and used to amplify full-length transcript from leaf-derived cDNA. Total Total RNA was isolated from leaf, and used to generate cDNA. A degenerate primer was designed based upon the highly conserved PTCGETC motif (SEQ ID NO:13), and used in combination with oligo-dT to isolate partial transcripts from cDNA. Analysis of PCR products revealed a single 402 bp band. Following cloning, sequence analysis of independently amplified clones revealed that partial cyclotide sequence was embedded within a precursor protein with a strikingly different (atypical) gene architecture compared to all previously determined cyclotide gene sequences.

In all cyclotide genes elucidated to date, mature cyclotide domains are followed by a small C-terminal region (CTR) tail of 3-11 amino acids comprising a small amino acids (Gly or Ala), a strictly conserved Leu in the second position which has been postulated to play a critical role in docking to a specific binding pocket of asparaginyl endoprotease during peptide excision and ligation reactions (Koradi, R., et al., (1996) *J. Mol. Graph.* 14, 29-32). In the case of the *C. ternatea*-derived sequence, the sequence of the mature peptide is flanked on the C-terminus by a 74 amino acid tail, in which the Gly and the 'critical' Leu notably absent. BLAST searching of this C-terminal tail region revealed that it possessed high sequence homology to the C-terminal portion of albumin-1 proteins from a variety of Fabaceae species.

Following 5' RACE amplification and alignment to previous sequences, a 514 bp consensus sequence was obtained. To confirm that this sequence represented a single mRNA expressed in *C. ternatea* leaf, primers were designed within the 5' and 3' untranslated regions, and a single 418 bp PCR product was amplified. Sequence analysis revealed this product was as predicted, and encoding a predicted protein of 127 amino acids (FIG. 10). The full protein sequence of the novel Fabaceae cyclotide precursor was aligned to the homologous albumin proteins identified in the initial BLAST search FIG. 18).

Figure 19:
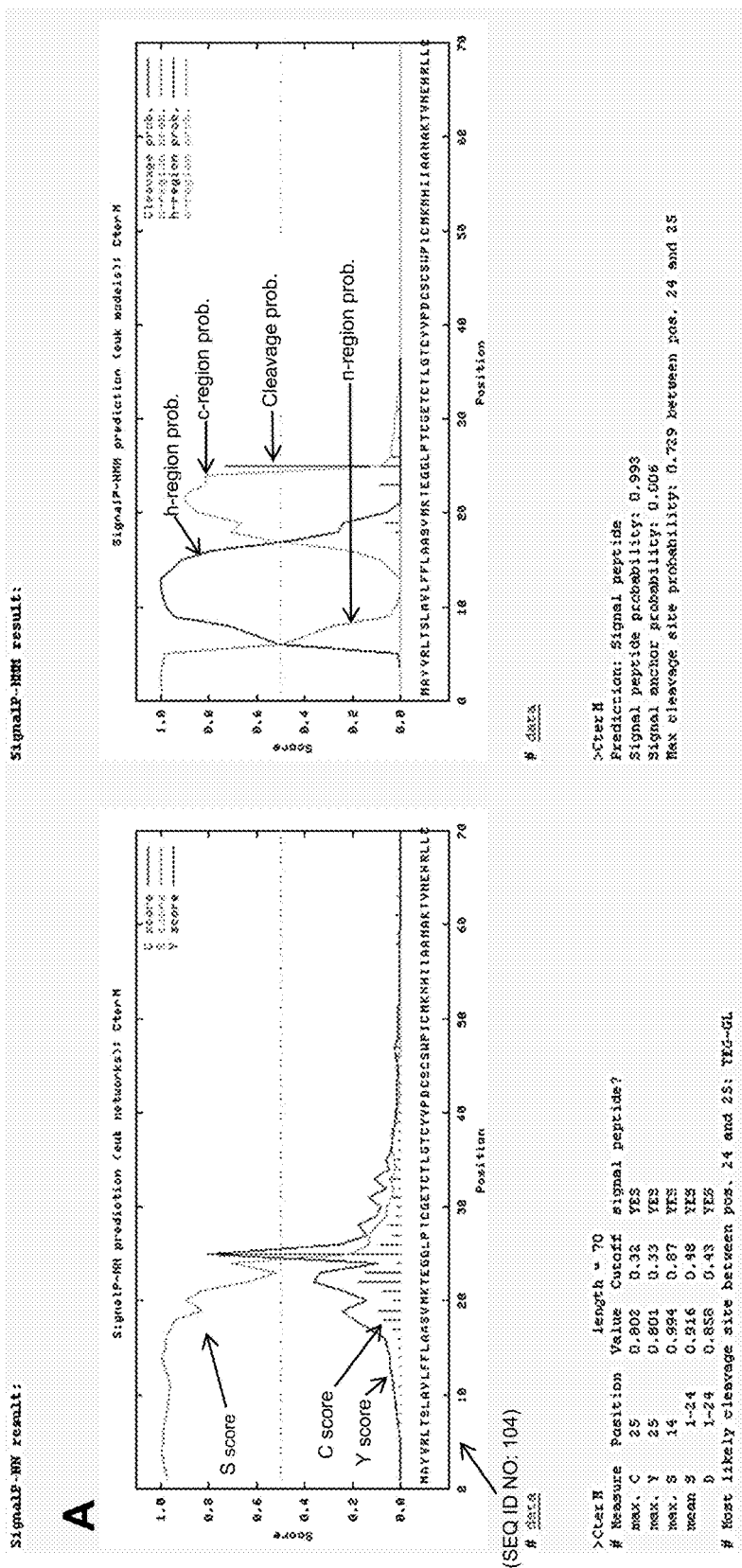
FIG. 19A-19F provides SignalP analysis of Cter M, kalata B1 and selected albumin-1 precursors from Fabaceae. Panel A-SignalP (Bendtsen, J. D., et al., (2004), *J. Mol. Biol.* 340, 783-795) analysis of Cter M precursor protein (partial sequence shown as SEQ ID NO:104) predicts signal peptidase cleavage at the proto-N-terminus of the mature cyclotide sequence, between signal peptide residues 24 and 25 (72.9% probability). Panel B—SignalP analysis of kalata B1 precursor protein (partial sequence shown as SEQ ID NO:105) predicts signal peptidase cleavage between precursor protein residues 22 and 23 (82.5% probability). As in all previously characterized cyclotide genes, a pro-region and an N-terminal repeat region are encoded prior to the start of the first cyclotide domain. Panels C through F—Respective SignalP analyses of albumin-1 precursor proteins from *Pisum sativum, Medicago truncatula, Phaseolus vulgaris*, and *Glycine max* (partial sequences shown as SEQ ID NOS:106-109, respectively) predict signal peptidase cleavage at the proto-N-termini of mature PA1b peptide sequences. Cleavages are predicted between residues 26 and 27 (53.0%), 22 and 23 (51.1%), 27 and 28 (69.7%), and 19 and 20 (98.6%) respectively.
Figure 19:
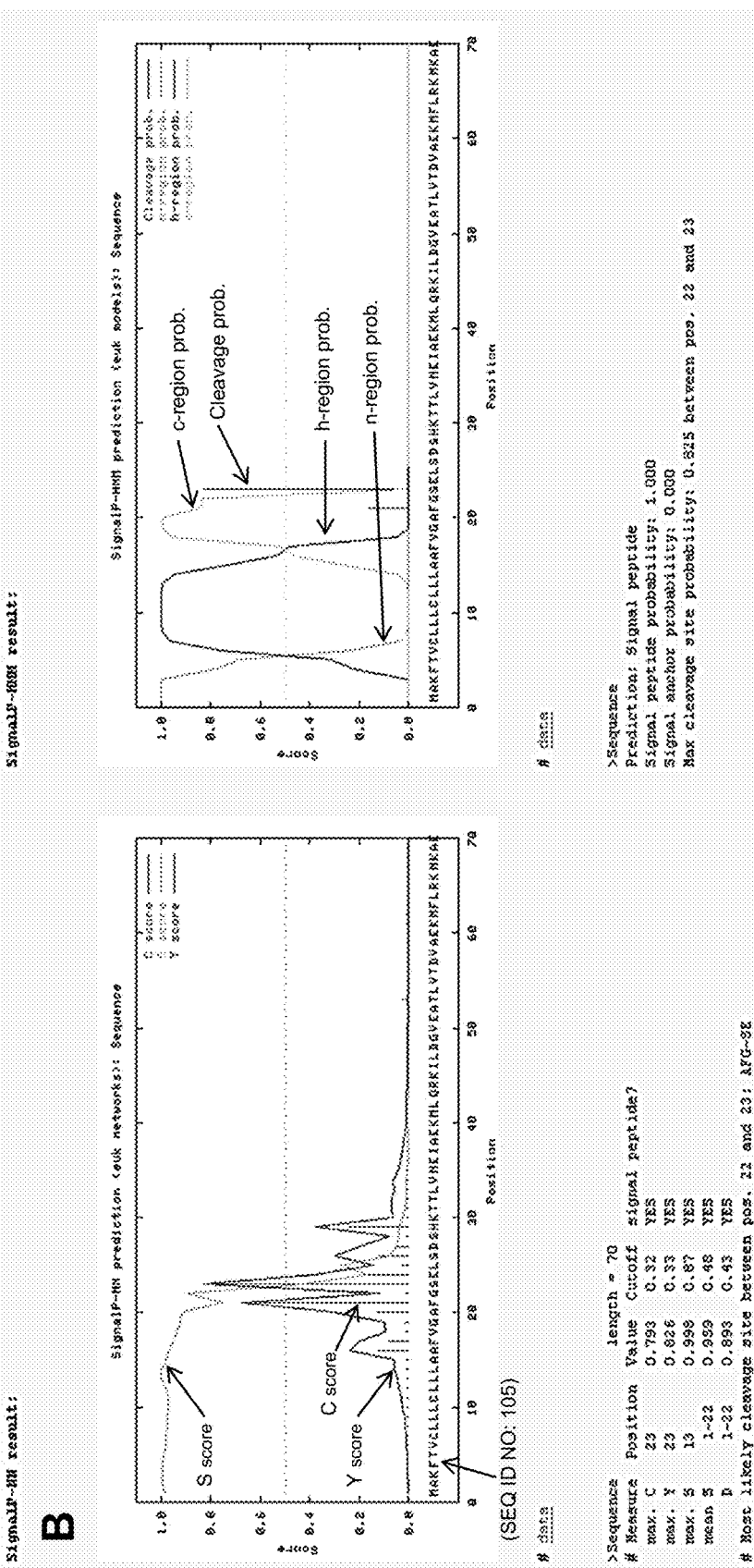
Figure 19:
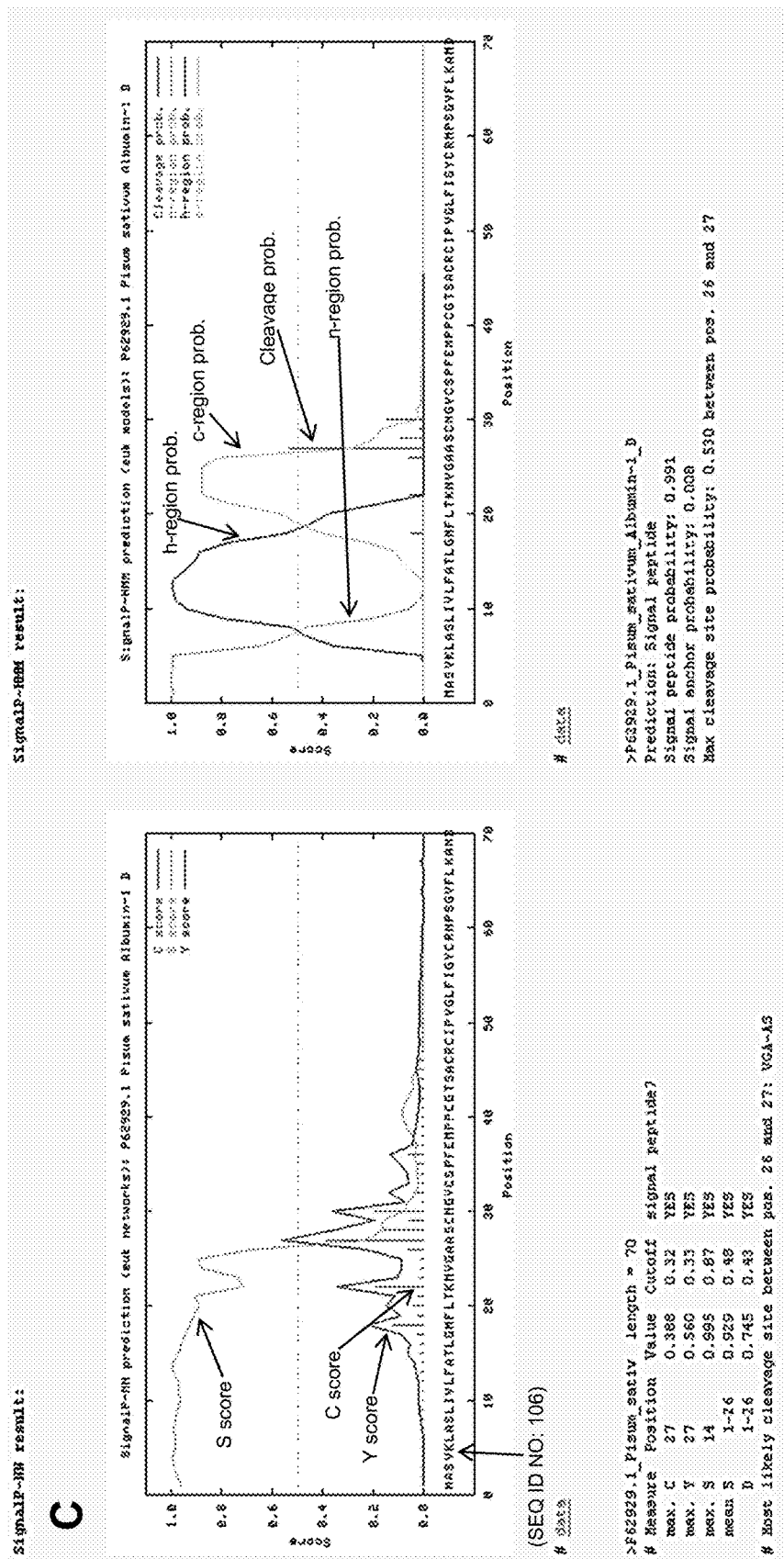
Figure 19:
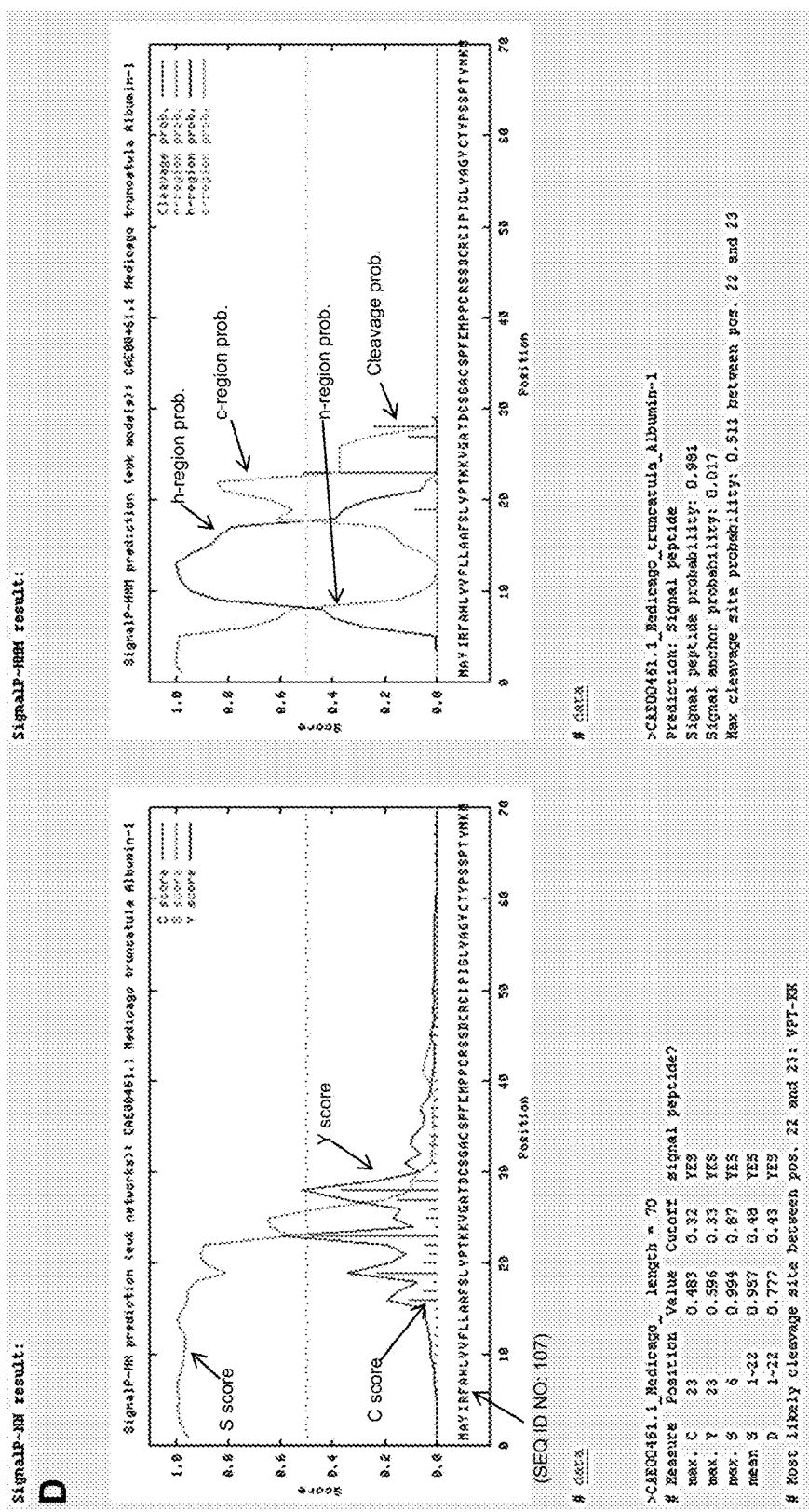
Figure 19:
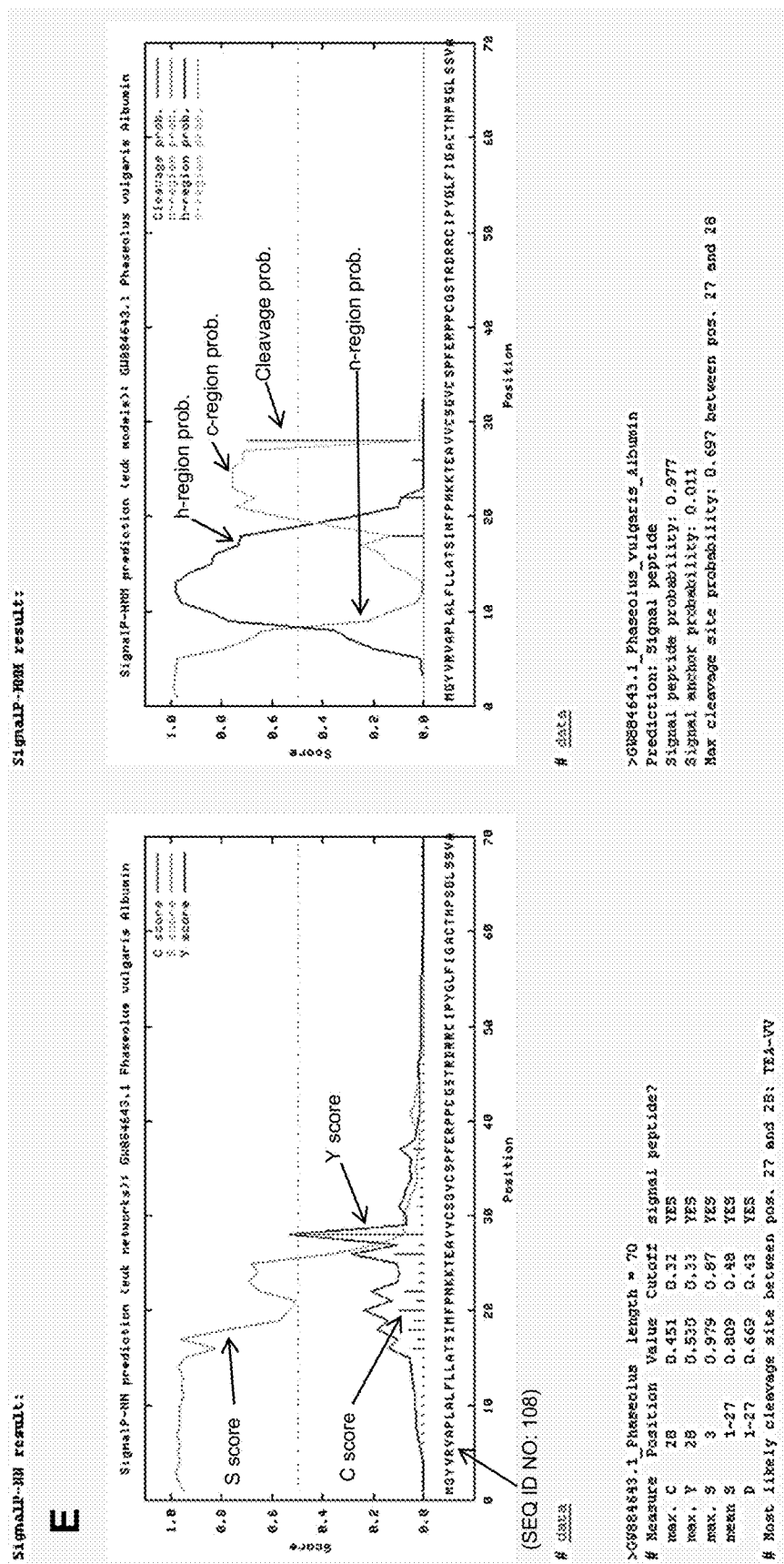
Figure 19:
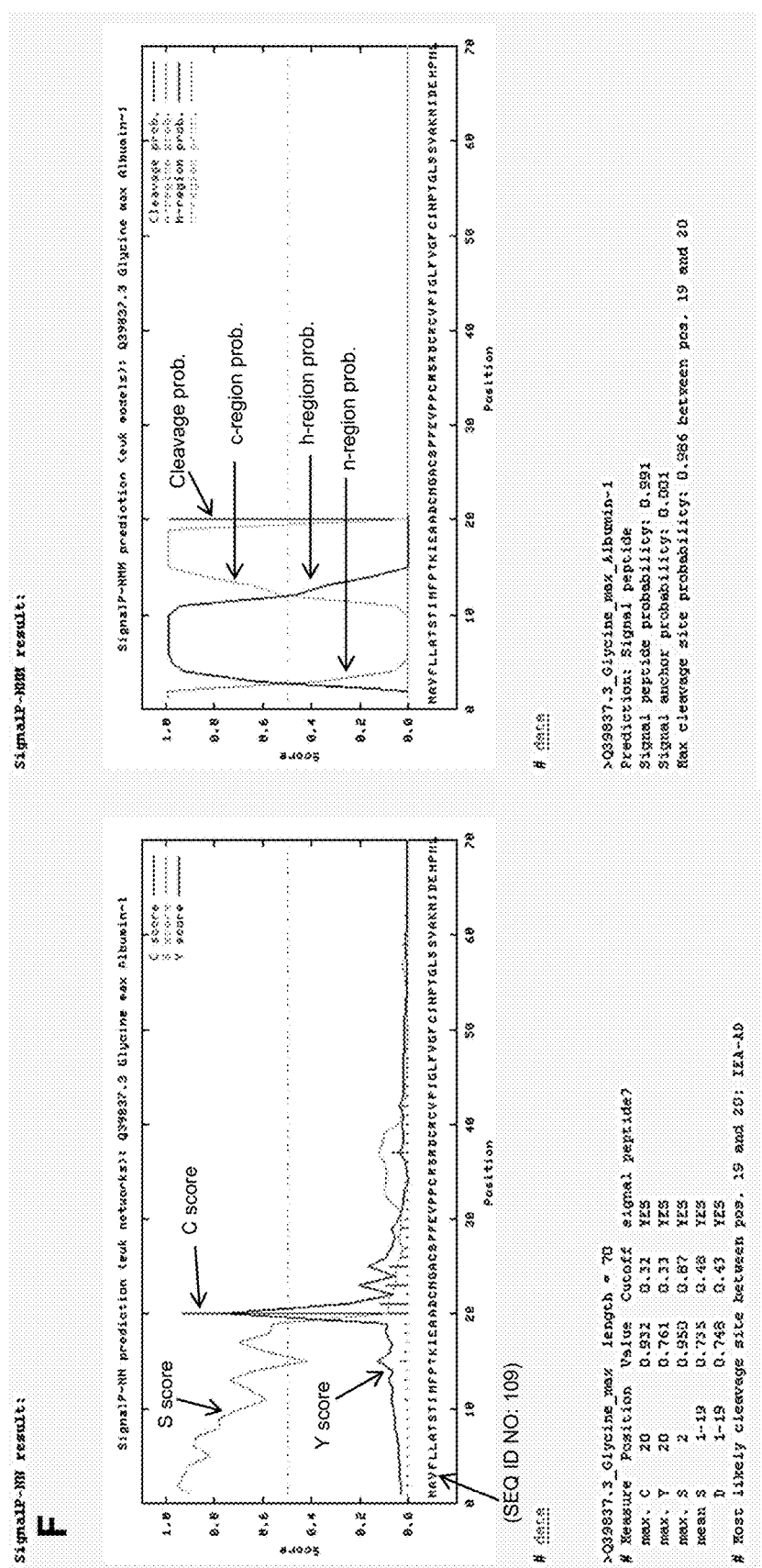
Figure 20:
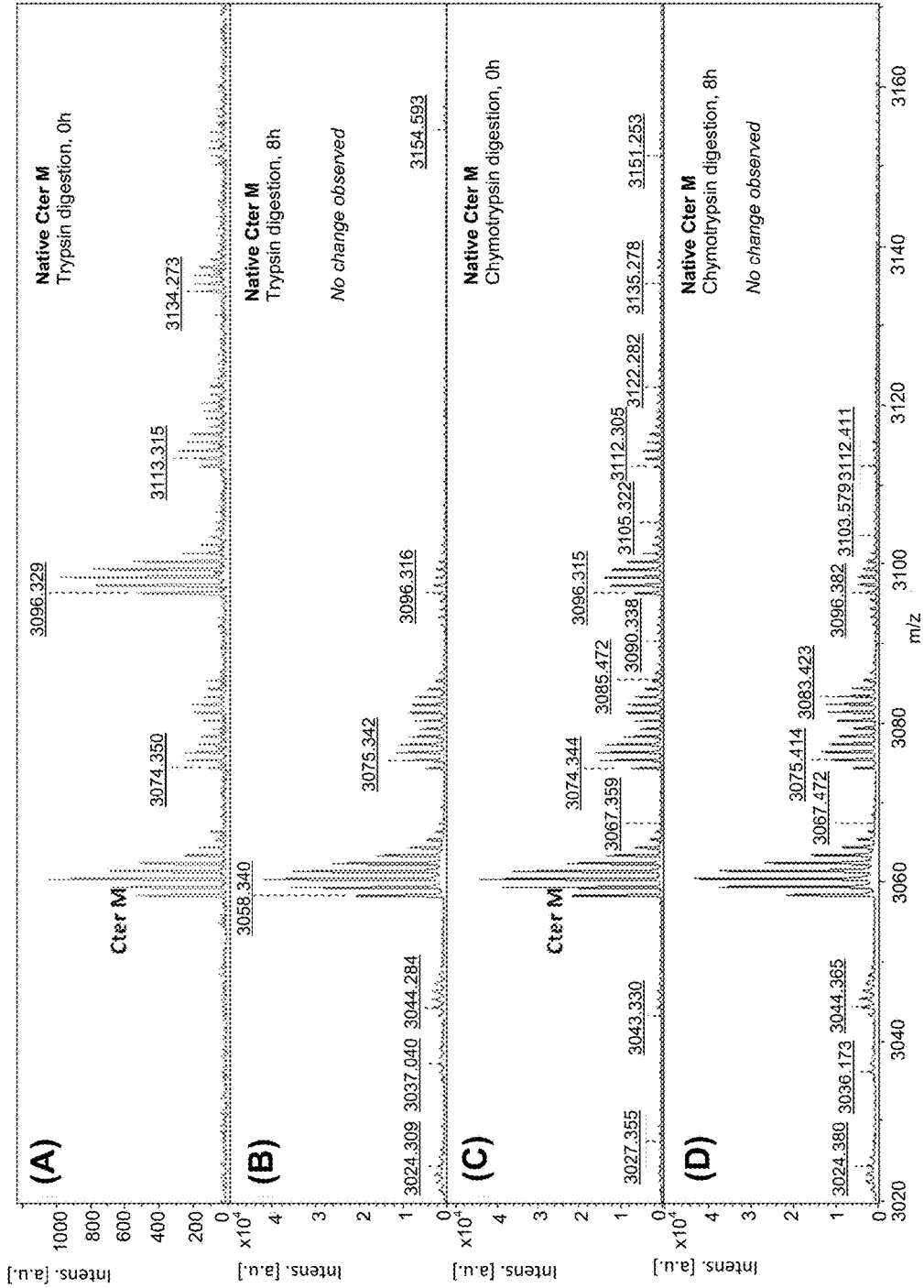
FIG. 20 shows that Cter M is resistant to proteolysis by trypsin and chymotrypsin. Leaf extract showing native Cter M at m/z 3058.3 (A, C) was subjected to trypsin (B) and chymotrypsin (D) digestion with no observed hydrolysis. The reduced and alkylated peptide, m/z 3407.6 (E, G, I) underwent proteolytic cleavage by trypsin (F) and chymotrypsin (H, J). As there is only a single tryptic site, the trypsin digestion product is observed at m/z 3424.6, whereas there were three chymotryptic sites resulting in the formation of major products at m/z 1450.7, 1511.7 and 1931.8 corresponding to KNGLPTCGETCL (SEQ ID NO:129), VPDCSCSWPICM (SEQ ID NO:130) and KNGLPTCGET-CLGTCY (SEQ ID NO:131) respectively.
Figure 20:
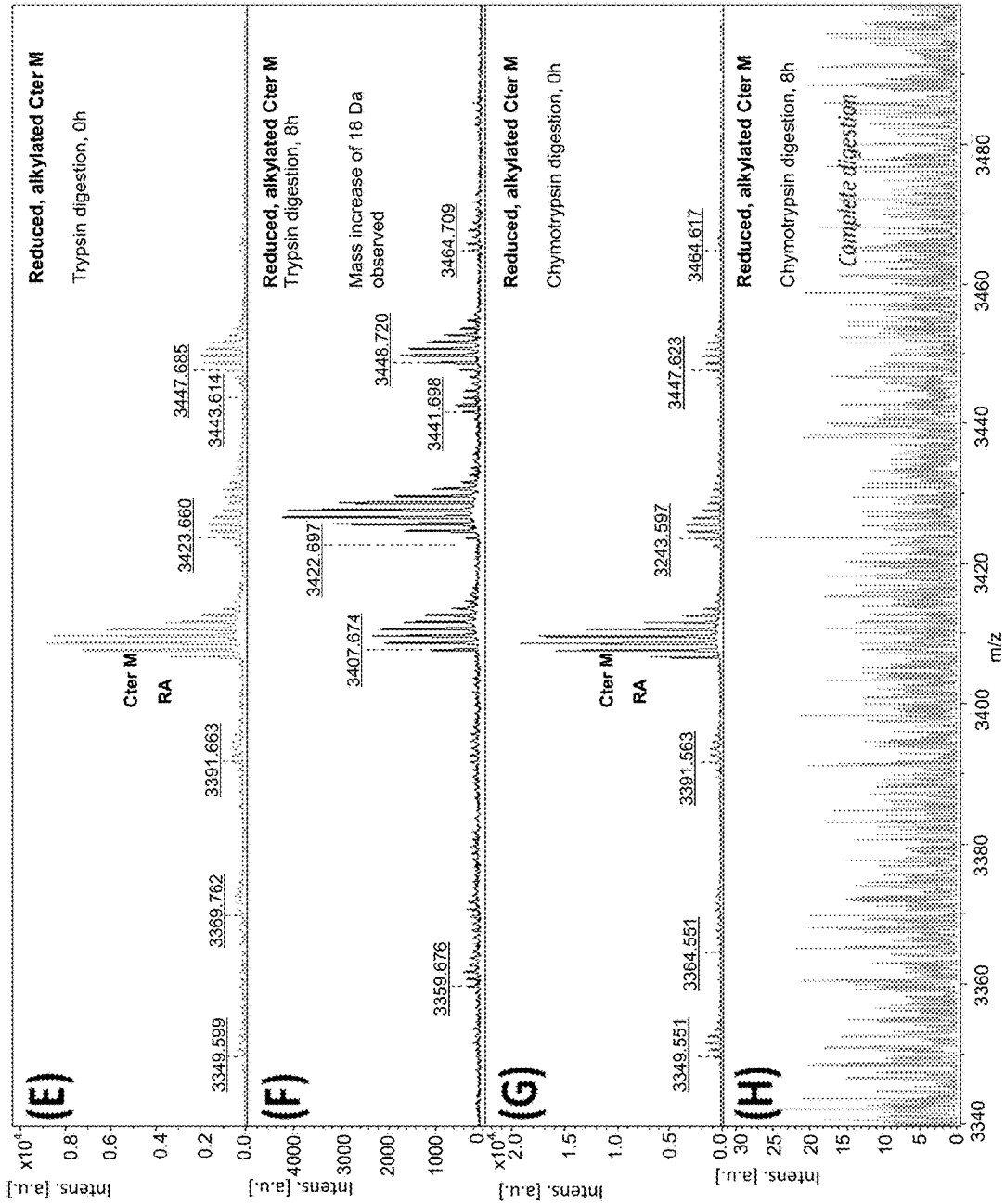
Figure 20:
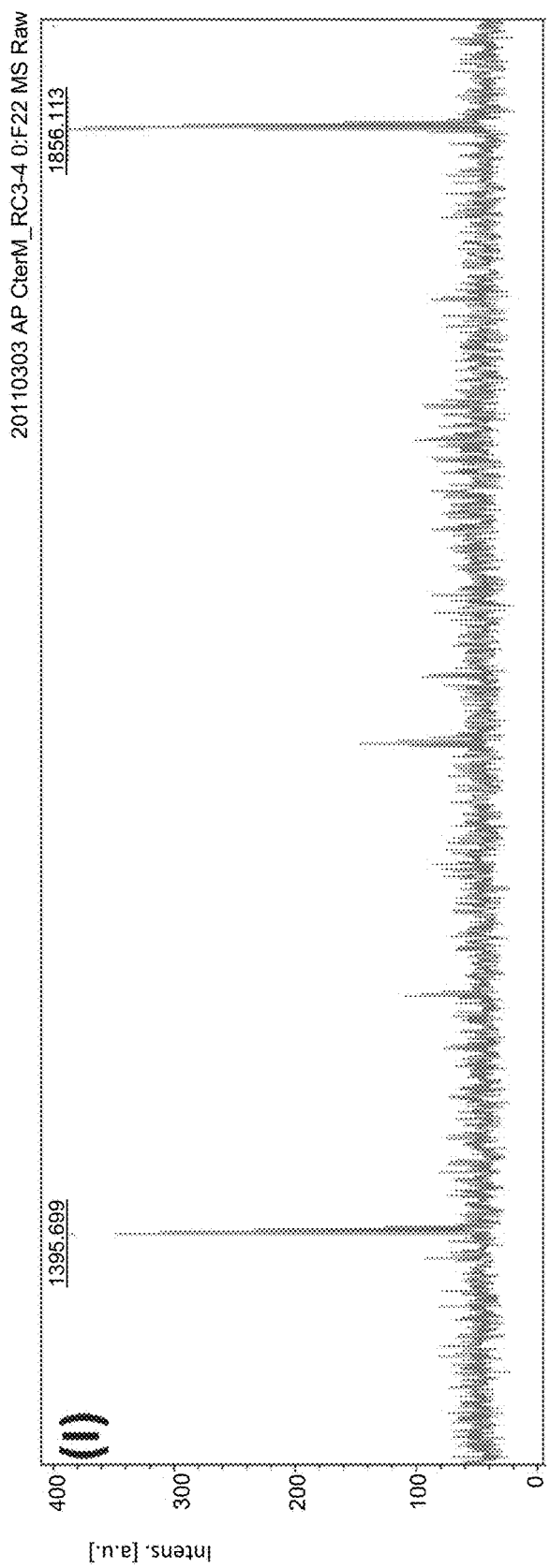
Figure 20:
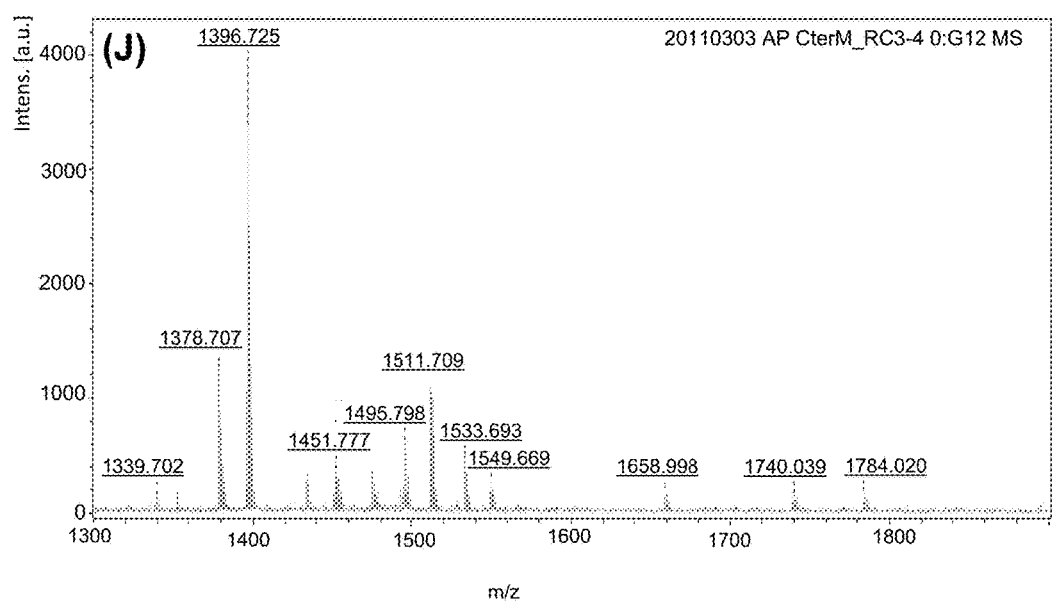

In the precursor protein encoding the prototypic cyclotide, kalata B1, the mature peptide sequence is flanked by 69 amino acids at the N-terminus and seven amino acids at the C-terminus, with each of the six cysteines in the precursor located within the mature kB1 sequence. In contrast, the Cter M precursor has a typical endoplasmic reticulum (ER) signal sequence of 24 amino acids, but the predicted signal peptide cleavage site immediately precedes the N-terminus of the mature cyclotide (FIGS. 11 and 19). In addition to the six cysteines present within the cyclotide domain, four cysteines are present within the albumin-like a-chain. Examples of nucleic acid encoding ER signal peptide and the corresponding peptides of Fabaceae include but are not limited to the following:

```
Fabaceae albumin-1 ER signal sequences:

Clitoria ternatea (JF501210):
Nucleotide sequence
ATGGCTTACGTTAGACTTACTTCTCTTGCCGTTCTCTTCTTCCTTGCTGCTTCCGTTAT
GAAGACAGAAGGA (SEQ ID NO: 127)
Amino acid sequence
MAYVRLTSLAVLFFLAASVMKTEG (SEQ ID NO: 128)

Phaseolus vulgaris (HM240265.1):
Nucleotide sequence
ATGGGTTATGTTAGGGTTGCTCCTTTGGCTCTCTTCTTGCTTGCCACTTCCATGATGTTTTC
GATGAAGAAGATAGAAGCT (SEQ ID NO: 150)
Amino acid sequence
MGYVRVAPLALFLLATSMMFSMKKIEA (SEQ ID NO: 151)

Phaseolus vulgaris (GW898230.1):
Nucleotide sequence
ATGGGTTATGTTAGGGTTGCTCCTTTGGCTCTCTTCTTGCTTGCCACTTCCATAATGTTTCC
GATGAAGAAGACAGAGGCA (SEQ ID NO: 152)
Amino acid sequence
MGYVRVAPLALFLLATSIMFPMKKTEA (SEQ ID NO: 153)

Pisum sativum (AJ276882.1):
Nucleotide sequence
ATGGCTTCCGTTAAACTCGCTTCTTTGATCGTCTTGTTTGCCACATTAGGTATGTTCCTGAC
AAAAAACGTAGGGGCA (SEQ ID NO: 154)
Amino acid sequence
MASVKLASLIVLFATLGMFLTKNVGA (SEQ ID NO: 155)

Medicago truncatula (BT053249.1):
Nucleotide sequence
ATGACTTATGTTAAGCTCATTACTTTGGCTCTATTCCTGGTTACCACACTCTTAATGTTTCA
GACAAAGAATGTTGAAGCA (SEQ ID NO:156)
Amino acid sequence
MTYVKLITLALFLVTTLLMFQTKNVEA (SEQ ID NO: 157)

Medicago truncatula (BG584516.1):
Nucleotide sequence
ATGGCTTATGTTAAGCTTGCTTCTTTTGCTGTCTTCTTGCTTGCTGCATTCGTAATGTTTCC
GATGAAAAAAGTAGAAGGA (SEQ ID NO: 158)
Amino acid sequence
MAYVKLASFAVFLLAAFVMFPMKKVEG (SEQ ID NO:159)

Glycine max (D17396.1):
Nucleotide sequence
ATGGCTGTCTTCTTGCTTGCCACTTCCACCATAATGTTCCCAACGAAGATAGAAGCA
(SEQ ID NO: 160)
```

Fabaceae albumin-1 ER signal sequences:

Amino acid sequence
MAVFLLATSTIMFPTKIEA (SEQ ID NO: 161)

Synthesis

Figure 22:
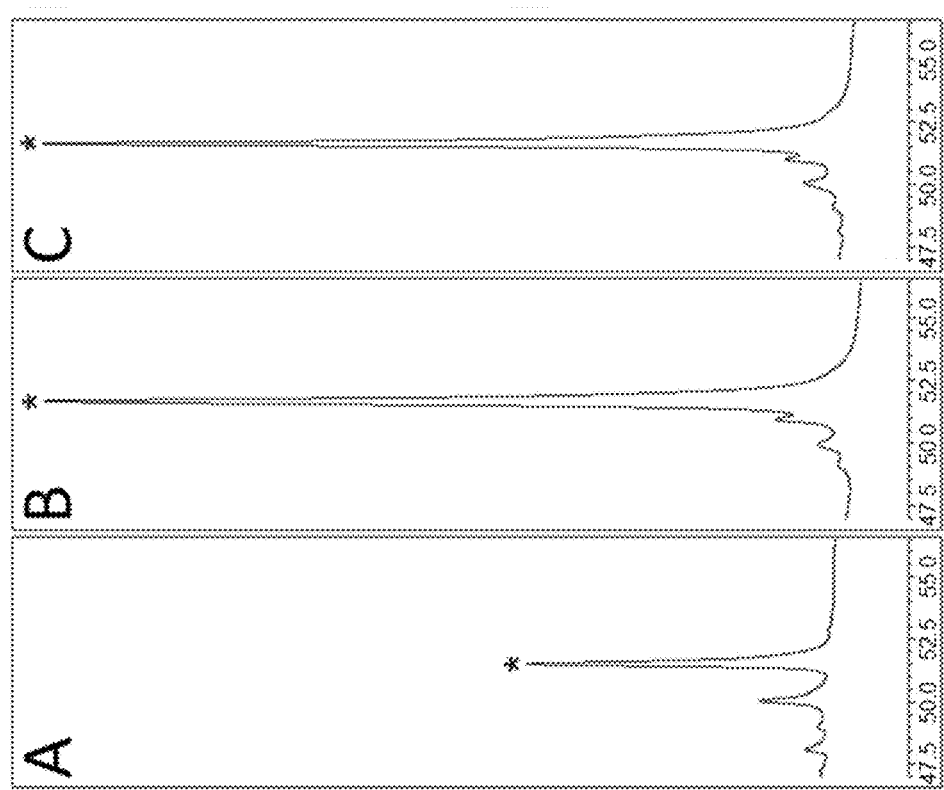
FIG. 22 shows analytical HPLC and mass spectrometric analysis showing that native and synthetic Cter M are identical. (A) Native Cter M; (B) Synthetic Cter M; and (C) Co-elution of Native and Synthetic Cter M. MALDI-TOF mass spectra of (D) Native Cter M extracted from *Clitoria ternatea* leaf material and (E) Synthetic Cter M.
Figure 22:
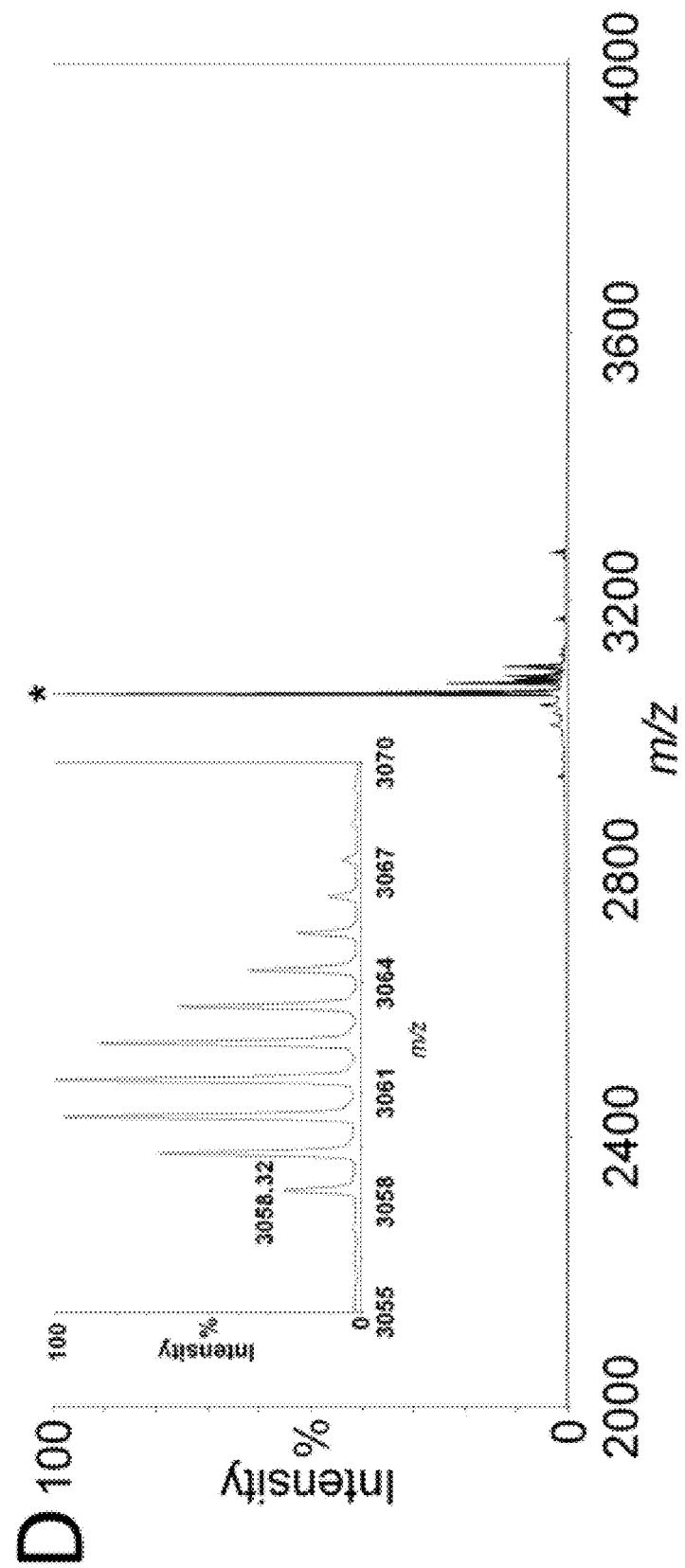
Figure 22:
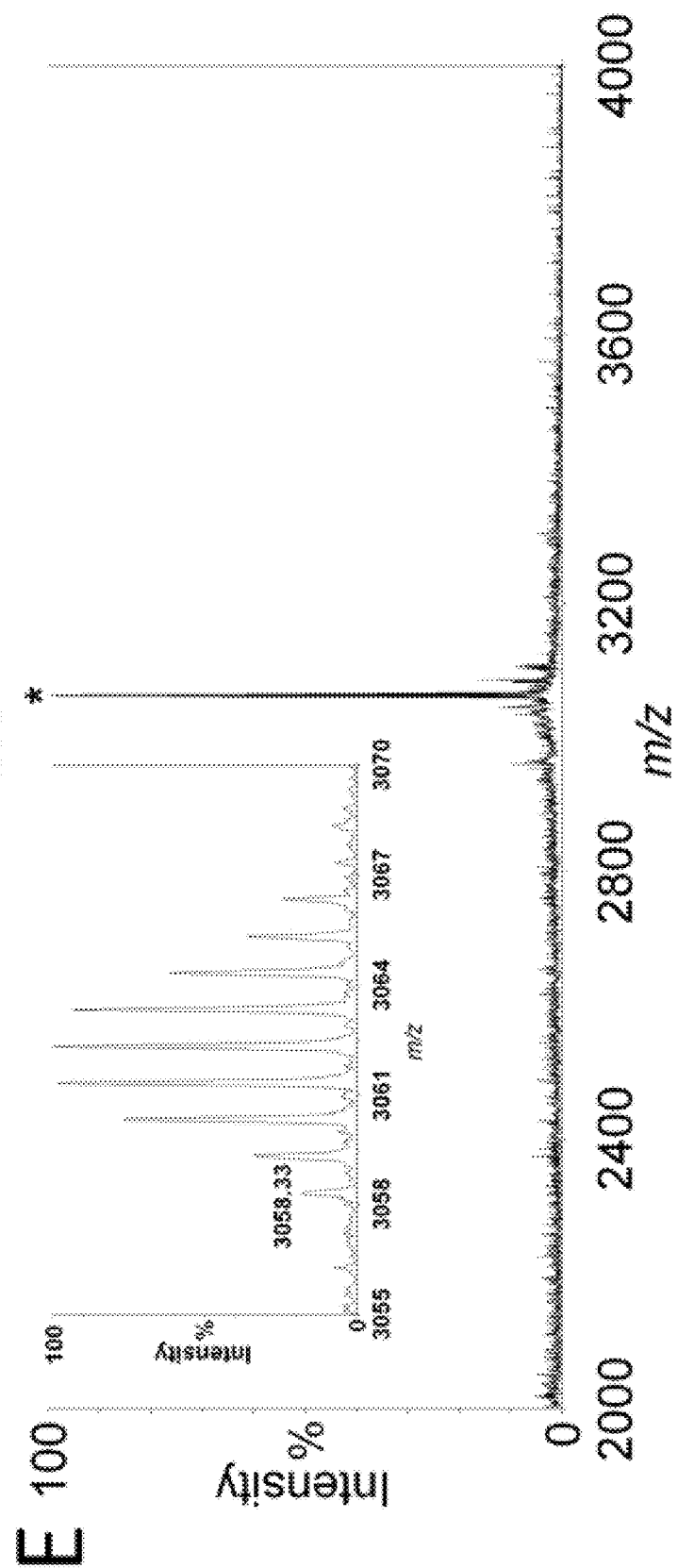

Cter M was synthesized using solid phase peptide synthesis and folded using conditions earlier established for other cyclotides (Daly, N. L., et al., (1999) *Biochemistry* 38, 10606-10614) including the use of 50% isopropanol in buffer. The synthetic peptide was identical to the native peptide by MS and HPLC (FIG. 22) and was noted to have relatively low solubility in water. The addition of acetonitrile greatly improved the solubility and the spectra of Cter M were thus recorded in the presence of acetonitrile. The NMR spectra of the native and synthetic Cter M peptides were recorded and found to be identical. The three-dimensional structure of Cter M was calculated with 398 distance restraints and 11 angle restraints using a simulated annealing protocol in CNS. The resulting family of structures had good structural and energetic statistics, as shown in Table 4, below.

TABLE 4

NMR and refinement statistics for Cter M.

| NMR distance & dihedral constraints Distance constraints | |
|---|---|
| Total NOE | 398 |
| Intra-residue | 84 |
| Sequential (\|i − j\| = 1) | 149 |
| Medium-range (\|i − j\| < 4) | 51 |
| Long-range (\|i − j\| > 5) | 114 |
| Total dihedral angle restraints | 11 |
| Structure Statistics Violations (mean and s.d.) | |
| Distance constraints (Å) | 0.02 ± 0.002 |
| Dihedral angle constraints (°) | 0.6 ± 0.13 |
| Max. dihedral angle violation (°) | 3 |
| Max. distance constraint violation (Å) | 0.3 |
| Deviations from idealized geometry | |
| Bond lengths (Å) | 0.003 ± 0.0002 |
| Bond angles (°) | 0.59 ± 0.03 |
| Impropers (°) | 0.49 ± 0.03 |
| Average pairwise r.m.s.d.** (Å) | |
| Backbone | 0.3 ± 0.08 |
| Heavy | 0.67 ± 0.18 |
| Ramachandran statistics | |
| % in most favoured region | 71.4 |
| % in additionally allowed region | 27.3 |
| % in generously allowed region | 1.4 |

**Pairwise r.m.s.d. was calculated among 20 refined structures.

Figure 14:
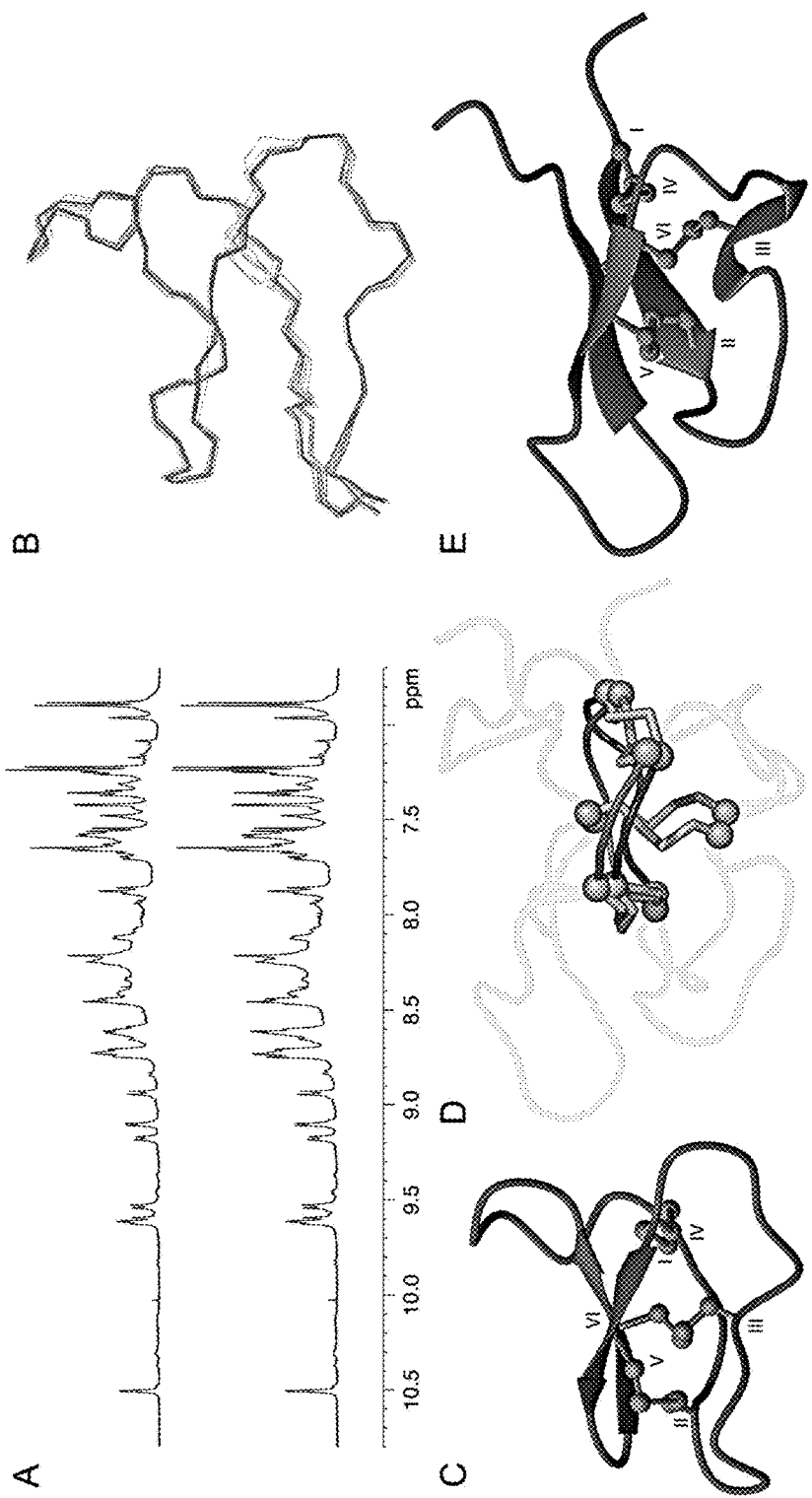
FIG. 14 shows the NMR spectra and three-dimensional structure of Cter M. (A) One-dimensional spectra of Cter M recorded before (top) and after (bottom) heating to 95° C. for 5 minutes. (B) Superposition of the 20 lowest energy structures of Cter M. Secondary structure of Cter M (C) and PA1b (E; PDB code 1P8B). The strands are shown as arrows and the helical turns as thickened ribbons. The disulfide bonds are shown in ball-and-stick format. The structure figures were generated using MOLMOL (Koradi, R., Billeter, M. & Wüthrich, K. (1996) *J. Mol. Graph.* 14, 29-32). Superimposition of Cter M and PA1b (D) showing cystine knot motif; disulfide bonds are indicated, and the aC are represented by spheres.

The structure of Cter M is extremely stable evidenced by its resistance to heat denaturation. Spectra were recorded before and after heating the peptide at 95° C. for 5 minutes and no changes were observed in the spectra as shown in FIG. 14a. An ensemble and ribbon representation of the three dimensional structure is shown in FIG. 14 along with a comparison with PA1b, the pea albumin whose precursor shares high sequence homology with the Cter gene. While variation in the loop regions of the two peptides is apparent, the eight-membered ring formed between loops 1 and 4 and the inter-connecting disulfide bonds (cysteine knot) shows striking similarities as evidenced by the superimposition in FIG. 14d.

Analysis of the structures of Cter M with PROMOTIF identified a type I β-turn between residues 9-12, a type II β-turn between residues 16-19 and a type VIaI β-turn between residues 22-25. A β-hairpin is recognized between residues 20-27, as shown in FIG. 14c. This β-hairpin is invariably present in inhibitor cystine knot proteins (Pallaghy, P. K., et al., (1994) *Protein Sci.* 3, 1833-1839; Craik, D. J., et al., (2001) *Toxicon* 39, 43-60).

Example 4

Haemolytic Activity Assays

Figure 15:
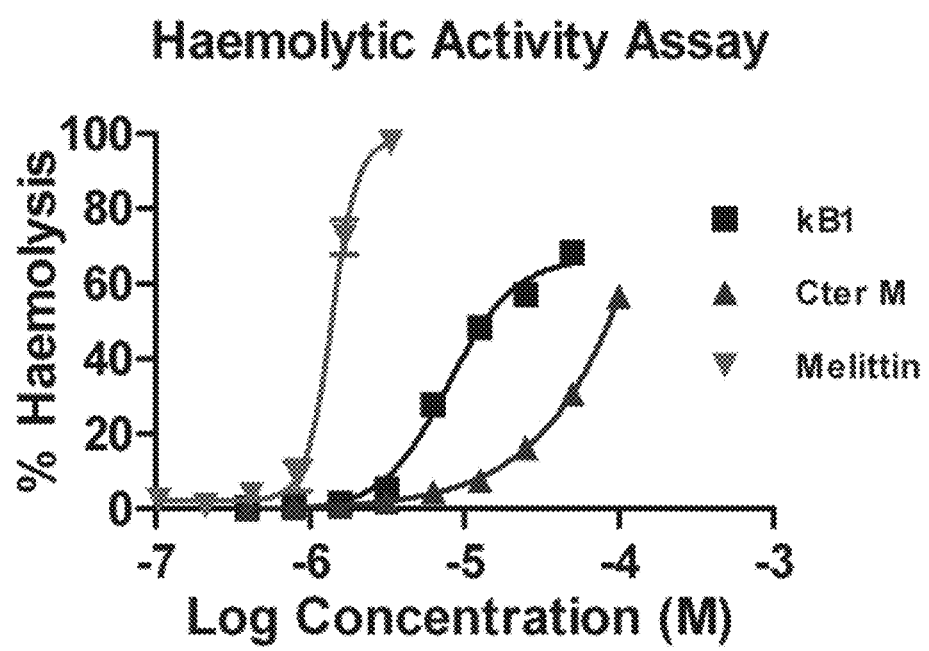
FIG. 15 provides a graph comparing haemolytic activity of Cter M with the prototypic cyclotide kalata B1 and the known pore-forming agent from bee venom, melittin.

Serially diluted peptide solutions were incubated with washed human red blood cells. Following incubation, the supernatant was transferred before the UV absorbance was measured. The amount of haemolysis was calculated as the percentage of maximum lysis (1% Triton X-100 control) after adjusting for minimum lysis (PBS control). Synthetic melittin was used for comparison. The haemolytic dose necessary to lyse 50% of the RBCs ($HD_{50}$) was calculated using the regression constant from the linear portion of the haemolytic titration curve (Graphpad Prism software). Results are presented in FIG. 15. The $HD_{50}$ was determined to be 1.4 µM for melittin, 7.8 µM for kB1 and >100 µM for Cter M, showing Cter M to be mildly haemolytic.

Example 5

Larval Migration Assays

Larval Migration Assays.

The effect of kB1 and Cter M on the motility of L3-stage larvae of *Haemonchus contortus* was assessed using a previously described method (Colgrave, et al., 2010, *Antimicrob. Agents Ch.* 54:2160-2166). The larvae were incubated in PBS containing a range of peptide concentrations for 24 h in the dark in a 96-well plate format. The motility of the worms was assessed wherein sinusoidal motion was indicative of health and loss of motility or the degree of motility was indicative of poor health. Nematodes that had been incubated with cyclotides were compared to control (no-peptide) wells.

Figure 16:
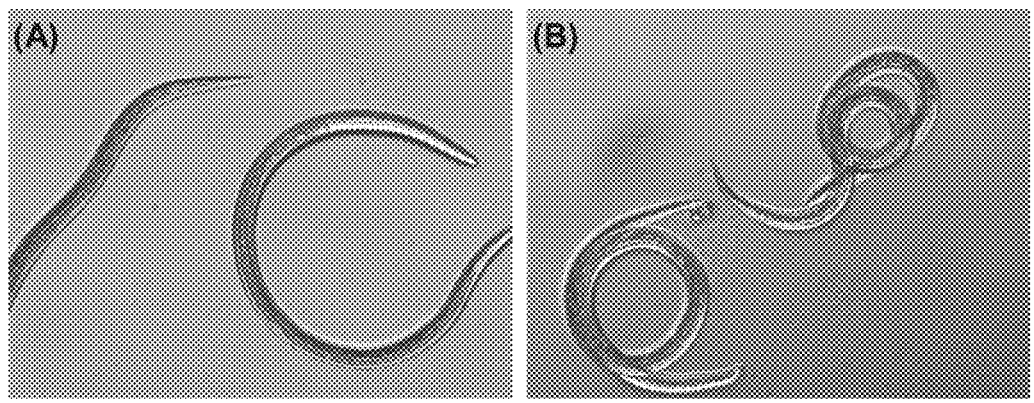
FIG. 16 illustrates the results following exposure of nematodes to control (no peptide) and Cter M cyclotide solutions. The effect of Cter M of the motility of L3 larvae of *Haemonchus contortus*: control worms (A) and cyclotide treated worms (B).
Figure 18A:
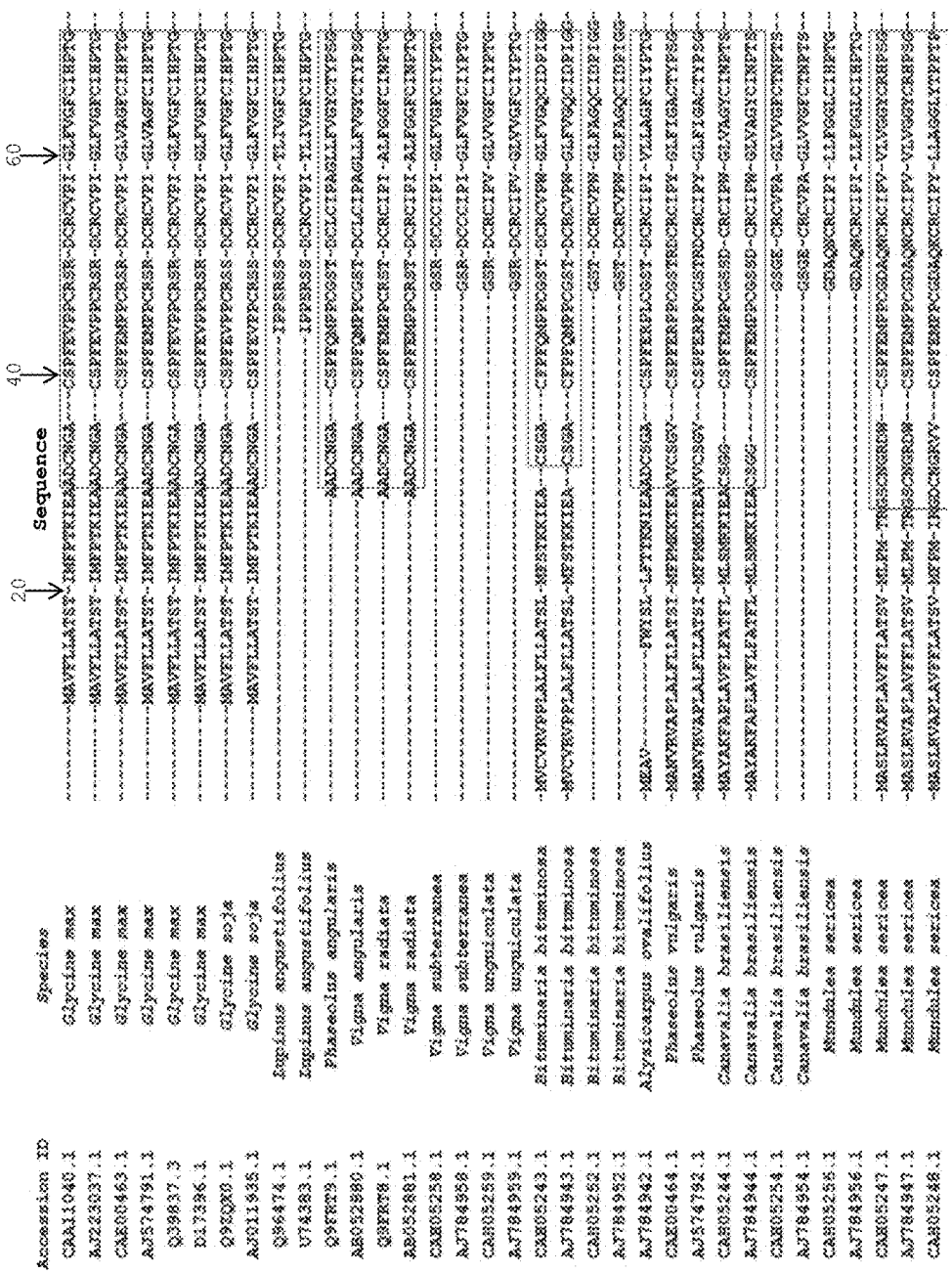
FIGS. 18A-B show a ClustalW2 alignment of Cter M with BLASTP- and TBLASTN-matched Fabaceae albumin-1 precursor proteins, in order from Accession ID No.CAA11040.1 to Accession No. CAH05248.1 (SEQ ID NO:37 through SEQ ID NO:70).
Figure 18B:
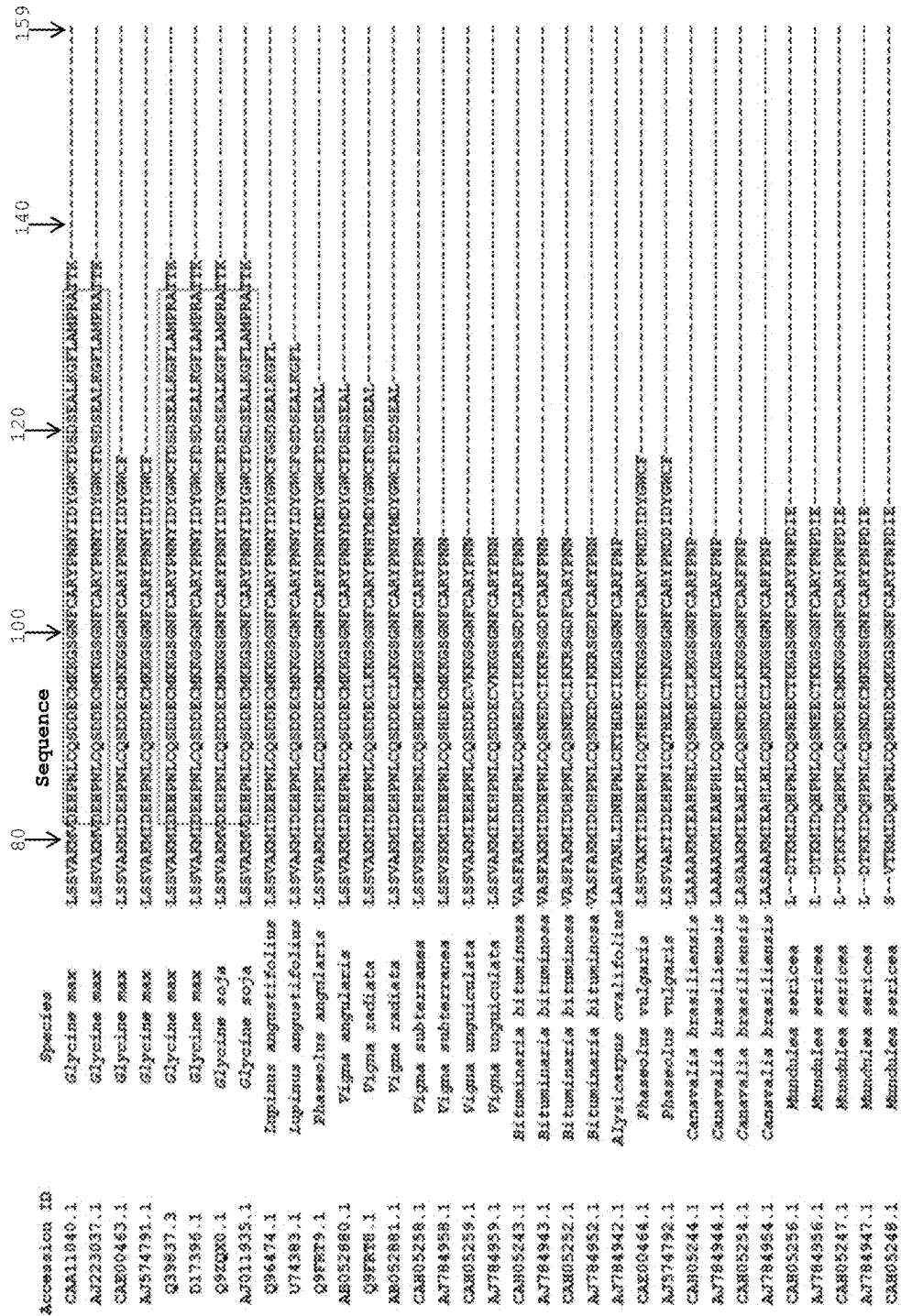
Figure 18C:
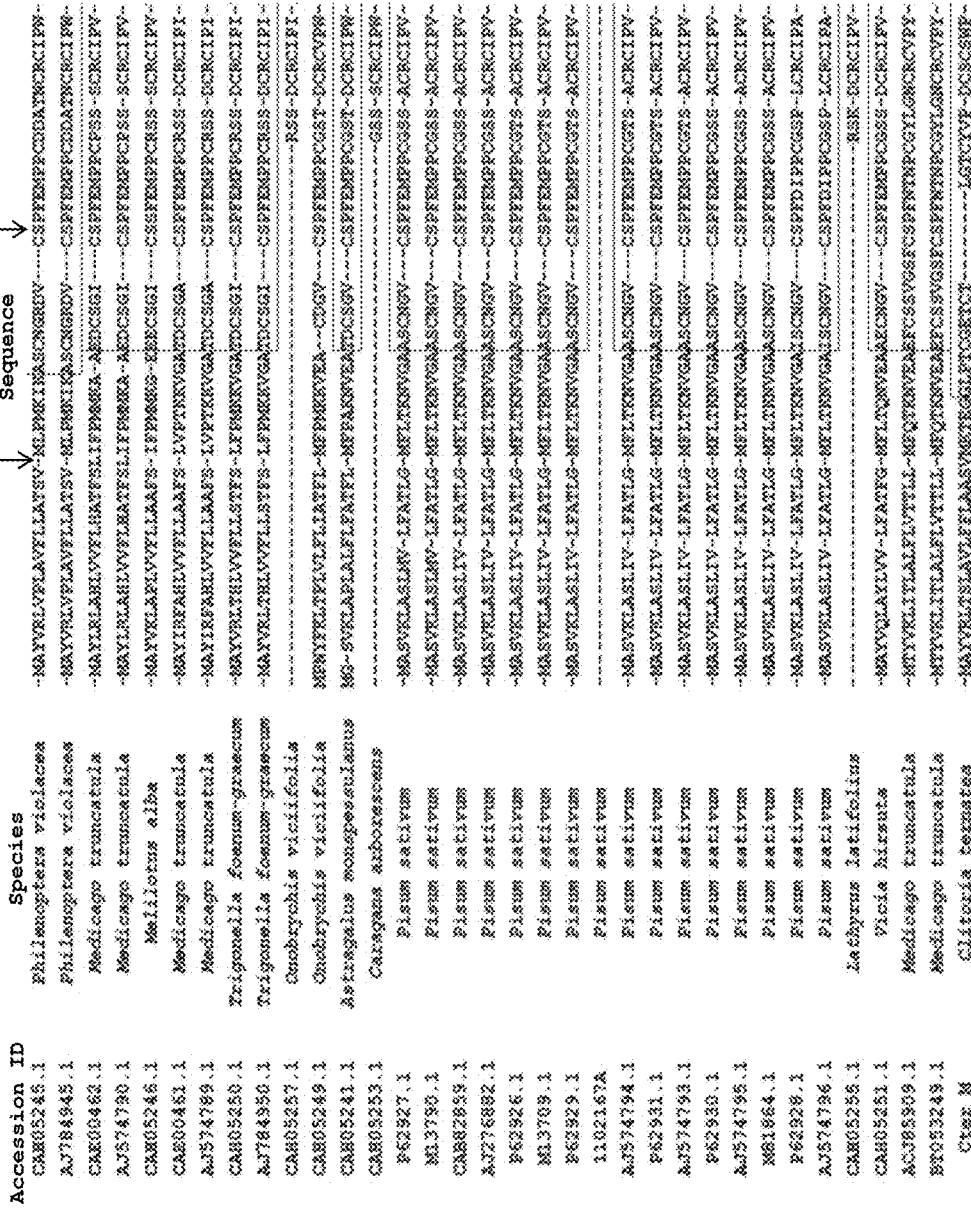
FIGS. 18C-D show a ClustalW2 alignment of Cter M with BLASTP- and TBLASTN-matched Fabaceae albumin-1 precursor proteins, in order from Accession ID No. CAH05245.1 to Accession ID No. BT053249.1 (SEQ ID NO:71 through SEQ ID NO:103), followed by Cter M (SEQ ID NO:28). N-terminal boxed regions outline mature PA1 chain-b peptide sequence in Fabaceae albumins, and the mature sequence of cyclotide Cter M. C-terminal boxed regions outline predicted mature PA1 chain-a peptide sequence.
Figure 18D:
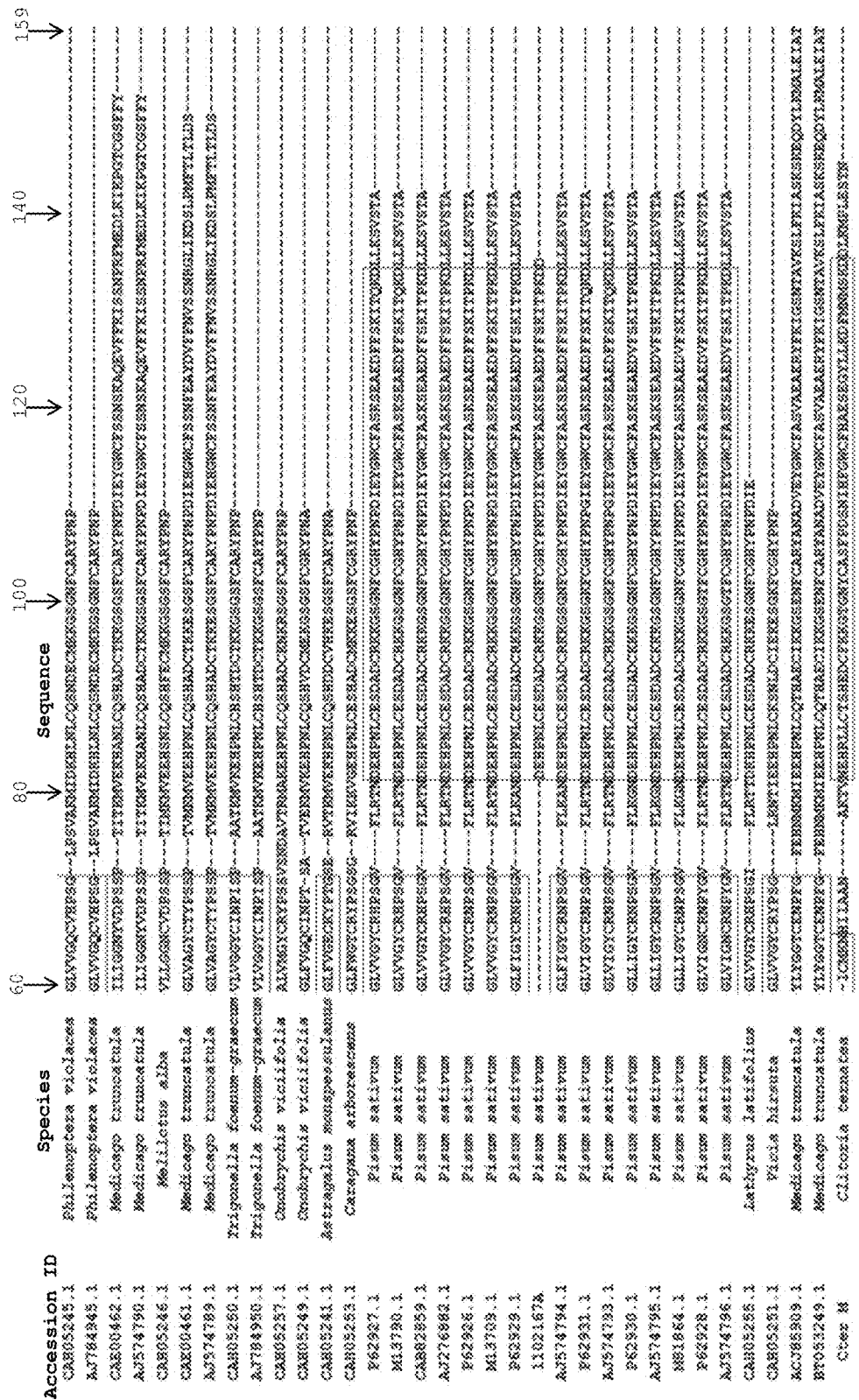

The results are shown in FIG. 16. Incubation with the cyclotides resulted in decreased motility of the nematodes as evidenced in the images. The control nematodes exhibited sinusoidal movement indicative of health (appeared extended in image on left, A), whereas the nematodes that had been treated with high concentrations of the peptides were coiled and showed very little movement or only a slight twitching (image on right, B).

Example 6

Insecticidal Assay

*H. armigera* larvae were obtained from the Queensland Department of Employment, Economic Development & Innovation. A feeding trial was conducted for 48 h with larvae maintained at 25° C. throughout the experiment. Larvae were given diets consisting of wheat germ, yeast, and soy flour. The test diets contained the peptide Cter M or kalata B1 (used as a positive control (Jennings, C., et al., (2001) *Proc Nat'l Acad Sci USA* 98, 10614-10619) and the control diet did not have any added peptide. Larvae were weighed at 0, 24 and 48 h. Following this, the larvae were photographed. Statistical differences were analyzed using a paired t-test or ANOVA test. Results are presented in FIG. 17.

Example 7

Expression of a Cyclotide-Encoding Gene in a Fabaceae Crop Plant

One aspect of this invention is the construction of transgenic plants to express either the entire cDNA encoding a cyclotide, such as Cter M (peptide sequence GLPTCGETCTLGTCYVPDCSCSWPICMKN (SEQ ID NO:25) and the PA1a albumin domain, or part thereof. Transgenic plant species may include many belonging to Fabaceae family, including soybeans (*Glycine max*), bean (*Phaseolus vulgaris*), pea (*Pisum sativum*), broadbean (*Vicia faba*), chickpea (*Cicer arietinum*), pigeonpea (*Cajanus cajan*), lupin (*Lupinus* spp), lentil (*Lens culinaris*) and cowpea (*Vigna unguiculata*). All of these species have been demonstrated to be amenable to genetic transformation and transgenesis (Eapen, (2008), *Biotechnol Adv,* 26, 162-168).

Expression cassettes are initially generated for transformation into soybean (*Glycine max*) using a modified pMON expression vector (Rogers, S. G., et al., (1987) *Methods Enzymol.* 153, 253-277). The coding sequence of the Cter M encoding gene with or without the PA1a albumin domain is fused with eGFP and cloned into the pMON530 binary vector under the control of the cauliflower mosaic virus 35S promoter or tissue specific promoters (see below). Transformation is performed as described above, and transformants are selected using 50 mg L21 kanamycin. The GFP fluorescence of transgenic plants is observed using a Zeiss confocal laser scanning microscope.

A range of promoters are utilised for assessment of CterM-GFP expression, including but not limited to CMV35S (Ealing, P. M., et al., (1994) *Transgenic Res.,* 3, 344-354), polyubiquitin promoter (Gmubi) from soybean (*Glycine max*) (Hernandez-Garcia, C. M., et al., (2009) *Plant Cell Rep.,* 28, 837-849), and monocot tissue-specific promoter from sorghum γ-kafirin seed storage protein gene (Defreitas, F. A., et al., (1994) *Mol. Gen. Genet.,* 245, 177-186). Expression cassettes are then introduced in the soybean plant genome using *Agrobacterium*-mediated transformation (Eapen, S. (2008) *Biotechnol Adv,* 26, 162-168) (Krishnamurthy, K. V., et al., (2000) *Plant Cell Rep.,* 19, 235-240); (Sharma, K. K., et al., (2006) *In Vitro Cell. Dev. Pl.,* 42, 165-173). Assessment of recombinant polypeptide in various tissues and sub-cellular compartments is via fluorescence studies and proteomic analysis of tissues for presence of cyclotides. These techniques have been used successfully for many transgenic plants including cowpea, chickpea, peanut and other members of the Fabaceae family (Collinge, D. B., et al., (2010) *Ann. Rev. Phytopathol.* 48, 269-291).

The nucleotide sequences of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence homology to the nucleic acid sequence in FIG. 10, or to nucleic acids encoding the polypeptides of SEQ ID NOs 1-12 and 14-26 as set forth herein or to fragments thereof are encompassed by the embodiments.

All publications and patents mentioned in the above specification are herein incorporated by reference herein in their entireties, for all purposes. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

TABLE 2

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TACA1_TACTR | Horseshoe_crab | 6 | 11 | 0 | 4 | 11 | — | 0 | QLQGFN | VVRSYGLPTIP | | RGLT | RSYFPGSTYGR | |
| TACA2_TACTR | Horseshoe_crab | 6 | 11 | 0 | 4 | 11 | — | 1 | QLQGFN | VVRSYGLPTIP | | RGLT | RSYFPGSTYGR | |
| TACB1_TACTR | Horseshoe_crab | 6 | 7 | 0 | 4 | 11 | — | 1 | LFRGAR | RVYSGRS | | FGYY | RRDFPGSIFGT | |
| TACB2_TACTR | Horseshoe_crab | 6 | 7 | 0 | 4 | 11 | — | 1 | LFRGAR | RVYSGRS | | FGYY | RRDFPGSIFGT | |
| A0ZSG4_FUGRU | agouti | 6 | 6 | 0 | 5 | 10 | — | 0 | LPLGGS | KSPGTE | | DFCAF | QCRLFRTVCY | |
| A0ZSG5_FUGRU | agouti | 6 | 5 | 0 | 5 | 10 | — | 0 | SQLTQS | VPQFG | | HPQAL | HCRFFNAICF | |
| A0ZSG6_FUGRU | agouti | 6 | 6 | 0 | 5 | 10 | — | 0 | IPHQQS | LGYPLP | | DPCDT | YCRFFNAICY | |
| A0ZSG7_FUGRU | agouti | 6 | 5 | 0 | 5 | 10 | — | 0 | SRLMES | SPYTP | | DPCAS | HCRLFNTICN | |
| A1YL76_9PRIM | agouti | 6 | 6 | 0 | 5 | 10 | — | 0 | VATRGS | KPPAPA | | HPCAS | QCRFFRSACS | |
| A2ALT3_MOUSE | agouti | 6 | 6 | 0 | 5 | 10 | — | 0 | VATRDS | KPPAPA | | DPCAS | QCRFFGSACT | |
| A4GVF2_CANLU | agouti | 6 | 6 | 0 | 5 | 10 | — | 0 | VATRNS | KSPAPA | | DPCAS | QCRFFRSACT | |
| A5JUA3_9GALL | agouti | 6 | 6 | 0 | 5 | 10 | — | 0 | VRLLES | LGHQIP | | DPCAT | YCRFFNAFCY | |
| A5JUA4_TRATE | agouti | 6 | 6 | 0 | 5 | 10 | — | 0 | VRLLES | LGHQIP | | DPCAT | YCRFFNAFCY | |
| A5JUA5_TRASA | agouti | 6 | 6 | 0 | 5 | 10 | — | 0 | VRLLES | LGHQIP | | DPCAT | YCRFFNAFCY | |
| A5JUA6_SYRRE | agouti | 6 | 6 | 0 | 5 | 10 | — | 0 | VRLLES | LGHQIP | | DPCAT | YCRFFNAFCY | |
| A5JUA7_ROLRO | agouti | 6 | 6 | 0 | 5 | 10 | — | 0 | VRLLES | LGHQIP | | DPCAT | YCRFFNAFCY | |
| A5JUA8_PERPE | agouti | 6 | 6 | 0 | 5 | 10 | — | 0 | VRLLES | LGHQIP | | DPCAT | YCRFFNAFCY | |
| A5JUA9_POLMA | agouti | 6 | 6 | 0 | 5 | 10 | — | 0 | VRLLES | LGHQIP | | DPCAT | YCRFFNAFCY | |
| A5JUB0_PAVMU | agouti | 6 | 6 | 0 | 5 | 10 | — | 0 | VRLLES | LGHQIP | | DPCAT | YCRFFNAFCY | |
| A5JUB1_9GALL | agouti | 6 | 6 | 0 | 5 | 10 | — | 0 | VRLLES | LGHQIP | | DPCAT | YCRFFNAFCY | |
| A5JUB2_POLEM | agouti | 6 | 6 | 0 | 5 | 10 | — | 0 | VRLLES | LGHQIP | | DPCAT | YCRFFNAFCY | |
| A5JUB3_PHACC | agouti | 6 | 6 | 0 | 5 | 10 | — | 0 | VRLLES | LGHQIP | | DPCAT | YCRFFNAFCY | |
| A5JUB4_PAVCR | agouti | 6 | 6 | 0 | 5 | 10 | — | 0 | VRLLES | LGHQIP | | DPCAT | YCRFFNAFCY | |
| A5JUB6_MELGA | agouti | 6 | 6 | 0 | 5 | 10 | — | 0 | VRLLES | LGHQIP | | DPCAT | YCRFFNAFCY | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| A5JUB7_9GALL | agouti | 6 | 6 | 0 | 5 | 10 | — | 0 | VRLLES | LGHQIP | | DPCAT | YCRFFNAFCY | |
| A5JUB9_LOPNY | agouti | 6 | 6 | 0 | 5 | 10 | — | 0 | VRLLES | LGHQIP | | DPCAT | YCRFFNAFCY | |
| A5JUC0_LAGLG | agouti | 6 | 6 | 0 | 5 | 10 | — | 0 | VRLLES | LGHQIP | | DPCAT | YCRFFNAFCY | |
| A5JUC1_LOPIM | agouti | 6 | 6 | 0 | 5 | 10 | — | 0 | VRLLES | LGHQIP | | DPCAT | YCRFFNAFCY | |
| A5JUC2_LOPED | agouti | 6 | 6 | 0 | 5 | 10 | — | 0 | VRLLES | LGHQIP | | DPCAT | YCRFFNAFCY | |
| A5JUC3_LOPDI | agouti | 6 | 6 | 0 | 5 | 10 | — | 0 | VRLLES | LGHQIP | | DPCAT | YCRFFNAFCY | |
| A5JUC4_GALSO | agouti | 6 | 6 | 0 | 5 | 10 | — | 0 | VRLLES | LGHQIP | | DPCAT | YCRFFNAFCY | |
| A5JUC5_FRAPO | agouti | 6 | 6 | 0 | 5 | 10 | — | 0 | VRLLES | LGHQIP | | DPCAT | YCRFFNAFCY | |
| A5JUC6_9GALL | agouti | 6 | 6 | 0 | 5 | 10 | — | 0 | VRLLES | LGHQIP | | DPCAT | YCRFFNAFCY | |
| A5JUC7_CATWA | agouti | 6 | 6 | 0 | 5 | 10 | — | 0 | VRLLES | LGHQIP | | DPCAT | YCRFFNAFCY | |
| A5JUC8_CROMA | agouti | 6 | 6 | 0 | 5 | 10 | — | 0 | VRLLES | LGHQIP | | DPCAT | YCRFFNAFCY | |
| A5JUC9_COTJA | agouti | 6 | 6 | 0 | 5 | 10 | — | 0 | VRLLES | LGHQIP | | DPCAT | YCRFFNAFCY | |
| A5JUD0_COTCO | agouti | 6 | 6 | 0 | 5 | 10 | — | 0 | VRLLES | LGHQIP | | DPCAT | YCRFFNAFCY | |
| A5JUD1_CROCS | agouti | 6 | 6 | 0 | 5 | 10 | — | 0 | VRLLES | LGHQIP | | DPCAT | YCRFFNAFCY | |
| A5JUD4_ALECH | agouti | 6 | 6 | 0 | 5 | 10 | — | 0 | VRLLES | LGHQIP | | DPCAT | YCRFFNAFCY | |
| A5JUD5_AFRCO | agouti | 6 | 6 | 0 | 5 | 10 | — | 0 | VRLLES | LGHQIP | | DPCAT | YCRFFNAFCY | |
| A5JUD6_ARGAR | agouti | 6 | 6 | 0 | 5 | 10 | — | 0 | VRLLES | LGHQIP | | DPCAT | YCRFFNAFCY | |
| A5JUD7_ALERU | agouti | 6 | 6 | 0 | 5 | 10 | — | 0 | VRLLES | LGHQIP | | DPCAT | YCRFFNAFCY | |
| A7YMS3_PERMA | agouti | 6 | 6 | 0 | 5 | 10 | — | 0 | VATRDS | KPPAPA | | DPCAS | QCRFFRSVCS | |
| A7YMS6_PERPL | agouti | 6 | 6 | 0 | 5 | 10 | — | 0 | VATRDS | KPPAPA | | DPCAS | QCRFFRSVCS | |
| A7YMS8_PERPL | agouti | 6 | 6 | 0 | 5 | 10 | — | 0 | VATRDS | KPPAPA | | DPCAS | QCRFFRSVCS | |
| A9EDH6_COTJA | agouti | 6 | 6 | 0 | 5 | 10 | — | 0 | VPNFKT | KPHLNS | | NYCAL | KCRIFQTICQ | |
| A9EDI0_COTJA | agouti | 6 | 6 | 0 | 5 | 10 | — | 0 | VPNFKT | KPHLNS | | NYCAL | KCRIFQTICQ | |
| A9JPS5_CAPHI | agouti | 6 | 6 | 0 | 5 | 10 | — | 0 | VATRDS | KPPAPA | | DPCAF | QCRFFRSACS | |
| AGRP_BOVIN | agouti | 6 | 6 | 0 | 5 | 10 | — | 0 | VRLHES | LGHQVP | | DPCAT | YCRFFNAFCY | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| AGRP_HUMAN | agouti | 6 | 6 | 0 | 5 | 10 | — | 2 | VRLHES | LGQQVP | | DPCAT | YCRFFNAFCY | |
| AGRP_MOUSE | agouti | 6 | 6 | 0 | 5 | 10 | — | 0 | VRLHES | LGQQVP | | DPCAT | YCRFFNAFCY | |
| AGRP_PIG | agouti | 6 | 6 | 0 | 5 | 10 | — | 0 | VRLHES | LGHQVP | | DPCAT | YCRFFNAFCY | |
| ASIP_BOVIN | agouti | 6 | 6 | 0 | 5 | 10 | — | 0 | VATRDS | KPPAPA | | DPCAF | QCRFFRSACS | |
| ASIP_CALGE | agouti | 6 | 6 | 0 | 5 | 10 | — | 0 | VSTRGS | KPPAPA | | HPCAS | QCRFFRSACS | |
| ASIP_CALGO | agouti | 6 | 6 | 0 | 5 | 10 | — | 0 | VSTRGS | KPPAPA | | HPCAS | QCRFFRSACS | |
| ASIP_CALJA | agouti | 6 | 6 | 0 | 5 | 10 | — | 0 | VATRNS | KSPAPA | | DPCAS | QCRFFRSACS | |
| ASIP_CANFA | agouti | 6 | 6 | 0 | 5 | 10 | — | 0 | VSTRGS | KPPAPA | | HPCAS | QCRFFRSACT | |
| ASIP_CEBPY | agouti | 6 | 6 | 0 | 5 | 10 | — | 0 | VATRDS | KPPAPA | | DPCAS | QCRFFRSACS | |
| ASIP_CERAE | agouti | 6 | 6 | 0 | 5 | 10 | — | 0 | VATRDS | KPPAPA | | DPCAS | QCRFFRSACS | |
| ASIP_CERMI | agouti | 6 | 6 | 0 | 5 | 10 | — | 0 | VATRNS | KPPAPA | | DPCAS | QCRFFRSACS | |
| ASIP_COLPO | agouti | 6 | 6 | 0 | 5 | 10 | — | 0 | VSTRGS | KPPAPA | | DPCAS | QCRFFRSACS | |
| ASIP_ERYPA | agouti | 6 | 6 | 0 | 5 | 10 | — | 0 | VSTRGS | KPPAPA | | DPCAS | QCRFFRSACS | |
| ASIP_FELCA | agouti | 6 | 6 | 0 | 5 | 10 | — | 0 | VATRDS | KPPAPA | | DPCAS | QCRFFRSACS | |
| ASIP_GORGO | agouti | 6 | 6 | 0 | 5 | 10 | — | 0 | VATRNS | KPPAPA | | DPCAS | QCRFFRSACS | |
| ASIP_HORSE | agouti | 6 | 6 | 0 | 5 | 10 | — | 2 | VATRNS | KPPAPA | | DPCAS | QCRFFRSACS | |
| ASIP_HUMAN | agouti | 6 | 6 | 0 | 5 | 10 | — | 0 | VSTRGS | KPPAPA | | HPCAS | QCRFFRSACS | |
| ASIP_LEOCY | agouti | 6 | 6 | 0 | 5 | 10 | — | 0 | VSTRGS | KPPAPA | | HPCAS | QCRFFRSACS | |
| ASIP_LEORO | agouti | 6 | 6 | 0 | 5 | 10 | — | 0 | VATRDS | KPPAPA | | DPCAS | QCRFFRSACS | |
| ASIP_MACAR | agouti | 6 | 6 | 0 | 5 | 10 | — | 0 | VATRDS | KPPAPA | | DPCAS | QCRFFRSACS | |
| ASIP_MACAS | agouti | 6 | 6 | 0 | 5 | 10 | — | 0 | VATRDS | KPPAPA | | DPCAS | QCRFFRSACS | |
| ASIP_MACCY | agouti | 6 | 6 | 0 | 5 | 10 | — | 0 | VATRDS | KPPAPA | | DPCAS | QCRFFRSACS | |
| ASIP_MACFA | agouti | 6 | 6 | 0 | 5 | 10 | — | 0 | VATRDS | KPPAPA | | DPCAS | QCRFFRSACS | |
| ASIP_MACFU | agouti | 6 | 6 | 0 | 5 | 10 | — | 0 | VATRDS | KPPAPA | | DPCAS | QCRFFRSACS | |
| ASIP_MACHE | agouti | 6 | 6 | 0 | 5 | 10 | — | 0 | VATRDS | KPPAPA | | DPCAF | QCRFFRSACS | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| ASIP_MACMR | agouti | 6 | 6 | 0 | 5 | 10 | — | 0 | VATRDS | KPPAPA | | DPCAS | QCRFFRSACS | |
| ASIP_MACMU | agouti | 6 | 6 | 0 | 5 | 10 | — | 0 | VATRDS | KPPAPA | | DPCAS | QCRFFRSACS | |
| ASIP_MACNE | agouti | 6 | 6 | 0 | 5 | 10 | — | 0 | VATRDS | KPPAPA | | DPCAS | QCRFFRSACS | |
| ASIP_MACNG | agouti | 6 | 6 | 0 | 5 | 10 | — | 0 | VATRDS | KSPAPA | | DPCAS | QCRFFRSACS | |
| ASIP_MACNR | agouti | 6 | 6 | 0 | 5 | 10 | — | 0 | VATRDS | KPPAPA | | DPCAS | QCRFFRSACS | |
| ASIP_MACRA | agouti | 6 | 6 | 0 | 5 | 10 | — | 0 | VATRDS | KPPAPA | | DPCAS | QCRFFRSACS | |
| ASIP_MACSI | agouti | 6 | 6 | 0 | 5 | 10 | — | 0 | VATRDS | KPPAPA | | DPCAS | QCRFFRSACS | |
| ASIP_MACSL | agouti | 6 | 6 | 0 | 5 | 10 | — | 0 | VTTRDS | KPPAPA | | DPCAS | QCRFFRSACS | |
| ASIP_MACSY | agouti | 6 | 6 | 0 | 5 | 10 | — | 0 | VATRDS | KPPAPA | | DPCAS | QCRFFGSACT | |
| ASIP_MOUSE | agouti | 6 | 6 | 0 | 5 | 10 | — | 0 | VATRDS | KPPAPA | | DPCAS | QCRFFRSACS | |
| ASIP_PANPA | agouti | 6 | 6 | 0 | 5 | 10 | — | 0 | VATRNS | KPPAPA | | DPCAS | QCRFFRSACS | |
| ASIP_PANTR | agouti | 6 | 6 | 0 | 5 | 10 | — | 0 | VATRNS | KPPAPA | | DPCAS | QCRFFRSACS | |
| ASIP_PAPAN | agouti | 6 | 6 | 0 | 5 | 10 | — | 0 | VANRDS | KPPALA | | DPCAF | QCRFFRSACS | |
| ASIP_PIG | agouti | 6 | 6 | 0 | 5 | 10 | — | 0 | VATRNS | KPPAPA | | DPCAS | QCRFFRSACS | |
| ASIP_PONPY | agouti | 6 | 6 | 0 | 5 | 10 | — | 0 | VATRDS | KPPAPA | | NPCAS | QCRFFGSACS | |
| ASIP_RAT | agouti | 6 | 6 | 0 | 5 | 10 | — | 0 | VATRYS | KPPAPA | | DPCAS | QCRFFRSACS | |
| ASIP_SEMEN | agouti | 6 | 6 | 0 | 5 | 10 | — | 0 | VATRDS | KPPAPA | | DPCAS | QCRFFRSACT | |
| ASIP_TRAAU | agouti | 6 | 6 | 0 | 5 | 10 | — | 0 | VATRDS | KPPAPA | | DPCAS | QCRFFRSACS | |
| ASIP_TRACR | agouti | 6 | 6 | 0 | 5 | 10 | — | 0 | VATRDS | KPPAPA | | DPCAS | QCRFFRSACS | |
| ASIP_TRAFR | agouti | 6 | 6 | 0 | 5 | 10 | — | 0 | VATRDS | KPPAPA | | DPCAS | QCRFFRSACS | |
| ASIP_TRAOB | agouti | 6 | 6 | 0 | 5 | 10 | — | 0 | VATRNS | KSPAPA | | DPCAS | QCRFFRSACT | |
| ASIP_VULVU | agouti | 6 | 6 | 0 | 5 | 10 | — | 0 | VATRDS | KPPAPV | | DPCAS | QCRFFRSVCT | |
| B0B577_RABIT | agouti | 6 | 6 | 0 | 5 | 10 | — | 0 | VPNFKT | KPHLNS | | NYCAL | KCRIFQTICQ | |
| B0ZDU0_COTJA | agouti | 6 | 6 | 0 | 5 | 10 | — | 0 | VPNFKT | KPHLNS | | NYCAL | KCRIFQTICQ | |
| B0ZDU2_CHICK | agouti | | | | | | | | | | | | | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| B0ZDU3_CHICK | agouti | 6 | 6 | 0 | 5 | 10 | — | 0 | VPNFKT | KPHLNS | | NYCAL | KCRIFQTICQ | |
| B0ZDU4_CHICK | agouti | 6 | 6 | 0 | 5 | 10 | — | 0 | VPNFKT | KPHLNS | | NYCAL | KCRIFQTICQ | |
| Q3UU47_MOUSE | agouti | 6 | 6 | 0 | 5 | 10 | — | 0 | VRLHES | LGQQVP | | DPCAT | YCRFFNAFCY | |
| Q4JNX9_CAPHI | agouti | 6 | 6 | 0 | 5 | 10 | — | 0 | VATRDS | KPPAPA | | DPCAF | QCRFFRSACS | |
| Q4SEW0_TETNG | agouti | 6 | 6 | 0 | 5 | 10 | — | 0 | IPHQQS | LGYPLP | | DPCDT | YCRFFNAICY | |
| Q4SP72_TETNG | agouti | 6 | 5 | 0 | 5 | 10 | — | 0 | SRLKDS | SPYMP | | DPCAS | HCRLFNTICN | |
| Q5CC33_CARAU | agouti | 6 | 6 | 0 | 5 | 10 | — | 0 | VPLWGS | KTPSAA | | DQCAF | HCRLFKTVCY | |
| Q5CC34_CARAU | agouti | 6 | 6 | 0 | 5 | 10 | — | 0 | VPLWGS | KTPSAA | | DQCAF | HCRLFKTVCY | |
| Q5CC35_CARAU | agouti | 6 | 6 | 0 | 5 | 10 | — | 0 | VPLWGS | KTPSAA | | DQCAF | HCRLFKTVCY | |
| Q5IRA5_CANFA | agouti | 6 | 6 | 0 | 5 | 10 | — | 0 | VATRNS | KSPAPA | | DPCAS | QCRFFRSACT | |
| Q68GX9_CANLU | agouti | 6 | 6 | 0 | 5 | 10 | — | 0 | VATRNS | KSPAPA | | DPCAS | QCRFFRSACT | |
| Q68GY0_CANLA | agouti | 6 | 6 | 0 | 5 | 10 | — | 0 | VATRNS | KSPAPA | | DPCAS | QCRFFRSACT | |
| Q6J648_SHEEP | agouti | 6 | 6 | 0 | 5 | 10 | — | 0 | VRLHES | LGHQVP | | DPCAT | YCRFFNAFCY | |
| Q70Q61_CARAU | agouti | 6 | 6 | 0 | 5 | 10 | — | 0 | IPHQQS | LGHHLP | | NPCDT | YCRFFKAFCY | |
| Q70Q62_CARAU | agouti | 6 | 6 | 0 | 5 | 10 | — | 0 | IPHQQS | LGHHLP | | NPCDT | YCRFFKAFCY | |
| Q90WY7_COTJA | agouti | 6 | 6 | 0 | 5 | 10 | — | 0 | VRLLES | LGHQIP | | DPCAT | YCRFFNAFCY | |
| Q9GLM5_PIG | agouti | 6 | 6 | 0 | 5 | 10 | — | 0 | VRLHES | LGHQVP | | DPCAT | YCRFFNAFCY | |
| Q9PWG2_CHICK | agouti | 6 | 6 | 0 | 5 | 10 | — | 0 | VRLLES | LGQQVP | | DLCAT | YCRFFKTCY | |
| Q9QX13_RAT | agouti | 6 | 6 | 0 | 5 | 9 | — | 0 | VRLLES | LGHQIP | | DPCAT | YCRFFNAFCY | |
| Q9W7R0_CHICK | agouti | 6 | 6 | 0 | 5 | 10 | — | 0 | VRLLES | LGHQIP | | DPCAT | YCRFFNAFCY | |
| 1AAL_AMAHP | alpha_amylase | 6 | 6 | 0 | 4 | 7 | — | 3 | IPKWNR | GPKMDGVP | | EPYT | TSDYYGN | |
| ADO1_AGRDO | bug | 6 | 6 | 0 | 4 | 6 | — | 1 | LPRGSK | LGENKQ | | KGTT | MFYANR | |
| IOB1_ISYOB | bug | 6 | 6 | 0 | 4 | 6 | — | 0 | LPRGSK | LGENKQ | | EKTT | MFYANR | |
| PTU1_PEITU | bug | 6 | 6 | 0 | 5 | 6 | — | 1 | LAPGAP | FGTDKP | | NPRAW | SSYANK | |
| A11GB | conoserver_frame-workVIVII | 6 | 8 | 0 | 3 | 3 | — | 0 | QRANFV | DAFHHAAV | | EGV | VLV | |
| ABVIA | conoserver_frame-workVIVII | 6 | 5 | 0 | 3 | 6 | — | 0 | SPPGSY | FGPAA | | SNF | STLSDV | |
| ABVIB | conoserver_frame-workVIVII | 6 | 5 | 0 | 3 | 6 | — | 0 | TPPGGA | GGHAH | | SQS | DILAST | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| ABVIC | conoserver_frame-workVIVII | 6 | 5 | 0 | 3 | 6 | — | 0 | TPPGGA | GGHAH | | SQS | NILAST | |
| ABVID | conoserver_frame-workVIVII | 6 | 5 | 0 | 3 | 6 | — | 0 | TPRHGV | FYSYF | | SKA | NPSSKR | |
| ABVIE | conoserver_frame-workVIVII | 6 | 5 | 0 | 3 | 4 | — | 0 | TPPEVG | LFAYE | | SKI | WRPR | |
| ABVIF | conoserver_frame-workVIVII | 6 | 5 | 0 | 3 | 6 | — | 0 | TPPGGY | YHPDP | | SQV | NFPRKH | |
| ABVIF mutant 1 | conoserver_frame-workVIVII | 6 | 5 | 0 | 3 | 6 | — | 0 | TPPGGY | YHPDP | | SQY | NFPRKH | |
| ABVIG | conoserver_frame-workVIVII | 6 | 5 | 0 | 3 | 6 | — | 0 | TAPGGA | YAAYT | | SNA | NLNTKK | |
| ABVIG mutant 1 | conoserver_frame-workVIVII | 6 | 5 | 0 | 3 | 6 | — | 0 | TAPGGA | YADNT | | SNA | NLNTKK | |
| ABVIH | conoserver_frame-workVIVII | 6 | 5 | 0 | 3 | 6 | — | 0 | TPAGDA | DATTK | | IPF | NLATKK | |
| ABVII | conoserver_frame-workVIVII | 6 | 5 | 0 | 3 | 6 | — | 0 | TPAGDA | DATTE | | ILF | NLATKK | |
| ABVIJ | conoserver_frame-workVIVII | 6 | 5 | 0 | 3 | 6 | — | 0 | TPAGDA | DATTE | | ILF | NLATKE | |
| ABVIK | conoserver_frame-workVIVII | 6 | 5 | 0 | 3 | 6 | — | 0 | TPAGGA | DATTE | | ILF | NLATKK | |
| ABVIL | conoserver_frame-workVIVII | 6 | 5 | 0 | 3 | 6 | — | 0 | TPGGEA | DATTN | | FLT | NLATNK | |
| ABVIM | conoserver_frame-workVIVII | 6 | 5 | 0 | 3 | 4 | — | 0 | LGSGEL | VRDTS | | SMS | TNNI | |
| ABVIN | conoserver_frame-workVIVII | 6 | 5 | 0 | 3 | 4 | — | 0 | LGSREQ | VRDTS | | SMS | TNNI | |
| ABVIO | conoserver_frame-workVIVII | 6 | 5 | 0 | 3 | 4 | — | 0 | LGSREL | VRDTS | | SMS | TNNI | |
| AVIA | conoserver_frame-workVIVII | 6 | 6 | 0 | 3 | 3 | — | 0 | SNAGAF | GIHPGL | | SEI | IVW | |
| Ai6.1 | conoserver_frame-workVIVII | 6 | 6 | 0 | 3 | 4 | — | 0 | KQSGEM | NLLDQN | | EGY | IVLV | |
| Ai6.2 | conoserver_frame-workVIVII | 6 | 6 | 0 | 3 | 4 | — | 0 | TQSGEL | DVIDPD | | NNF | IIFF | |
| Ai6.3 | conoserver_frame-workVIVII | 6 | 5 | 0 | 3 | 3 | — | 0 | YDGGTS | NTGNQ | | SGW | IFL | |
| Am2766 | conoserver_frame-workVIVII | 6 | 6 | 0 | 3 | 3 | — | 1 | KQAGES | DIFSQN | | VGT | AFI | |
| Ar6.1 | conoserver_frame-workVIVII | 6 | 6 | 0 | 3 | 3 | — | 0 | LEKGVL | DPSAGN | | SGE | VLV | |
| Ar6.10 | conoserver_frame-workVIVII | 6 | 4 | 0 | 4 | 7 | — | 0 | ADLGEE | YTRF | | PGLR | KDLQVPT | |
| Ar6.11 | conoserver_frame-workVIVII | 6 | 4 | 0 | 4 | 8 | — | 0 | GEQGEG | ATRP | | AGLS | VGSRPGGL | |
| Ar6.12 | conoserver_frame-workVIVII | 6 | 4 | 0 | 4 | 6 | — | 0 | GNLGES | SAHR | | PGLM | MGEASI | |
| Ar6.13 | conoserver_frame-workVIVII | 6 | 6 | 0 | 3 | 8 | — | 0 | SNFGSD | IPATHD | | SGE | FGFEDMGL | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Ar6.14 | conoserver_framework VI VII | 6 | 5 | 0 | 3 | 6 | — | 0 | TPVGGY | SRHHH | | SNH | IKSIGR | |
| Ar6.15 | conoserver_framework VI VII | 6 | 5 | 0 | 3 | 6 | — | 0 | TPVGGY | FDHHH | | SNH | IKSIGR | |
| Ar6.16 | conoserver_framework VI VII | 6 | 5 | 0 | 3 | 6 | — | 0 | TPVGGY | SRHYH | | SNH | IKSIGR | |
| Ar6.17 | conoserver_framework VI VII | 6 | 5 | 0 | 3 | 6 | — | 0 | TPVGGS | SRHYH | | SLY | NKNIGQ | |
| Ar6.18 | conoserver_framework VI VII | 6 | 5 | 0 | 3 | 6 | — | 0 | SPNGGS | SRHYH | | SLW | NKDSGV | |
| Ar6.19 | conoserver_framework VI VII | 6 | 6 | 0 | 3 | 8 | — | 0 | TVDSDF | DPDNHD | | SGR | IDEGGSGV | |
| Ar6.2 | conoserver_framework VI VII | 6 | 8 | 0 | 3 | 3 | — | 0 | VDGGTF | GFPKIGGP | | SGW | IFV | |
| Ar6.20 | conoserver_framework VI VII | 3 | 6 | 0 | 8 | 3 | — | 0 | EES | EEEEKT | | GEXDGEPV | ARF | |
| Ar6.21 | conoserver_framework VI VII | 3 | 6 | 0 | 8 | 3 | — | 0 | EEY | EDEEKT | | GLEDGEPV | ATT | |
| Ar6.22 | conoserver_framework VI VII | 3 | 6 | 0 | 8 | 3 | — | 0 | EEY | EEEEKT | | GEEDGEPV | AEF | |
| Ar6.24 | conoserver_framework VI VII | 3 | 6 | 0 | 8 | 3 | — | 0 | EEY | EDEEKT | | GEEDGEPV | ARF | |
| Ar6.25 | conoserver_framework VI VII | 3 | 6 | 0 | 7 | 3 | — | 0 | EES | EEEEKH | | HENNGVYT | LRY | |
| Ar6.26 | conoserver_framework VI VII | 3 | 6 | 0 | 7 | 3 | — | 0 | EEN | EEEEKH | | NTNNGPS | APQ | |
| Ar6.27 | conoserver_framework VI VII | 3 | 6 | 0 | 7 | 3 | — | 0 | EES | EDEEKH | | NTNNGPS | APQ | |
| Ar6.28 | conoserver_framework VI VII | 3 | 6 | 0 | 8 | 3 | — | 0 | EES | EEEEKT | | GLENGQPF | SRI | |
| Ar6.3 | conoserver_framework VI VII | 6 | 9 | 0 | 3 | 3 | — | 0 | RALGEY | GLPYVHNSR | | SQL | GFI | |
| Ar6.4 | conoserver_framework VI VII | 6 | 6 | 0 | 2 | 4 | — | 0 | LPPLSL | TMADDE | | HD | ILFL | |
| Ar6.5 | conoserver_framework VI VII | 6 | 6 | 0 | 2 | 4 | — | 0 | LPPLSL | TMDDDE | | DD | ILFL | |
| Ar6.6 | conoserver_framework VI VII | 6 | 6 | 0 | 2 | 4 | — | 0 | LPPLSL | TMDDDE | | DD | XLFL | |
| Ar6.7 | conoserver_framework VI VII | 6 | 6 | 0 | 2 | 4 | — | 0 | LPPLHW | NMVDDE | | HF | VLLA | |
| Ar6.8 | conoserver_framework VI VII | 6 | 6 | 0 | 2 | 4 | — | 0 | LPPLSL | NMADDD | | ND | VLFL | |
| Ar6.9 | conoserver_framework VI VII | 6 | 4 | 0 | 4 | 7 | — | 0 | ADLGEE | HTRF | | PGLR | EDLQVPT | |
| AsVIIA | conoserver_framework VI VII | 6 | 5 | 0 | 3 | 10 | — | 0 | KQKGEG | SLDVE | | SSS | KPCGPLFDFD | |
| At6.1 | conoserver_framework VI VII | 6 | 5 | 0 | 3 | 5 | — | 0 | TPPGTY | VGPST | | SDV | SMSNV | |
| At6.2 | conoserver_framework VI VII | 6 | 5 | 0 | 3 | 6 | — | 0 | TPPSGY | YHPYY | | SRA | NLTRKR | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| At6.3 | conoserver_frame-workVIVII | 6 | 5 | 0 | 3 | 6 | — | 0 | THAYEA | DATTN | | YMT | NLPTRK | |
| At6.4 | conoserver_frame-workVIVII | 6 | 5 | 0 | 3 | 6 | — | 0 | TSPDGA | NTPPQ | | SKY | ISISTT | |
| At6.5 | conoserver_frame-workVIVII | 6 | 5 | 0 | 3 | 6 | — | 0 | THPGGA | AGHHH | | SQS | NTAANS | |
| At6.6 | conoserver_frame-workVIVII | 6 | 5 | 0 | 3 | 6 | — | 0 | TPPGGA | YYHSQ | | GDF | QRYINS | |
| At6.7 | conoserver_frame-workVIVII | 6 | 5 | 0 | 3 | 6 | — | 0 | TPPEGA | NHPSH | | EDF | DRGRNR | |
| At6.8 | conoserver_frame-workVIVII | 6 | 5 | 0 | 3 | 6 | — | 0 | TPPEGY | TYHRD | | DLY | NKTTNV | |
| Au6.1 | conoserver_frame-workVIVII | 6 | 6 | 0 | 3 | 3 | — | 0 | KAENEL | NIFIQN | | DGT | LLI | |
| Au6.2 | conoserver_frame-workVIVII | 6 | 6 | 0 | 2 | 4 | — | 0 | LEFGEL | NFFFPT | | GY | VLLV | |
| Au6.3 | conoserver_frame-workVIVII | 6 | 8 | 0 | 3 | 3 | — | 0 | EPPGNF | GMIKIGPP | | SGW | FFA | |
| BVIA | conoserver_frame-workVIVII | 6 | 6 | 0 | 3 | 3 | — | 0 | SAPGAF | LIRPGL | | SEF | FFA | |
| BeB42 | conoserver_frame-workVIVII | 6 | 5 | 0 | 3 | 6 | — | 0 | NDPGGS | TRHYH | | QLY | NKQESV | |
| BeB54 | conoserver_frame-workVIVII | 6 | 5 | 0 | 3 | 4 | — | 0 | KGWSVY | SWDWE | | SGE | TRYY | |
| Bromosleeper peptide | conoserver_frame-workVIVII | 3 | 6 | 0 | 7 | 3 | — | 0 | EET | NVTFKT | | GPPGDWQ | VEA | |
| C6.1 | conoserver_frame-workVIVII | 6 | 6 | 0 | 3 | 3 | — | 0 | SNAGAF | GIHPGL | | SEL | LGW | |
| C6.2 | conoserver_frame-workVIVII | 6 | 6 | 0 | 3 | 4 | — | 0 | KGKGAS | RRTSYD | | TGS | RSGR | |
| C6.3 | conoserver_frame-workVIVII | 6 | 6 | 0 | 3 | 4 | — | 0 | KGKGAS | RRTSYG | | TGS | RSGR | |
| C6.4 | conoserver_frame-workVIVII | 6 | 6 | 0 | 3 | 4 | — | 0 | KSTGAS | RRTPYD | | TGS | RSGR | |
| C6.5 | conoserver_frame-workVIVII | 6 | 6 | 0 | 3 | 4 | — | 0 | QGRGAS | RKTMYN | | SGS | RSGR | |
| C6.6 | conoserver_frame-workVIVII | 6 | 6 | 0 | 3 | 4 | — | 0 | QGRGAS | RKTSYD | | TGS | RSGR | |
| C6.7 | conoserver_frame-workVIVII | 6 | 6 | 0 | 3 | 4 | — | 0 | KSTGAS | RRTSYD | | TGS | DRGR | |
| C6.8 | conoserver_frame-workVIVII | 6 | 6 | 0 | 3 | 4 | — | 0 | QGRGAS | RRTSYD | | TGS | RSGR | |
| CVIA | conoserver_frame-workVIVII | 6 | 6 | 0 | 3 | 4 | — | 0 | KSTGAS | RRTSYD | | TGS | RSGR | |
| CVIB | conoserver_frame-workVIVII | 6 | 6 | 0 | 3 | 4 | — | 0 | KGKGAS | RKTMYD | | RGS | RSGR | |
| CVIC | conoserver_frame-workVIVII | 6 | 6 | 0 | 3 | 5 | — | 0 | KGKGQS | SKLMYD | | TGS | SRRGK | |
| CVID | conoserver_frame-workVIVII | 6 | 6 | 0 | 3 | 8 | — | 0 | KSKGAK | SKLMYD | | SGS | SGTVGR | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| CVIE | conoserver_frame-workVIVII | 6 | 6 | 0 | 3 | 3 | — | 0 | SNAGAF | GIHPGL | | SEL | LVW | |
| Ca6.1 | conoserver_frame-workVIVII | 6 | 6 | 0 | 3 | 3 | — | 0 | VDPGEF | GPGFGD | | TGF | LLV | |
| CaFr179 | conoserver_frame-workVIVII | 3 | 6 | 0 | 7 | 3 | — | 0 | EED | EDEEKH | | NTNNGPS | ARL | |
| CaHr91 | conoserver_frame-workVIVII | 6 | 6 | 0 | 4 | 8 | — | 0 | REQSQG | TNTSPP | | SGLR | SGQSQGGV | |
| Cn6.1 | conoserver_frame-workVIVII | 6 | 6 | 0 | 3 | 3 | — | 0 | YNAGTF | GIRPGL | | SEF | FLW | |
| CnVIA | conoserver_frame-workVIVII | 6 | 6 | 0 | 3 | 4 | — | 0 | YSTGTF | GINGGL | | SNL | LFFV | |
| CnVIIA | conoserver_frame-workVIVII | 6 | 6 | 0 | 3 | 6 | — | 0 | KGKGAP | TRLMYD | | HGS | SSSKGR | |
| Co6.1 | conoserver_frame-workVIVII | 6 | 5 | 0 | 3 | 6 | — | 0 | TPPGSH | TGHSD | | SDF | STMSDV | |
| Co6.2 | conoserver_frame-workVIVII | 6 | 5 | 0 | 3 | 6 | — | 0 | TPRNGV | FYSYF | | SRA | NPSTKR | |
| Co6.3 | conoserver_frame-workVIVII | 6 | 5 | 0 | 3 | 6 | — | 0 | TSPGGA | YSAST | | SKA | NLTTKR | |
| Co6.4 | conoserver_frame-workVIVII | 6 | 5 | 0 | 3 | 6 | — | 0 | MHPEGG | RFSYE | | SKI | YTPSFT | |
| Co6.5 | conoserver_frame-workVIVII | 6 | 5 | 0 | 3 | 6 | — | 0 | TPAGKA | DATAT | | VLF | NLVTNK | |
| Co6.6 | conoserver_frame-workVIVII | 6 | 5 | 0 | 3 | 6 | — | 0 | TDPGGA | GNPGH | | SKF | ITTSST | |
| Co6.7 | conoserver_frame-workVIVII | 6 | 5 | 0 | 3 | 5 | — | 0 | RLPGDL | AGDAS | | EHS | NIVHT | |
| Conotoxin-1 | conoserver_frame-workVIVII | 6 | 5 | 0 | 3 | 8 | — | 0 | DEEGTG | SSDSE | | SGR | TPEGLFEF | |
| Conotoxin-10 | conoserver_frame-workVIVII | 6 | 4 | 0 | 4 | 9 | — | 0 | GGQGEG | YTQP | | PGLR | RGGGTGGG A | |
| Conotoxin-12 | conoserver_frame-workVIVII | 6 | 4 | 0 | 4 | 9 | — | 0 | GGQGKG | YTQP | | PGLR | RGGGTGGG V | |
| Conotoxin-15 | conoserver_frame-workVIVII | 6 | 5 | 0 | 2 | 4 | — | 0 | RPSGSP | GVTSI | | GR | SRGK | |
| Conotoxin-2 | conoserver_frame-workVIVII | 6 | 4 | 0 | 4 | 9 | — | 0 | GGQGEG | YTQP | | PGLR | RGGGTGGG V | |
| Conotoxin-2/7 | conoserver_frame-workVIVII | 6 | 9 | 0 | 3 | 3 | — | 0 | IADDMP | GFGLFGGPL | | SGW | LFV | |
| Conotoxin-3 | conoserver_frame-workVIVII | 6 | 5 | 0 | 2 | 6 | — | 0 | ESYGKP | GIYND | | NA | DPAKKT | |
| Conotoxin-5 | conoserver_frame-workVIVII | 6 | 7 | 0 | 3 | 3 | — | 0 | REGGEF | GTLYEER | | SGW | FFV | |
| Conotoxin-6 | conoserver_frame-workVIVII | 6 | 7 | 0 | 3 | 3 | — | 0 | REGGEF | GTLYEER | | SGW | FFV | |
| Conotoxin-8 | conoserver_frame-workVIVII | 6 | 4 | 0 | 4 | 9 | — | 0 | GGQGEG | YTQP | | PGLR | RGGGTGGG S | |
| Conotoxin-9 | conoserver_frame-workVIVII | 6 | 6 | 0 | 3 | 3 | — | 0 | SSGGTF | GIHPGL | | SEF | FLW | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Cv conotoxin | conoserver_frame-workVIVII | 6 | 8 | 0 | 3 | 3 | — | 0 | IAVGQL | VFWNIGRP | | SGL | VFA | |
| Da6.1 | conoserver_frame-workVIVII | 6 | 6 | 0 | 4 | 4 | — | 0 | RKEHQL | DLIFQN | | RGWY | LLRP | |
| Da6.2 | conoserver_frame-workVIVII | 6 | 6 | 0 | 4 | 4 | — | 0 | SEEGQL | DPLSQN | | RGWH | VLVS | |
| Da6.3 | conoserver_frame-workVIVII | 6 | 6 | 0 | 2 | 4 | — | 0 | LGGGEV | DIFFPQ | | GY | ILLF | |
| Da6.4 | conoserver_frame-workVIVII | 6 | 6 | 0 | 3 | 4 | — | 0 | AQSSEL | DALDSD | | SGV | MVFF | |
| Da6.5 | conoserver_frame-workVIVII | 6 | 5 | 0 | 3 | 3 | — | 0 | YDGGTG | DSGNQ | | SGW | IFV | |
| Da6.6 | conoserver_frame-workVIVII | 6 | 9 | 0 | 4 | 4 | — | 0 | QEKWDY | PVPFLGSRY | | DGFI | PSFF | |
| Da6.7 | conoserver_frame-workVIVII | 6 | 9 | 0 | 4 | 4 | — | 0 | QGEWEF | IVPVLGFVY | | PWLI | GPFV | |
| De7a | conoserver_frame-workVIVII | 6 | 7 | 0 | 3 | 4 | — | 0 | IPGGEN | DVFRPYR | | SGY | ILLL | |
| DeVIIA | conoserver_frame-workVIVII | 6 | 7 | 0 | 3 | 4 | — | 0 | KPKNNL | AITEMAE | | SGF | LIYR | |
| Di6.1 | conoserver_frame-workVIVII | 6 | 6 | 0 | 2 | 4 | — | 0 | LGFGEA | LMLYSD | | SY | VGAV | |
| Di6.2 | conoserver_frame-workVIVII | 6 | 6 | 0 | 3 | 4 | — | 0 | YLLVHF | GINGGL | | SNL | LFFV | |
| Di6.3 | conoserver_frame-workVIVII | 6 | 5 | 0 | 3 | 6 | — | 0 | NEAQEH | TQNPD | | SES | NKFVGR | |
| E6.1 | conoserver_frame-workVIVII | 6 | 6 | 0 | 3 | 4 | — | 0 | KPKGRK | FPHQKD | | NKT | TRSK | |
| E6.2 | conoserver_frame-workVIVII | 6 | 5 | 0 | 2 | 6 | — | 0 | TPHGGS | GLVST | | GR | SVPRNK | |
| EVIA | conoserver_frame-workVIVII | 6 | 9 | 0 | 3 | 3 | — | 2 | IKXYGF | SLPILKNGL | | SGA | VGV | |
| EVIB | conoserver_frame-workVIVII | 6 | 6 | 0 | 3 | 4 | — | 0 | YPPGTF | GIKPGL | | SEL | LPAV | |
| Eb6.1 | conoserver_frame-workVIVII | 6 | 5 | 0 | 3 | 6 | — | 0 | THSGGA | NSHDQ | | NAF | DTATRT | |
| Eb6.10 | conoserver_frame-workVIVII | 6 | 5 | 0 | 3 | 6 | — | 0 | TRSGGA | NSHTQ | | DDF | DTATRT | |
| Eb6.11 | conoserver_frame-workVIVII | 6 | 5 | 0 | 3 | 6 | — | 0 | TRSGGA | NSHTQ | | NAF | DTATRT | |
| Eb6.12 | conoserver_frame-workVIVII | 6 | 5 | 0 | 3 | 6 | — | 0 | TRSGGA | NSHTQ | | DDF | STATST | |
| Eb6.13 | conoserver_frame-workVIVII | 6 | 5 | 0 | 3 | 6 | — | 0 | TQTNGA | YHRDT | | SKS | NLTINR | |
| Eb6.2 | conoserver_frame-workVIVII | 6 | 5 | 0 | 3 | 6 | — | 0 | AHSGGA | NSHDQ | | NAF | DTATRT | |
| Eb6.3 | conoserver_frame-workVIVII | 6 | 5 | 0 | 3 | 6 | — | 0 | THSGGA | NSHDQ | | NAF | DTATRA | |
| Eb6.4 | conoserver_frame-workVIVII | 6 | 5 | 0 | 3 | 6 | — | 0 | THSGGA | NSHDQ | | NTF | DTATRT | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Eb6.5 | conoserver_frame-workVIVII | 6 | 5 | 0 | 3 | 6 | — | 0 | TRSGGA | NSHDQ | | NAF | DTATRT | |
| Eb6.6 | conoserver_frame-workVIVII | 6 | 5 | 0 | 3 | 6 | — | 0 | THSGGA | NSHNQ | | NAF | DTATRT | |
| Eb6.8 | conoserver_frame-workVIVII | 6 | 5 | 0 | 3 | 6 | — | 0 | THSGGA | NSHTQ | | DDF | STATST | |
| Eb6.9 | conoserver_frame-workVIVII | 6 | 5 | 0 | 3 | 6 | — | 0 | TRSGGA | NSHTQ | | DDF | STATST | |
| Ep6.1 | conoserver_frame-workVIVII | 6 | 6 | 0 | 2 | 4 | — | 0 | LGFGEA | LMLYSD | | SY | VALV | |
| G6.1 | conoserver_frame-workVIVII | 6 | 8 | 0 | 3 | 3 | — | 0 | EPPGDF | GFFKIGPP | | SGW | FLW | |
| GVIA | conoserver_frame-workVIVII | 6 | 6 | 0 | 2 | 6 | — | 3 | KSPGSS | SPTSYN | | RS | NPYTKR | |
| GVIIA | conoserver_frame-workVIVII | 6 | 6 | 0 | 2 | 6 | — | 0 | KSPGTP | SRGMRD | | TS | LLYSNK | |
| GVIIB | conoserver_frame-workVIVII | 6 | 6 | 0 | 2 | 6 | — | 0 | KSPGTP | SRGMRD | | TS | LSYSNK | |
| Ge6.1 | conoserver_frame-workVIVII | 6 | 8 | 0 | 3 | 3 | — | 0 | LDPGYF | GTPFLGAY | | GGI | LIV | |
| Gla(1)-TxVI | conoserver_frame-workVIVII | 6 | 5 | 0 | 3 | 3 | — | 0 | KDGLTT | LAPSE | | SED | EGS | |
| Gla(2)-TxVI/A | conoserver_frame-workVIVII | 6 | 5 | 0 | 3 | 3 | — | 0 | SDDWQY | ESPTD | | SWD | DW | |
| Gla(2)-TxVI/B | conoserver_frame-workVIVII | 6 | 5 | 0 | 3 | 3 | — | 0 | SDDWQY | ESPTD | | SWD | DW | |
| Gla(3)-TxVI | conoserver_frame-workVIVII | 6 | 5 | 0 | 3 | 4 | — | 0 | PDYTEP | SHAHE | | SWN | YNGH | |
| Gm6.1 | conoserver_frame-workVIVII | 6 | 8 | 0 | 3 | 3 | — | 0 | RLGAES | DVISQN | | QGT | VFF | |
| Gm6.2 | conoserver_frame-workVIVII | 6 | 6 | 0 | 3 | 3 | — | 0 | KQADES | NVFSLD | | TGL | LGF | |
| Gm6.3 | conoserver_frame-workVIVII | 6 | 6 | 0 | 3 | 3 | — | 0 | VPYEGP | NWLTQN | | DEL | VFF | |
| Gm6.4 | conoserver_frame-workVIVII | 6 | 5 | 0 | 3 | 3 | — | 0 | YDGGTG | DSGNQ | | SGW | IFA | |
| Gm6.5 | conoserver_frame-workVIVII | 6 | 9 | 0 | 4 | 4 | — | 0 | QALWDY | PVPLLSSGD | | YGLI | GPFV | |
| GmVIA | conoserver_frame-workVIVII | 6 | 6 | 0 | 4 | 3 | — | 0 | RKEGQL | DPIFQN | | RGWN | VLF | |
| Im6.1 | conoserver_frame-workVIVII | 4 | 5 | 0 | 5 | 8 | — | 0 | DPYY | NDGKV | | PEYPT | GDSTGKLI | |
| J6.1 | conoserver_frame-workVIVII | 6 | 5 | 0 | 3 | 6 | — | 0 | TRPGGA | YYDSH | | RHV | HEVFNT | |
| J6.2 | conoserver_frame-workVIVII | 6 | 5 | 0 | 3 | 6 | — | 0 | TPPGGA | NIHPH | | EEF | DMANNR | |
| King-Kong 1 | conoserver_frame-workVIVII | 6 | 6 | 0 | 3 | 4 | — | 0 | IEQFDP | EMIRHT | | VGV | FLMA | |
| King-Kong 2 | conoserver_frame-workVIVII | 6 | 6 | 0 | 3 | 4 | — | 0 | APFLHP | TFFFPN | | NSY | VQFI | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| LVVICa | conoserver_frame-workVIVII | 6 | 5 | 0 | 3 | 6 | — | 0 | TPRNGF | RYHSD | | SNF | HTWAIM | |
| LeD51 | conoserver_frame-workVIVII | 6 | 5 | 0 | 3 | 3 | — | 0 | KDGLTT | LAPSE | | SGN | EQN | |
| LiC42 | conoserver_frame-workVIVII | 6 | 4 | 0 | 4 | 8 | — | 0 | GHSGAG | YTRP | | PGLH | SGGHAGGL | |
| LiC53 | conoserver_frame-workVIVII | 6 | 5 | 0 | 3 | 4 | — | 0 | TAPSGY | DYPEE | | EVE | GRHY | |
| LiCr173 | conoserver_frame-workVIVII | 3 | 6 | 0 | 8 | 3 | — | 0 | NEY | EERDRN | | GKANGEPR | ARM | |
| LiCr95 | conoserver_frame-workVIVII | 6 | 6 | 0 | 3 | 8 | — | 0 | DPPGDS | SRWYNH | | SKL | TSRNSGPT | |
| Lp6.1 | conoserver_frame-workVIVII | 6 | 9 | 0 | 3 | 3 | — | 0 | VELGEI | ATGFFLDEE | | TGS | HVF | |
| LI7b | conoserver_frame-workVIVII | 6 | 5 | 0 | 3 | 3 | — | 0 | TDWLGS | SSPSE | | YDN | ETY | |
| LtVIA | conoserver_frame-workVIVII | 6 | 4 | 0 | 4 | 7 | — | 0 | AYISEP | DILP | | PGLK | NEDFVPI | |
| LtVIB | conoserver_frame-workVIVII | 6 | 5 | 0 | 3 | 6 | — | 0 | SSPDES | TYHYN | | QLY | NKEENV | |
| LtVIC | conoserver_frame-workVIVII | 6 | 5 | 0 | 2 | 6 | — | 0 | KVAGSP | GLVSE | | GT | NVLRNR | |
| LtVID | conoserver_frame-workVIVII | 6 | 6 | 0 | 3 | 8 | — | 0 | TDEGGD | DPGNHN | | RGS | LVLQHKAV | |
| LtVIE | conoserver_frame-workVIVII | 6 | 6 | 0 | 3 | 8 | — | 0 | TDEGGD | DPGNHN | | RGS | LVLQHKAV | |
| LtVIIA | conoserver_frame-workVIVII | 6 | 5 | 0 | 3 | 4 | — | 0 | LGWSNY | TSHSI | | SGE | ILSY | |
| Lv6.1 | conoserver_frame-workVIVII | 6 | 6 | 0 | 3 | 4 | — | 0 | PNTGEL | DWEQN | | YTY | FIVV | |
| LvVIA 1 | conoserver_frame-workVIVII | 6 | 5 | 0 | 4 | 6 | — | 0 | SPAGEV | TSKSP | | TGFL | SHIGGM | |
| LvVIA 2 | conoserver_frame-workVIVII | 6 | 5 | 0 | 4 | 6 | — | 0 | SPAGEV | TSKSP | | TGFL | THIGGM | |
| LvVIA 3 | conoserver_frame-workVIVII | 6 | 5 | 0 | 4 | 6 | — | 0 | SPGGEV | TSKSP | | TGFL | SHIGGM | |
| LvVIB 1 | conoserver_frame-workVIVII | 6 | 5 | 0 | 4 | 6 | — | 0 | SPGGEV | TRHSP | | TGFL | NHIGGM | |
| LvVIB 2 | conoserver_frame-workVIVII | 6 | 5 | 0 | 4 | 6 | — | 0 | SPGGEV | TRHSP | | TGFL | NHIGGM | |
| LvVICb | conoserver_frame-workVIVII | 6 | 5 | 0 | 3 | 6 | — | 0 | TPRNGF | RYHSH | | SNF | HTWAIM | |
| LvVID | conoserver_frame-workVIVII | 6 | 5 | 0 | 3 | 6 | — | 0 | TPRNGA | GYHSH | | SNF | HTWANV | |
| M1 | conoserver_frame-workVIVII | 6 | 5 | 0 | 3 | 6 | — | 0 | TPSGGA | YVAST | | SNA | NLNSNK | |
| M12 | conoserver_frame-workVIVII | 6 | 5 | 0 | 3 | 6 | — | 0 | TPRHGV | FYSYF | | SKA | NPSSKR | |
| M15 | conoserver_frame-workVIVII | 6 | 5 | 0 | 3 | 6 | — | 0 | TPPGGS | GGHAH | | SKS | NIMAST | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| M19 | conoserver_framework VI VII | 6 | 5 | 0 | 3 | 4 | — | 0 | LGSGEQ | VRDTS | | SMS | TNNI | |
| M23 | conoserver_framework VI VII | 6 | 5 | 0 | 3 | 6 | — | 0 | SPPGSY | FGPAA | | SNF | STMSDV | |
| M25 | conoserver_framework VI VII | 6 | 5 | 0 | 3 | 4 | — | 0 | TPPEGG | LSSYE | | SKI | WRPR | |
| M26 | conoserver_framework VI VII | 6 | 5 | 0 | 3 | 6 | — | 0 | TPAGDA | DATTN | | ILF | NLATKK | |
| M6.1 | conoserver_framework VI VII | 6 | 6 | 0 | 3 | 3 | — | 0 | KQADEP | DVFSLE | | TGI | LGF | |
| M6.2 | conoserver_framework VI VII | 6 | 6 | 0 | 3 | 4 | — | 0 | YNAGTF | GIKPGL | | SAI | LSFV | |
| MVIA | conoserver_framework VI VII | 6 | 6 | 0 | 3 | 3 | — | 0 | YNAGTF | GIRPGL | | SEF | FLW | |
| MVIB | conoserver_framework VI VII | 6 | 6 | 0 | 3 | 3 | — | 0 | YNAGSF | GIHPGL | | SEF | ILW | |
| MVIC | conoserver_framework VI VII | 6 | 6 | 0 | 3 | 4 | — | 0 | YPPGTF | GIKPGL | | SAI | LSFV | |
| MVID | conoserver_framework VI VII | 6 | 6 | 0 | 3 | 4 | — | 0 | YNAGTF | GIKPGL | | SAI | LSFV | |
| MVIIA | conoserver_framework VI VII | 6 | 6 | 0 | 3 | 4 | — | 5 | KGKGAK | SRLMYD | | TGS | RSGK | |
| MVIIB | conoserver_framework VI VII | 6 | 6 | 0 | 3 | 4 | — | 0 | KGKGAS | HRTSYD | | TGS | NRGK | |
| MVIIC | conoserver_framework VI VII | 6 | 6 | 0 | 3 | 5 | — | 2 | KGKGAP | RKTMYD | | SGS | GRRGK | |
| MVIID | conoserver_framework VI VII | 6 | 6 | 0 | 3 | 4 | — | 0 | QGRGAS | RKTMYN | | SGS | NRGR | |
| MaI51 | conoserver_framework VI VII | 6 | 5 | 0 | 3 | 3 | — | 0 | EDVWMP | TSNWE | | SLD | EMY | |
| MaIr137 | conoserver_framework VI VII | 6 | 8 | 0 | 3 | 3 | — | 0 | EPPGDF | GFFKIGPP | | SGW | FLW | |
| MaIr193 | conoserver_framework VI VII | 6 | 8 | 0 | 3 | 3 | — | 0 | RPPGMV | GFPKPGPY | | SGW | FAV | |
| MaIr332 | conoserver_framework VI VII | 6 | 6 | 0 | 3 | 4 | — | 0 | LDGGEI | GILFPS | | SGW | IVLV | |
| MaIr34 | conoserver_framework VI VII | 6 | 9 | 0 | 3 | 3 | — | 0 | LEADYY | VLPFVGNGM | | SGI | VFV | |
| MaIr94 | conoserver_framework VI VII | 6 | 8 | 0 | 3 | 10 | — | 0 | LESGSL | EAGYGHSS | | SGA | LDYGGLGVGA | |
| MgJ42 | conoserver_framework VI VII | 6 | 5 | 0 | 3 | 6 | — | 0 | NNRGGG | SQHPH | | SGT | NKITFGV | |
| MgJr112 | conoserver_framework VI VII | 6 | 5 | 0 | 4 | 4 | — | 0 | DPKWTI | NNDAE | | FPYS | ENSN | |
| MgJr93 | conoserver_framework VI VII | 6 | 5 | 0 | 3 | 6 | — | 0 | NNRGGG | SQHPH | | SGT | NKIFGV | |
| MgJr94 | conoserver_framework VI VII | 6 | 5 | 0 | 3 | 7 | — | 0 | KGKGAG | DYSHE | | SRQ | TGRIFQT | |
| MiEr92 | conoserver_framework VI VII | 6 | 6 | 0 | 4 | 8 | — | 0 | KHQNDS | AEEGEE | | SDLR | MTSGAGAI | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| MiEr93 | conoserver_frame-workVIVII | 6 | 5 | 0 | 3 | 6 | — | 0 | NDRGGG | SQHPH | | GGT | NKLIGV | |
| MiEr95 | conoserver_frame-workVIVII | 6 | 5 | 0 | 4 | 8 | — | 0 | REKGQG | TNTAL | | PGLE | EGQSQGGL | |
| MiK41 | conoserver_frame-workVIVII | 6 | 5 | 0 | 3 | 6 | — | 0 | RSSGRY | RSPYD | | RRY | RRITDA | |
| MiK42 | conoserver_frame-workVIVII | 6 | 6 | 0 | 2 | 9 | — | 0 | DAPNAP | EKFDND | | DA | MLREKQQPI | |
| MI6.1 | conoserver_frame-workVIVII | 6 | 5 | 0 | 3 | 6 | — | 0 | TPPGSD | NGHSD | | SNV | STMSYV | |
| MI6.2 | conoserver_frame-workVIVII | 6 | 5 | 0 | 3 | 6 | — | 0 | TPRNGY | YYRYF | | SRA | NLTIKR | |
| MI6.3 | conoserver_frame-workVIVII | 6 | 5 | 0 | 3 | 6 | — | 0 | TPSGGA | YYDYF | | SMT | NFNSKS | |
| MI6.4 | conoserver_frame-workVIVII | 6 | 6 | 0 | 2 | 8 | — | 0 | ADGGDL | DPSSDN | | SE | IDEGGSGV | |
| Mr6.1 | conoserver_frame-workVIVII | 6 | 6 | 0 | 3 | 4 | — | 0 | LDAGEM | DLFNSK | | SGW | IILF | |
| Mr6.2 | conoserver_frame-workVIVII | 6 | 6 | 0 | 3 | 4 | — | 0 | PNTGEL | DVVEQN | | YTY | FIVV | |
| Mr6.3 | conoserver_frame-workVIVII | 6 | 6 | 0 | 3 | 4 | — | 0 | PNTGEL | DVVEQN | | YTY | FIVV | |
| MrVIA | conoserver_frame-workVIVII | 6 | 9 | 0 | 4 | 4 | — | 0 | RKKWEY | IVPIIGFIY | | PGLI | GPFV | |
| MrVIB | conoserver_frame-workVIVII | 6 | 9 | 0 | 4 | 4 | — | 1 | SKKWEY | IVPILGFVY | | PGLI | GPFV | |
| NgVIA | conoserver_frame-workVIVII | 6 | 6 | 0 | 3 | 4 | — | 0 | FSPGTF | GIKPGL | | SVR | FSLF | |
| Om6.1 | conoserver_frame-workVIVII | 6 | 6 | 0 | 4 | 4 | — | 0 | VPHEGP | NWLTQN | | SGYN | IIFF | |
| Om6.2 | conoserver_frame-workVIVII | 6 | 6 | 0 | 3 | 3 | — | 0 | LAEHET | NIFTQN | | EGV | IFI | |
| Om6.3 | conoserver_frame-workVIVII | 6 | 6 | 0 | 3 | 4 | — | 0 | IPHFDP | DPIRHT | | FGL | LLLA | |
| Om6.4 | conoserver_frame-workVIVII | 6 | 6 | 0 | 2 | 4 | — | 0 | LGFGEA | LILYSD | | GY | VGAI | |
| Om6.5 | conoserver_frame-workVIVII | 6 | 8 | 0 | 3 | 3 | — | 0 | EPPGNF | GMIKIGPP | | SGW | FFA | |
| Om6.6 | conoserver_frame-workVIVII | 6 | 9 | 0 | 4 | 4 | — | 0 | QRRWDF | PGSLVGVIT | | GGLI | FLFF | |
| P2a | conoserver_frame-workVIVII | 6 | 6 | 0 | 3 | 4 | — | 0 | KTPGRK | FPHQKD | | GRA | IITI | |
| P2b | conoserver_frame-workVIVII | 6 | 6 | 0 | 3 | 4 | — | 0 | KKSGRK | FPHQKD | | GRA | IITI | |
| P2c | conoserver_frame-workVIVII | 6 | 6 | 0 | 3 | 4 | — | 0 | KKTGRK | FPHQKD | | GRA | IITI | |
| P6.1 | conoserver_frame-workVIVII | 6 | 6 | 0 | 3 | 4 | — | 0 | YPPGTF | GIKPGL | | SEL | LPAV | |
| PVIA | conoserver_frame-workVIVII | 6 | 6 | 0 | 3 | 4 | — | 0 | YAPGTF | GIKPGL | | SEF | LPGV | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| PVIIA | conoserver_frame-workVIVII | 6 | 6 | 0 | 3 | 5 | — | 2 | RIPNQK | FQHLDD | | SRK | NRFNK | |
| Pn6.1 | conoserver_frame-workVIVII | 6 | 6 | 0 | 3 | 4 | — | 0 | VKYLDP | DMLRHT | | FGL | VLIA | |
| Pn6.10 | conoserver_frame-workVIVII | 3 | 6 | 0 | 8 | 3 | — | 0 | EES | EDEEKH | | HENNGVYT | LRY | |
| Pn6.11 | conoserver_frame-workVIVII | 3 | 6 | 0 | 8 | 3 | — | 0 | EEY | EDEEKT | | GLEDGEPV | ATT | |
| Pn6.12 | conoserver_frame-workVIVII | 6 | 5 | 0 | 3 | 3 | — | 0 | FESWVA | ESPKR | | SHV | LFV | |
| Pn6.13 | conoserver_frame-workVIVII | 6 | 6 | 0 | 3 | 3 | — | 0 | IAESEP | NIITQN | | DGK | LFF | |
| Pn6.14 | conoserver_frame-workVIVII | 6 | 9 | 0 | 4 | 4 | — | 0 | QRRWDF | PGALVGVIT | | GGLI | LGVM | |
| Pn6.2 | conoserver_frame-workVIVII | 6 | 6 | 0 | 2 | 4 | — | 0 | LGFGEV | NFFFPN | | SY | VALV | |
| Pn6.3 | conoserver_frame-workVIVII | 6 | 6 | 0 | 3 | 4 | — | 0 | IPQFDP | DMVRHT | | KGL | VLIA | |
| Pn6.5 | conoserver_frame-workVIVII | 6 | 6 | 0 | 3 | 3 | — | 0 | KAESEA | NIITQN | | DGK | LFF | |
| Pn6.6 | conoserver_frame-workVIVII | 6 | 5 | 0 | 3 | 3 | — | 0 | FESWVA | ESPKR | | SHV | LFV | |
| Pn6.7 | conoserver_frame-workVIVII | 6 | 9 | 0 | 3 | 3 | — | 0 | LEVDYF | GIPFVNNGL | | SGN | VFV | |
| Pn6.8 | conoserver_frame-workVIVII | 6 | 5 | 0 | 3 | 3 | — | 0 | SDQWKS | SYPHE | | RWS | NRY | |
| Pn6.9 | conoserver_frame-workVIVII | 6 | 5 | 0 | 3 | 3 | — | 0 | DDWLAA | TTPSQ | | TEV | DGF | |
| PnVIA | conoserver_frame-workVIVII | 6 | 9 | 0 | 3 | 3 | — | 0 | LEVDYF | GIPFANNGL | | SGN | VFV | |
| PnVIB | conoserver_frame-workVIVII | 6 | 8 | 0 | 3 | 3 | — | 0 | EPPGNF | GMIKIGPP | | SGW | FFA | |
| PnVIIA | conoserver_frame-workVIVII | 6 | 5 | 0 | 3 | 4 | — | 0 | TSWFGR | TVNSE | | SNS | DQTY | |
| Pu6.1 | conoserver_frame-workVIVII | 6 | 6 | 0 | 3 | 3 | — | 0 | VEDGDF | GPGYEE | | SGF | LYV | |
| PuIA | conoserver_frame-workVIVII | 6 | 9 | 0 | 3 | 3 | — | 0 | RPVGQY | GIPYEHNWR | | SQL | AII | |
| PuIIA | conoserver_frame-workVIVII | 6 | 5 | 0 | 3 | 6 | — | 0 | NTPTQY | TLHRH | | SLY | HKTIHA | |
| Qc6.1 | conoserver_frame-workVIVII | 6 | 9 | 0 | 3 | 3 | — | 0 | AAAGEA | VIPIIGNVF | | KGY | LFV | |
| Qc6.2 | conoserver_frame-workVIVII | 6 | 8 | 0 | 3 | 3 | — | 0 | QDSGVV | GFPKPEPH | | SGW | LFV | |
| QcVIA | conoserver_frame-workVIVII | 2 | 3 | 0 | 4 | 4 | — | 0 | PW | GFT | | LPNY | QGLT | |
| RVIA | conoserver_frame-workVIVII | 6 | 6 | 0 | 2 | 6 | — | 0 | KPPGSP | RVSSYN | | SS | KSYNKK | |
| RVIIA | conoserver_frame-workVIVII | 6 | 5 | 0 | 3 | 4 | — | 0 | TYWLGP | EVDDT | | SAS | ESKF | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| S6.1 | conoserver_framework VI VII | 6 | 6 | 0 | 3 | 4 | — | 0 | KAAGKS | SRIAYN | | TGS | RSGK | |
| S6.10 | conoserver_framework VI VII | 6 | 5 | 0 | 3 | 6 | — | 0 | TPDDGA | AEPVQ | | STF | NPVTNM | |
| S6.11 | conoserver_framework VI VII | 6 | 5 | 0 | 3 | 4 | — | 0 | RTWNAP | SFTSQ | | FGK | AHHR | |
| S6.2 | conoserver_framework VI VII | 6 | 5 | 0 | 2 | 4 | — | 0 | RSSGSP | GVTGI | | GR | YRGK | |
| S6.6 | conoserver_framework VI VII | 6 | 6 | 0 | 3 | 5 | — | 0 | KGKGAP | RKTMYD | | SGS | GRRGK | |
| S6.7 | conoserver_framework VI VII | 6 | 6 | 0 | 2 | 8 | — | 0 | MEAGSY | GSTTRI | | GY | AYSASKNV | |
| S6.8 | conoserver_framework VI VII | 6 | 6 | 0 | 3 | 3 | — | 0 | SNAGGF | GIHPGL | | SEI | LVW | |
| SO3 | conoserver_framework VI VII | 6 | 6 | 0 | 3 | 4 | — | 1 | KAAGKP | SRIAYN | | TGS | RSGK | |
| SO4 | conoserver_framework VI VII | 6 | 7 | 0 | 2 | 6 | — | 0 | IEAGNY | GPTVMKI | | GF | SPYSKI | |
| SO5 | conoserver_framework VI VII | 6 | 6 | 0 | 2 | 6 | — | 0 | MEAGSY | GSTTRI | | GY | AYFGKK | |
| SVIA | conoserver_framework VI VII | 6 | 5 | 0 | 2 | 4 | — | 0 | RSSGSP | GVTSI | | GR | YRGK | |
| SVIA mutant 1 | conoserver_framework VI VII | 6 | 5 | 0 | 2 | 4 | — | 0 | RPSGSP TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Ts6.3 | conoserver_framework_VIVII | 6 | 5 | 0 | 3 | 3 | — | 0 | TPWLGG | TSPEE | | PGN | ETY | |
| Ts6.4 | conoserver_framework_VIVII | 3 | 6 | 0 | 8 | 3 | — | 0 | NEY | DDRNKE | | GRTNGHPR | ANV | |
| Ts6.5 | conoserver_framework_VIVII | 3 | 6 | 0 | 8 | 3 | — | 0 | NEH | EDRNKE | | GRTNGHPR | ANV | |
| Ts6.6 | conoserver_framework_VIVII | 3 | 6 | 0 | 8 | 3 | — | 0 | NEY | DDRNKE | | GRTNGHPR | ANV | |
| Ts6.7 | conoserver_framework_VIVII | 3 | 6 | 0 | 8 | 3 | — | 0 | DEY | EDLNKN | | GLSNGEPV | AIA | |
| Tx6.1 | conoserver_framework_VIVII | 6 | 6 | 0 | 4 | 4 | — | 0 | RKEHQL | DLIFQN | | RGWY | VVLS | |
| Tx6.2 | conoserver_framework_VIVII | 6 | 6 | 0 | 3 | 4 | — | 0 | APFLHL | TFFFPN | | NGY | VQFI | |
| Tx6.3 | conoserver_framework_VIVII | 6 | 5 | 0 | 3 | 4 | — | 0 | YDSGTS | NTGNQ | | SGW | IFVS | |
| Tx6.4 | conoserver_framework_VIVII | 6 | 8 | 0 | 3 | 3 | — | 0 | EPPGNF | GMIKIGPP | | SGW | FFA | |
| TxIA/TxVIA | conoserver_framework_VIVII | 6 | 6 | 0 | 3 | 4 | — | 2 | KQSGEM | NLLDQN | | DGY | IVLV | |
| TxIB/TxVIB | conoserver_framework_VIVII | 6 | 6 | 0 | 3 | 4 | — | 0 | KQSGEM | NVLDQN | | DGY | IVFV | |
| TxMEKL-011 | conoserver_framework_VIVII | 6 | 5 | 0 | 3 | 3 | — | 0 | KDGLTT | LAPSE | | SGN | EQN | |
| TxMEKL-022/TxMEKL-021 | conoserver_framework_VIVII | 6 | 5 | 0 | 3 | 5 | — | 0 | TSWLAT | TDASQ | | TGV | YKRAY | |
| TxMEKL-0511/TxMEKL-0512 | conoserver_framework_VIVII | 6 | 5 | 0 | 3 | 4 | — | 0 | MAWFGL | SKDSE | | SNS | DVTR | |
| TxMEKL-053 precursor | conoserver_framework_VIVII | 6 | 5 | 0 | 3 | 4 | — | 0 | GIWFSR | TKDSE | | SNS | DQTY | |
| TxMEKL-P2 | conoserver_framework_VIVII | 6 | 5 | 0 | 4 | 6 | — | 0 | RGYDAP | SSGAP | | DWWT | SARTNR | |
| TxMKLT1-0111 | conoserver_framework_VIVII | 6 | 6 | 0 | 3 | 4 | — | 0 | KQSGEM | NLLDQN | | DGY | IVFV | |
| TxMKLT1-0141 | conoserver_framework_VIVII | 6 | 6 | 0 | 2 | 4 | — | 0 | LDAGEI | DFFFPT | | GY | ILLF | |
| TxMKLT1-015 | conoserver_framework_VIVII | 6 | 6 | 0 | 3 | 4 | — | 0 | IEQFDP | DMIRHT | | VGV | FLMA | |
| TxMKLT1-0211 | conoserver_framework_VIVII | 6 | 5 | 0 | 3 | 3 | — | 0 | YDGGTS | DSGIQ | | SGW | IFV | |
| TxMKLT1-031 | conoserver_framework_VIVII | 6 | 9 | 0 | 4 | 4 | — | 0 | QEKWDF | PAPFFGSRY | | FGLF | TLFF | |
| TxO1 | conoserver_framework_VIVII | 6 | 6 | 0 | 2 | 4 | — | 0 | LDAGEV | DFFFPT | | GY | ILLF | |
| TxO2 | conoserver_framework_VIVII | 6 | 5 | 0 | 3 | 3 | — | 0 | YDSGTS | NTGNQ | | SGW | IFV | |
| TxO3 | conoserver_framework_VIVII | 6 | 5 | 0 | 3 | 3 | — | 0 | YDGGTS | DSGIQ | | SGW | IFV | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TxO4 | conoserver_frame-workVIVII | 6 | 8 | 0 | 3 | 3 | — | 0 | EPPGNF | GMIKIGPP | | SGW | FFA | |
| TxO5 | conoserver_frame-workVIVII | 6 | 6 | 0 | 3 | 4 | — | 0 | VPYEGP | NWLTQN | | DAT | VVFW | |
| TxO6 | conoserver_frame-workVIVII | 6 | 9 | 0 | 4 | 4 | — | 0 | QEKWDY | PVPFLGSRY | | DGLF | TLFF | |
| TxVII | conoserver_frame-workVIVII | 6 | 6 | 0 | 3 | 3 | — | 1 | KQADEP | DVFSLD | | TGI | LGV | |
| TxVIIA | conoserver_frame-workVIVII | 6 | 5 | 0 | 3 | 4 | — | 0 | GGYSTY | EVDSE | | SDN | VRSY | |
| Vc6.3 | conoserver_frame-workVIVII | 6 | 8 | 0 | 2 | 4 | — | 0 | YGFGEA | LVLYTD | | GY | VLAV | |
| Vc6.4 | conoserver_frame-workVIVII | 6 | 8 | 0 | 3 | 3 | — | 0 | EPPGNF | GMIKVGPP | | SGW | FFA | |
| Vc6.6 | conoserver_frame-workVIVII | 6 | 5 | 0 | 3 | 3 | — | 0 | YDGGTG | DSGNQ | | SGW | IFV | |
| VcVIA | conoserver_frame-workVIVII | 6 | 6 | 0 | 2 | 4 | — | 0 | LSGGEV | DFLFPK | | NY | ILLF | |
| VcVIB | conoserver_frame-workVIVII | 6 | 6 | 0 | 4 | 3 | — | 0 | HEEGQL | DPFLQN | | LGWN | VFV | |
| VcVIC | conoserver_frame-workVIVII | 6 | 6 | 0 | 3 | 4 | — | 0 | IPFLHP | TFFFPD | | NSI | AQFI | |
| VeG52 | conoserver_frame-workVIVII | 6 | 5 | 0 | 3 | 4 | — | 0 | RLWSNG | RKHKE | | SNH | KGIY | |
| ViKr35 | conoserver_frame-workVIVII | 6 | 5 | 0 | 4 | 8 | — | 0 | RRRGQG | TQSTP | | DGLR | DGQRQGG M | |
| ViKr92 | conoserver_frame-workVIVII | 6 | 8 | 0 | 3 | 3 | — | 0 | LDPGYF | GTPFLGAY | | GGI | LIV | |
| Vn6.1 | conoserver_frame-workVIVII | 6 | 5 | 0 | 3 | 4 | — | 0 | SGWSVY | TQHSE | | SGE | TGNY | |
| Vn6.10 | conoserver_frame-workVIVII | 6 | 8 | 0 | 3 | 3 | — | 0 | RPGGMI | GFPKPGPY | | SGW | FVV | |
| Vn6.11 | conoserver_frame-workVIVII | 6 | 8 | 0 | 3 | 3 | — | 0 | EAGGRF | GFPKIGEP | | SGW | FFV | |
| Vn6.12 | conoserver_frame-workVIVII | 6 | 10 | 0 | 3 | 3 | — | 0 | IEDKKY | GILPFANSGV | | SYL | IFV | |
| Vn6.13 | conoserver_frame-workVIVII | 6 | 6 | 0 | 3 | 3 | — | 0 | RQPGEF | FPVVAK | | GGT | LVI | |
| Vn6.14 | conoserver_frame-workVIVII | 6 | 5 | 0 | 3 | 4 | — | 0 | LASGET | WRDTS | | SFS | TNNV | |
| Vn6.15 | conoserver_frame-workVIVII | 6 | 5 | 0 | 3 | 4 | — | 0 | LGSGET | WLDSS | | SFS | TNNV | |
| Vn6.16 | conoserver_frame-workVIVII | 6 | 4 | 0 | 4 | 8 | — | 0 | SGSGYG | KNTP | | AGLT | RGPRQGPl | |
| Vn6.17 | conoserver_frame-workVIVII | 6 | 4 | 0 | 4 | 8 | — | 0 | SGSGYG | KNTP | | DGLT | RGPHQGPI | |
| Vn6.18 | conoserver_frame-workVIVII | 4 | 4 | 0 | 4 | 8 | — | 0 | STAG | KNVP | | EGLV | TGPSQGPV | |
| Vn6.19 | conoserver_frame-workVIVII | 3 | 7 | 0 | 8 | 3 | — | 0 | EEY | EDRDKKT | | GLENGEPF | ATL | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Vn6.2 | conoserver_frame-workVIVII | 6 | 5 | 0 | 3 | 4 | — | 0 | SGWSVM | TQHSD | | SGE | TGSY | |
| Vn6.20 | conoserver_frame-workVIVII | 3 | 6 | 0 | 8 | 3 | — | 0 | KEY | EDRDKT | | GLENGQPD | ANL | |
| Vn6.21 | conoserver_frame-workVIVII | 3 | 6 | 0 | 8 | 3 | — | 0 | YEY | KEQNKT | | GISNGRPI | VGG | |
| Vn6.22 | conoserver_frame-workVIVII | 3 | 6 | 0 | 8 | 3 | — | 0 | EEY | KEQNKT | | GLTNGRPR | VGV | |
| Vn6.3 | conoserver_frame-workVIVII | 6 | 5 | 0 | 3 | 4 | — | 0 | RGWSNG | TTNSD | | SNN | DGTF | |
| Vn6.4 | conoserver_frame-workVIVII | 6 | 5 | 0 | 3 | 3 | — | 0 | TGWLDG | TSPAE | | TAV | DAT | |
| Vn6.5 | conoserver_frame-workVIVII | 6 | 5 | 0 | 3 | 6 | — | 0 | RTWYAP | NFPSQ | | SEV | SSKTGR | |
| Vn6.6 | conoserver_frame-workVIVII | 6 | 7 | 0 | 4 | 3 | — | 0 | VGLSSY | GPWNNPP | | SWYT | DYY | |
| Vn6.7 | conoserver_frame-workVIVII | 6 | 7 | 0 | 4 | 3 | — | 0 | VGWSSY | GPWNNPP | | SWYT | DYY | |
| Vn6.8 | conoserver_frame-workVIVII | 6 | 8 | 0 | 3 | 3 | — | 0 | VAGGHF | GFPKIGGP | | SGW | FFV | |
| Vn6.9 | conoserver_frame-workVIVII | 6 | 8 | 0 | 3 | 3 | — | 0 | AAGGQF | GFPKIGGP | | SGW | LGV | |
| VxVIA | conoserver_frame-workVIVII | 6 | 5 | 0 | 3 | 6 | — | 0 | NNRGGG | SQHPH | | SGT | NKTFGV | |
| VxVIB | conoserver_frame-workVIVII | 6 | 6 | 0 | 3 | 8 | — | 0 | TDDSQF | DPNDHD | | SGE | IDEGGRGV | |
| conotoxin-GS | conoserver_frame-workVIVII | 6 | 3 | 0 | 4 | 7 | — | 1 | SGRGSR | PPQ | | MGLR | GRGNPQK | |
| ArXIA | conoserver_frame-workXI | 6 | 5 | 0 | 3 | 5 | — | 0 | SRRGHR | IRDSQ | | GGM | CQGNR | |
| Au11.6 | conoserver_frame-workXI | 6 | 5 | 0 | 3 | 5 | — | 0 | SWPGQE | EHDSD | | GSF | CVGRR | |
| BeTX | conoserver_frame-workXI | 6 | 5 | 0 | 3 | 4 | — | 0 | RAEGTY | ENDSQ | | LNE | CWGG | |
| Bt11.1 | conoserver_frame-workXI | 6 | 5 | 0 | 3 | 5 | — | 0 | LSLGQR | ERHSN | | GYL | CFYDK | |
| Bt11.4 | conoserver_frame-workXI | 6 | 5 | 0 | 3 | 5 | — | 0 | LSLGQR | GRHSN | | GYL | CFYDK | |
| Cp1.1 | conoserver_frame-workXI | 6 | 5 | 0 | 3 | 4 | — | 0 | FPPGVY | TRHLP | | RGR | CSGW | |
| Em11.10 | conoserver_frame-workXI | 6 | 5 | 0 | 3 | 3 | — | 0 | FPPGIY | TPYLP | | WGI | CGT | |
| Ep11.1 | conoserver_frame-workXI | 6 | 5 | 0 | 3 | 5 | — | 0 | SGIGQG | GQDSN | | GDM | CYGQI | |
| Ep11.12 | conoserver_frame-workXI | 6 | 5 | 0 | 3 | 4 | — | 0 | LSEGSP | SMSGS | | HKS | CRST | |
| Fi11.11 | conoserver_frame-workXI | 6 | 5 | 0 | 3 | 4 | — | 0 | HHEGLP | TSGDG | | GME | CGGV | |
| Fi11.1a | conoserver_frame-workXI | 6 | 5 | 0 | 1 | 5 | — | 0 | GKDGRA | DYHAD | | N | CLGGI | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Fi11.6 | conoserver_framework XI | 6 | 5 | 0 | 1 | 5 | — | 0 | KKDRKP | SYHAD | | N | CLSGI | |
| Fi11.8 | conoserver_framework XI | 6 | 5 | 0 | 1 | 5 | — | 0 | KADEEP | EYHAD | | N | CLSGI | |
| Im11.1 | conoserver_framework XI | 6 | 5 | 0 | 3 | 4 | — | 0 | LRDGQS | GYDSD | | RYS | CWGY | |
| Im11.2 | conoserver_framework XI | 6 | 5 | 0 | 3 | 4 | — | 0 | RLEGSS | RRSYQ | | HKS | CIRE | |
| Im11.3 | conoserver_framework XI | 6 | 5 | 0 | 3 | 4 | — | 0 | TSEGYS | SSDSN | | KNV | CWNV | |
| L11.5 | conoserver_framework XI | 6 | 5 | 0 | 3 | 5 | — | 0 | SGSGEG | DYHSE | | GER | CIESM | |
| Mi11.1a | conoserver_framework XI | 6 | 5 | 0 | 1 | 5 | — | 0 | GKDGRQ | RNHAD | | N | CPIGT | |
| Mi11.2 | conoserver_framework XI | 6 | 5 | 0 | 3 | 5 | — | 0 | SNKGQQ | GDDSD | | WHL | CVNNK | |
| Mi11.5 | conoserver_framework XI | 6 | 5 | 0 | 1 | 5 | — | 0 | GKDGRK | GYHAD | | N | CLSGI | |
| Mi11.1 | conoserver_framework XI | 6 | 5 | 0 | 3 | 4 | — | 0 | FPPGTF | SRYLP | | SGR | CSGW | |
| R11.1 | conoserver_framework XI | 6 | 5 | 0 | 1 | 5 | — | 0 | GKDGRK | GYHAD | | N | CLSGI | |
| R11.10 | conoserver_framework XI | 6 | 5 | 0 | 1 | 5 | — | 0 | GKDGRK | GYHAD | | N | CLSGI | |
| R11.11 | conoserver_framework XI | 6 | 5 | 0 | 1 | 5 | — | 0 | GKDGRA | DYHAD | | N | CLGGI | |
| R11.12 | conoserver_framework XI | 6 | 5 | 0 | 1 | 5 | — | 0 | GKDRRK | GYHAD | | N | CLSGI | |
| R11.13 | conoserver_framework XI | 6 | 5 | 0 | 1 | 5 | — | 0 | GKDGRK | GYHAD | | N | CLSGI | |
| R11.15 | conoserver_framework XI | 6 | 5 | 0 | 1 | 5 | — | 0 | GKDGRK | GYHTH | | N | CLSGI | |
| R11.16 | conoserver_framework XI | 6 | 5 | 0 | 1 | 5 | — | 0 | GKDGRK | SYHAD | | N | CLSGI | |
| R11.17 | conoserver_framework XI | 6 | 5 | 0 | 1 | 5 | — | 0 | KANGKP | RNHAD | | N | CLSGI | |
| R11.18 | conoserver_framework XI | 6 | 5 | 0 | 1 | 5 | — | 0 | GKDGRQ | RNHAD | | N | CPFGT | |
| R11.2 | conoserver_framework XI | 6 | 5 | 0 | 1 | 5 | — | 0 | GKDGRQ | RNHAD | | N | CPIGT | |
| R11.3 | conoserver_framework XI | 6 | 5 | 0 | 3 | 5 | — | 0 | WVGRVH | TYHKD | | PSV | CFKGR | |
| R11.5 | conoserver_framework XI | 6 | 5 | 0 | 1 | 5 | — | 0 | GKDGRQ | RNHAD | | N | CPIGT | |
| R11.7 | conoserver_framework XI | 6 | 5 | 0 | 1 | 5 | — | 0 | KADEKP | EYHSD | | N | CLSGI | |
| RXIA | conoserver_framework XI | 6 | 5 | 0 | 1 | 5 | — | 1 | KADEKP | EYHAD | | N | CLSGI | |
| RXIB | conoserver_framework XI | 6 | 5 | 0 | 1 | 5 | — | 0 | KANGKP | SYHAD | | N | CLSGI | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| RXIC | conoserver_frameworkXI | 6 | 5 | 0 | 1 | 5 | — | 0 | KADEKP | KYHAD | | N | CLGGI | |
| RXID | conoserver_frameworkXI | 6 | 5 | 0 | 1 | 5 | — | 0 | KKDRKP | SYHAD | | N | CLSGI | |
| RXIE | conoserver_frameworkXI | 6 | 5 | 0 | 3 | 5 | — | 0 | KTNKMS | SLHEE | | RFR | CFHGK | |
| RgXIA | conoserver_frameworkXI | 6 | 5 | 0 | 5 | 8 | — | 0 | QAYGES | SAWR | | DPNAV | CQYPEDAV | |
| S11.2a | conoserver_frameworkXI | 6 | 5 | 0 | 1 | 5 | — | 0 | KKDRKP | SYQAD | | N | CPIGT | |
| S11.3 | conoserver_frameworkXI | 6 | 5 | 0 | 3 | 4 | — | 0 | VPPSRY | TRHRP | | RGT | CSGL | |
| SiXIA | conoserver_frameworkXI | 6 | 5 | 0 | 3 | 4 | — | 0 | RTEGMS | EENQQ | | WRS | CRGE | |
| Sx11.2 | conoserver_frameworkXI | 6 | 5 | 0 | 3 | 4 | — | 0 | RAEGTY | ENDSQ | | LNE | CWGG | |
| TxXI | conoserver_frameworkXI | 6 | 5 | 0 | 3 | 4 | — | 0 | IPEGSS | SSSGS | | HKS | CRWT | |
| ViTx | conoserver_frameworkXI | 6 | 5 | 0 | 3 | 3 | — | 0 | FPPGIY | TPYLP | | WGI | CGT | |
| Vx11.1 | conoserver_frameworkXI | 6 | 5 | 0 | 3 | 3 | — | 0 | FPPGIY | TPYLP | | WGI | CDT | |
| Vx11.2 | conoserver_frameworkXI | 6 | 5 | 0 | 3 | 3 | — | 0 | FPPGIY | TPYLP | | WGI | CDT | |
| AVR9_CLAFU | fungi1 | 3 | 5 | 3 | 2 | 6 | — | 0 | NSS | TRAFD | LGQ | GR | DFHKLQ | |
| U499_ASPCL | fungi1 | 3 | 5 | 3 | 2 | 6 | — | 0 | GQL | FNNKD | GGP | PK | NTKEGV | |
| U499_ASPTN | fungi1 | 3 | 5 | 3 | 2 | 4 | — | 0 | GQV | TGKND | SGE | NK | VNFV | |
| U499_NEOFI | fungi1 | 3 | 5 | 3 | 2 | 6 | — | 0 | GQV | LNKTG | GGK | PK | DMRSLT | |
| A6RPC6_BOTFB | fungi2 | 6 | 6 | 0 | 4 | 12 | — | 0 | IAKGEV | HQTGET | | DGFK | ALAHGGKA DVGF | |
| A6SKI6_BOTFB | fungi2 | 6 | 6 | 0 | 4 | 4 | — | 0 | LPQGES | MMQHDK | | HGLM | NSGE | |
| A7EBW4_SCLS1 | fungi2 | 6 | 6 | 0 | 4 | 12 | — | 0 | IKNGEV | HLTGES | | DGFK | ALAHGGKA NVGY | |
| B0CWT3_LACBS | fungi2 | 6 | 7 | 0 | 4 | 9 | — | 0 | LGRDHD | DPDGREL | | RGLI | APFGPFGGS | |
| B0DJS7_LACBS | fungi2 | 6 | 5 | 0 | 3 | 10 | — | 0 | VTKGKI | SKDSD | | KKV | FPVPFGNGG V | |
| B0DQK7_LACBS | fungi2 | 6 | 5 | 0 | 3 | 12 | — | 0 | FIALTP | AADKD | | SGL | KISLSAVGL GLR | |
| B0DQL1_LACBS | fungi2 | 6 | 5 | 0 | 3 | 16 | — | 0 | LMDGSY | MSNSD | | SEL | VVFESSPLS RTVFVDW | |
| B0DQL3_LACBS | fungi2 | 6 | 5 | 0 | 3 | 11 | — | 0 | YVRGDY | QTDSD | | GRI | YPFAPEMV YGF | |
| B0DU64_LACBS | fungi2 | 6 | 5 | 0 | 3 | 11 | — | 0 | FGLGSP | SFNSN | | SGY | LIIPPTIVLG F | |
| B0DVV7_LACBS | fungi2 | 6 | 5 | 0 | 3 | 11 | — | 0 | FALGTL | SFDSN | | SGH | NSIPLIFVLG F | |
| U499_CHAGB | fungi2 | 6 | 5 | 0 | 4 | 8 | — | 0 | HSILTS | RVDTD | | AGLK | GIFDEDAL | |
| U499_NEUCR | fungi2 | 6 | 5 | 0 | 4 | 8 | — | 0 | RAILTT | RVTSD | | SGMK | VSADGESV | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| A0MK33 | grow_factors | 28 | 3 | 31 | 31 | 1 | — | 0 | RRHSLYVDFSDV GWNDWIVAPPG YHAFY | QGE | PFPLADHLNSTNH AIVQTLVNSVNTN IPKAC | VPTDLSPVSLLYLD EYERVILKNYQDM VVEG | G | |
| A0MK34 | grow_factors | 28 | 3 | 31 | 31 | 1 | — | 0 | RRHPLYVDFSDV GWNEWIVAPPG YHAFY | NGE | PFPLSDHLNSTNH AIVQTLVNSVNSN IPRAC | VPTELSPISLLYLDE YEKVVLKNYQDM VVEG | G | |
| A0MK35 | grow_factors | 28 | 3 | 31 | 31 | 1 | — | 0 | RRHALYVDFSDV GWNDWIVAPPG YQAYY | HGE | PFPLADHLNSTNH AIVQTLVNSVNSN IPKAC | VPTELSAISMLYLD ETDRVVLKNYQEM VVEG | G | |
| A0MK36 | grow_factors | 28 | 3 | 31 | 31 | 1 | — | 0 | KRHVLYVDFSDV GWNEWIVAPPG YDAFY | HGE | PFPLPDHLNATNH AVVQTLVNSVNS NIPKAC | VPTELSPISLLYLDE FEKVTLKNYQDM VVDG | G | |
| A0MK37 | grow_factors | 28 | 3 | 31 | 31 | 1 | — | 0 | RRHTLYVDFSDV GWNDWIVAPPG YQAYY | HGE | PFPLADHLNSTNH AIVQTLVNSVNN NIPKAC | VPTELSAISMLYLD EYDKVVLKNYQE MVVEG | G | |
| A0SLB5 | grow_factors | 28 | 3 | 32 | 31 | 1 | — | 0 | RRHPLYVDFSDV HWNDWIVAPAG YQAYY | HGE | PFPLAEHLNTTNH AIVQTLVNSVNPA LVPKAC | VPTELSAISMLYLD EYEKVVLKNYQD MVVEG | G | |
| A0SLB6 | grow_factors | 28 | 3 | 32 | 31 | 1 | — | 0 | QRHRLFVSFRDV GWEDWILAPMG YQAYY | DGE | PFPLGERLNGTNH AIIQTLVNSIDSRA VPKVC | APTKLSGISMLYFD NNENVVLRQYED MVVEA | G | |
| A1KXV9 | grow_factors | 28 | 3 | 31 | 31 | 1 | — | 0 | KRHALYVDFSDV GWNEWIVAPPG YHAFY | HGE | PFPLADHLNSTNH AIVQTLVNSVNSN IPRAC | VPTDLSPISLLYLD EYEKVILKNYQDM VVEG | G | |
| A1XP54 | grow_factors | 30 | 3 | 6 | 33 | 1 | — | 0 | QVREILVDIFQEY PEEVEYIFKPSCV PLMR | AGC | NDESLE | VSTESYNITMQIMK IKPHISQHIMDMSF QQHSH | E | |
| A2A2V4 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| A2AII0 | grow_factors | 28 | 3 | 32 | 31 | 1 | — | 0 | SRKPLHVNFKEL GWDDWIIAPLEY EAYH | EGV | DFPLRSHLEPTNH AIIQTLMNSMDPG STPPSC | VPTKLTPISILYIDA GNNVYKQYEDM VVES | G | |
| A2ARK2 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| A2AUJ3 | grow_factors | 28 | 3 | 32 | 31 | 1 | — | 0 | KKHELYVSFRDL GWQDWIIAPEGY AAYY | EGE | AFPLNSYMNATIN HAIVQTLVHFINP DTVPKPC | APTQLNAISVLYFD DSSNVILKKYRNM VVRA | G | |
| A4UY01 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| A4VCG6 | grow_factors | 30 | 3 | 6 | 33 | 1 | — | 0 | RPREMLVEIQQE YPDDTEHIFIPSC WLTR | AGC | NDEMME | TPTVTYNITLEIKRL KPLRHQGDIFMSFA EHSE | Q | |
| A5GFN1 | grow_factors | 28 | 3 | 32 | 31 | 1 | — | 0 | KKHELYVSFRDL GWQDWIIAPEGY AAYY | EGE | AFPLNSYMNATIN HAIVQTLVHFINP ETVPKPC | APTQLNAISVLYFD DSSNVILKKYRNM VVRA | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| A5GFN2 | grow_factors | 28 | 3 | 32 | 31 | 1 | — | 0 | KKHELYVSFRDL GWQDWIIAPEGY AAYY | EGE | AFPLNSYMNATN HAIVQTLVHFINP ETVPKPC | APTQLNAISVLYFD DSSNVILKKYRNM VVRA | G | |
| A5HMF8 | grow_factors | 28 | 3 | 31 | 31 | 1 | — | 0 | RRHALYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| A5HMF9 | grow_factors | 28 | 3 | 31 | 31 | 1 | — | 0 | RRHALYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| A5JL80 | grow_factors | 30 | 3 | 6 | 33 | 1 | — | 0 | QPRELLVDILQE YPEEVEHIFIPSC WLKR | AGC | NDEMLQ | TPTETYNITMEIKRI KPQRQQNDIFMSFT EHSA | E | |
| A5PII9 | grow_factors | 28 | 3 | 31 | 31 | 1 | — | 0 | KRHPLYVDFSDV GWNDWIVAPPG YHAFY | HGE | PFPLADHLNSTNH AIVQTLVNSVNSK IPKAC | VPTELSAISMLYLD ENEKVVLKNYQD MVVEG | G | |
| A6N998 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| A7L634 | grow_factors | 28 | 3 | 31 | 31 | 1 | — | 0 | KRHPLYVDFSDV GWNDWIVAPPG YHAFY | HGE | PFPLADHLNSTNH AIVQTLVNSVNSK IPKAC | VPTELSAISMLYLD ENEKVVLKNYQD MVVEG | G | |
| A7LCK8 | grow_factors | 28 | 3 | 32 | 31 | 1 | — | 0 | KKHELYVSFRDL GWQDWIIAPEGY AAYY | EGE | AFPLNSYMNATN HAIVQTLVHFIDP DTVPKPC | APTQLNAISVLYFD DSSNVILKKYRNM VVRA | G | |
| A7LJT9 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| A7RQJ0 | grow_factors | 28 | 3 | 32 | 31 | 1 | — | 0 | QRQALHVSFRKL RWQDWVIAPEG YSAFY | SGE | SFPLNANMNATN HAIVQTLVHFLMN PKTVPKPC | APTELSPISVLYFD QDNNVVLKKYNK MVVKA | G | |
| A7SAY4 | grow_factors | 28 | 3 | 31 | 32 | 1 | — | 0 | QRHPLYVDFTDV GWNDWIVAPPG YHAFY | TGV | PYPIAKHLNATNH AIVQTIMNTVDSN VPNAC | IPTTLNPISILSLNEF DKVVLKNYKDMVI EG | G | |
| A7SZ10 | grow_factors | 28 | 3 | 32 | 32 | 1 | — | 0 | RRKRMYVDFRL LGWSDWIIAPQG YDAYL | EGE | KYPIDNYLRPTNH ATVQTIVNSLDPSI APKAC | TPNELSPISIILYTED GSNNVVYKNYKD MVVER | G | |
| A8E7N9 | grow_factors | 28 | 3 | 32 | 31 | 1 | — | 0 | SKKPLHVNFREL GWDDWVIAPLD YEAYH | EGM | DFPLRSHLEPTNH AIIQTLMNSMNPS NMPPSC | VPSKLSPISILYIDA GNNVVYKQYEDM VVES | G | |
| A8K571 | grow_factors | 28 | 3 | 32 | 31 | 1 | — | 0 | KKHELYVSFRDL GWQDWIIAPEGY AAYY | EGE | AFPLNSYMNATN HAIVQTLVHFINP ETVPKPC | APTQLNAISVLYFD DSSNVILKKYRNM VVRA | G | |
| A8K694 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| A8S3P5 | grow_factors | 28 | 3 | 32 | 31 | 1 | — | 0 | KKHELYVSFRDL GWQDWIIAPEGY AAYY | EGE | AFPLNSYMNATN HAIVQTLVHFINP ETVPKPC | APTQLNAISVLYFD DSSNVILKKYRNM VVRA | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| A8VTF8 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVALKNYQE MVVEG | G | |
| A9ULK0 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTDLSAISMLYLD EYDKVVLKNYQE MVVEG | G | |
| B0BMQ3 | grow_factors | 30 | 3 | 6 | 33 | 1 | — | 0 | QVREILVDIFQEY PDEVEYIFKPSCV PLMR | AGC | NDESLE | VPTESYNITMQIMK IKPHISQHIMDMSF QQHSQ | E | |
| B0CM38 | grow_factors | 28 | 3 | 31 | 31 | 1 | — | 0 | RRHSLYVDFSDV GWNOWIVAPPG YQAFY | HGD | PFPLADHLNSTNH AIVQTLVNSVNSS IPKAC | VPTELSAISMLYLD EYDKVVLKNYQE MVVEG | G | |
| B0CM78 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B0FN90 | grow_factors | 30 | 3 | 6 | 33 | 1 | — | 0 | RPIETLVDIFQEY PDEIEFIFKPSCVP LMR | GGC | NDESLE | VPTEEFNITMQIMR IKPHQNQHIGEMSF LQHNK | E | |
| B0KWL9 | grow_factors | 28 | 3 | 32 | 31 | 1 | — | 1 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B0VXV3 | grow_factors | 30 | 3 | 6 | 34 | 1 | — | 0 | QTREMLVSILDE HPDEVAHLFRPS CVTVLR | GGC | TDESLM | TATGKRSVGREIM RVDPRKETSKIQV MQFTEHTK | E | |
| B0VXV4 | grow_factors | 30 | 3 | 6 | 34 | 1 | — | 0 | QTREMLVSILDE HPDEVAHLFRPS CVTVLR | GGC | TDESLM | TATGKRSVGREIM RVDPRKETSKIEV MQFTEHTE | E | |
| B0WCI2 | grow_factors | 28 | 3 | 32 | 31 | 1 | — | 0 | QRRPLYVDFSDV GWSDWIAPPG YEAFY | QGD | QFPIADHLNTTNH AIVQTLVNSISPSY APKAC | VPTQLSSISMLYLN EQNKVVLKNYQD MTVVG | G | |
| B1AKZ9 | grow_factors | 28 | 3 | 32 | 31 | 1 | — | 0 | KKHELYVSFRDL GWQDWIIAPEGY AAYY | EGE | AFPLNSYMNATN HAIVQTLVHFINP ETVPKPC | APTQLNAISVLYFD DSSNVILKKYRNM VVRA | G | |
| B1MTM2 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B1P8C3 | grow_factors | 28 | 3 | 31 | 31 | 1 | — | 0 | RRHPLYVDFSDV GWNDWIVAPPG YHAFY | HGD | PFPLADHMNSTN HAIVQTLVNSVN ANIPKAC | VPTELSAISMLYLD ENEKVVLKNYQD MVVEG | G | |
| B2C4I5 | grow_factors | 30 | 3 | 6 | 33 | 1 | — | 0 | RPIETLVDIFQEY PDEIEYIFKPSCV PLMR | AGC | NDESLE | VPTEEFNITMQIMR IKPHQGQHIGEMSF LQHNK | E | |
| B2C4I6 | grow_factors | 30 | 3 | 6 | 33 | 1 | — | 0 | RPIETLVDIFQEY PDEIEYIFKPSCV PLMR | AGC | NDESLE | VPTEEFNITMQIMR IKPHQGQHIGEMSF LQHNK | E | |
| B2KI82 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| B2KIC7 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B2KL65 | grow_factors | 28 | 3 | 32 | 31 | 1 | — | 0 | RKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| B2KL66 | grow_factors | 28 | 3 | 32 | 31 | 1 | — | 0 | RKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| B2RRV6 | grow_factors | 28 | 3 | 32 | 31 | 1 | — | 0 | KKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| B2ZP8 | grow_factors | 28 | 3 | 32 | 31 | 1 | — | 0 | KKHELYVSFRDL GWQDWIIAPEGY AAYY | EGE | AFPLNSYMNATN HAIVQTLVHFINP ETVPKPC | APTQLNAISVLYFD DSSNVILKKYRNM VVRA | G | |
| B3D186 | grow_factors | 28 | 3 | 31 | 31 | 1 | — | 0 | RRHSLYVDFSDV GWNDWIVAPPG YHAFY | QGE | PFPLADIHLNSTNH AIVQTLVNSVSN IPRAC | VPTDLSPVSLLYLD EYERVILKNYQDM VVEG | G | |
| B3D143 | grow_factors | 28 | 3 | 32 | 31 | 1 | — | 0 | SKKPLHVNFREL GWDDWVIAPLD YEAYH | EGM | DFPLRSHLEPTNH AIIQTLMNSMNPS NMPPSC | VPSKLSPISILYIDA GNNVVYKQYEDM VVES | G | |
| B3FNR0 | grow_factors | 28 | 3 | 32 | 31 | 1 | — | 0 | RRHELYVDFSDV HWNDWIVAPAG YQAYY | RGE | PFPLAEHLNTTNH AIVQTLVNSVNPA LVPKAC | VPTELSAISMLYLD EYEKVVLKNYQD MVVEG | G | |
| B3NA13 | grow_factors | 28 | 3 | 32 | 31 | 1 | — | 0 | RRHSLYVDFSDV GWDDWIVAPLG YDAYY | HGK | PFPLADHFNSTNH AVVQTLVNNMNP GKVPKAC | VPTQLDSVAMLYL NDQSTVVLKNYQE MTVVG | G | |
| B3RF16 | grow_factors | 28 | 3 | 31 | 31 | 1 | — | 0 | RRHSLYVDFSDV GWNDWIVAPPG YQAFY | HGD | PFPLADHLNSTNH AIVQTLVNSVSS IPKAC | VPTELSAISMLYLD EYDKVVLKNYQE MVVEG | G | |
| B3RF47 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B3Y026 | grow_factors | 28 | 3 | 32 | 31 | 1 | — | 0 | RRKELNVDFKAV GWNDWIFAPPG YNAYY | DGS | HWPYDDHMNVT NHAIVQDLVNSID PRAAPKC | VPTELSSLSLLYTD EHGTVVLKVYQD MVVEG | G | |
| B4DUF7 | grow_factors | 28 | 3 | 32 | 31 | 1 | — | 0 | RKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| B4JAU3 | grow_factors | 28 | 3 | 32 | 31 | 1 | — | 0 | RRHSLYVDFQDV GWSDWIVAPPG YDAFY | HGK | PFPLADHLNSTNH AVVQTLVNNLNP GKVPKAC | VPTQLEGISMLYLN DQRTVLKNYPD MTVVG | G | |
| B4KGU4 | grow_factors | 28 | 3 | 32 | 31 | 1 | — | 0 | RRHSLYVDFQDV GWSDWIVAPPG YDAYY | HGK | PFPLADHLNSTNH AVVQTLVNNINP GKVPKAC | VPTQLEGISMLYLN DQRTVLKNYQD MITVVG | G | |
| B4LUE0 | grow_factors | 28 | 3 | 32 | 31 | 1 | — | 0 | RRHSLYVDFQDV GWSDWIVAPPG YDAYY | HGK | QFPLADIHLNSTNH AVVQTLVNNLNP GKVPKAC | VPTQLEGISMLYLN DQRTVLKNYQD MITVVG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| B4MU02 | grow_factors | 28 | 3 | 32 | 31 | 1 | — | 0 | RRHSLYVDFADV GWSDWIVAPPG YDAF | HGK | PFPLADHLNSTNH AVVQTLVNNIDP GKVPKAC | VPTQLEGISMLYLN DQSTVVLKNYQD MITVVG | G | |
| B4NWQ1 | grow_factors | 28 | 3 | 32 | 31 | 1 | — | 0 | RRHSLYVDFSDV GWDDWIVAPLG YDAYY | HGK | PFPLADHFNSTNH AVVQTLVNNMNP GKVPKAC | VPTQLDSVAMLYL NDQSTVVLKNYQE MITVVG | G | |
| B4Q848 | grow_factors | 28 | 3 | 32 | 31 | 1 | — | 0 | RRHSLYVDFSDV GWDDWIVAPLG YDAYY | HGK | PFPLADHFNSTNH AVVQTLVNNMNP GKVPKAC | VPTQLDSVAMLYL NDQSTWLKNYQE MITVVG | G | |
| B4YYD6 | grow_factors | 30 | 3 | 6 | 33 | 1 | — | 0 | RPIETLVDIFQEY PDEIEYIFKPSCV PLMR | GGC | NDEGLE | VPTEEFNITMQIMR IKPHQGQHIGEMSF LQHNK | E | |
| B5BNX6 | grow_factors | 28 | 3 | 32 | 31 | 1 | — | 0 | SKKPLHVNFKD MGWDDWIIAPLE YEAYH | EGL | EFPLRSHLEPTNH AVIQTLMNSMDP ETTPPTC | VPTRLSPISILYTDS ANNVVYKQYEDM VVES | G | |
| B5BU86 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| B5DEK7 | grow_factors | 30 | 3 | 6 | 33 | 1 | — | 0 | RPIETLVDIFQYP DEIEYIFKPSCVP LMR | AGC | NDEALE | VPTSESSNVTMQIM RIKPHQSQHIGEMS FLQHSR | E | |
| B5FW32 | grow_factors | 28 | 3 | 31 | 31 | 1 | — | 0 | RRHSLYVDFSDV GWNDWIVAPPG YQAF | HGD | PFPLADHLNSTNH AIVQTLVNSVNSS IPKAC | VPTELSAISMLYLD EYDKVVLKNYQE MVVEG | G | |
| B5FW51 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| B5X135 | grow_factors | 28 | 3 | 31 | 31 | 1 | — | 0 | RRHALYVDFSDV GWNDWIVAPPG YQAYY | HGE | PFPLADHLNSTNH AIVQTLVNSVNTN IPKAC | VPTELSAISMLYLD EHDKVVLKNYQE MVVEG | G | |
| B6DXF1 | grow_factors | 30 | 3 | 6 | 33 | 1 | — | 0 | RALERLVDIVSV YPSEVEHMFSPS CVSLLR | TGC | GDENLH | VPVETVNVTMQLL KIRSGDRPSYVELT FSQHVR | E | |
| B6LU94 | grow_factors | 28 | 3 | 32 | 31 | 1 | — | 0 | KRRKLYIRFKDV GWDDWIIAPQGY MAYH | SGE | PFPLNEHLNGTNH AVIQTLVNSLTPD SVPPAC | APTKWSSISMLYFD NNGDVVLRQYED MVVDG | G | |
| B6LUA7 | grow_factors | 28 | 3 | 32 | 31 | 1 | — | 0 | KRRKLYIRFKDV GWDDWIIAPQGY MAYH | SGE | PFPLNEHLNGTNH AVIQTLVNSLTPD SVPPAC | APTKWSSISMLYFD NNGDVVLRQYED MVVDG | G | |
| B6NUD9 | grow_factors | 28 | 3 | 32 | 31 | 1 | — | 0 | MRRSLQVSFHDL GWDDWIIAPTNY DAHY | AGA | SFPLRSHLEPTNH AIVQTLVNSMNPR AVEKVC | VPTKLSPISILYIDG KDTVVYKKYDDM VADQ | G | |
| B6NVZ7 | grow_factors | 28 | 3 | 32 | 31 | 1 | — | 0 | RRHSLYVDFSDV GWNDWIVAPPG YQAYY | HGE | PFPLADHLNSTNH AIVQTLVNSVNPL AVPKAC | VPTDLSPISMLYLN ENDQVVLKNYQD MVVEG | G | |
| B8NVZ8 | grow_factors | 28 | 3 | 32 | 31 | 1 | — | 0 | RRLHLYVDFREV GWQDWIIAPPGY HAYY | AGD | PFPLNEKLNGTNH AIIQTLVNTVAPA AVPRPC | APTALSAISMLYFD ESGNVVLRQYEDM VVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| B6P6C2 | grow_factors | 28 | 3 | 32 | 31 | 1 | — | 0 | MRRSLQVSFHDLGWDDWIIAPTNYDAHY | AGA | SFPLRSHLEPTNHAIVQTLVNSMNPRAVEKVC | VPTKLSPISILYIDGKDTVVYKKYDDMVADQ | G | |
| B6SCR4 | grow_factors | 28 | 3 | 32 | 31 | 1 | — | 0 | QRHPLYVDFSEVGWNDWIVAPPGYQGFY | KGE | PFHIADHLNTTNHAIVQTLMNSVNPNNVPPAC | VPTTLDAISMLFMNEHSKVVLKNYQDMVVDG | G | |
| B6SCR5 | grow_factors | 28 | 3 | 32 | 31 | 1 | — | 0 | QRHPLYVDFSEVGWNDWIVAPPGYQGFY | KGE | PFPLADHLNTTNHAIVQTLMNSVNPNNVPPAC | VPTTLDAISMLFMNEHSKVVLKNYQDMVVDG | G | |
| B6VAE7 | grow_factors | 30 | 3 | 6 | 36 | 1 | — | 0 | KPRETWRIGDEYPSLISQRFSPPCVSVMR | GGC | NDESLE | VPTEEANITMEVMSVSVSSTGSNPGMQNMQFVEHLR | D | |
| B6VAE8 | grow_factors | 30 | 3 | 6 | 36 | 1 | — | 0 | KPRETWRISDEYPSLTSQRFSPPCVSVMR | GGC | NDESLE | VPTEEANITMEVMSVSVSSTDSNPGMQNMQFVEHLH | D | |
| B6ZHB6 | grow_factors | 28 | 3 | 32 | 31 | 1 | — | 0 | HRRRLHVNFKEMGWDDWIIAPLEYDAYH | DGA | DFPIRSHLEPTNHAIIQTLINSMDPESTPPTC | VPTRLSPISILYIDSANNWYKQYEDMVVES | G | |
| B7NZI8 | grow_factors | 28 | 3 | 32 | 31 | 1 | — | 0 | SRKALHVNFKDMGWDDWIIAPLEYEAFH | EGL | EFPLRSHLEPTNHAVIQTLMNSMDPESTPPTC | VPTRLSPISILFIDSANNWYKQYEDMVVES | G | |
| B7QHX4 | grow_factors | 28 | 3 | 32 | 31 | 1 | — | 0 | RRFPLRVEFSHVGWNDWIVAPPSYEAYY | HGV | PFPLPDHLNGTNHAIVQTLVNSMRAGGVPNAC | VPTELSPVSLLYVDAFERVLKNYQDMVVEG | G | |
| B7ZPR8 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKWLKNYQEMVVEG | G | |
| B7ZQN5 | grow_factors | 28 | 3 | 32 | 31 | 1 | — | 0 | SKKPLHVNFKELGWDDWIIAPLEYEAHH | EGV | DFPLRSHLEPTNHAIIQTLMNSMNPGSTPPSC | VPTKLTPISILYIDAGNNWYKQYEDMVVES | G | |
| B7ZRN7 | grow_factors | 28 | 3 | 31 | 31 | 1 | — | 0 | RRHPLYVDFSDVGWNDWIVAPPGYHAFY | HGE | PFPLADHLNSTNHAIVQTLVNSVNTNIPKAC | VPTELSAISMLYLDENEKWLKNYQDMVVEG | G | |
| B8A4Z0 | grow_factors | 30 | 3 | 6 | 33 | 1 | — | 0 | RPREMLVEIQQEYPDDTEHIFIPSCWLTR | AGC | NDEMME | TPTVTYNITLEIKRLKPLRHQGDIFMSFAEHSE | Q | |
| B8XA45 | grow_factors | 28 | 3 | 31 | 31 | 1 | — | 0 | RRHALYVDFSDVGWNDWIVAPPGYQAYY | HGE | PFPLADHLNSTNHAIVQTLVNSVNTNIPKAC | VPTELSAISMLYLDEHDKVVLKNYQEMVVEG | G | |
| B8XRZ3 | grow_factors | 28 | 3 | 31 | 31 | 1 | — | 0 | RRHALYVDFSDVGWNDWIVAPPGYQAYY | HGE | PFPLADHLNSTNHAIVQTLVNSVNTNIPKAC | VPTELSAISMLYLDEHDKVVLKNYQEMVVEG | G | |
| B8YPW1 | grow_factors | 28 | 3 | 32 | 31 | 1 | — | 0 | QRRPLFVDFAEVGWSDWIVAPPGYEAYF | QGD | PFPLADHLNGTNHAIVQTLVNSVDPALVPKAC | IPTQLSPISMLYMDEHNQVALKNYQDMMVMG | G | |
| B9EJ18 | grow_factors | 28 | 3 | 32 | 31 | 1 | — | 0 | KKHELYVSFRDLGWQDWILAPEGYAAFY | DGE | SFPLNAHMNATNHAIVQTLVHLMFPDHVPKPC | APTKLNAISVLYFDDSSNVILKKYRNMVVRS | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| C0HBA5 | grow_factors | 28 | 3 | 31 | 31 | 1 | — | 0 | RRHALYVDFSDVGWNEWIVAPPGYHAFY | HGE | PFPLADHLNSTNHAIVQTLVNSVNSNIPRAC | VPTELSPISLLYLDEYEKVILKNYQDMVVEG | G | |
| C0K3N1 | grow_factors | 30 | 3 | 6 | 34 | 1 | — | 0 | QPRETLVSILEEYPDKISKIFRPSCVAVLR | GGC | SDESLT | TSVGERITVELQVMQVTPKTLSSKIKVMKFREHTA | E | |
| C0K3N2 | grow_factors | 30 | 3 | 6 | 34 | 1 | — | 0 | QTRETLVSILEEHPHEISHLFKPSCVTVLR | GGC | SDESLT | TSTGKRSVGREIMRVDPHKETSKIEVMQFTEHTD | E | |
| C0K3N3 | grow_factors | 30 | 3 | 6 | 34 | 1 | — | 0 | QTREMLVSILDEYPSEVAHLFRPSCVTVLR | GGC | TDESLT | TATGKRSVGREIMRVDPRKGTSKIEVMQFTEHTE | E | |
| C0K3N4 | grow_factors | 30 | 3 | 6 | 33 | 1 | — | 0 | RPIETMVDIFQEYPDEVEYILKPPCVALMR | GGC | NDEALE | VPTELYNVTMEIMKLKPYQSQHHPMSFQQHSK | E | |
| C0K3N5 | grow_factors | 30 | 3 | 6 | 33 | 1 | — | 0 | RPVETMVDIFQEYPDEVEYIFKPSCVALMR | GGC | NDEALE | VPTEVYNVTMEIMKLKPFQSQHHPMSFQQHSK | E | |
| C0K3N6 | grow_factors | 30 | 3 | 6 | 34 | 1 | — | 0 | QTRETLVPILKEYPDEVSHLFKPSCVPVLR | GGC | SDESLT | TATGKHSVGREIMRVDPHKGTSKMEVMQFKEHTA | E | |
| C0K3N7 | grow_factors | 30 | 3 | 6 | 33 | 1 | — | 0 | RPIETMVDIFQDYPDEVEYILKPPCVALMR | GGC | NDEALE | VPTELYNVTMEIMKLKPYQSQHHPMSFQQHSK | E | |
| C0K3N8 | grow_factors | 30 | 3 | 6 | 34 | 1 | — | 0 | QARETLVPILQEYPDEISDIFRPSCVAVLR | SGC | TDESLK | TPVGKHTVDLQIMRVNPRITQSSKMEVMKFTEHTA | E | |
| C0K3N9 | grow_factors | 30 | 3 | 6 | 34 | 1 | — | 0 | QTRETLVSILQEHPDEISDIFRPSCVAVLR | SGC | TDESMK | TPVGKHTADIQIMRMNPRTHSSKMEVMKFMEHTA | E | |
| C1BJY6 | grow_factors | 30 | 3 | 6 | 33 | 1 | — | 0 | RPRELLVEILQEYPEEVEHIYIPSCWLTR | AGC | NDEMLQ | TPTSTHNITMEIKRIKPQRQQNDIFMSFTEHNS | E | |
| C3KGR8 | grow_factors | 30 | 3 | 6 | 33 | 1 | — | 0 | RPMEQLVDVEQEYPGEVEYIYMPACVPLWR | SGC | MDENLE | QASLKSNITLEVMRIHPMISMHHVLLTFVEHQR | E | |
| C3PT60 | grow_factors | 28 | 3 | 32 | 31 | 1 | — | 0 | SRKALHVNFKDMGWDDWIIAPLEYEAFH | EGL | EFPLRSHLEPTNHAVIQTLMNSMDPESTPPTC | VPTRLSPISILFIDSANNVYKQYEDMVVES | G | |
| C3SB59 | grow_factors | 28 | 3 | 31 | 31 | 1 | — | 0 | KRHPLYVDFSDVGWNDWIAPPGYHAFY | HGE | PFPLADHLNSTNHAIVQTLVNSVNSKIPKAC | VPTELSAISMLYLDENEKVVLKNYQDMVVEG | G | |
| O13107 | grow_factors | 28 | 3 | 31 | 31 | 1 | — | 0 | RRHALYVDFSDVGWNDWIVAPPGYQAYY | HGE | PFPLADHLNSTNHAIVQTLVNSVNTNIPKWC | VPTELSAISMLYLDETDRVVLKNYQEMVVEG | G | |
| O13108 | grow_factors | 28 | 3 | 31 | 31 | 1 | — | 0 | RRHALYVDFSDVGWNEWIVAPPGYHAFY | HGE | PFPLPDHLNSTNHAIVQTLVNSVNSNIPKAC | IPTELSPISLLYLDEYEKVILKNYQDMVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| O13109 | grow_factors | 28 | 3 | 31 | 31 | 1 | — | 0 | RRHSLYVDFSDVGWNDWIAPPGYHAFY | QGE | PFPLADHLNSTTNAMVQTLVNSVNSNIPRAC | VPTDLSPVSLLYLDEYERVILKNYQDMVVEG | G | |
| O19006 | grow_factors | 28 | 3 | 31 | 31 | 1 | — | 0 | KRHPLYVDFSDVGWNDWIAPPGYHAFY | HGE | PFPLADHLNSTNHAIVQTLVNSVNSKIPKAC | VPTELSAISMLYLDENEKVLKNYQDMVVEG | G | |
| O42303 | grow_factors | 28 | 3 | 32 | 31 | 1 | — | 0 | NRKQLHVNFKEMGWDDWIIAPLEYEAFH | DGV | DFPIRSHLEPTNHAIIQTLMNSMDPRSTPPTC | VPTRLSPISILYIDSANNVVYKQYEDMVVES | G | |
| O42571 | grow_factors | 30 | 3 | 6 | 33 | 1 | — | 0 | QVREILVDIFQEYPDEVEYIFKPSCVPLMR | AGC | NDESLE | VPTECYNITMQIMKIKPHISQHIMDMSFQQHSQ | E | |
| O42572 | grow_factors | 30 | 3 | 6 | 33 | 1 | — | 0 | QVREILVDIFQEYPDEVEYIFKPSCVPLMR | AGC | NDESLE | VPTECYNITMQIMKIKPHISQHIMDMSFQQHSQ | E | |
| O46564 | grow_factors | 28 | 3 | 31 | 31 | 1 | — | 0 | KRHPLYVDFSDVGWNDWIAPPGYHAFY | HGE | PFPLADHLNSTNHAIVQTLVNSVNSKIPKAC | VPTELSAISMLYLDENEKVLKNYQDMVVEG | G | |
| O46576 | grow_factors | 28 | 3 | 31 | 31 | 1 | — | 0 | RRHALYVDFSDVGWNDWIAPPGYQAFY | HGD | PFPLADHFNSTNHAIVQTLVNSVNSSIPKAC | VPTELSAISMLYLDEYDKVVLKNYQEMVVEG | G | |
| O57573 | grow_factors | 28 | 3 | 31 | 31 | 1 | — | 0 | RRHALYVDFSDVGWNEWIAPPGYHAFY | HGE | PFPLPDHLNSTNHAIVQTLVNSVNSNIPKAC | IPTELSPISLLYLDEYEKVILKNYQQDMVVEG | G | |
| O57574 | grow_factors | 28 | 3 | 31 | 31 | 1 | — | 0 | RRHALYVDFSDVGWNDWIAPPGYQAYY | HGE | PFPLADHLNSTNHAIVQTLVNSVNTNIPKAC | VPTELSAISMLYLDETDRVVLKNYQQEMVVEG | G | |
| O73682 | grow_factors | 30 | 3 | 6 | 33 | 1 | — | 0 | KTRELLVDIIQEYPDEIEHTYIPSCVVLMR | AGC | NDEALE | VPTETRNVTMEVLRVKQRVSQHNFQLSFTEHTK | E | |
| O73682-2 | grow_factors | 30 | 3 | 6 | 33 | 1 | — | 0 | KTRELLVDIIQEYPDEIEHTYIPSCVVLMR | AGC | NDEALE | VPTETRNVTMEVLRVKQRVSQHNFQLSFTEHTK | E | |
| O73818 | grow_factors | 28 | 3 | 31 | 31 | 1 | — | 0 | RRHSLYVDFSDVGWNDWIAPPGYQAFY | HGD | PFPLADHLNSTNHAIVQTLVNSVNASIPKAC | VPTELSAISMLYLDEYDKVVLKNYQEMVVEG | G | |
| O76851 | grow_factors | 28 | 3 | 32 | 31 | 1 | — | 0 | QRQDLYVDFSDVNWDDWIAPHGYHAFY | NGE | PFPLAEYMNATNHAIVQTLVNSVDPSLTPKPC | VPTELSPIAMLYVDECELVLKTYQQMAVEG | G | |
| O77643 | grow_factors | 30 | 3 | 6 | 33 | 1 | — | 0 | RPIETLVDIFQEYPDEIEFIFKPSCVPLMR | GGC | NDESLE | VPTEEFNITMQIMRIKPHQSQHIGEMSFLQHNK | E | |
| O88911 | grow_factors | 30 | 3 | 6 | 14 | 1 | — | 0 | RPIETLVDIFQEYPDEIEYIFKPSCVPLMR | AGC | NDEALE | VPTSESNVTMQTCK | S | |
| O93369 | grow_factors | 28 | 3 | 31 | 31 | 1 | — | 0 | RRHALYVDFSDVGWNEWIAPPGYHAFY | HGE | PFPLPDHLNSTNHAIVQTLVNSVNSNIPKAC | IPTELSPISLLYLDEYEKVILKNYQDMVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| O93573 | grow_factors | 28 | 3 | 32 | 31 | 1 | — | 0 | SRKPLHVNFKEL GWDDWIIAPLDY EAYH | EGV | DFPLRSHLEPTNH AIIQTLMNSMDPE STPSC | VPSKLSPISILYIDS GNNVVYKQYEDM VVET | G | |
| O96504 | grow_factors | 28 | 3 | 32 | 31 | 1 | — | 0 | RRHSLYVDFSDV GWNDWIVAPPG YQAYY | HGE | PFPLADHLNSTNH AIVQTLVNSVNPL AVPKAC | VPTDLSPISMLYLN ENDQVVLKNYQD MVVEG | G | |
| O97390 | grow_factors | 28 | 3 | 32 | 31 | 1 | — | 0 | RRKELNVDFKAV GWNDWIFAPPG YNAYY | DGS | HWPYDDHMNVT NHAIVQDLVNSID PRAAPKPC | VPTELSSLSLLYTD EHGAVVLKVYQD MVVEG | G | |
| P07713 | grow_factors | 28 | 3 | 32 | 31 | 1 | — | 0 | RRHSLYVDFSDV GWDDWIVAPLG YDAYY | HGK | PFPLADHFNSTNH AVVQTLVNNMNP GKVPKAC | VPTQLDSVAMLYL NDQSTVLKNYQE MTVVG | G | |
| P12643 | grow_factors | 28 | 3 | 31 | 31 | 1 | — | 0 | KRHPLYVDFSDV GWNDWIVAPPG YHAFY | HGE | PFPLADHLNSTNH AIVQTLVNSVNSK IPKAC | VPTELSAISMLYLD ENEKVVLKNYQD MVVEG | G | |
| P12644 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| P15691 | grow_factors | 30 | 3 | 6 | 33 | 1 | — | 0 | RPIETLVDIFQEY PDEIEFIFKPSCVP LMR | GGC | NDESLE | VPTEEFNITMQIMR IKPHQSQHIGEMSF LQHNK | E | |
| P15691-2 | grow_factors | 30 | 3 | 6 | 33 | 1 | — | 1 | RPIETLVDIFQEY PDEIEFIFKPSCVP LMR | GGC | NDESLE | VPTEEFNITMQIMR IKPHQSQHIGEMSF LQHNK | E | |
| P15692 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-10 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-2 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSFLI KQHNK | E | |
| P15692-3 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-4 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-5 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-6 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-7 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| P15692-8 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P15692-9 | grow_factors | 30 | 3 | 6 | 33 | 1 | — | 1 | HPIETLVDIFQEY PDEIEYIFKPSCV PLMR | GGC | NDEGLE | VPTEESNITMQIMR IKPHQGQHIGEMSF LQHNK | E | |
| P16612 | grow_factors | 30 | 3 | 6 | 33 | 1 | — | 0 | RPIETLVDIFQEY PDEIEYIFKPSCV PLMR | AGC | NDEALE | VPTSESNVTMQIM RIKPHQSQHIGEMS FLQHSR | E | |
| P16612-2 | grow_factors | 30 | 3 | 6 | 33 | 1 | — | 0 | RPIETLVDIFQEY PDEIEYIFKPSCV PLMR | AGC | NDEALE | VPTSESNVTMQIM RIKPHQSQHIGEMS FLQHSR | E | |
| P16612-3 | grow_factors | 30 | 3 | 6 | 33 | 1 | — | 0 | RPIETLVDIFQEY PDEIEYIFKPSCV PLMR | AGC | NDEALE | VPTSESNVTMQIM RIKPHQSQHIGEMS FLQHSR | E | |
| P16612-4 | grow_factors | 30 | 3 | 6 | 33 | 1 | — | 0 | RPIETLVDIFQEY PDEIEYIFKPSCV PLMR | AGC | NDEALE | VPTSESNVTMQIM RIKPHQSQHIGEMS FLQHSR | E | |
| P18075 | grow_factors | 28 | 3 | 32 | 31 | 1 | — | 0 | KKHELYVSFRDL GWQDWIIAPEGY AAFY | EGE | AFPLNSYMNATN HAIVQTLVHFINP ETVPKPC | APTQLNAISVLYFD DSSNVILKKYRNM VVRA | G | |
| P20722 | grow_factors | 28 | 3 | 32 | 31 | 1 | — | 0 | KKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| P21274 | grow_factors | 28 | 3 | 31 | 31 | 1 | — | 0 | KRHPLYVDFSDV GWNDWIVAPPG YHAFY | HGE | PFPLADHLNSTNH AIVQTLVNSVNSK IPKAC | VPTELSAISMLYLD ENEKVLKNYQDM VVEG | G | |
| P21275 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVLKNYQEM VVEG | G | |
| P22003 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| P22004 | grow_factors | 28 | 3 | 32 | 31 | 1 | — | 0 | RKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| P23359 | grow_factors | 28 | 3 | 32 | 31 | 1 | — | 0 | KKHELYVSFRDL GWQDWIIAPEGY AAFY | EGE | AFPLNSYMNATN HAIVQTLVHFINP DTVPKPC | APTQLNAISVLYFD DSSNVILKKYRNM VVRA | G | |
| P25703 | grow_factors | 28 | 3 | 31 | 31 | 1 | — | 0 | RRHPLYVDFSDV GWNDWIVAPPG YHAFY | HGE | PFPLADHLNSTNH AIVQTLVNSVNTN IPKAC | VPTELSAISMLYLD ENEKVLKNYQD MVVEG | G | |
| P26617 | grow_factors | 30 | 3 | 6 | 33 | 1 | — | 0 | RPIEMLVDIFQEY PDEIEYIFKPSCV PLMR | GGC | NDESLE | VPTEEFNITMQIMR IKPHQGQHIGEMSF LQHSK | E | |
| P30884 | grow_factors | 28 | 3 | 31 | 31 | 1 | — | 0 | RRHPLYVDFSDV GWNDWIVAPPG YHAFY | HGE | PFPLADHLNSTNH AIVQTLVNSVNTN IPKAC | VPTELSAISMLYLD ENEKVVLKNYQD MVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| P30885 | grow_factors | 28 | 3 | 31 | 31 | 1 | — | 0 | RRHSLYVDFSDVGWNDWIAPPGYQAFY | HGD | PFPLADHLNSTNHAIVQTLVNSVNSSIPKAC | VPTELSAISMLYLDEYDKVVLKNYQEMVVEG | G | |
| P35621 | grow_factors | 28 | 3 | 32 | 31 | 1 | — | 0 | KPRRLYIDFKDVGWQDWIIAPQGYLANY | HGE | PFPLSESLNGTNHAIIQTLVHSFDPKGTPQPC | VPIKLSPISMLYYDNNDNVVLRHYEDMVVDE | G | |
| P43026 | grow_factors | 28 | 3 | 32 | 31 | 1 | — | 0 | SRKALHVNFKDMGWDDWIIAPLEYEAFH | EGL | EFPLRSHLEPTNHAVIQTLMNSMDPESTPPTC | VPTRLSPISILFIDSANNVVYKQYEDMVVES | G | |
| P43027 | grow_factors | 28 | 3 | 32 | 31 | 1 | — | 0 | SRKALHVNFKDMGWDDWIIAPLEYEAFH | EGL | EFPLRSHLEPTNHAVIQTLMNSMDPESTPPTC | VPTRLSPISILFIDSANNVVYKQYEDMVVES | G | |
| P43028 | grow_factors | 28 | 3 | 32 | 31 | 1 | — | 0 | SRKPLHVNFKELGWDDWIIAPLEYEAYH | EGV | DFPLRSHLEPTNHAIIQTLMNSMDPGSTPSC | VPTKLTPISILYIDAGNNVVYKQYEDMMVVRA | G | |
| P43029 | grow_factors | 28 | 3 | 32 | 31 | 1 | — | 0 | SRKSLHVDFKELGWDDWIIAPLDYEAYH | EGV | DFPLRSHLEPTNHAIIQTLLNSMAPDAAPASC | VPARLSPISILYIDAANNVVYKQYEDMVVEA | G | |
| P43029-2 | grow_factors | 28 | 3 | 32 | 31 | 1 | — | 0 | SRKSLHVDFKELGWDDWIIAPLDYEAYH | EGV | DFPLRSHLEPTNHAIIQTLLNSMAPDAAPASC | VPARLSPISILYIDAANNVVYKQYEDMVVEA | G | |
| P48969 | grow_factors | 28 | 3 | 32 | 31 | 1 | — | 0 | KRKNLFVNFEDLDWQEWIIAPLGYVAFY | QGE | AFPLNGHANATNHAIVQTLVHHMSPSHVPQPC | APTKLSPITVLYYDDSRNVVLKKYKNMVVRA | G | |
| P48970 | grow_factors | 28 | 3 | 32 | 31 | 1 | — | 0 | QRHRLFVSFRDVGWENWIIAPMGYQAYY | DGE | PFPLGERLNGTNHAIIQTLVNSIDNRAVPKVC | APTKLSGISMLYFDNNENVVLRQYEDMVVEA | G | |
| P49001 | grow_factors | 28 | 3 | 31 | 31 | 1 | — | 0 | KRHPLYVDFSDVGWNDWIAPPGYHAFY | HGE | PFPLADHLNSTNHAIVQTLVNSVNSKIPKAC | VPTELSAISMLYLDENEKVVLKNYQDMVVEG | G | |
| P49003 | grow_factors | 28 | 3 | 32 | 31 | 1 | — | 0 | KKHELYVSFRDLGWQDWIIAPEGYAAFY | DGE | SFPLNAHMNATNHAIVQTLVHLMFPDHVPKPC | APTKLNAISVLYFDDSSNVILKKYRNMVVRS | G | |
| P49151 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHNK | E | |
| P49763 | grow_factors | 30 | 3 | 6 | 33 | 1 | — | 0 | RALERLVDVVSEYPSEVEHMFSPSCVSLLR | TGC | GDENLH | VPVETANVTMQLLKIRSGDRPSYVELTFSQHVR | E | |
| P49763-2 | grow_factors | 30 | 3 | 6 | 33 | 1 | — | 0 | RALERLVDVVSEYPSEVEHMFSPSCVSLLR | TGC | GDENLH | VPVETANVTMQLLKIRSGDRPSYVELTFSQHVR | E | |
| P49763-3 | grow_factors | 30 | 3 | 6 | 33 | 1 | — | 0 | RALERLVDVVSEYPSEVEHMFSPSCVSLLR | TGC | GDENLH | VPVETANVTMQLLKIRSGDRPSYVELTFSQHVR | E | |
| P49764 | grow_factors | 30 | 3 | 6 | 34 | 1 | — | 0 | RPMEKLVYILDEYPDEVSHIFSPSCVLLSR | SGC | GDEGLH | VPIKTANITMQILKIPPNRDPHFYVEMTFSQDVL | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| P50412 | grow_factors | 30 | 3 | 6 | 33 | 1 | — | 0 | RPIETLVDIFQEY PDEIEFIFKPSCVP LMR | GGC | NDESLE | VPTEEFNTMQIMR IKPHQSQHIGEMSF LQHNK | E | |
| P55106 | grow_factors | 28 | 3 | 32 | 31 | 1 | — | 0 | SKKPLHVNFKEL GWDDWIIAPLEY EAYH | EGV | DFPLRSHLEPTNH AIIQTLMNSMDPG STPPSC | VPTKLTPISILYIDA GNNVVYNEYEEM VVES | G | |
| P67860 | grow_factors | 30 | 3 | 6 | 33 | 1 | — | 0 | RPIETMVDIFQDY PDEVEYILKPPCV ALMR | GGC | NDEALE | VPTELYNVTMEIM KLKPYQSQHHPM SFQQHSK | E | |
| P67860-2 | grow_factors | 30 | 3 | 6 | 33 | 1 | — | 0 | RPIETMVDIFQDY PDEVEYILKPPCV ALMR | GGC | NDEALE | VPTELYNVTMEIM KLKPYQSQHHPM SFQQHSK | E | |
| P67860-3 | grow_factors | 30 | 3 | 6 | 33 | 1 | — | 0 | RPIETMVDIFQDY PDEVEYILKPPCV ALMR | GGC | NDEALE | VPTELYNVTMEIM KLKPYQSQHHPM SFQQHSK | E | |
| P67861 | grow_factors | 30 | 3 | 6 | 34 | 1 | — | 0 | QTRETLVSILQEH PDEISDIFRPSCV AVLR | SGC | TDESMK | TPVGKHTADIQIMR MNPRTHSSKMEV MKFMEHTA | E | |
| P67862 | grow_factors | 30 | 3 | 6 | 34 | 1 | — | 0 | QTRETLVPILKEY PDEVSHLFKPSC VPVLR | GGC | SDESLT | TATGKHSVGREIM RVDPHKGTSKMEV MQFKEHTA | E | |
| P67863 | grow_factors | 30 | 3 | 6 | 34 | 1 | — | 0 | QARETLVPILQE YPDEISDIFRPSC VAVLR | SGC | TDESLK | TPVGKHTVDLQIM RVNPRTQSSKMEV MKFTEHTA | E | |
| P67964 | grow_factors | 30 | 3 | 6 | 33 | 1 | — | 0 | RTIETLVQIFQEY PDEVEYIFRPSCV PLMR | AGC | GDEGLE | VPVDVYNVTMEIA RIKPHQSQHIAHMS FLQHSK | D | |
| P67965 | grow_factors | 30 | 3 | 6 | 33 | 1 | — | 0 | RTIETLVDIFQEY PDEVEYIFRPSCV PLMR | AGC | GDEGLE | VPVDVYNVTMEIA RIKPHQSQHIAHMS FLQHSK | D | |
| P67965-2 | grow_factors | 30 | 3 | 6 | 33 | 1 | — | 0 | RTIETLVDIFQEY PDEVEYIFRPSCV PLMR | AGC | GDEGLE | VPVDVYNVTMEIA RIKPHQSQHIAHMS FLQHSK | D | |
| P67965-3 | grow_factors | 30 | 3 | 6 | 33 | 1 | — | 0 | RTIETLVDIFQEY PDEVEYIFRPSCV PLMR | AGC | GDEGLE | VPVDVYNVTMEIA RIKPHQSQHIAHMS FLQHSK | D | |
| P67985-4 | grow_factors | 30 | 3 | 6 | 33 | 1 | — | 0 | RTIETLVDIFQEY PDEVEYIFRPSCV PLMR | AGC | GDEGLE | VPVDVYNVTMEIA RIKPHQSQHIAHMS FLQHSK | D | |
| P82475 | grow_factors | 30 | 3 | 6 | 34 | 1 | — | 0 | QARETLVSILQE YPDEISDIFRPSC VAVLR | SGC | TDESLK | TPVGKHTVDMQIM RVNPRTQSSKMEV MKFTEHTA | E | |
| P83906 | grow_factors | 30 | 3 | 6 | 33 | 1 | — | 0 | RPVETMVDIFQE YPDEVEYIFKPSC VALMR | GGC | NDEALE | VPTEMYNVTMEV MKLKPFQSQHIHP VSFQQHSK | E | |
| P83942 | grow_factors | 30 | 3 | 6 | 34 | 1 | — | 0 | QARETLVSILQE YPDEISDIFRPSC VAVLR | SGC | TDESLK | TPVGKHTVDLQIM RVNPRTQSSKMEV MKFTEHTA | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| P85857 | grow_factors | 28 | 3 | 32 | 31 | 1 | — | 0 | SKKALHVNFKEL GWDDWIIAPLDY EAYH | EGV | DFPLRSHLEPTNH AIIQTLMNSMDPN STPSC | VPTKLSPISILYIDS GNNVVYKQYEDM VVEQ | G | |
| P87373 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| P91706 | grow_factors | 28 | 3 | 32 | 31 | 1 | — | 0 | RRHSLYVDFSDV GWDDWIVAPLG YDAYY | HGK | PFPLADHFNSTNH AWQTLVNNMNP GKVPKAC | VPTQLDSVAMLYL NDQSTVVLKNYQE MTVVG | G | |
| P91720 | grow_factors | 28 | 3 | 32 | 31 | 1 | — | 0 | RRHSLYVDFQDV GWSDWIVAPPG YDAYY | HGK | QFPLADHLNSTNH AWQTLVNNLNPG KVPKAC | VPTQLEGISMLYLN DQRTVLKNYQD MTVVG | G | |
| Q00731 | grow_factors | 30 | 3 | 6 | 33 | 1 | — | 0 | RPIETLVDIFQEY PDEIEYIFKPSCV PLMR | AGC | NDEALE | VPTSESNITMQIMR IKPHQSQHIGEMSF LQHSR | E | |
| Q00731-2 | grow_factors | 30 | 3 | 6 | 33 | 1 | — | 0 | RPIETLVDIFQEY PDEIEYIFKPSCV PLMR | AGC | NDEALE | VPTSESNITMQI MRIKPHQSQHIGE MSFLQHSR | E | |
| Q00731-3 | grow_factors | 30 | 3 | 6 | 33 | 1 | — | 0 | RPIETLVDIFQEY PDEIEYIFKPSCV PLMR | AGC | NDEALE | VPTSESNITMQIMR IKPHQSQHIGEMSF LQHSR | E | |
| Q00731-4 | grow_factors | 30 | 3 | 6 | 40 | 1 | — | 0 | RPIETLVDIFQEY PDEIEYIFKPSCV PLMR | AGC | NDEALE | VPTSESNITMQVGT CGTGDGAGAGGG RRTVQGGALEGC L | L | |
| Q04906 | grow_factors | 28 | 3 | 32 | 31 | 1 | — | 0 | KKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| Q06826 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| Q07G81 | grow_factors | 30 | 3 | 6 | 33 | 1 | — | 0 | QVREILVDIFQEY PDEVEYIFKPSCV PLMR | AGC | NDESLE | VPTESYNITMQIMK IKPHISQHIMDMSF QQHSQ | E | |
| Q0P6N0 | grow_factors | 28 | 3 | 31 | 31 | 1 | — | 0 | QRHPLYVDFTDV GWNDWIVAPPG YHAFY | TGV | PYPIAKHLNATNH AIVQTIMNTVDSN VPNAC | IPTTLNPISILSLNEF DKVVLKNYKDMVI EG | G | |
| Q0QY10 | grow_factors | 30 | 3 | 6 | 33 | 1 | — | 0 | RPREMLVEIQQE YPDDTEHIFIPSC WLTR | AGC | NDEMME | TPTVTYNITLEIKRL KPLRHQGDIFMSFA EHSE | Q | |
| Q17JZ3 | grow_factors | 28 | 3 | 32 | 31 | 1 | — | 0 | QRRPLYVDFSDV GWSDWIVAPPG YEAYY | HGD | QFPIADHLNTTNH AIVQTLVNSINPSL APKAC | VPTQLSSISMLYLN EQNKVVLKNYQD MTVVG | G | |
| Q19T09 | grow_factors | 30 | 3 | 6 | 33 | 1 | — | 0 | RPIETLVOIFQEY PDEIEFIFKPSCVP LMR | GGC | NDESLE | VPTEEFNITMQIMR IKPHQSQHIGEMSF LQHNK | E | |
| Q1ANK8 | grow_factors | 30 | 3 | 6 | 33 | 1 | — | 0 | RPREMLVEIQQE YPDDTEHIFIPSC WLTR | AGC | NDEMME | TPTVTYNITLEIKRL KPLRHQGDIFMSFA EHSE | Q | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q1ECU5 | grow_factors | 30 | 3 | 6 | 33 | 1 | — | 0 | RPREMLVEIQQEYPDDTEHIFIPSCWLTR | AGC | NDEMME | TPTVTYNITLEIKRLKPLRHQGDIFMSFAEHSE | Q | |
| Q1PHR6 | grow_factors | 28 | 3 | 32 | 31 | 1 | — | 0 | KKRSLWSFRELGWQDWIIAPDGYSAFY | NGE | SFPLNAHMNATNHAIVQTLVHLMDPEAVPKPC | APTKLNAISVLYFDDSSNVILKKYRNMIVKS | G | |
| Q1PHR7 | grow_factors | 28 | 3 | 32 | 31 | 1 | — | 0 | KRHELYVDFNDVGWNDWIVAPPGYHAFY | HGE | PFPIAEHLNSTNHAIVQTLVNSVSPDSVPKAC | VPTDLSPISMLYLDEFDKVVLKNYQDMVVEG | G | |
| Q1WKY6 | grow_factors | 28 | 3 | 32 | 31 | 1 | — | 0 | RRHSLYVDFSDVGWDDWIVAPLGYDAYY | HGK | PFPLADHFNSTNHAVVQTLVNNMNPGKVPKAC | VPTQLDSVAMLYLNDQSTVVLKNYQEMTVVG | G | |
| Q1WKY7 | grow_factors | 28 | 3 | 32 | 31 | 1 | — | 0 | RRHSLYVDFSDVGWDDWIVAPLGYDAYY | HGK | PFPLADHFNSTNHAVVQTLVNNMNPGKVPKAC | VPTQLDSVAMLYLNDQSTVVLKNYQEMTVVG | G | |
| Q1WKY8 | grow_factors | 28 | 3 | 32 | 31 | 1 | — | 0 | RRHSLYVDFSDVGWDDWIVAPLGYDAYY | HGK | PFPLADHFNSTNHAVVQTLVNNMNPGKVPKAC | VPTQLDSVAMLYLNDQSTVVLKNYQEMTVVG | G | |
| Q25211 | grow_factors | 28 | 3 | 32 | 31 | 1 | — | 0 | QRRPLFVDFADVGWSDWIVAPHGYDAYY | QGD | PFPLSDHLNGTNHAIVQTLVNSVNPAAVPKAC | VPTQLSSISMLYMDEVNNVVLKNYQDMMVVG | G | |
| Q264B8 | grow_factors | 28 | 3 | 32 | 31 | 1 | — | 0 | RRHPLYVDFREVGWDDWIVAPPGYEGWY | HGD | PFPLSAHMNSTNHAVVQTLMNSMNPGLVPKAC | IPTQLTSISMLYLDEESKVVLKNYHEMAVVG | G | |
| Q27W10 | grow_factors | 28 | 3 | 32 | 31 | 1 | — | 0 | QRQALHVSFRKLRWQDWVIAPEGYSAFY | SGE | SFPLNANMNATNHAIVQTLVHLMNPKTVPKPC | APTELSPISVLYFDQDNNVVLKKYNKMVVKA | G | |
| Q29607 | grow_factors | 28 | 3 | 32 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q2KJH1 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q2KT33 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEA | G | |
| Q2NKW7 | grow_factors | 28 | 3 | 32 | 31 | 1 | — | 0 | SRKALHVNFKDMGWDDWIIAPLEYEAFH | EGL | EFPLRSHLEPTNHAVIQTLMNSMDPESTPPTC | VPTRLSPISILFIDSANNVYKQYEDMVVES | G | |
| Q2VEW5 | grow_factors | 28 | 3 | 31 | 31 | 1 | — | 0 | RRHPLYVDFSDVGWNDWIVAPPGYHAFY | QGD | PFPLTDHLNSTNHAIVQTLVNSVNSSIPRAC | VPTELSAISMLYLDEYDKVVLKNYQEMVVEG | G | |
| Q2WBX0 | grow_factors | 28 | 3 | 32 | 31 | 1 | — | 0 | RRHPLYVDFSDVGWDDWIVAPPGYRAYF | NGE | GFPLPEYTNATNHAIVQTLVHSVNPEAVPRPC | VPTELSPISMLYVDEHDKVTLKNYQDMVVVG | G | |
| Q330H7 | grow_factors | 28 | 3 | 32 | 32 | 1 | — | 0 | RRKRMYVDFRLLGWSDWIIAPQGYDAYL | EGE | KYPIDNYLRPTNHATVQTIVNSLDPSIAPKAC | TPNELSPISILYTEDGSNNVVYKNYKDMVVER | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q330KB | grow_factors | 30 | 3 | 6 | 34 | 1 | — | 0 | QTREMLVPILKE YPNEVSHLFKPS CVPVLR | GGC | SDESLT | TATGKRSVGREVM RVDPHKGTSKIEV MQFKEHTA | E | |
| Q38KY2 | grow_factors | 30 | 3 | 6 | 33 | 1 | — | 0 | RPRELLVDIYQE YPEEIEHTYIPSC WLMR | GGC | NDEALE | VPVATRNVTLEVK RVKLHVTQHNFLIS FTEHTS | D | |
| Q3LSL9 | grow_factors | 28 | 3 | 32 | 31 | 1 | — | 0 | RRHNLYVDFSDV GWNDWIAPPG YQAYY | HGE | PFPLADHLNSTNH AIVQTLVNSVNPQ LVPKAC | VPTELSPISMLYLD EADKVVLKNYQD MVVEG | G | |
| Q3LSM3 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVYKQYEDMV VES | G | |
| Q3ULR1 | grow_factors | 28 | 3 | 31 | 31 | 1 | — | 0 | RRHSLYVDFSDV GWNDWIAPPG YQAFY | HGD | PFPLADHLNSTNH AIVQTLVNSVNSS IPKAC | VPTELSAISMLYLD EYDKVVLKNYQE MVVEG | G | |
| Q3UXB2 | grow_factors | 28 | 3 | 32 | 31 | 1 | — | 0 | KKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| Q3V114 | grow_factors | 28 | 3 | 31 | 31 | 1 | — | 0 | KRHPLYVDFSDV GWNDWIAPPG YHAFY | HGE | PFPLADHLNSTNH AIVQTLVNSVNSQ IPKAC | VPTELSAISMLYLD ENEKVVLKNYQD MVVEG | G | |
| Q496P8 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD OSSNVILKKYRNM VVRS | G | |
| Q496P9 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| Q497W8 | grow_factors | 28 | 3 | 31 | 31 | 1 | — | 0 | KRHPLYVDFSDV GWNDWIAPPG YHAFY | HGE | PFPLADHLNSTNH AIVQTLVNSVNSK IPKAC | VPTELSAISMLYLD ENEKVVLKNYQD MVVEG | G | |
| Q4H2P7 | grow_factors | 28 | 3 | 32 | 31 | 1 | — | 0 | QRHSMWVDFEE MGWSDWVIAPR AFQSYR | AGE | PFPLSGKLNGTNH AMLMTMMNSVD PSNTPMPC | VPTRLSSVSMLYL DKKDNVVLRLYED MVVEA | G | |
| Q4JCQ2 | grow_factors | 28 | 3 | 32 | 31 | 1 | — | 0 | RKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| Q4LEV0 | grow_factors | 28 | 3 | 31 | 31 | 1 | — | 0 | RRHSLYVDFSDV GWNDWIAPPG YQAFY | HGD | PFPLADHLNSTNH AIVQTLVNSVNSS IPKAC | VPTELSAISMLYLD EYDKVVLKNYQE MVVEG | G | |
| Q4R5W6 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| Q4RLY8 | grow_factors | 30 | 3 | 6 | 34 | 1 | — | 0 | RITEKLVEWQEY PTEVEYITYSPSCV PLVR | AGC | GDEKLE | HPTTTNVTMQLL KIRPSEPHKEYVH MITVEHQT | E | |
| Q4RMK1 | grow_factors | 28 | 3 | 31 | 31 | 1 | — | 0 | RRHSLYVDFSDV GWNDWIAPPG YQAYY | HGD | PFPLADHLNSTNH AIVQTLVNSVNSN IPKAC | VPTELSAISMLYLD EHDKVVLKNYQE MVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q4RQB0 | grow_factors | 28 | 3 | 32 | 31 | 1 | — | 0 | KKHELYVSFRDLGWQDWILAPEGYAAFY | DGE | AFPLNAHMNATNHAIVQTLVHLMFPDNVPKPC | APTKLNAISVLYFDDSSNVILKKYRNMVVRS | G | |
| Q4SCW7 | grow_factors | 30 | 3 | 6 | 34 | 1 | — | 0 | QPMEQLVDVEQEYPGELEYTYMPSCVPLKR | SGC | GDEHLE | QPTLESNVTLQVIKIQQTWSMHYVEITFVEHQR | E | |
| Q4SSW6 | grow_factors | 28 | 3 | 32 | 31 | 1 | — | 0 | SRKALHVNFKELGWDDWILAPLDYEAHH | EGV | DFPLRSHLEPTNHAIIQTLMNSMDPNSTPPSC | VPTKLSPISILYIDSGNNVVYKQYEDMVVEQ | G | |
| Q4SV40 | grow_factors | 30 | 3 | 6 | 33 | 1 | — | 0 | QPRDVLVDVFQAYPEDTEHIYTPSCVVLKR | GGC | NDEGKE | VPAESRNVTLQLQRFRPRVIKEVVDLSFTEHVL | V | |
| Q4SZ19 | grow_factors | 28 | 3 | 32 | 31 | 1 | — | 0 | KARRLYIDFKDVGWQDWILAPQGYMANY | HGE | PFPLSDSLNGTNHAILQTLVHSLDPHGTPQPC | VPIRLSPISMLYYDNNDNVVLRHYQDMVVDE | G | |
| Q4U4G1 | grow_factors | 30 | 3 | 6 | 33 | 1 | — | 0 | KPRPMVFRVHDEYPTLTSQRFNPPCVTLMR | GGC | NDESLE | VPTEEANVTMQLMGASVSGGNGMQHLSFVEHKK | D | |
| Q4VBA3 | grow_factors | 28 | 3 | 32 | 31 | 1 | — | 0 | RKHELYVSFQDLGWQDWILAPKGYAANY | DGE | SFPLNAHMNATNHAIVQTLVHLMNPEYVPKPC | APTKLNAISVLYFDDNSNVILKKYRNMVVRA | G | |
| Q53XC5 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q53XY6 | grow_factors | 30 | 3 | 6 | 33 | 1 | — | 0 | RALERLVDVVSEYPSEVEHMFSPSCVSLLR | TGC | GDENLH | VPVETANVTMQLLKIRSGDRPSYVELTFSQHVR | E | |
| Q54OI2 | grow_factors | 30 | 3 | 6 | 33 | 1 | — | 0 | RTIETLVDIFQEYPDEVEYIFRPSCVPLMR | AGC | GDEGLE | VPVDVYNVTMEIARIKPHQSQHIAHMSFLQHSK | D | |
| Q54IS7 | grow_factors | 30 | 3 | 6 | 33 | 1 | — | 0 | RPIETLVDIFQEYPDEIEYIFKPSCVPLMR | AGC | NDEALE | VPTSESNVTMQIMRIKPHQSQHIGEMSFLQHSR | E | |
| Q544A5 | grow_factors | 30 | 3 | 6 | 34 | 1 | — | 0 | RPMEKLVYILDEYPDEVSHIFSPSCVLLSR | SGC | GDEGLH | VPIKTANITMQILKIPPNRDPHFYVEMTFSQDVL | E | |
| Q58E94 | grow_factors | 28 | 3 | 31 | 31 | 1 | — | 0 | RRHPLYVDFSDVGWNDWIVAPPGYHAFY | HGE | PFPLADHLNSTNHAIVQTLVNSVNTNIPKAC | VPTELSAISMLYLDENEKVVLKNYQDMVVEG | G | |
| Q58G88 | grow_factors | 28 | 3 | 32 | 33 | 1 | — | 0 | QRHSLYVSFREVGWQDWILAPMGYQAYF | SGE | PFPLNDRLNGTNHAIIQTLVNSMDPSSVPKVC | APTKLSAISMLYFDNDENVVLRQYEDMVVEA | G | |
| Q59FH5 | grow_factors | 30 | 3 | 6 | 33 | 1 | — | 1 | HPIETLVDIFQEYPDEIEYIFKPSCVPLMR | GGC | NDEGLE | VPTEESNTTMQIMRIKPHQGQHIGEMSFLQHNK | E | |
| Q5I4I9 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q5RHW5 | grow_factors | 30 | 3 | 6 | 33 | 1 | — | 0 | RPREMLVEIQQEYPDDTEHIFPSCWLTR | AGC | NDEMME | TPTVTYNITLEIKRLKPLRHQGDIFMSFAEHSE | Q | |
| Q5RKN7 | grow_factors | 28 | 3 | 32 | 31 | 1 | — | 0 | KPRRLYIDFKDVGWQDWIIAPQGYLANY | HGE | PFPLSESLNGTNHAILQTLVHSFDPKGTPQPC | VPIKLSPISMLYYDNNDNVVLRHYEDMVVDE | G | |
| Q5YJC3 | grow_factors | 28 | 3 | 32 | 32 | 1 | — | 0 | RRKRMYDFRLLGWSDWIIAPQGYDAYL | EGE | KYPIONYLRPTNHAIVQTIVNSLDPSIAPKAC | TPNELSPISILYTEDGSNNVVYKNYKDMVVER | G | |
| Q63434 | grow_factors | 30 | 3 | 6 | 34 | 1 | — | 0 | RPMEKLVYIADEHPNEVSHIFSPSCVLLSR | SGC | GDEGLH | VALKTANITMQILKIPPNRDPHSYVEMTFSQDVL | E | |
| Q64FZ6 | grow_factors | 30 | 3 | 6 | 33 | 1 | — | 0 | RPIETLVDIFQEYPDEIEYIFKPSCVPLMR | AGC | NDEALE | VPTSESNVTMQIMRIKPHQSQHIGEMSFLQHSR | E | |
| Q66KL4 | grow_factors | 28 | 3 | 32 | 31 | 1 | — | 0 | KKRRLYIDFKDVGWQNWVIAPRGYMANY | YGE | PYPLTEMLRGTNHAVLQTLVHSVEPESTPLPC | APTKLSPISMLYYDNNDNVVLRHYEDMVVDE | G | |
| Q68KG0 | grow_factors | 28 | 3 | 32 | 32 | 1 | — | 0 | SKKPLHVNFKDMGWDDWIIAPLEYEAYH | EGL | EFPLRSHLEPTNHAVIQTLMNSMDPETTPPTC | VPTRLSPISILYTDSANNVVYKQYEDMVVES | G | |
| Q6AYU9 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q6EH35 | grow_factors | 28 | 3 | 31 | 31 | 1 | — | 0 | KRHPLYVDFNDVGWNDWIAPPGYGAFY | HGE | PFPLADHLNTTNHAIVQTLVNSVNSKIPKAC | VPTELSAISMLYLDENEKVVLKNYQDMVVEG | G | |
| Q6H8S7 | grow_factors | 30 | 3 | 6 | 33 | 1 | — | 0 | RTREMLVDVFQEYPDEIEHTYIPSCWLMR | AGC | NDEALE | VPTETKNVTMEVIQVKQRVSQHHFLLSFTEHRK | E | |
| Q6H8S8 | grow_factors | 30 | 3 | 6 | 33 | 1 | — | 0 | RTREMLVDVFQEYPDEIEHTYIPSCVVLMR | AGC | NDEALE | VPTETKNVTMEVIQVKQRVSQHHFLLSFTEHRK | E | |
| Q6HA10 | grow_factors | 28 | 3 | 32 | 31 | 1 | — | 0 | SRKPLHVNFKELGWDDWIIAPLEYEAYH | EGV | DFPLRSHLEPTNHAIIQTLMNSMDPGSTPPSC | VPTKLTPISILYIDAGNNVVYKQYEDMVVES | G | |
| Q63S4 | grow_factors | 28 | 3 | 31 | 31 | 1 | — | 0 | QRQPLYVDFREVGWDDWIVAPPGYNAYF | QGE | PFPLADHLNSTNHAIVQTLVNSVNASIPRAC | VPTELSPISMLYMDEYEKVVLKNYQDMVVEG | G | |
| Q63S5 | grow_factors | 28 | 3 | 31 | 31 | 1 | — | 0 | RRHALYVDFREVGWNDWIVAPPGYHAYF | HGE | PFPLADHLNSTNHAIVQTLVNSVNASIPRAC | VPTELSPISMLYLDEYGKVVLKNYQDMVVEG | G | |
| Q63S6 | grow_factors | 28 | 3 | 31 | 31 | 1 | — | 0 | ARYPLYVDFSDVGWNDWIVAPPGYNAFF | QGE | HFPLPQHLNSTNHAIVQTLVNSVNPEVPRAC | IPTELTPIALLYLDEYEKVVLKNYQDMVVEG | G | |
| Q6J936 | grow_factors | 30 | 3 | 6 | 34 | 1 | — | 0 | QPRETLVSILEEYPGELAHIFRPSCVTALR | GGC | TDESLE | TATGKRSVGREIMRLSPHKGTSEKEVMQFTEHTD | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q6KF10 | grow_factors | 28 | 3 | 32 | 31 | 1 | — | 0 | SKKPLHVNFKEL GWDDWILAPLEY EAYH | EGV | DFPLRSHLEPTNH AIIQTLMNSMDPG STPSC | VPTKLTPISILYIDA GNNVYKQYEDM VVES | G | |
| Q6P4J4 | grow_factors | 28 | 3 | 32 | 31 | 1 | — | 0 | KKHELYVSFKDL GWQDWILAPEGY AAFY | EGE | AFPLNSYMNATN HAIVQTLVHFINP DTVPKPC | APTQLNPISVLYFD DSSNVILKKYRNM VVRA | G | |
| Q6PAF3 | grow_factors | 28 | 3 | 31 | 31 | 1 | — | 0 | RRHSLYVDFSDV GWNDWIAPPG YQAFY | HGD | PFPLADHLNSTNH AIVQTLVNSVNAS IPKAC | VPTELSAISMLYLD EYDKVVLKNYQE MVVEG | G | |
| Q6R5A5 | grow_factors | 30 | 3 | 6 | 45 | 1 | — | 0 | RPMPTTVRVSDE YPNDTSERYNPQ CVTLMR | GGC | NDESLE | VPTETSNVTMQLM VTSAHNGGSNDNG SGGGIGSGMREMS FLQHNK | E | |
| Q6RF65 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| Q6TVI2 | grow_factors | 30 | 3 | 6 | 41 | 1 | — | 0 | QPMKTPVKVSDE YPDNTNDRHSPP CVTLMR | GGC | NDESLE | VPTETSNVTMQIM TTSAYNDGGTSGGI SSGMREMSFLQHN K | E | |
| Q6WZM0 | grow_factors | 30 | 3 | 6 | 37 | 1 | — | 0 | HPIETLVDIFQEY PDEIEYIFKPSCV PLMR | GGC | NDEGLE | VPTEESNITMQVGI FGKWGKGGIGRGV TLWEQWPGR | L | |
| Q6XDQ0 | grow_factors | 28 | 3 | 31 | 31 | 1 | — | 0 | KRHPLYVDFENDV GWNDWIVAPPG YSAFY | HGE | PFPLADHLNSTNH AIVQTLVNSVNSK IPKAC | VPTELSAISMLYLD ENEKVVLKNYQD MVVEG | G | |
| Q6YLN3 | grow_factors | 30 | 3 | 6 | 33 | 1 | — | 0 | RPIETLVDIFQEY PDEIEYIFKPSCV PLMR | AGC | NDEALE | VPTSESNITMQIMR IKPHQSQHIGEMSF LQHSR | E | |
| Q75N54 | grow_factors | 28 | 3 | 31 | 31 | 1 | — | 0 | KRHALYVDFSDV GWNEWIVAPPG YHAFY | HGE | PFPLADHLNSTNH AIVQTLVNSVNSN IPRAC | VPTDLSPISLLYLD EYEKVILKNYQDM VVEG | G | |
| Q75RY1 | grow_factors | 28 | 3 | 32 | 31 | 1 | — | 0 | SRKPLHVDFKEL GWDDWILAPLDY EAYH | EGL | DFPLRSHLEPTNH AIIQTLLNSMAPD AAPASC | VPARLSPISILYIDA ANNVYKQYEDM VVEA | G | |
| Q75WK6 | grow_factors | 28 | 3 | 32 | 31 | 1 | — | 0 | RRHPLYVDFVDV GWNDWIVAPPG YDAFY | HGD | PFPLADHLNSTNH AIVQTLVYSTPN IVPKAC | VPTALSSISMLYLD EENKVVLKNYQD MAVLG | G | |
| Q772M8 | grow_factors | 30 | 3 | 6 | 33 | 1 | — | 0 | KPRPMVFRVHDE HPELTSQRFNPPC VTLMR | GGC | NDESLE | VPTEEANVTMQLM GASVSGGNGMQH LSFVEHKK | D | |
| Q78DH3 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q7BDH4 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q78DH5 | grow_factors | 28 | 3 | 31 | 31 | 1 | — | 0 | RRHALYVDFSDV GWNDWIVAPPG YQAFY | HGE | PFPLADHLNSTNH AIVQTLVNSVNN NIPKAC | VPTELSAISMLYLD EHDKVVLKNYQE MVVEG | G | |
| Q78DH6 | grow_factors | 28 | 3 | 31 | 31 | 1 | — | 0 | RRHALYVDFSDV GWNDWIVAPPG YQAFY | HGE | PFPLADHLNSTNH AIVQTLVNSVNN NIPKAC | VPTELSAISMLYLD EHDKVVLKNYQE MVVEG | G | |
| Q7Q3Q7 | grow_factors | 28 | 3 | 32 | 31 | 1 | — | 0 | QRKPLYVDFSDV GWNDWIVAPPG YEAFY | QGD | RFPIADHLNTTNH AIVQTLVNSYNPT LAPKAC | VPTQLSSISMLYLN EQNKVVLKNYQD MTVVG | G | |
| Q7T288 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DNVPKPC | APTKLNAISVLYFD DSSNVILKKYRNM VVRS | G | |
| Q7Z4P5 | grow_factors | 28 | 3 | 32 | 31 | 1 | — | 0 | SRKPLHVDFKEL GWDDWIIAPLDY EAYH | EGL | DFPLRSHLEPTNH AIIQTLLNSMAPD AAPASC | VPARLSPISILYIDA ANNVVYKQYEDM VVEA | G | |
| Q804S2 | grow_factors | 28 | 3 | 31 | 31 | 1 | — | 0 | KRHALYVDFSDV GWNEWIVAPPG YHAFY | QGE | PFPLADHLNSTNH AIVQTLVNSVNSN IPRAC | VPTDLSPISLLYLD EYEKVILKNYQDM VVEG | G | |
| Q804S3 | grow_factors | 28 | 3 | 31 | 31 | 1 | — | 0 | KRHALYVDFSDV GWNEWIVAPPG YHAFY | QGE | PFPLADHLNSTNH AIVQTLVNSVNSN IPRAC | VPTDLSPISLLYLD EYEKVILKNYMDM VVEG | G | |
| Q811S3 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| Q866G4 | grow_factors | 30 | 3 | 6 | 33 | 1 | — | 0 | QPIETLVDIFQEY PDEIEYIFKPSCV PLVR | GGC | NDESLE | VPTEEFNVTMQIM RIKPHQGQHIGEMS FLQHNK | E | |
| Q869A4 | grow_factors | 28 | 3 | 32 | 31 | 1 | — | 0 | RRHALYVDFSDV GWNDWIIAPPGY NAYF | HGD | PFPLPDHLNTTNH AIVQTLVNSANPA AVPRAC | VPTELSPISMLYKD KFDNVVLKNYQD MVVEG | G | |
| Q86RL7 | grow_factors | 28 | 3 | 32 | 31 | 1 | — | 0 | RRHALYVDFQEV GWEQWIVAPDG YNAYF | QGD | NFPLAQHLNSTNH AIVQTLVNSVDPT AVSKAC | VPTELSAISMLYLN ERGKVQLKNYQD MVVEA | G | |
| Q8BRW3 | grow_factors | 28 | 3 | 32 | 31 | 1 | — | 0 | KKHELYVSFQDL GWQDWIIAPKGY AANY | DGE | SFPLNAHMNATN HAIVQTLVHLMN PEYVPKPC | APTKLNAISVLYFD DNSNVILKKYRNM VVRA | G | |
| Q8BRW9 | grow_factors | 28 | 3 | 32 | 31 | 1 | — | 0 | SRKALHVNFKD MGWDDWIIAPLE YEAFH | EGL | EFPLRSHLEPTNH AVIQTLMNSMDP ESTPPTC | VPTRLSPISILFIDSA NNVVYKQYEDMV VES | G | |
| Q8CCE0 | grow_factors | 28 | 3 | 32 | 31 | 1 | — | 0 | KKHELYVSFRDL GWQDWIIAPEGY AAFY | DGE | SFPLNAHMNATN HAIVQTLVHLMFP DHVPKPC | APTKLNAISVLYFD DSSNVILKKYRNM VVRS | G | |
| Q8HY70 | grow_factors | 30 | 3 | 6 | 33 | 1 | — | 0 | RPIETLVDIFQEY PDEIEYIFKPSCV PLMR | GGC | NDEGLE | VPTEEFNTMQIMR IKPHQGQHIGEMSF LQHSK | E | |
| Q8HY75 | grow_factors | 30 | 3 | 6 | 33 | 1 | — | 0 | RPVERLVDIVSE YPSEVEHMFSPS CVSLMR | TGC | SDETMH | MPLETANVTMQL MKYHSLDQPFFVE MSFSQHVR | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q8IAE3 | grow_factors | 28 | 3 | 32 | 31 | 1 | — | 0 | SKHSLYVDFAIV GWDSWLAPEGY QAYY | QGE | PYPMPEHLNPTNH AIVQTIVHSADPSS VPKAC | VPTELDTLNMLYL NEKEQIILKNYKD MIVTS | G | |
| Q8JFE2 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ2 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ3 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ4 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ5 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ6 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ7 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ8 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIJ9 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIK0 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIK1 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8JIK2 | grow_factors | 28 | 3 | 31 | 31 | 1 | — | 0 | RRHALYVDFSDV GWNDWIVAPPG YQAYY | HGE | PFPLADHLNSTNH AIVQTLVNSVNN NIPKAC | VPTELSAISMLYLD EHDKVVLKNYQE MVVEG | G | |
| Q8MJV5 | grow_factors | 28 | 3 | 31 | 31 | 1 | — | 0 | RRHSLYVDFSDV GWNDWIVAPPG YQAFY | HGD | PFPLADHLNSTNH AIVQTLVNSVNSS IPKAC | VPTELSAISMLYLD EYDKVVLKNYQE MVVEG | G | |
| Q8MWG4 | grow_factors | 28 | 3 | 32 | 31 | 1 | — | 0 | KRHVLYVDFGD VGWNDWIVAPP GYNAYF | RGE | PFPMGQHLNSTH HAVMQTLVHSVD PTAVPKAC | VPSDLSAISMLYLD ELDKVVLKNYQD MVVEG | G | |
| Q8MXC2 | grow_factors | 28 | 3 | 32 | 31 | 1 | — | 0 | QRHPLYVDFSEV GWNDWIAPPG YQGFY | KGE | PFPLADHLNTTNH AIVQTLMNSVNP NNVPPAC | VPTTLEAISMLFMN EHSKVVLKNYQD MVVDG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q8MXZ3 | grow_factors | 28 | 3 | 32 | 31 | 1 | — | 0 | KRKNLFVNFEDLDWQEWIIAPLGYVAFY | QGE | AFPLNGHANATNHAIVQTLVHHMSPSTVPQPC | APTKLSPITVLYYDDSRNVLKKYKNMVVRA | G | |
| Q8SPL5 | grow_factors | 30 | 3 | 6 | 33 | 1 | — | 0 | RPIETLVDIFQEYPDEIEYIFKPSCVPLMR | GGC | NDEGLE | VPTAEFNITMQIMRIKPHQSQHIGEMSFLQHSK | E | |
| Q8SP29 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHNK | E | |
| Q8WMQ4 | grow_factors | 30 | 3 | 6 | 33 | 1 | — | 0 | RPIETLVDIFQEYPDEIEYIFKPSCVPLMR | GGC | NDEGLE | VPTEEFNIAMQIMRIKPHQGQHIGEMSFLQHNK | E | |
| Q8WS99 | grow_factors | 28 | 3 | 32 | 31 | 1 | — | 0 | RRHPLYVDFTDVGWNSWIVAPAGYQAYY | QGE | PFPLVDHLNATNHAIVQTLVNSASPQLAPKAC | VPTDLSAISMLYLDDSDSVILRNYQDMVVEG | G | |
| Q90723 | grow_factors | 28 | 3 | 32 | 31 | 1 | — | 0 | KPRRLYISFSDVGWENWIIAPQGYMANY | LGE | PFPLTAELNSTNHAILQTMVHSLDPEGTPQPC | VPVRLSPISILYYDNSDNVVLRHYEDMVVDE | G | |
| Q90751 | grow_factors | 28 | 3 | 31 | 31 | 1 | — | 0 | KRHPLYVDFNDVGWNDWIVAPPGYSAFY | HGE | PFPLADHLNSTNHAIVQTLVNSVNSKIPKAC | VPTELSAISMLYLDENEKVVLKNYQDMVVEG | G | |
| Q90752 | grow_factors | 28 | 3 | 31 | 31 | 1 | — | 0 | RRHALYVDFESDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q90X23 | grow_factors | 30 | 3 | 6 | 34 | 1 | — | 0 | QPRETLVSILEEYPGEISHIFRPSCVTALR | GGC | TDESLE | TATGKRSVGREIMRLSPHKGTSEKEVMQFTEHTD | E | |
| Q90X24 | grow_factors | 30 | 3 | 6 | 34 | 1 | — | 0 | QTRETLVSILEEHPDEVSHIFRPSCVTALR | GGC | TDESLK | TATGKRSVGREIMRVDPHKGTSKTEVMQFTEHTD | E | |
| Q90Y81 | grow_factors | 28 | 3 | 31 | 31 | 1 | — | 0 | RRHALYVDFREVGWNDWIVAPPGYHAYF | HGE | PFPLADHLNSTNHAIVQTLVNSVNASIPRAC | VPTELSPISMLYLDEYGKVVLKNYQDMVVEG | G | |
| Q90Y82 | grow_factors | 28 | 3 | 31 | 31 | 1 | — | 0 | ARYPLYVDFSDVGWNDWIVAPPGYNAFF | QGE | HFPLPQHLNSTNHAIVQTLVNSVNPEVPRAC | IPTELTPIALLYLDEYEKVVLKNYQDMVVEG | G | |
| Q90YD6 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTDLSAISMLYLDEYDKVVLKNYQEMVVEG | G | |
| Q90YD7 | grow_factors | 28 | 3 | 31 | 31 | 1 | — | 0 | RRHPLYVDFSDVGWNDWIVAPPGYHAFY | HGE | PFPLADHLNSTNHAIVQTLVNNVNPNIPKAC | VPTELSAISMLYLDENEKVVLKNYQDMVVEG | G | |
| Q91403 | grow_factors | 28 | 3 | 32 | 31 | 1 | — | 0 | KKHELYVSFRDLGWQDWIIAPEGYAAYY | EGE | AFPLNSYMNATNHAIVQTLVHFINPETVPKPC | APTQLNAISVIYFDDSSNVILKKYRNMVVRA | G | |
| Q91703 | grow_factors | 28 | 3 | 31 | 31 | 1 | — | 0 | RRHSLYVDFSDVGWNDWIAPPGYQAFY | HGD | PFPLADHLNSTNHAIVQTLVNSVNASIPKAC | VPTELSAISMLYLDEYDKVVLKNYQEMVVEG | G | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q95LQ4 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHSK | E | |
| Q95NE5 | grow_factors | 30 | 3 | 6 | 33 | 1 | — | 1 | HPIETLVDIFQEYPDEIEYIFKPSCVPLMR | GGC | NDEGLE | VPTEESNITMQIMRIKPHQGQHIGEMSFLQHNK | E | |
| Q95W38 | grow_factors | 28 | 3 | 32 | 31 | 1 | — | 0 | RRHPLYVDFREVGWDDWIVAPPGYEAWY | HGD | PFPLSAHMNSTNHAWQTLMNSMNPGLVPKAC | VPTQLTSISMLYLDEESKWLKNYHEMAVVG | G | |
| Q98950 | grow_factors | 28 | 3 | 32 | 31 | 1 | — | 0 | KPRRLYISFSDVGWENWIIAPQGYMANY | LGE | PFPLTAELNSTNHAILQTMVHSLDPEGTPQPC | VPVRLSPISILYYDNSDNVVLRHYEDMVVDE | G | |
| Q99PS1 | grow_factors | 30 | 3 | 6 | 33 | 1 | — | 0 | HPIETLVDIFQEYPDEIEYIFKPSCVPLMR | GGC | SDEALE | VPTSESNITMQIMRVKPHQSQHIGEMSFLQHSR | E | |
| Q9BDP7 | grow_factors | 30 | 3 | 6 | 33 | 1 | — | 1 | HPIETLVDIFQEYPDEIEYIFKPSCVPLMR | GGC | NDEGLE | VPTEESNITMQIMRIKPHQGQHIGEMSFLQHNK | E | |
| Q9BDW8 | grow_factors | 28 | 3 | 32 | 31 | 1 | — | 0 | SRKPLHVDFKELGWDDWILAPLDYEAYH | EGV | DFPLRSHLEPTNHAIIQTLLNSMAPDAAPASC | VPARLSPISILYIDAANNVVYKQYEDMVVEA | G | |
| Q9BDW9 | grow_factors | 28 | 3 | 32 | 31 | 1 | — | 0 | SRKPLHVDFKELGWDDWILAPLDYEAYH | EGV | DFPLRSHLEPTNHAIIQTLLNSMAPDAAPASC | VPARLSPISILYIDAANNVVYKQYEDMVVEA | G | |
| Q9DGN4 | grow_factors | 28 | 3 | 32 | 31 | 1 | — | 0 | SKKPLLVNFKELGWDDWILAPLDYEAYH | EGV | DFPLRSHLEPTNHAIIQTLMNSMDPESTPPSC | VPSKLSPISILYIDSGNNVVYKQYEDMVVES | S | |
| Q9ERL6 | grow_factors | 30 | 3 | 6 | 33 | 1 | — | 0 | HPIETLVDIFQEYPDEIEYIFKPSCVPLMR | GGC | SDEALE | VPTSESNITMQIMRVKPHQSQHIGEMSFLQHSR | E | |
| Q9GK00 | grow_factors | 30 | 3 | 6 | 33 | 1 | — | 0 | HPIETLVDIFQEYPDEIEYIFKPSCVPLMR | GGC | NDEGLE | VPTEEFNITMQIMRIKPHQGQHIGEMSFLQHSK | E | |
| Q9GKR0 | grow_factors | 30 | 3 | 6 | 33 | 1 | — | 0 | RPIETLVDIFQEYPDEIEYIFKPSCVPLMR | GGC | NDEGLE | VPTAEFNITMQIMRIKPHQSQHIGEMSFLQHSK | E | |
| Q9I8T6 | grow_factors | 28 | 3 | 32 | 31 | 1 | — | 0 | KKHELYVSFRDLGWQDWIIAPEGYAAYY | EGE | AFPLNSYMNATNHAIVQTLVHFINPETVPKPC | APTQLNAISVLYFDDSSNVILKKYRNMVVRA | G | |
| Q9MYV3 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHSK | E | |
| Q9MYV3-2 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHSK | E | |
| Q9MYV3-3 | grow_factors | 30 | 3 | 6 | 33 | 1 | — | 0 | RPIETLVDIFQEYPDEIEYIFKPSCVPLMR | GGC | NDEGLE | VPTEEFNITMQIMRIKPHQGQHIGEMSFLQHSK | E | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q9MZB1 | grow_factors | 30 | 3 | 6 | 33 | 1 | — | 0 | RPIETLVDIFQEYPDEIEFIFKPSCVPLMR | GGC | NDESLE | VPTEEFNITMQIMRIKPHQSQHIGEMSFLQHNK | E | |
| Q9MZV5 | grow_factors | 28 | 3 | 31 | 31 | 1 | — | 0 | RRHSLYVDFSDVGWNDWIVAPPGYQAFY | HGD | PFPLADHLNSTNHAIVQTLVNSVNSSIPKAC | VPTELSAISMLYLDEYDKVVLKNYQEMVVEG | G | |
| Q9PTF9 | grow_factors | 28 | 3 | 32 | 31 | 1 | — | 0 | KKHELYVSFRDLGWQDWIIAPEGYAAFY | EGE | VFPLNSYMNATNHAIVQTLVHFINPETVPKPC | APTQLHGISVLYFDDSSNVILKKYRNMVVRA | G | |
| Q9QX39 | grow_factors | 30 | 3 | 6 | 33 | 1 | — | 0 | HPIETLVDIFQEYPDEIEYIFKPSCVPLMR | GGC | NDEALE | VPTSESNITMQIMRIKPHQSQHIGEMSFLQHNR | E | |
| Q9U418 | grow_factors | 28 | 3 | 32 | 31 | 1 | — | 0 | RRHSLYVDFSDVGWNDWIVAPPGYQAYY | HGE | PFPLADHLNSTNHAIVQTLVNSVNPLAVPKAC | VPTDLSPISMLYLNENDQVVLKNYQDMVVEG | G | |
| Q9U5E8 | grow_factors | 28 | 3 | 32 | 31 | 1 | — | 0 | RRRSLYVDFSDVGWNDWIVAPPGYNAFY | DGE | PFPLADHLNSTNHAIVQTLVHSVKASAVPQAC | VPTELSPISMLYLDEYDKVILKNYQEMVVEG | G | |
| Q9W6C0 | grow_factors | 28 | 3 | 32 | 31 | 1 | — | 0 | SRKPLHVNFKELGWDDWIIAPLDYEAYH | EGL | DFPLRSHLEPTNHAIIQTLMNSMDPESTPPSC | VPSKLSPISILYIDSGNNVVYKQYEDMVVES | G | |
| Q9W6G0 | grow_factors | 28 | 3 | 32 | 31 | 1 | — | 0 | SRKALHVNFKDMGWDDWIIAPLEYEAYH | EGL | EFPLRSHLEPTNHAVIQTLMNSMDPESTPPTC | VPTRLSPISILFIDSANNVVYKQYEDMVVES | G | |
| Q9W753 | grow_factors | 28 | 3 | 32 | 31 | 1 | — | 0 | SKKPLHVNFKELGWDDWIIAPLEYEAHH | EGV | DFPLRSHLEPTNHAIIQTLMNSMNPGSTPPSC | VPTKLTPISILYIDAGNNVVYKQYEDMVVES | G | |
| Q9XS47 | grow_factors | 30 | 3 | 6 | 33 | 1 | — | 0 | RPVERLVDIVSEYPSEMEHLFSPSCVSLMR | TGC | SDESMH | VPLETANVTMQLMKYRSLDQPFFVEMSFSQHVR | E | |
| Q9XYQ7 | grow_factors | 28 | 3 | 32 | 31 | 1 | — | 0 | RRHPLYVDFSDVHWNDWIVAPAGYQAYY | HGE | PFPLAEHLNTTNHAIVQTLVNSVNPALVPKAC | GPTELSAISMLYLDEYEKVVLKNYQDMVVEG | G | |
| Q9XYQ8 | grow_factors | 28 | 3 | 32 | 31 | 1 | — | 0 | RRHELYVDFSDVHWNDWIVAPAGYQAYY | RGE | PFPLAEHLNTTNHAIVQTLVNSVNPALVPKAC | VPTELSAISMLYLDEYEKVVLKNYQDMVVEG | G | |
| Q9ZG69 | grow_factors | 28 | 3 | 32 | 31 | 1 | — | 0 | RRHPLYVDFSDVHWNDWIVAPAGYQAYY | HGE | PFPLAEHLNTTNHAIVQTLVNSVNPALVPKAC | VPTELSAISMLYLDEYEKVVLKNYQDMVVEG | G | |
| Q9YGH7 | grow_factors | 28 | 3 | 32 | 31 | 1 | — | 0 | KKHELYVSFKDLGWQDWIIAPEGYAAFY | EGE | APPLNSYMNATNHAIVQTLVHFINPDTVPKPC | APTQLNAISVLYFDDSSNVILKKYRNMVVRA | G | |
| Q9YGV1 | grow_factors | 28 | 3 | 32 | 31 | 1 | — | 0 | KKRRLYIDFKDVGWQNWVIAPRGYMANY | HGE | PYPLTEMLRGTNHAVLQTLVHSVEPENTPLPC | APTKLSPISMLYYDNNDNVVLRHYEDMVVDE | G | |
| Q9YMF3 | grow_factors | 30 | 3 | 6 | 33 | 1 | — | 0 | KPRPMVFRVHDEHPELTSQRFNPPCVTLMR | GGC | NDESLE | VPTEEANVTMQLMGASVSGGNGMQHLSFVEHKK | D | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| GUR_GYMSY | gurmarine | 6 | 6 | 0 | 4 | 9 | — | 2 | VKKDEL | IPYYLD | | EPLE | KKVNWWDHK | |
| ALO1_ACRLO | insect_anti-microbial | 6 | 8 | 0 | 3 | 10 | — | 0 | IKNGNG | QPDGSQGN | | SRY | HKEPGWVAGY | |
| ALO2_ACRLO | insect_anti-microbial | 6 | 8 | 0 | 3 | 10 | — | 0 | IANRNG | QPDGSQGN | | SGY | HKEPGWVAGY | |
| ALO3_ACRLO | insect_anti-microbial | 6 | 8 | 0 | 3 | 10 | — | 1 | IKNGNG | QPNGSQGN | | SGY | HKQPGWVAGY | |
| CVP3_PIMHY | insect_anti-microbial | 6 | 5 | 0 | 4 | 9 | — | 0 | GFPGRR | SPTEE | | EGLV | QPRKNGPSM | |
| CVP5_PIMHY | insect_anti-microbial | 6 | 6 | 0 | 2 | 6 | — | 0 | SSMGAS | QIGSAT | | GV | NVHTLR | |
| Q2MJU0_LYSTE | insect_anti-microbial | 6 | 5 | 0 | 6 | 6 | — | 0 | SPPGFF | QTDDD | | FTKLFR | LEIVGR | |
| Q2PQC7_BEMTA | insect_anti-microbial | 6 | 8 | 0 | 3 | 11 | — | 0 | ISNWTK | KPDGSIGN | | SGY | FQEKPDWEYGI | |
| Q2PQC8_BEMTA | insect_anti-microbial | 6 | 8 | 0 | 3 | 10 | — | 0 | LTKGAS | KGDGSMGN | | SGF | WQANPSSPGS | |
| Q2PQC9_BEMTA | insect_anti-microbial | 6 | 8 | 0 | 3 | 14 | — | 0 | LSDGAA | QSDGSIGN | | SGF | LQYVEPGLHATPGT | |
| Q2PQD0_BEMTA | insect_anti-microbial | 6 | 8 | 0 | 3 | 12 | — | 0 | LPDGAP | QADGSMGN | | TTF | LQHEQPGGTPGH | |
| Q3LTD6_9DIPT | insect_anti-microbial | 6 | 8 | 0 | 3 | 10 | — | 0 | IPDGGR | HESDPGPG | | SGF | YRERNWKDGD | |
| FSPM_SOLLC | metallocarboxy-peptidase_inhibitor | 3 | 5 | 5 | 2 | 13 | — | 0 | NEP | SSNSD | IGITL | QF | KEKTDQYGLTYRT | |
| MCPI_SOLLC | metallocarboxy-peptidase_inhibitor | 3 | 5 | 5 | 2 | 6 | — | 0 | HKP | STQDD | SGGTF | QA | WRFAGT | |
| MCPI_SOLTU | metallocarboxy-peptidase_inhibitor | 3 | 5 | 5 | 2 | 6 | — | 2 | NKP | KTHDD | SGAWF | OA | WNSART | |
| O24372_SOLTU | metallocarboxy-peptidase_inhibitor | 3 | 5 | 5 | 2 | 13 | — | 0 | NDY | NTNAD | LGITL | PW | KLKKSSSGFTYSE | |
| O24373_SOLTU | metallocarboxy-peptidase_inhibitor | 3 | 5 | 5 | 2 | 13 | — | 0 | NDY | TTNAD | FGITL | PW | KLKKSPSGGTYSE | |
| O24639_SOLTU | metallocarboxy-peptidase_inhibitor | 3 | 5 | 5 | 2 | 13 | — | 0 | NDY | TTNAD | IGITF | PW | KLKKSPSGFTYSE | |
| Q3S480_SOLTU | metallocarboxy-peptidase_inhibitor | 3 | 5 | 5 | 2 | 13 | — | 0 | NDY | TRNSD | FGITL | PW | KLKKSPGGGTYSE | |
| Q3S486_SOLTU | metallocarboxy-peptidase_inhibitor | 3 | 5 | 5 | 2 | 13 | — | 0 | NDY | NTNAD | FGLTL | PW | KLKKSSSGFTYSE | |
| Q41432_SOLTU | metallocarboxy-peptidase_inhibitor | 3 | 5 | 5 | 2 | 13 | — | 0 | NDY | NTNAD | FGITL | PW | KLKKSPSGFTYSE | |
| Q948Z8_SOLTU | metallocarboxy-peptidase_inhibitor | 3 | 5 | 5 | 2 | 13 | — | 0 | NDY | TTNAD | FGITL | PW | KLKKSPSGGTYSE | |
| Q949A1_SOLBR | metallocarboxy-peptidase_inhibitor | 3 | 5 | 5 | 2 | 14 | — | 0 | NYY | TSNSD | IGITF | QW | KVKTNPYDGSASRT | |
| Q9SBH8_SOLTU | metallocarboxy-peptidase_inhibitor | 3 | 5 | 5 | 2 | 6 | — | 0 | NKP | KTHDD | SGAWF | OA | WNSART | |
| Q9SXP0_HYONI | metallocarboxy-peptidase_inhibitor | 3 | 5 | 5 | 2 | 11 | — | 0 | FKY | NVESD | SDGWL | YN | VPSAFEGWRSQ | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| POL_MUSDO | phenol-oxidase_inhibitor | 6 | 5 | 0 | 3 | 6 | — | 0 | LANGSK | YSHDV | | TKR | HNYAKK | |
| Q170Q5_AEDAE | phenol-oxidase_inhibitor | 6 | 5 | 0 | 3 | 6 | — | 0 | AANGEY | LTHSE | | SGS | LSFSYK | |
| Q170Q6_AEDAE | phenol-oxidase_inhibitor | 6 | 5 | 0 | 3 | 6 | — | 0 | AANGEY | LTHSE | | SGS | LSFSYK | |
| Q5BN34_ANOGA | phenol-oxidase_inhibitor | 6 | 5 | 0 | 3 | 6 | — | 0 | AKNNEY | LTHRD | | SGS | LSFSYK | |
| AMP1_MESCR | plant_anti-microbial | 6 | 8 | 0 | 3 | 10 | — | 0 | IKNGKG | REDQGPPF | | SGF | YRQVGWARGY | |
| AMP1_MIRJA | plant_anti-microbial | 6 | 8 | 0 | 3 | 10 | — | 0 | IGNGGR | NENVGPPY | | SGF | LRQPGQGYGY | |
| AMP2_MIRJA | plant_anti-microbial | 6 | 8 | 0 | 3 | 10 | — | 0 | IGNGGR | NENVGPPY | | SGF | LRQPNQGYGV | |
| PAFP_PHYAM | plant_anti-microbial | 6 | 8 | 0 | 3 | 10 | — | 1 | IKNGGR | NASAGPPY | | SSY | FQIAGQSYGV | |
| Q54AI2_PHYAM | plant_anti-microbial | 6 | 8 | 0 | 3 | 10 | — | 0 | IKNGGR | NASAGPPY | | SSY | FQIAGQSYGV | |
| Q9SDS1_PHYAM | plant_anti-microbial | 6 | 8 | 0 | 3 | 10 | — | 0 | IKNGGR | VASGGPPY | | SNY | LQIAGQSYGV | |
| DEF1_PETHY | plant_defensin | 6 | 5 | 2 | 10 | 6 | — | 1 | PTWDSV | INKKP | VA | CKKAKFSDGH | SKILRR | |
| DEF2_PETHY | plant_defensin | 6 | 5 | 2 | 12 | 6 | — | 0 | PTWEGI | INKAP | VK | CKAQPEKFTDGH | SKILRR | |
| ALB1A_PEA | plant_toxin | 3 | 7 | 4 | 1 | 9 | — | 0 | NGV | SPFEMPP | GTSA | R | IPVGLVVGY | |
| ALB1B_PEA | plant_toxin | 3 | 7 | 4 | 1 | 9 | — | 1 | NGV | SPFEMPP | GSSA | R | IPVGLVVGY | |
| ALB1C_PEA | plant_toxin | 3 | 7 | 4 | 1 | 9 | — | 0 | NGV | SPFDIPP | GSPL | R | IPAGLVIGN | |
| ALB1D_PEA | plant_toxin | 3 | 7 | 4 | 1 | 9 | — | 0 | NGV | SPFEMPP | GTSA | R | IPVGLFIGY | |
| ALB1E_PEA | plant_toxin | 3 | 7 | 4 | 1 | 9 | — | 0 | NGV | SPFEMPP | GSSA | R | IPVGLLIGY | |
| ALB1F_PEA | plant_toxin | 3 | 7 | 4 | 1 | 9 | — | 0 | NGV | SPFEVPP | GTSA | R | IPVGLVIGY | |
| ALB1_GLYSO | plant_toxin | 3 | 7 | 4 | 1 | 9 | — | 0 | NGA | SPFEVPP | RSSD | R | VPIGLFVGF | |
| ALB1_PHAAN | plant_toxin | 3 | 7 | 4 | 1 | 10 | — | 0 | NGA | SPFQMPP | GSTD | L | IPAGLLFVGY | |
| ALB1_PHAAU | plant_toxin | 3 | 7 | 4 | 1 | 9 | — | 0 | NGA | SPFEMPP | RSTD | R | IPIALFGGF | |
| ALB1_SOYBN | plant_toxin | 3 | 7 | 4 | 1 | 9 | — | 1 | NGA | SPFEVPP | RSRD | R | VPIGLFVGF | |
| O24095_MEDTR | plant_toxin | 6 | 7 | 5 | 1 | 11 | — | 0 | PTAGTA | SQRRGNS | GGIE | I | VSQGYPYDGGI | |
| O24100_MEDTR | plant_toxin | 6 | 7 | 5 | 1 | 9 | — | 0 | ARVGMR | SRALPNP | GDIVT | R | VHLHLVGST | |
| O48617_MEDTR | plant_toxin | 6 | 7 | 5 | 1 | 11 | — | 0 | PFAGRV | SQYESNA | GDSEE | I | VSEWSHYDGGI | |
| Q6A1C7_9FABA | plant_toxin | 3 | 7 | 4 | 1 | 9 | — | 0 | NGV | SPFEMPP | GSSD | R | IPVGLVVGY | |
| Q6A1C8_TRIFG | plant_toxin | 3 | 7 | 4 | 1 | 9 | — | 0 | SGI | SSFEMPP | RSSD | R | IPIVLVGGY | |
| Q6A1C9_ONOVI | plant_toxin | 3 | 7 | 4 | 1 | 9 | — | 0 | DGV | SPFEMPP | GSTD | R | VPWGLFVGQ | |
| Q8A1D1_9FABA | plant_toxin | 5 | 7 | 5 | 1 | 9 | — | 0 | NGRDW | SPFEMPP | GDAQN | R | IPWIVGGY | |
| Q6A1D2_MELAB | plant_toxin | 3 | 7 | 4 | 1 | 9 | — | 0 | SGI | SSFEMPP | RSSS | R | IPWLLGGN | |
| Q6A1D3_LONCA | plant_toxin | 5 | 7 | 5 | 1 | 9 | — | 0 | NGRDV | SPFEMPP | DDATN | R | IPWGLWGQ | |
| Q6A1D4_CANBR | plant_toxin | 3 | 7 | 4 | 1 | 9 | — | 0 | SGG | SPFEMPP | GSSD | R | IPWGLVAG | |
| Q6A1D5_9FABA | plant_toxin | 3 | 7 | 4 | 1 | 9 | — | 0 | SGA | FPFQMPP | GSTD | R | VPWGLFVGQ | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q6AID6_9FABA | plant_toxin | 3 | 7 | 4 | 1 | 9 | — | 0 | SGA | SPFERPL | GSTD | R | IPIVLLAGF | |
| Q6AID7_9FABA | plant_toxin | 3 | 7 | 4 | 1 | 9 | — | 0 | SGV | SPFEMPP | GSTD | R | IPWGLFVGE | |
| Q7XZC2_PHAVU | plant_toxin | 3 | 7 | 5 | 1 | 9 | — | 0 | SGV | SPFERPP | GSTRD | R | IPYGLFIGA | |
| Q7XZC3_SOYBN | plant_toxin | 3 | 7 | 4 | 1 | 9 | — | 0 | NGA | SPFEMPP | RSRD | R | VPIGLVAGF | |
| Q7XZC5_MEDTR | plant_toxin | 3 | 7 | 4 | 1 | 9 | — | 0 | SGA | SPFEMPP | RSSD | R | IPIGIVAGY | |
| SCCT_MESMA | scorpion1 | 2 | 10 | 2 | 6 | 4 | — | 0 | GP | FTTDANMARK | RE | CGGIGK | FGPQ | |
| SCCX_MESMA | scorpion1 | 2 | 10 | 2 | 6 | 4 | — | 0 | GP | FTTDANMARK | RE | CGGNGK | FGPQ | |
| SCIT_MESTA | scorpion1 | 2 | 10 | 2 | 7 | 4 | — | 0 | GP | FTTDPQTQAK | SE | CGRKGGV | KGPQ | |
| SCX1_BUTEU | scorpion1 | 2 | 10 | 2 | 6 | 4 | — | 0 | MP | FTTRPDMAQQ | RA | CKGRGK | FGPQ | |
| SCX1_BUTSI | scorpion1 | 2 | 10 | 2 | 8 | 4 | — | 0 | KP | FTTDPQMSKK | AD | CGGKGKGK | YGPQ | |
| SCX1_LEIQH | scorpion1 | 2 | 10 | 2 | 6 | 4 | — | 0 | GP | FTTDHQMEQK | AE | CGGIGK | YGPQ | |
| SCX3_BUTEU | scorpion1 | 2 | 10 | 2 | 7 | 3 | — | 0 | MP | FTTDHQTARR | RD | CGGRGRK | FGQ | |
| SCX3_MESTA | scorpion1 | 2 | 10 | 2 | 6 | 4 | — | 0 | PP | FTTNPNMEAD | RK | CGGRGY | ASYQ | |
| SCX4_BUTEU | scorpion1 | 2 | 10 | 2 | 6 | 4 | — | 0 | MP | FTTDHNMAKK | RD | CGGNGK | FGPQ | |
| SCX5_BUTEU | scorpion1 | 2 | 10 | 2 | 6 | 4 | — | 1 | MP | FTTDPNMAKK | RD | CGGNGK | FGPQ | |
| SCX8_LEIQH | scorpion1 | 2 | 10 | 2 | 8 | 4 | — | 0 | SP | FTTDQQMTKK | YD | CGGKGKGK | YGPQ | |
| SCXL_BUTSI | scorpion1 | 2 | 10 | 2 | 6 | 4 | — | 0 | GP | FTKDPETEKK | AT | CGGIGR | YGPQ | |
| SCXL_LEIQU | scorpion1 | 2 | 10 | 2 | 8 | 4 | — | 1 | MP | FTTDHQMARK | DD | CGGKGRGK | YGPQ | |
| SCXP_ANDMA | scorpion1 | 2 | 10 | 2 | 6 | 4 | — | 0 | GP | FTTDPYTESK | AT | CGGRGK | VGPQ | |
| SCXS_BUTEU | scorpion1 | 2 | 10 | 2 | 6 | 4 | — | 0 | MP | FTTDPNMANK | RD | CGGGKK | FGPQ | |
| IPTXA_PANIM | scorpion2 | 6 | 5 | 0 | 3 | 10 | — | 1 | LPHLKR | KADND | | GKK | KRRGTNAE KR | |
| SCX1_OPICA | scorpion2 | 6 | 5 | 0 | 3 | 10 | — | 0 | LPHLKR | KENND | | SKK | KRRGTNPE KR | |
| SCX2_OPICA | scorpion2 | 6 | 5 | 0 | 3 | 10 | — | 0 | LPHLKR | KENND | | SKK | KRRGANPE KR | |
| SCXC1_MESMA | scorpion2 | 6 | 5 | 0 | 5 | 8 | — | 0 | NRLNKK | NSDGD | | RYGER | ISTGVNYY | |
| SCXC_SCOMA | scorpion2 | 6 | 5 | 0 | 3 | 10 | — | 1 | LPHLKL | KENKD | | SKK | KRRGTNIEK R | |
| KGX11_CENNO | scorpion3 | 5 | 8 | 2 | 10 | 4 | — | 2 | VDKSR | AKYGYYQE | QD | CKNAGHNGGT | MFFK | |
| KGX12_CENEL | scorpion3 | 5 | 8 | 2 | 10 | 4 | — | 0 | VDKSR | AKYGYYQE | TD | CKKYGHNGGT | MFFK | |
| KGX13_CENGR | scorpion3 | 5 | 8 | 2 | 10 | 4 | — | 0 | VDKSR | AKYGHYQE | TD | CKKYGHNGGT | MFFK | |
| KGX14_CENSC | scorpion3 | 5 | 8 | 2 | 10 | 4 | — | 0 | VDKSR | AKYGYYQE | QD | CKKAGHNGGT | MFFK | |
| KGX15_CENLL | scorpion3 | 5 | 8 | 2 | 10 | 4 | — | 0 | VDKSR | SKYGYYQE | QD | CKKAGHSGGT | MFFK | |
| KGX16_CENEX | scorpion3 | 5 | 8 | 2 | 10 | 4 | — | 0 | VDKSR | AKYGYYQE | QD | CKKAGHKGGT | MFFK | |
| KGX31_CENNO | scorpion3 | 5 | 8 | 2 | 10 | 4 | — | 0 | VNKSR | AKYGYYSQ | EV | CKKAGHRGGT | DFFK | |
| KGX32_CENEL | scorpion3 | 5 | 8 | 2 | 10 | 4 | — | 0 | VDKSR | AKYGYYQQ | EI | CKKAGHRGGT | EFFK | |
| KGX33_CENSC | scorpion3 | 5 | 8 | 2 | 10 | 4 | — | 0 | VDKSR | AKYGYYGQ | EV | CKKAGHRGGT | DFFK | |
| KGX34_CENGR | scorpion3 | 5 | 8 | 2 | 10 | 4 | — | 0 | VDKSR | QKYGNYAQ | TA | CKKAGHNKGT | VYFK | |
| KGX41_CENLL | scorpion3 | 5 | 8 | 2 | 10 | 4 | — | 0 | VDKSK | SKYGYYGQ | DE | CKKAGHNGGT | VYYK | |
| KGX42_CENNO | scorpion3 | 5 | 8 | 2 | 10 | 4 | — | 0 | VDKSK | GKYGYYGQ | QD | CKNAGHNGGT | VYYK | |
| KGX43_CENEX | scorpion3 | 5 | 8 | 2 | 10 | 4 | — | 0 | VDKSR | GKYGYYGQ | DE | CKKAGDRAGI | EYFK | |
| KGX44_CENEX | scorpion3 | 5 | 8 | 2 | 10 | 4 | — | 0 | VDKSR | AKYGYYYY | DE | CKKAGDRAGT | EYFK | |
| KGX45_CENEL | scorpion3 | 5 | 8 | 2 | 10 | 4 | — | 0 | VDKSK | SKYGYYGQ | DK | CKKAGDRAGN | VYFK | |
| KGX46_CENLL | scorpion3 | 5 | 8 | 2 | 10 | 4 | — | 0 | VDKSQ | AKYGYYGQ | DE | CKKAGDRAGN | VYLK | |
| KGX47_CENLL | scorpion3 | 5 | 8 | 2 | 10 | 4 | — | 0 | VDKSK | GKYGYYHQ | DD | CKKAGDRAGT | VYYK | |
| KGX48_CENEL | scorpion3 | 5 | 8 | 2 | 10 | 4 | — | 0 | VDKSR | GKYGYYGQ | DE | CKKAGDRAGI | VYYK | |
| KGX49_CENSC | scorpion3 | 5 | 8 | 2 | 10 | 4 | — | 0 | VDKSR | GKYGYYGQ | DE | CKKAGERVGT | VYYK | |
| KGX4A_CENSC | scorpion3 | 5 | 8 | 2 | 10 | 4 | — | 0 | VDKSR | GKYGYYGQ | DE | CKKAGDRAGI | VYYK | |
| KGX4B_CENNO | scorpion3 | 5 | 8 | 2 | 10 | 4 | — | 0 | VDKSQ | GKYGYYGQ | DE | CKKAGDRAGT | VYYK | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| KGX4C_CENSC | scorpion3 | 5 | 8 | 2 | 10 | 4 | — | 0 | VEKSK | GKYGYYGQ | DE | CKKAGDRAGT | VYYK | |
| KGX4D_CENNO | scorpion3 | 5 | 8 | 2 | 10 | 4 | — | 0 | VDKSK | GKYGYYGQ | DE | CKKAGDRAGT | VYYK | |
| KGX51_CENSC | scorpion3 | 5 | 8 | 2 | 10 | 4 | — | 0 | VDKSK | AKYGYYGQ | EV | CKKAGHNGGT | MFFK | |
| KGX52_CENGR | scorpion3 | 5 | 8 | 2 | 10 | 4 | — | 0 | VDKSR | QKYGPYGQ | TD | CKKAGHTGGT | IYFK | |
| A6N2U8_MOMCH | serine_protein-ase_inhib | 6 | 5 | 3 | 1 | 4 | — | 0 | PRIWME | KRDSD | MAQ | I | VDGH | |
| IELI_MOMCH | serine_protein-ase_inhib | 6 | 5 | 3 | 1 | 4 | — | 0 | PLIWME | KRDSD | LAQ | I | VDGH | |
| ITI1_LAGLE | serine_protein-ase_inhib | 6 | 5 | 3 | 1 | 5 | — | 0 | PRIYME | KHDSD | LAD | V | LEHGI | |
| ITI1_CITLA | serine_protein-ase_inhib | 6 | 5 | 3 | 1 | 5 | — | 0 | PRIYME | KRDAD | LAD | V | LQHGI | |
| ITR1_CUCMA | serine_protein-ase_inhib | 6 | 5 | 3 | 1 | 5 | — | 7 | PRILME | KKDSD | LAE | V | LEHGY | |
| ITR1_LUFCY | serine_protein-ase_inhib | 6 | 5 | 3 | 1 | 5 | — | 0 | PRILME | SSDSD | LAE | I | LEQGF | |
| ITR1_MOMCH | serine_protein-ase_inhib | 6 | 5 | 3 | 1 | 5 | — | 0 | PRILKQ | KRDSD | PGE | I | MAHGF | |
| ITR1_MOMCO | serine_protein-ase_inhib | 6 | 5 | 3 | 1 | 5 | — | 0 | PKILQR | RRDSD | PGA | I | RGNGY | |
| ITR1_MOMRE | serine_protein-ase_inhib | 6 | 5 | 3 | 1 | 5 | — | 0 | PRILME | KRDSD | LAQ | V | KRQGY | |
| ITR1_TRIKI | serine_protein-ase_inhib | 6 | 5 | 3 | 1 | 5 | — | 0 | PRILMP | KVNDD | LRG | K | LSNGY | |
| ITR2B_CUCSA | serine_protein-ase_inhib | 6 | 5 | 3 | 1 | 6 | — | 0 | PKILMK | KHDSD | LLD | V | LEDIGY | |
| ITR2_BRYDI | serine_protein-ase_inhib | 6 | 5 | 3 | 1 | 5 | — | 0 | PKILMR | KRDSD | LAG | V | QKNGY | |
| ITR2_ECBEL | serine_protein-ase_inhib | 6 | 5 | 3 | 1 | 5 | — | 7 | PRILMR | KQDSD | LAG | V | GPNGF | |
| ITR2_LUFCY | serine_protein-ase_inhib | 6 | 5 | 3 | 1 | 6 | — | 0 | PRILME | SSDSD | LAE | I | LEQDGF | |
| ITR2_MOMCH | serine_protein-ase_inhib | 6 | 5 | 3 | 1 | 4 | — | 1 | PRIWME | KRDSD | MAQ | I | VDGH | |
| ITR2_MOMCO | serine_protein-ase_inhib | 6 | 5 | 3 | 1 | 5 | — | 3 | PKILKK | RRDSD | PGA | I | RGNGY | |
| ITR2_SECED | serine_protein-ase_inhib | 6 | 5 | 3 | 1 | 5 | — | 0 | PKILMR | KRDSD | LAK | T | QESGY | |
| ITR3_CUCMC | serine_protein-ase_inhib | 6 | 5 | 3 | 1 | 5 | — | 0 | PKILMK | KKDSD | LLD | V | LKEGF | |
| ITR3_CUCPE | serine_protein-ase_inhib | 6 | 5 | 3 | 1 | 5 | — | 2 | PKILME | KKDSD | LAE | I | LEHGY | |
| ITR3_CYCPE | serine_protein-ase_inhib | 6 | 5 | 3 | 1 | 5 | — | 0 | PRILME | KADSD | LAQ | I | EESGF | |
| ITR3_LUFCY | serine_protein-ase_inhib | 6 | 5 | 3 | 1 | 5 | — | 0 | PRILME | SSDSD | LAE | I | LENGF | |
| ITR3_MOMCH | serine_protein-ase_inhib | 6 | 5 | 3 | 1 | 5 | — | 0 | PRILKQ | KQDSD | PGE | I | MAHGF | |
| ITR3_MOMCO | serine_protein-ase_inhib | 6 | 5 | 3 | 1 | 5 | — | 0 | PRILKK | RRDSD | PGE | I | KENGY | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| ITR4_CUCMA | serine_protein-ase_inhib | 6 | 5 | 3 | 1 | 5 | — | 0 | PRILMK | KKDSD | LAE | V | LEHGY | |
| ITR4_CUCSA | serine_protein-ase_inhib | 6 | 5 | 3 | 1 | 6 | — | 0 | PRILMK | KHDSD | LPG | V | LEHIEY | |
| ITR4_CYCPE | serine_protein-ase_inhib | 6 | 5 | 3 | 1 | 5 | — | 0 | PRILME | KADSD | LAQ | I | QENGF | |
| ITR4_LUFCY | serine_protein-ase_inhib | 6 | 5 | 3 | 1 | 5 | — | 0 | PRILMP | SSDSD | LAE | I | LENGF | |
| ITR5_CYCPE | serine_protein-ase_inhib | 6 | 5 | 3 | 1 | 5 | — | 0 | PRILME | KADSD | LAQ | I | QESGF | |
| ITR5_LUFCY | serine_protein-ase_inhib | 6 | 5 | 3 | 1 | 5 | — | 0 | PRILMP | KTDDD | MLD | R | LSNGY | |
| ITR5_SECED | serine_protein-ase_inhib | 6 | 5 | 3 | 1 | 5 | — | 0 | PRILMP | KLDTD | FPT | T | RPSGF | |
| ITR6_CYCPE | serine_protein-ase_inhib | 6 | 5 | 3 | 1 | 5 | — | 0 | PRILMK | KKDSD | LAE | I | EEHGF | |
| ITR7_CYCPE | serine_protein-ase_inhib | 6 | 5 | 3 | 1 | 5 | — | 0 | PRILMK | KKDSD | LAE | I | QEHGF | |
| ITRA_MOMCH | serine_protein-ase_inhib | 6 | 5 | 3 | 1 | 4 | — | 1 | PRIWME | TRDSD | MAK | I | VAGH | |
| Q9S8D2_CUCME | serine_protein-ase_inhib | 6 | 5 | 3 | 1 | 5 | — | 0 | PRILMK | KTDRD | LTG | T | KRNGY | |
| Q9S8W2_CUCME | serine_protein-ase_inhib_2 | 6 | 5 | 3 | 1 | 5 | — | 0 | PKILMK | KQDSD | LLD | V | LKEGF | |
| Q9S8W3_CUCME | serine_protein-ase_inhib_2 | 6 | 5 | 3 | 1 | 5 | — | 0 | PKILMK | KQDSD | LLD | V | LKEGF | |
| ITR1_MIRJA | serine_protein-ase_inhib_2 | 6 | 7 | 0 | 3 | 10 | — | 0 | AKTDQI | PPNAPNY | | SGS | VPHPRLRIFV | |
| ITR1_SPIOL | serine_protein-ase_inhib_2 | 6 | 8 | 0 | 3 | 10 | — | 0 | SPSGAI | SGFGPPEQ | | SGA | VPHPILRIFV | |
| ITR2_SPIOL | serine_protein-ase_inhib_2 | 6 | 8 | 0 | 3 | 10 | — | 0 | SPSGAI | SGFGPPEQ | | SGA | VPHPILRIFV | |
| ITR3_SPIOL | serine_protein-ase_inhib_2 | 6 | 8 | 0 | 3 | 10 | — | 0 | SPSGAI | SGFGPPEQ | | SGA | VPHPILRIFV | |
| 29C0_ANCSP | spider | 5 | 4 | 0 | 10 | 9 | — | 0 | TKQAD | AEDE | | LDNLFFKRPY | EMRYGAGKR | |
| A5A3H0_ATRRO | spider | 6 | 5 | 0 | 3 | 13 | — | 0 | IPSGQP | PYNEH | | SGS | TYKENENG NTVQR | |
| A5A3H1_ATRRO | spider | 6 | 5 | 0 | 3 | 13 | — | 0 | TPTGQP | PYNES | | SGS | QEQLNENG HTVKR | |
| A5A3H3_ATRRO | spider | 6 | 5 | 0 | 3 | 13 | — | 0 | IPSGQP | PYNEN | | SQS | TFKENENG NTVKR | |
| A5A3H4_ATRRO | spider | 6 | 5 | 0 | 3 | 13 | — | 0 | IPSGQP | PYNEN | | SKS | TYKENENG NTVQR | |
| A5A3H5_ATRRO | spider | 6 | 5 | 0 | 3 | 13 | — | 0 | IPSGQP | PYNEN | | SQS | TFKENETG NTVKR | |
| A9XDF9_GEOA2 | spider | 6 | 6 | 0 | 4 | 19 | — | 0 | ITWRNS | MHNDKG | | FPWS | VCWSQTVS RNSSRKEK KCQ | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| A9XDG0_GEOA2 | spider | 6 | 6 | 0 | 4 | 19 | — | 0 | ITWRNS | MHNDKG | | FPWS | VCWSQTVS RNSSRKEK KCQ | |
| A9XDG1_GEOA2 | spider | 6 | 6 | 0 | 4 | 19 | — | 0 | ITWRNS | MHNDKG | | FPWS | VCWSQTVS RNSSGKEK KCQ | |
| A9XDG2_GEOA2 | spider | 6 | 6 | 0 | 4 | 19 | — | 0 | ITWRNS | MHNDKG | | FPWS | VCWSQTVP RNSSRKEK KCQ | |
| A9XDG3_GEOA2 | spider | 6 | 6 | 0 | 4 | 19 | — | 0 | ITWRNS | MHYDKG | | FPWT | VCWSQTVS RNSSRKEK KCQ | |
| A9XDG4_GEOA2 | spider | 6 | 6 | 0 | 4 | 19 | — | 0 | TTWRNS | MHNDKG | | FPWS | VCWSQTVS RNSSRKEK KCQ | |
| A9XDG5_GEOA2 | spider | 6 | 6 | 0 | 4 | 19 | — | 0 | ITWRNS | VHNDKG | | FPWS | VCWSQTVS RNSSRKEK KCQ | |
| AF1_GRARO | spider | 6 | 5 | 0 | 4 | 3 | — | 0 | QKWLWT | DSERK | | EDMV | RLW | |
| AF2_GRARO | spider | 6 | 5 | 0 | 4 | 3 | — | 0 | QKWMWT | DEERK | | EGLV | RLW | |
| B1P1A0_CHIJI | spider | 6 | 5 | 0 | 4 | 6 | — | 0 | KKMFGG | TVHSD | | AHLG | KPTLKY | |
| B1P1A1_CHIJI | spider | 6 | 6 | 0 | 4 | 6 | — | 0 | GGFWWK | GRGKPP | | KGYA | SKTWGW | |
| B1P1A2_CHIJI | spider | 6 | 5 | 0 | 4 | 7 | — | 0 | RWMFGG | TTDSD | | EHLG | RWEKPSW | |
| B1P1A3_CHIJI | spider | 6 | 6 | 0 | 4 | 6 | — | 0 | GGLMAG | DGKSTF | | SGYN | SPTWKW | |
| B1P1A4_CHIJI | spider | 6 | 6 | 0 | 4 | 6 | — | 0 | GGLMAG | DGKSTF | | SGYN | SPTWKW | |
| B1P1B0_CHIJI | spider | 6 | 5 | 0 | 4 | 9 | — | 0 | IEEGKW | PKKAP | | GRLE | KGPSPKQK K | |
| B1P1B1_CHIJI | spider | 6 | 5 | 0 | 4 | 9 | — | 0 | IEEGKW | PKKAP | | GRLE | KGPSPKQK K | |
| B1P1B2_CHIJI | spider | 6 | 5 | 0 | 4 | 9 | — | 0 | IEEGKW | PKKAP | | GRLE | KGPSPKQK K | |
| B1P1B3_CHIJI | spider | 6 | 5 | 0 | 4 | 9 | — | 0 | FKEGHS | PKTAP | | RPLV | KGPSPNTK K | |
| B1P1B4_CHIJI | spider | 6 | 7 | 0 | 2 | 4 | — | 0 | EPSGKP | RPLMRIP | | GS | VRGK | |
| B1P1B5_CHIJI | spider | 6 | 5 | 0 | 4 | 3 | — | 0 | QKWMWT | DSERK | | EGYV | ELW | |
| B1P1B6_CHIJI | spider | 6 | 5 | 0 | 4 | 3 | — | 0 | QKWMWT | DSERK | | EGYV | ELW | |
| B1P1B7_CHIJI | spider | 6 | 6 | 0 | 4 | 6 | — | 0 | GQFWWK | GEGKPP | | ANFA | KIGLYL | |
| B1P1B8_CHIJI | spider | 6 | 6 | 0 | 4 | 6 | — | 0 | GQFWWK | GEGKPP | | ANFA | KIGLYL | |
| B1P1B9_CHIJI | spider | 6 | 5 | 0 | 4 | 6 | — | 0 | GTMWSP | STEKP | | DNFS | QPAIKW | |
| B1P1C0_CHIJI | spider | 6 | 6 | 0 | 4 | 6 | — | 0 | QKFFWT | HPGQPP | | SGLA | TWPTEI | |
| B1P1C1_CHIJI | spider | 6 | 6 | 0 | 4 | 6 | — | 0 | QKFFWT | HPGQPP | | SGLA | TWPTEI | |
| B1P1C2_CHIJI | spider | 6 | 6 | 0 | 4 | 6 | — | 0 | GGLMAG | GGKSTF | | SGYN | SPTWKW | |
| B1P1C3_CHIJI | spider | 6 | 6 | 0 | 4 | 6 | — | 0 | GGLMDG | DGKSTF | | SGYN | SPTWKW | |
| B1P1C4_CHIJI | spider | 6 | 6 | 0 | 4 | 6 | — | 0 | GGLMDG | DGKSTF | | SGFN | SPTWKW | |
| B1P1C6_CHIJI | spider | 6 | 6 | 0 | 4 | 6 | — | 0 | GGLMDG | DGKSTF | | SGFN | SPTWKW | |
| B1P1C8_CHIJI | spider | 6 | 6 | 0 | 4 | 6 | — | 0 | GEFMWK | GAGKPT | | SGYD | SPTWKW | |
| B1P1C9_CHIJI | spider | 6 | 6 | 0 | 4 | 6 | — | 0 | GEFMWK | GAGKPT | | SGYD | SPTWKW | |
| B1P1D0_CHIJI | spider | 6 | 6 | 0 | 4 | 6 | — | 0 | GEFMWK | GAGKPT | | SGYD | SPTWKW | |
| B1P1D1_CHIJI | spider | 6 | 5 | 0 | 4 | 6 | — | 0 | KGFQVK | KKDSE | | SSYV | GSQWKW | |
| B1P1D2_CHIJI | spider | 6 | 5 | 0 | 4 | 6 | — | 0 | KGFQVK | KKDSE | | SSYV | GSQWKW | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| B1P1D3_CHJI | spider | 6 | 5 | 0 | 4 | 6 | — | 0 | KGFQVK | KKDSE | | SSYV | GRQWKW | |
| B1P1D4_CHJI | spider | 6 | 5 | 0 | 4 | 6 | — | 0 | YDIGEL | SSDKP | | SGYY | SPRWGW | |
| B1P1D5_CHJI | spider | 6 | 6 | 0 | 4 | 6 | — | 0 | GGFWWK | GSGKPA | | PKYV | SPKWGL | |
| B1P1D6_CHJI | spider | 6 | 6 | 0 | 4 | 6 | — | 0 | GGFWWK | GSGKPA | | PKYV | SPKWGL | |
| B1P1D7_CHJI | spider | 6 | 5 | 0 | 4 | 6 | — | 0 | RKMFGG | SKHED | | AHLA | KRTFNY | |
| B1P1D8_CHJI | spider | 6 | 5 | 0 | 4 | 6 | — | 0 | RKMFGG | SKHED | | AHLA | KRTFNY | |
| B1P1D9_CHJI | spider | 6 | 5 | 0 | 4 | 6 | — | 0 | RKMFGG | SVDSD | | AHLG | KPTLKY | |
| B1P1E0_CHJI | spider | 6 | 5 | 0 | 4 | 6 | — | 0 | RKMFGG | SVDSD | | AHLG | KPTLKY | |
| B1P1E1_CHJI | spider | 6 | 5 | 0 | 4 | 6 | — | 0 | RKMFGG | SVDSD | | AHLG | KPTLKY | |
| B1P1E2_CHJI | spider | 6 | 5 | 0 | 4 | 6 | — | 0 | RKMFGG | SVDSD | | AHLG | KPTLKY | |
| B1P1E3_CHJI | spider | 6 | 5 | 0 | 4 | 6 | — | 0 | RKMFGG | SVDSD | | AHLG | KPTLKY | |
| B1P1E4_CHJI | spider | 6 | 5 | 0 | 4 | 6 | — | 0 | RKMFGG | SVHSD | | AHLG | KPTLKY | |
| B1P1E5_CHJI | spider | 6 | 5 | 0 | 4 | 5 | — | 0 | GGWMAK | ADSDD | | ETFH | TRFNV | |
| B1P1E6_CHJI | spider | 6 | 5 | 0 | 4 | 5 | — | 0 | GGWMAK | ADSDD | | ETFH | TRFNV | |
| B1P1E7_CHJI | spider | 6 | 5 | 0 | 4 | 5 | — | 0 | GGWMAK | ADSDD | | ETFH | TRFNV | |
| B1P1E8_CHJI | spider | 6 | 5 | 0 | 4 | 5 | — | 0 | GGWMAK | ADSDD | | EAFH | TRFNV | |
| B1P1F0_CHJI | spider | 6 | 6 | 0 | 4 | 5 | — | 0 | RGYGLP | TPEKND | | QRLY | SQHRL | |
| B1P1F1_CHJI | spider | 6 | 6 | 0 | 4 | 6 | — | 0 | LGMFSS | NPDNDK | | EGRK | DRRDQW | |
| B1P1F2_CHJI | spider | 6 | 6 | 0 | 4 | 6 | — | 0 | LGLFSS | NPDNDK | | EGRK | NRRDKW | |
| B1P1F3_CHJI | spider | 6 | 5 | 0 | 4 | 6 | — | 0 | TKFLGG | SEDSE | | PHLG | KDVLYY | |
| B1P1F4_CHJI | spider | 6 | 5 | 0 | 4 | 6 | — | 0 | TKFLGG | SEDSE | | PHLG | KDVLYY | |
| B1P1F5_CHJI | spider | 6 | 5 | 0 | 4 | 6 | — | 0 | TKLLGG | TKDSE | | PHLG | RKKWPYH | |
| B1P1F6_CHJI | spider | 6 | 5 | 0 | 4 | 7 | — | 0 | RYLMGG | SKDGD | | EHLV | RTKWPYH | |
| B1P1F7_CHJI | spider | 6 | 5 | 0 | 4 | 7 | — | 0 | REWLGG | SKDAD | | AHLE | RKKWPYH | |
| B1P1F8_CHJI | spider | 6 | 5 | 0 | 4 | 7 | — | 0 | RALYGG | TKDED | | KHLA | RRTLPTY | |
| B1P1F9_CHJI | spider | 6 | 5 | 0 | 4 | 7 | — | 0 | RALYGG | TKDED | | KHLA | RRTLPTY | |
| B1P1G0_CHJI | spider | 6 | 5 | 0 | 4 | 7 | — | 0 | RWLFGG | EKDSD | | EHLG | RRAKPSW | |
| B1P1G2_CHJI | spider | 6 | 5 | 0 | 4 | 7 | — | 0 | RWLFGG | EKDSD | | EHLG | RRAKPSW | |
| B1P1G3_CHJI | spider | 6 | 5 | 0 | 4 | 7 | — | 0 | RWLFGG | EKDSD | | EHLG | RRAKPSW | |
| B1P1G4_CHJI | spider | 6 | 5 | 0 | 4 | 7 | — | 0 | RWLFGG | EKDSD | | EHLG | RRAKPSW | |
| B1P1G5_CHJI | spider | 6 | 5 | 0 | 4 | 7 | — | 0 | RWLFGG | EKDSD | | EHLG | RRTKPSW | |
| B1P1G6_CHJI | spider | 6 | 5 | 0 | 4 | 7 | — | 0 | RWMFGG | TTDSD | | EHLG | RWEKPSW | |
| B1P1G7_CHJI | spider | 6 | 5 | 0 | 4 | 7 | — | 0 | RWMFGG | TTDSD | | EHLG | RWEKPSW | |
| B1P1G8_CHJI | spider | 6 | 5 | 0 | 4 | 6 | — | 0 | KWYLGD | KAHED | | EHLR | HSRWDW | |
| B1P1G9_CHJI | spider | 6 | 5 | 0 | 4 | 5 | — | 0 | GEKNDR | KTNQD | | SGFR | TKFRR | |
| B1P1H0_CHJI | spider | 6 | 5 | 0 | 4 | 5 | — | 0 | GEKNDR | KTNQD | | SGFR | TKFRR | |
| B1P1H1_CHJI | spider | 6 | 5 | 0 | 4 | 6 | — | 0 | RKMFGG | SVDSD | | AHLG | KPTLKY | |
| B1P1H2_CHJI | spider | 6 | 6 | 0 | 4 | 6 | — | 0 | LGLFWI | NYMDDK | | PGYK | ERSSPW | |
| B1P1H3_CHJI | spider | 6 | 7 | 0 | 4 | 9 | — | 0 | IERMQT | EVEAGLP | | SGAP | ICPYIGDCI | |
| B1P1H4_CHJI | spider | 6 | 7 | 0 | 4 | 9 | — | 0 | IERMQT | EVEAGLP | | SGAP | ICPYIGDCI | |
| B1P1H5_CHJI | spider | 6 | 7 | 0 | 4 | 9 | — | 0 | IERMQT | GVEAGLP | | SGAP | ICPYIGDCI | |
| B1P1H6_CHJI | spider | 6 | 6 | 0 | 4 | 14 | — | 0 | WGANVP | EDENSP | | SPLK | EKTFGYGW WYGSPF | |
| B1P1H7_CHJI | spider | 6 | 6 | 0 | 4 | 14 | — | 0 | WGANVP | EDENSP | | PPLK | EKTFGYGW WYGSPF | |
| B1P1H8_CHJI | spider | 6 | 9 | 0 | 4 | 4 | — | 0 | GHLHDP | PNDRPGHRT | | IGLQ | RYGS | |
| B1P1H9_CHJI | spider | 6 | 5 | 0 | 4 | 7 | — | 0 | RWFWGA | KSDSD | | RYLG | KRKWPNI | |
| B1P1I0_CHJI | spider | 6 | 5 | 0 | 10 | 9 | — | 0 | SRKTWP | ETSED | | DKNCSDTFWT | QLGYGCSR V | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| CALA_CALS5 | spider | 6 | 5 | 0 | 3 | 16 | — | 0 | ISARYP | SNSKD | | SGN | | GTFWTCYIR KDPCSKE |
| CALB_CALS5 | spider | 6 | 5 | 0 | 3 | 16 | — | 0 | ISARYP | SNSKD | | SGN | | GTFWTCFIR KDPCSKE |
| CALC_CALS5 | spider | 6 | 5 | 0 | 3 | 16 | — | 0 | ISARYP | SNSKD | | SGS | | GIFWTCYLR KDPCSKE |
| F256_OLIOR | spider | 6 | 5 | 0 | 3 | 8 | — | 0 | TYPGQQ | KSDDE | | HGT | KTAFIGRI | |
| JZT11_CHIJI | spider | 6 | 5 | 0 | 4 | 6 | — | 1 | RKMFGG | SVDSD | | AHLG | KPTLKY | |
| JZT12_CHIJI | spider | 6 | 5 | 0 | 4 | 3 | — | 0 | QKWMWT | DSERK | | EGYV | ELW | |
| JZTX1_CHIJI | spider | 6 | 6 | 0 | 4 | 6 | — | 0 | GQFWWK | GEGKPP | | ANFA | KIGLYL | |
| JZTX3_CHIJI | spider | 6 | 6 | 0 | 4 | 6 | — | 1 | GGFWWK | GRGKPP | | KGYA | SKTWGW | |
| JZTX5_CHIJI | spider | 6 | 5 | 0 | 4 | 3 | — | 0 | QKWMWT | DSKRA | | EGLR | KLW | |
| JZTX7_CHIJI | spider | 6 | 6 | 0 | 4 | 6 | — | 2 | GGLMAG | DGKSTF | | SGYN | SPTWKW | |
| MTX2_GRARO | spider | 6 | 5 | 0 | 4 | 3 | — | 1 | QKWMWT | DEERK | | EGLV | RLW | |
| MTX4_GRARO | spider | 6 | 6 | 0 | 5 | 6 | — | 2 | LEFWVK | NPNDDK | | RPKLK | SKLFKL | |
| Q5Y4U5_AGEOR | spider | 6 | 4 | 0 | 4 | 8 | — | 0 | AEKGIK | HNIH | | SGLT | KCKGSSCV | |
| Q5Y4U6_AGEOR | spider | 6 | 6 | 0 | 4 | 9 | — | 0 | VGENGH | RSWYND | | DGYY | SCMQPPNCI | |
| Q5Y4U7_AGEOR | spider | 6 | 6 | 0 | 4 | 9 | — | 0 | VGENGR | RDWYND | | DGFY | SCRQPPYCI | |
| Q5Y4U8_AGEOR | spider | 6 | 7 | 0 | 4 | 9 | — | 0 | VGENQQ | ADWAGLH | | SGYY | TCRYFPKCI | |
| Q5Y4U9_AGEOR | spider | 6 | 7 | 0 | 4 | 9 | — | 0 | VGENQQ | ADWARPH | | SGYY | TCRYFPKCI | |
| Q5Y4V0_AGEOR | spider | 6 | 7 | 0 | 4 | 9 | — | 0 | VGENQQ | ANWAGPH | | SGYY | TCRYFPKCI | |
| Q5Y4V1_AGEOR | spider | 6 | 7 | 0 | 4 | 9 | — | 0 | VGESQQ | ADWSGPY | | KGYY | TCQYFPKCI | |
| Q5Y4V2_AGEOR | spider | 6 | 7 | 0 | 4 | 9 | — | 0 | VGESQQ | ADWSGPY | | KGYY | TCRYFPKCI | |
| Q5Y4V3_AGEOR | spider | 6 | 7 | 0 | 4 | 9 | — | 0 | VGESQQ | ADWAGPH | | KGYY | TCRYFPKCI | |
| Q5Y4V4_AGEOR | spider | 6 | 7 | 0 | 4 | 9 | — | 0 | VGENQQ | ADWAGPH | | SGYY | TCRYFPKCI | |
| Q5Y4V5_AGEOR | spider | 6 | 7 | 0 | 4 | 9 | — | 0 | VGDGQR | ADWAGPY | | SGYY | SCRSMPYC R | |
| Q5Y4V6_AGEOR | spider | 6 | 7 | 0 | 4 | 9 | — | 0 | VGENQQ | ADWAGPH | | SGYY | TCRYFPKCI | |
| Q5Y4V7_AGEOR | spider | 6 | 7 | 0 | 4 | 9 | — | 0 | VGDGQR | ADWAGPY | | SGYY | SCRSMPYC R | |
| Q5Y4V8_AGEOR | spider | 4 | 5 | 0 | 4 | 9 | — | 0 | AAKNKR | ADWAGPW | | EGLY | SCRSYPGC M | |
| Q5Y4W0_AGEOR | spider | 6 | 5 | 0 | 4 | 10 | — | 0 | THGS | ENGET | | DGWR | RYTGRAVP FM | |
| Q5Y4W1_AGEOR | spider | 6 | 7 | 0 | 4 | 9 | — | 0 | VGENQQ | ADWAGPH | | SGLR | KELSIWDSR | |
| Q5Y4W2_AGEOR | spider | 6 | 7 | 0 | 4 | 9 | — | 0 | LPRNKF | NPSSGPR | | SGLT | KELNIWAN K | |
| Q5Y4W3_AGEOR | spider | 6 | 7 | 0 | 4 | 9 | — | 0 | LPRNKF | NPSSGPR | | SGLT | KELNIWDS R | |
| Q5Y4W4_AGEOR | spider | 6 | 7 | 0 | 4 | 9 | — | 0 | LPRNKF | NPSSGPR | | SGLT | KELNIWAS K | |
| Q5Y4W5_AGEOR | spider | 6 | 7 | 0 | 4 | 9 | — | 0 | LPHNRF | NALSGPR | | SGLT | KELNIWAS K | |
| Q5Y4W6_AGEOR | spider | 6 | 7 | 0 | 4 | 9 | — | 0 | LPHNRF | NALSGPR | | SGLK | KELTIWNT K | |
| Q5Y4W8_AGEOR | spicier | 6 | 7 | 0 | 4 | 9 | — | 0 | LPHNRF | NALTGPR | | SRLR | KELSIWDSI | |
| Q5Y4X0_AGEOR | spider | 6 | 7 | 0 | 4 | 9 | — | 0 | LPHNRF | NALSGPR | | SGLK | KELSIWDSI | |
| Q5Y4X1_AGEOR | spider | 6 | 7 | 0 | 4 | 9 | — | 0 | LPHNRF | NALSGPR | | TGLK | KELSIWDSR | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q5Y4X2_AGEOR | spider | 6 | 7 | 0 | 4 | 9 | — | 0 | LPHNRF | NALSGPR | | SGLR | KELSIRDSR | |
| Q5Y4X3_AGEOR | spider | 6 | 7 | 0 | 4 | 9 | — | 0 | LPHNRF | NALSGPR | | SGLK | KELSIWDST | |
| Q5Y4X4_AGEOR | spider | 6 | 7 | 0 | 4 | 9 | — | 0 | LPHNRF | NALSDPR | | SGLR | KELSIWDSR | |
| Q5Y4X8_AGEOR | spider | 6 | 7 | 0 | 4 | 9 | — | 0 | LPHNRF | NALSGPR | | SGLR | KELSIWDST | |
| Q5Y4Y0_AGEOR | spider | 6 | 7 | 0 | 4 | 9 | — | 0 | LPHNRF | NALSGPR | | SRLK | KELSIWDSR | |
| Q5Y4Y1_AGEOR | spider | 6 | 7 | 0 | 4 | 9 | — | 0 | LPRNRF | NALSGPR | | SGLR | KELSIWASK | |
| Q5Y4Y2_AGEOR | spider | 6 | 7 | 0 | 4 | 9 | — | 0 | LPHNRF | NALSGPR | | SGLK | KELSIYDSR | |
| Q5Y4Y4_AGEOR | spider | 6 | 7 | 0 | 4 | 9 | — | 0 | LPHNRF | NALSGPR | | SGLR | KELSIWDSR | |
| SFI1_SEGFL | spider | 6 | 7 | 0 | 4 | 17 | — | 0 | MTDGTV | YIHNHND | | GSCL | SNGPIARPW EMMVGNC M | |
| SFI2_SEGFL | spider | 6 | 7 | 0 | 4 | 17 | — | 0 | MADETV | YIHNHNN | | GSCL | LNGPYARP WEMLVGN CK | |
| SFI3_SEGFL | spider | 6 | 7 | 0 | 4 | 17 | — | 0 | MVDGTV | YIHNHND | | GSCL | LNGPIARPW EMMVGNC K | |
| SFI4_SEGFL | spider | 6 | 7 | 0 | 4 | 17 | — | 0 | MVDGTV | YIHNHND | | GSCL | LNGPIARPW KMMVGNC K | |
| SFI5_SEGFL | spider | 6 | 7 | 0 | 4 | 17 | — | 0 | MVDGTV | YIHNHND | | GSCL | PNGPLARP WEMLVGN CK | |
| SFI6_SEGFL | spider | 6 | 7 | 0 | 4 | 17 | — | 0 | MTDETV | YIHNHND | | GSCL | LNGPIARPW EMMVGNC K | |
| SFI7_SEGFL | spider | 6 | 7 | 0 | 4 | 17 | — | 0 | MADGTV | YIHNHND | | GSCL | PNGPLARP WEVLVGNC K | |
| SFI8_SEGFL | spider | 6 | 7 | 0 | 4 | 17 | — | 0 | MADGTV | YIHNHND | | GSCL | PNGPLARP WEMLVGN CK | |
| T244_PHONI | spider | 6 | 5 | 0 | 3 | 8 | — | 0 | RFNGQQ | TSDGQ | | YGK | RTAFLRMI | |
| TACHC_TACTR | spider | 6 | 7 | 0 | 4 | 4 | — | 0 | ATYGQK | RTWSPPN | | WNLR | KAFR | |
| TJT1A_HADFO | spider | 6 | 5 | 0 | 4 | 10 | — | 0 | TGADRP | AACCP | | PGTS | KGPEPNGV SY | |
| TJT1A_HADVE | spider | 6 | 5 | 0 | 4 | 10 | — | 0 | TGADRP | AACCP | | PGTS | QGPESNGV VY | |
| TJT1B_HADVE | spider | 6 | 5 | 0 | 4 | 10 | — | 0 | TGADRP | AACCP | | PGTS | QGPEPNGV SY | |
| TJT1C_HADVE | spider | 6 | 5 | 0 | 4 | 9 | — | 1 | TGADRP | AACCP | | PGTS | KAESNGVS Y | |
| TOG4A_AGEAP | spider | 7 | 6 | 0 | 4 | 10 | — | 3 | IAKDYGR | KWGGTP | | RGRG | ICSIMGTNC E | |
| TOG4B_AGEAP | spider | 7 | 6 | 0 | 4 | 10 | — | 3 | IAEDYGK | TWGGTK | | RGRP | RCSMIGTNC E | |
| TOM1A_MISBR | spider | 6 | 6 | 0 | 10 | 7 | — | 0 | TPSGQP | QPNTQP | | NNAEEQTIN SGS | NGNTVYR TYKENENG | |
| TOT1A_ATRRO | spider | 6 | 5 | 0 | 3 | 13 | — | 0 | IPSGQP | PYNEH | | | NTVQR | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TOT1A_HADIN | spider | 6 | 5 | 0 | 3 | 13 | — | 0 | TPTDQP | PYHES | | SGS | TYKANENG NQVKR | |
| TOT1A_HADVE | spider | 6 | 5 | 0 | 3 | 13 | — | 2 | IPSGQP | PYNEN | | SQS | TFKENENG NTVKR | |
| TOT1B_HADFO | spider | 6 | 5 | 0 | 3 | 13 | — | 0 | IRSGQP | PYNEN | | SQS | TFKTNENG NTVKR | |
| TOT1B_HADIN | spider | 6 | 5 | 0 | 3 | 13 | — | 0 | IPTGQP | PYNEN | | SQS | TYKANENG NQVKR | |
| TOT1B_HADVE | spider | 6 | 5 | 0 | 3 | 13 | — | 0 | IPSGQP | PYNEN | | SQS | TYKENENG NTVKR | |
| TOT1C_HADIN | spider | 6 | 5 | 0 | 3 | 13 | — | 0 | IRTDQP | PYNES | | SGS | TYKANENG NQVKR | |
| TOT1C_HADVE | spider | 6 | 5 | 0 | 3 | 13 | — | 0 | IPSGQP | PYNEN | | SQS | TFKENENG NTVKR | |
| TOT1D_HADVE | spider | 6 | 5 | 0 | 3 | 13 | — | 0 | IPSGQP | PYNEN | | SKS | TYKENENG NTVQR | |
| TOT1E_HADVE | spider | 6 | 5 | 0 | 3 | 13 | — | 0 | IPSGQP | PYNEN | | SQS | TYKENENG NTVKR | |
| TOT1F_HADVE | spider | 6 | 5 | 0 | 3 | 13 | — | 0 | IPSGQP | PYSKY | | SGS | TYKTNENG NSVQR | |
| TOT2A_ATRIL | spider | 5 | 5 | 0 | 5 | 4 | — | 0 | VLSRV | SPDAN | | GLTPI | KMGL | |
| TOT2A_HADIN | spider | 6 | 5 | 0 | 5 | 4 | — | 0 | VVNTLG | SSDKD | | GMTPS | TLGI | |
| TOT2A_HADVE | spider | 6 | 5 | 0 | 5 | 4 | — | 2 | LFGNGR | SSNRD | | ELTPV | KRGS | |
| TOT2B_ATRIL | spider | 5 | 5 | 0 | 5 | 4 | — | 0 | VLSRV | SPDAN | | GLTPI | KMGL | |
| TOT2B_HADIN | spider | 6 | 5 | 0 | 5 | 4 | — | 0 | VLNTLG | SSDKD | | GMTPS | TLGI | |
| TX13_CUPSA | spider | 6 | 6 | 0 | 8 | 14 | — | 0 | TLRNHID | TDDRHS | | RSKMFKDV | TCFYPSQAK KELCT | |
| TX13_PHONI | spider | 6 | 5 | 0 | 3 | 8 | — | 0 | RSNGQQ | TSDGQ | | YGK | MTAFMGKI | |
| TX17_PHORI | spider | 6 | 5 | 0 | 3 | 8 | — | 0 | RFNGQQ | TSDGQ | | NGR | INAFQGRI | |
| TX19_PHOKE | spider | 6 | 4 | 0 | 8 | 8 | — | 0 | ADAWKS | DNLP | | VVNGYSRT | MCSANRCN VCWSQTVS | |
| TX1A_GEOA2 | spider | 6 | 6 | 0 | 4 | 19 | — | 0 | ITWRNS | MHNDKG | | FPWS | RNSSRKEK KCQ | |
| TX1_CERCR | spider | 6 | 6 | 0 | 4 | 6 | — | 0 | LGWFKS | DPKNDK | | KNYT | SRRDRW | |
| TX1_GRARO | spider | 6 | 5 | 0 | 4 | 3 | — | 0 | QKWMWT | DSKRK | | EDMV | QLW | |
| TX1_HETMC | spider | 6 | 5 | 0 | 4 | 6 | — | 0 | RYLFGG | SSTSD | | KHLS | RSDWKY | |
| TX1_PSACA | spider | 6 | 5 | 0 | 4 | 6 | — | 0 | RWFMGG | DSTLD | | KHLS | KMGLYY | |
| TX1_SCOGR | spider | 6 | 5 | 0 | 4 | 6 | — | 1 | RYLFGG | KTTAD | | KHLA | RSDGKY | |
| TX1_STRCF | spider | 6 | 5 | 0 | 4 | 6 | — | 0 | TRMFGA | RRDSD | | PHLG | KPTSKY | |
| TX1_THEBL | spider | 6 | 6 | 0 | 4 | 6 | — | 0 | LGMFES | DPNNDK | | PNRE | NRKHKW | |
| TX21_PHOKE | spider | 6 | 5 | 0 | 3 | 8 | — | 0 | KYNGEQ | TSDGQ | | NGR | RTAFMGKI | |
| TX22_PHOKE | spider | 6 | 6 | 0 | 4 | 13 | — | 0 | IGHRRS | KEDRNG | | KLYT | NCWYPTPD DQWCK | |
| TX22_PHONI | spider | 6 | 5 | 0 | 4 | 9 | — | 0 | PKILKQ | KSDED | | RGWK | FGFSIKDKM | |
| TX24_PHONI | spider | 6 | 5 | 0 | 3 | 8 | — | 0 | RFNGQQ | TSDGQ | | YGK | RTAFMGKI | |
| TX27_PHONI | spider | 6 | 5 | 0 | 4 | 11 | — | 0 | APRFSL | NSDKE | | KGLR | KSRIANMW PTF | |
| TX27_PHORI | spider | 6 | 5 | 0 | 4 | 11 | — | 0 | APRGLL | FRDKE | | KGLT | KGRFVNTW PTF | |
| TX29_PHONI | spider | 5 | 5 | 0 | 4 | 8 | — | 0 | IPFKP | KSDEN | | KKFK | KTTGIVKL | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TX2_CERCR | spider | 6 | 6 | 0 | 4 | 6 | — | 0 | LGWFKS | DPKNDK | | KNYT | SRRDRW | |
| TX2_HETMC | spider | 6 | 5 | 0 | 4 | 10 | — | 0 | RYFWGE | NDEMV | | EHLV | KEKWPITYKI | |
| TX2_PSACA | spider | 6 | 5 | 0 | 4 | 6 | — | 0 | RWFLGG | KSTSD | | EHLS | KMGLDY | |
| TX2_THEBL | spider | 6 | 6 | 0 | 4 | 6 | — | 0 | LGMFSS | DPKNDK | | PNRV | RSRDQW | |
| TX31_PHONI | spider | 6 | 6 | 0 | 4 | 10 | — | 0 | AAVYER | GKGYKR | | EERP | KCNIVMDNCT | |
| TX325_SEGFL | spider | 6 | 10 | 0 | 4 | 20 | — | 0 | IESGKS | THSRSMKNGL | | PKSR | NCRQIQHRHDYLGKRKYSCR | |
| TX32_PHOKE | spider | 6 | 5 | 0 | 4 | 11 | — | 0 | APRGQL | FSDKL | | IGLR | KSRVANMWPTF | |
| TX32_PHONI | spider | 6 | 6 | 0 | 4 | 10 | — | 0 | AGLYKK | GKGASP | | EDRP | KCDLAMGNCI | |
| TX33A_PHONI | spider | 6 | 5 | 0 | 9 | 8 | — | 0 | ADAYKS | NHPRT | | DGYNGYKRA | ICSGSNCK | |
| TX35A_PHONI | spider | 6 | 6 | 0 | 4 | 13 | — | 0 | IGHRRS | KEDRNG | | RLYT | NCWYPTPGDQWCK | |
| TX35_PHONI | spider | 6 | 6 | 0 | 4 | 16 | — | 0 | IGRNES | KFDRHG | | WPWS | SCWNKEGQPESDVWCE | |
| TX37_PHORI | spider | 6 | 6 | 0 | 4 | 10 | — | 0 | AGLYKK | GKGVNT | | ENRP | KCDLAMGNCI | |
| TX3A_PHONI | spider | 6 | 6 | 0 | 4 | 9 | — | 0 | ADVYKE | WYPEKP | | KDRA | QCTLGMTCK | |
| TX3_CERCR | spider | 6 | 5 | 0 | 4 | 6 | — | 0 | RKLLGG | TIDDD | | PHLG | NKKYWH | |
| IX3_LOXIN | spider | 6 | 9 | 0 | 15 | 10 | — | 0 | IKYGDR | GSPHGLPSN | | NDWKYKGRCGCTMGV | TCGPNCPSRG | |
| TX3_PARSR | spider | 6 | 6 | 0 | 5 | 6 | — | 0 | LGFLWK | NPSNDK | | RPNLV | SRKDKW | |
| TX3_PSACA | spider | 6 | 5 | 0 | 4 | 6 | — | 0 | RWYLGG | KEDSE | | EHLQ | HSYWEW | |
| TX3_THEBL | spider | 6 | 6 | 0 | 4 | 6 | — | 0 | LGMFSS | DPNNDK | | PNRV | RVRDQW | |
| TX482_HYSGI | spider | 6 | 5 | 0 | 4 | 9 | — | 0 | RYMFGG | SVNDD | | PRLG | HSLFSY | |
| TX5A_HETVE | spider | 6 | 5 | 0 | 4 | 9 | — | 0 | GWIMDD | TSDSD | | PNWV | SKTGFVKNI | |
| TX5B_HETVE | spider | 6 | 5 | 0 | 4 | 9 | — | 0 | GWLFHS | ESNAD | | ENWA | ATTGRFRYL | |
| TXAG_AGEOP | spider | 6 | 7 | 0 | 4 | 9 | — | 1 | LPHNRF | NALSGPR | | SGLK | KELSIWDSR | |
| TXAG_AGEOR | spider | 6 | 7 | 0 | 4 | 9 | — | 0 | LPHNRF | NALSGPR | | SGLK | KELSIWDSR | |
| TXC1_CUPSA | spider | 6 | 6 | 0 | 8 | 17 | — | 0 | IPKHEE | TNDKHN | | RKGLFKLK | QCSTFDDESGQPTERCA | |
| TXC1_HOLCU | spider | 6 | 6 | 0 | 4 | 9 | — | 0 | VGEYGR | RSAYED | | DGYY | NCSQPPYCL | |
| TXC2_HOLCU | spider | 6 | 7 | 0 | 4 | 9 | — | 0 | VGDGQR | ADWAGPY | | SGYY | SCRSMPYCR | |
| TXC3_HOLCU | spider | 6 | 7 | 0 | 4 | 9 | — | 0 | VGDGQK | ADWFGPY | | SGYY | SCRSMPYCR | |
| TXC5_PHONI | spider | 6 | 4 | 0 | 4 | 8 | — | 0 | AQKGIK | HDIH | | TNLK | VREGSNRV | |
| TXC5_PHORI | spider | 6 | 4 | 0 | 4 | 10 | — | 0 | ADAYKS | DSLK | | NNRI | MCSMIGTNCT | |
| TXC9_CUPSA | spider | 6 | 6 | 0 | 8 | 17 | — | 0 | IPKHHE | TNDKKN | | KKGLTKMK | KCFTVADAKGATSERCA | |
| TXDP1_PARLU | spider | 6 | 7 | 0 | 4 | 9 | — | 1 | LGEGEK | ADWSGPS | | DGFY | SCRSMPYCR | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TXDP2_PARLU | spider | 6 | 7 | 0 | 4 | 9 | — | 1 | VGDGQR | ASWSGPY | | DGYY | SCRSMPYCR | |
| TXDP3_PARLU | spider | 6 | 7 | 0 | 4 | 9 | — | 0 | LNFGDW | ADWSGPS | | GEMW | SCPGFGKCR | |
| TXDP4_PARLU | spider | 6 | 7 | 0 | 4 | 9 | — | 0 | ATKNQR | ASWAGPY | | DGFY | SCRSYPGCM | |
| TXDT1_HADVE | spider | 6 | 5 | 0 | 4 | 10 | — | 1 | AKKRNW | GKTED | | CPMK | VYAWYNEQGS | |
| TXFK1_PSACA | spider | 6 | 8 | 0 | 4 | 4 | — | 1 | GILHDN | VYVPAQNP | | RGLQ | RYGK | |
| TXFK2_PSACA | spider | 6 | 8 | 0 | 2 | 4 | — | 0 | LPAGKT | VRGPMRVP | | GS | SQNK | |
| TXFU5_OLIOR | spider | 6 | 6 | 0 | 4 | 10 | — | 0 | VPVYKE | WYPQKP | | EDRV | QCSFGMTNCK | |
| TXG1D_PLEGU | spider | 6 | 6 | 0 | 4 | 6 | — | 0 | GGFWWK | GSGKPA | | PKYV | SPKWGL | |
| TXG1E_PLEGU | spider | 6 | 6 | 0 | 4 | 6 | — | 0 | GGFWWK | GSGKPA | | PKYV | SPKWGL | |
| TXG2_PLEGU | spider | 6 | 5 | 0 | 4 | 6 | — | 0 | RKMFGG | SVDSD | | AHLG | KPTLKY | |
| TXH10_ORNHU | spider | 6 | 8 | 0 | 2 | 4 | — | 1 | LPPGKP | YGATQKIP | | GV | SHNK | |
| TXH1_ORNHU | spider | 6 | 6 | 0 | 4 | 6 | — | 0 | KGVFDA | TPGKNE | | PNRV | SDKHKW | |
| TXH3_ORNHU | spider | 6 | 4 | 0 | 4 | 6 | — | 0 | AGYMRE | KEKL | | SGYV | SSRWKW | |
| TXH4_ORNHU | spider | 6 | 6 | 0 | 6 | 6 | — | 1 | LEIFKA | NPSNDQ | | KSSKIV | SRKTRW | |
| TXH5_ORNHU | spider | 6 | 5 | 0 | 4 | 6 | — | 0 | RWYLGG | SQDGD | | KHLQ | HSNYEW | |
| TXH9_ORNHU | spider | 6 | 5 | 0 | 4 | 10 | — | 0 | APEGGP | VAGIG | | AGLR | SGAKLGLAGS | |
| TXHA1_SELHA | spider | 6 | 6 | 0 | 4 | 6 | — | 1 | KGFGKS | VPGKNE | | SGYA | NSRDKW | |
| TXHA3_SELHA | spider | 6 | 6 | 0 | 4 | 6 | — | 1 | KGFGDS | TPGKNE | | PNYA | SSKHKW | |
| TXHA4_SELHA | spider | 6 | 6 | 0 | 6 | 6 | — | 3 | LGFGKG | NPSNDQ | | KSSNIV | SRKHRW | |
| TXHA5_SELHA | spider | 6 | 6 | 0 | 6 | 6 | — | 0 | LGFGKG | NPSNDQ | | KSANIV | SRKHRW | |
| TXHN1_GRARO | spider | 6 | 5 | 0 | 4 | 6 | — | 1 | RYLFGG | KTTSD | | KHLG | KFRDKY | |
| TXHN2_GRARO | spider | 6 | 5 | 0 | 4 | 6 | — | 0 | RYLFGG | KTTAD | | KHLG | KFRDKY | |
| TXHP1_HETVE | spider | 6 | 6 | 0 | 4 | 4 | — | 0 | GTTWHY | GTDQSE | | EGWK | SRQL | |
| TXHP2_HETVE | spider | 6 | 5 | 0 | 4 | 4 | — | 1 | GKLFSG | DTNAD | | EGYV | RLW | |
| TXHP3_HETVE | spider | 6 | 5 | 0 | 4 | 3 | — | 0 | GTLFSG | STHAD | | EGFI | KLW | |
| TXI11_DIGCA | spider | 7 | 4 | 0 | 13 | 13 | — | 0 | MKYKSGD | RGKT | | DQQYLWYKWRNLA | RCFTVEVFKKDCW | |
| TXI92_DIGCA | spider | 6 | 4 | 0 | 13 | 13 | — | 0 | KKYDVE | DSGE | | QKQYLWYKWRPLD | RCLKSGFFSSKCV | |
| TXJ1_HETVE | spider | 6 | 5 | 0 | 4 | 3 | — | 0 | GTLFSG | DTSKD | | EGYV | HLW | |
| TXL1_ORNHU | spider | 4 | 5 | 0 | 4 | 6 | — | 1 | LGDK | DYNNG | | SGYV | SRTWKW | |
| TXLT4_LASPA | spider | 6 | 6 | 0 | 4 | 14 | — | 0 | GGVDAP | DKDRPD | | SYAE | LRPSGYGWWHGTYY | |
| TXM10_MACGS | spider | 6 | 6 | 0 | 4 | 10 | — | 0 | LAEYQK | EGSTVP | | PGLS | SAGRFRKTKL | |
| TXM11_MACGS | spider | 6 | 5 | 0 | 4 | 3 | — | 0 | KLTFWR | KKDKE | | GWNI | TGL | |
| TXM31_OLIOR | spider | 6 | 6 | 0 | 4 | 1 | — | 0 | VPVYKE | WYPQKP | | EDRV | Q | |
| TXMG1_AGEAP | spider | 6 | 6 | 0 | 4 | 9 | — | 1 | VPENGH | RDWYDE | | EGFY | SCRQPPKCIVKTSGYW | |
| TXMG1_MACGS | spider | 6 | 5 | 0 | 4 | 13 | — | 0 | MGYDIH | TDRLP | | FGLE | WYKKTY | |
| TXMG2_AGEAP | spider | 6 | 7 | 0 | 4 | 9 | — | 0 | ATKNKR | ADWAGPW | | DGLY | SCRSYPGCM | |
| TXMG2_MACGS | spider | 6 | 5 | 0 | 6 | 13 | — | 0 | MGYDIE | NENLP | | KHRKLE | VETSGYWWYKRKY | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| TXMG3_AGEAP | spider | 6 | 7 | 0 | 4 | 9 | — | 0 | VGDGQR | ADWAGPY | | SGYY | SCRSMPYCR | |
| TXMG4_AGEAP | spider | 6 | 7 | 0 | 4 | 9 | — | 0 | VGENQQ | ADWAGPH | | DGYY | TCRYFPKCI | |
| TXMG5_AGEAP | spider | 6 | 7 | 0 | 4 | 9 | — | 0 | VGENKQ | ADWAGPH | | DGYY | TCRYFPKCI | |
| TXMG5_MACGS | spider | 6 | 5 | 0 | 4 | 4 | — | 1 | KLTFWK | KNKKE | | GWNA | ALGI | |
| TXMG6_AGEAP | spider | 6 | 7 | 0 | 4 | 9 | — | 0 | VGESQQ | ADWAGPH | | DGYY | TCRYFPKCI | |
| TXMG6_MACGS | spider | 4 | 9 | 0 | 4 | 9 | — | 0 | VDGS | DPYSSDAPR | | GSQI | QCIFFVPCY | |
| TXMG7_MACGS | spider | 6 | 5 | 0 | 4 | 10 | — | 0 | APEGGP | VVGIG | | KGYS | APGLLGLVGH | |
| TXMG8_MACGS | spider | 6 | 5 | 0 | 4 | 7 | — | 0 | KGLFRQ | KKSSE | | KGSS | ESDLTGL | |
| TXMG9_MACGS | spider | 6 | 4 | 0 | 4 | 10 | — | 0 | GTNGKP | VNGQ | | GALR | VVTYHYADGV | |
| TXP1_PARSR | spider | 6 | 5 | 0 | 4 | 3 | — | 1 | QKWMWT | DSARK | | EGLV | RLW | |
| TXP1_PSACA | spider | 6 | 6 | 0 | 4 | 9 | — | 1 | IPKWKG | VNRHGD | | EGLE | WKRRRSFEV | |
| TXP2_PARSR | spider | 6 | 5 | 0 | 4 | 3 | — | 0 | QKWMWT | DEERK | | EGLV | RLW | |
| TXP3_APTSC | spider | 6 | 5 | 0 | 3 | 15 | — | 0 | NSKGTP | TNADE | | GGK | AYNVWNCIGGGCSKT | |
| TXP5_BRASM | spider | 6 | 5 | 0 | 4 | 6 | — | 0 | VDFQTK | KKDSD | | GKLE | SSRWKW | |
| TXP7_APTSC | spider | 6 | 6 | 0 | 4 | 4 | — | 1 | ARVKEA | GPWEWP | | SGLK | DGSE | |
| TXPR1_THRPR | spider | 6 | 5 | 0 | 4 | 6 | — | 0 | RYWLGG | SAGQT | | KHLV | SRRHGW | |
| TXPR2_THRPR | spider | 6 | 5 | 0 | 4 | 3 | — | 0 | QKWMWT | DSERK | | EGMV | RLW | |
| TXPT6_MACGS | spider | 6 | 5 | 0 | 4 | 13 | — | 0 | MGYDIE | NERLH | | ADLE | VKTSGRWWYKKTY | |
| TXR3_MACRV | spider | 6 | 5 | 0 | 4 | 4 | — | 0 | KLTFWK | KNKKE | | GWNA | ALGI | |
| TXU2_HETVE | spider | 6 | 5 | 0 | 4 | 3 | — | 0 | GGLFSG | DSNAD | | EGYV | RLW | |
| TXVL2_CORVA | spider | 6 | 5 | 0 | 4 | 6 | — | 0 | SRAGEN | YKSGR | | DGLY | KAYVVT | |
| VSTX1_GRARO | spider | 6 | 5 | 0 | 4 | 6 | — | 0 | GKFMWK | KNSND | | KDLV | SSRWKW | |
| VSTX2_GRARO | spider | 6 | 5 | 0 | 4 | 3 | — | 0 | QKWMWT | DEERK | | EGLV | RLW | |
| VSTX3_GRARO | spider | 6 | 6 | 0 | 4 | 6 | — | 0 | LGWFKG | DPDNDK | | EGYK | NRRDKW | |
| WGRTX_GRARO | spider | 6 | 5 | 0 | 4 | 8 | — | 1 | VRFWGK | SQTSD | | PHLA | KSKWPRNI | |
| ASTAE_ASTSM | sponge | 6 | 7 | 0 | 6 | 9 | — | 0 | GLFGDL | TLDGTLA | | IALELE | IPLNDFVGI | |
| AX6A_TERSU | terebra | 3 | 5 | 0 | 4 | 10 | — | 0 | PEY | PHGNE | | EHHE | RYDPWSRELK | |
| A2Q0G4_9VIRU | virus1 | 6 | 8 | 0 | 16 | 7 | — | 0 | TPNYAD | MDLQFNKP | | RQQQLEVGQIIPEDFV | FRFGKGI | |
| A2Q0I8_9VIRU | virus1 | 6 | 8 | 0 | 16 | 7 | — | 0 | IPNYAH | TDIGRTEP | | RQQELRIGQTIPEDFI | FRFGIGK | |
| A2Q0M1_9VIRU | virus1 | 6 | 6 | 0 | 16 | 7 | — | 0 | IPQGSY | MDTVKP | | QPVVLNGFHVRHYERI | FIFGQGL | |
| A2Q0M3_9VIRU | virus1 | 6 | 6 | 0 | 16 | 7 | — | 0 | IPQGSY | MDTVKP | | QPAVLLNRHIRHYERI | FVFGQGL | |
| A2Q0M4_9VIRU | virus1 | 6 | 6 | 0 | 16 | 7 | — | 0 | IPEGSY | LDAIAP | | QPTVLRHGYDRHRENI | FIFGQGL | |
| O11874_CSV | virus1 | 6 | 6 | 0 | 16 | 7 | — | 0 | IDNWKY | RGINKP | | GQQLMEDGTLGPKHFV | FELGQGI | |
| Q5ZNS9_9VIRU | virus1 | 6 | 6 | 0 | 16 | 7 | — | 0 | LKLKSN | DLRSNS | | QESEIGNSSSLVKKIH | DYLGKRV | |
| Q5ZNZ4_9VIRU | virus1 | 6 | 6 | 0 | 17 | 7 | — | 0 | LPLGNP | MKSKLP | | KLTYQNSYLRLGEVPTT | FKFGKGI | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Q66216_CSV | virus1 | 6 | 6 | 0 | 5 | 7 | — | 0 | MANWDY | LGFGKP | | DQHSI | FKFGEGI | |
| Q66236_CSV | virus1 | 6 | 6 | 0 | 5 | 7 | — | 0 | MANWDY | LGFGKP | | DQHSI | FKFGEGI | |
| Q80KH5_CSV | virus1 | 6 | 6 | 0 | 14 | 7 | — | 0 | IGNETN | VHTTLP | | SRYEDGEISPRKFV | WRFGTGI | |
| Q80KH6_CSV | virus1 | 6 | 6 | 0 | 14 | 7 | — | 0 | IVNETN | VHTTLP | | SRYEDGEISPRKFV | WRFGTGI | |
| Q80KH7_CSV | virus1 | 6 | 6 | 0 | 17 | 7 | — | 0 | IKHYHR | RGVSKP | | GQEALPTSGVLVGQEYT | AVFGSGL | |
| Q80KH8_CSV | virus1 | 6 | 6 | 0 | 16 | 7 | — | 0 | IPNWSN | LHTTIP | | HQQSLERGQVLPHDFI | WRFGSGL | |
| Q80KH9_CSV | virus1 | 6 | 6 | 0 | 16 | 7 | — | 0 | LVPSHR | LHTTIP | | HQQSLERGQVLPHDFI | WRFGSGL | |
| Q80PW5_CSV | virus1 | 6 | 6 | 0 | 16 | 7 | — | 0 | IAYNDY | RFSLTP | | DHGLSTQGAWMSEEHT | SVFDSGR | |
| Q80S75_9VIRU | virus1 | 6 | 6 | 0 | 16 | 7 | — | 0 | IGNYQP | IESTKP | | RLEDRTSVRFGREEYI | QRFLGGL | |
| Q89632_CSV | virus1 | 6 | 6 | 0 | 16 | 7 | — | 2 | IGHYQK | VNADKP | | SKTVRYGDSKNVRKFI | DRDGEGV | |
| Q91H14_9VIRU | virus1 | 6 | 6 | 0 | 17 | 7 | — | 0 | IKQFDH | QGMNKP | | GEEAVPQLGIXFGVEFT | SVFDSGV | |
| Q99825_CSV | virus1 | 6 | 6 | 0 | 16 | 7 | — | 0 | IGNYQP | IESTKP | | RLEDRTSVQFGRKEYI | DRFFGGL | |
| A0EYV0_9ABAC | virus2 | 3 | 5 | 7 | 3 | 6 | 5 | 0 | TETGRN | KYSYE | TITALLG | SNA | SAAFGF | YNGIP |
| A8C6C4_NPVAP | virus2 | 3 | 5 | 6 | 3 | 6 | 5 | 0 | TEDGRN | QYSYE | ISAAIG | SGA | SALFKF | YRAIP |
| A9YMX2_9BBAC | virus2 | 3 | 5 | 7 | 3 | 6 | 5 | 0 | TETGRN | VWIP | TVTALLG | SGA | SAVFKY | YNTIP |
| B0FDX4_9ABAC | virus2 | 3 | 5 | 6 | 3 | 6 | 5 | 0 | AETGAV | VWIP | VTIVIG | SGA | SPVFNY | YNGIP |
| CXOL2_NPVOP | virus2 | 3 | 5 | 7 | 3 | 6 | 5 | 0 | TETGRN | VYLP | TVTALLG | SGA | SAAFGF | YNGIP |
| CXOL_NPVAC | virus2 | 3 | 5 | 7 | 3 | 6 | 5 | 0 | AETGAV | VWIP | TVTALLG | SGA | SPIFNY | YNGIP |
| Q06KN7_NPVAG | virus2 | 3 | 5 | 7 | 3 | 6 | 5 | 0 | TETGRN | QYSYE | TVTALLG | SGA | SAVFKY | YNGIP |
| Q0GYM0_9ABAC | virus2 | 3 | 5 | 7 | 3 | 6 | 5 | 0 | AETGAV | VHNDE | TVTALAG | SGA | SPIFNY | YNSIP |
| Q5Y4P1_NPVAP | virus2 | 3 | 5 | 7 | 3 | 6 | 5 | 0 | AETGAV | IHNDE | TITALAG | SGA | SPVFNY | YNSIP |
| Q8JM47_9ABAC | virus2 | 3 | 5 | 7 | 3 | 6 | 5 | 0 | TETGRN | KYSYE | TVTALVG | SGA | SAAFGF | YDGIP |
| Q8QLC7_9ABAC | virus2 | 3 | 5 | 7 | 3 | 6 | 5 | 0 | TDTGRN | KYSYE | TITALLG | SGA | SAAFGF | YHGIP |
| Q9PYR8_GVXN | virus2 | 3 | 5 | 6 | 3 | 6 | 5 | 0 | TETGRN | QYSYE | TITALLG | SGA | SAAFKY | YNGIP |
| Hypa_A | cybase_cyclotide | 3 | 4 | 7 | 1 | 4 | 5 | 0 | AES | VYIP | FTTIIG | S | KNKV | YNGIP |
| circulin_F | cybase_cyclotide | 3 | 4 | 6 | 1 | 4 | 5 | 0 | GES | VWIP | TVTALLIG | S | KNKV | YNGIP |
| cycloviolacin_B16 | cybase_cyclotide | 3 | 4 | 7 | 1 | 4 | 5 | 0 | AES | VWIP | | S | KDKV | YNSIP |
| cycloviolacin_B3 | cybase_cyclotide | 3 | 4 | 6 | 1 | 4 | 5 | 0 | AES | VYLP | | S | KDKV | YNGIP |
| cycloviolacin_B4 | cybase_cyclotide | 3 | 4 | 7 | 1 | 4 | 5 | 0 | AES | VWIP | | S | SNNV | YNGIP |
| cycloviolacin_H4 | cybase_cyclotide | 3 | 4 | 7 | 1 | 4 | 5 | 0 | AES | VYIP | | S | SNRV | YNGIP |
| cycloviolacin_O1 | cybase_cyclotide | 3 | 4 | 7 | 1 | 4 | 5 | 0 | AES | VYIP | | S | KSKV | YNSIP |
| cycloviolacin_O18 | cybase_cyclotide | 3 | 4 | 7 | 1 | 4 | 5 | 0 | GES | VWIP | | K | KSKV | YNSIP |
| cycloviolacin_O7 | cybase_cyclotide | 3 | 4 | 7 | 1 | 4 | 5 | 0 | GES | VYIP | | S | SDKV | YDGIP |
| cycloviolacin_Y5 | cybase_cyclotide | 3 | 4 | 7 | 1 | 4 | 5 | 0 | AES | VYIP | | K | QDKV | YHGIP |
| kalata_B16 | cybase_cyclotide | 3 | 4 | 7 | 1 | 4 | 5 | 0 | AES | VYLP | | K | KDQV | YNGIP |
| kalata_B17 | cybase_cyclotide | 3 | 4 | 6 | 1 | 4 | 5 | 0 | GES | VWIP | | K | SNKV | YHGIP |
| mram_3 | cybase_cyclotide | 3 | 4 | 7 | 1 | 4 | 5 | 0 | AES | VWIP | | K | QGKV | YNGIP |
| vhr1 | cybase_cyclotide | 3 | 4 | 4 | 1 | 4 | 5 | 1 | AES | VYIP | TVTALLIG | S | SNKV | KSAIS |
| vibi_E | cybase_cyclotide | 3 | 4 | 4 | 1 | 4 | 5 | 0 | GET | FKFK | YTPR | G | SYPV | YLNSIS |
| violacin_A | cybase_cyclotide | 3 | 4 | 6 | 1 | 4 | 6 | 0 | GES | VYIP | TVTALVG | T | KDKV | YWNSIS |
| Hyfl_A | cybase_cyclotide | 3 | 4 | 7 | 1 | 4 | 6 | 0 | GET | TTFN | WIPN | K | NHHDKV | |
| Hyfl_F | cybase_cyclotide | 3 | 4 | 4 | 1 | 6 | 6 | 0 | | | | | | |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| Hyfl_I | cybase_cyclotide | 3 | 4 | 6 | 1 | 4 | 6 | 0 | GES | VFIP | ISGVIG | S | KSKV | YRNGIP |
| Hyfl_J | cybase_cyclotide | 3 | 4 | 4 | 1 | 4 | 6 | 0 | GES | AYFG | WIPG | S | RNKV | YFNGIA |
| Hyfl_K | cybase_cyclotide | 3 | 4 | 6 | 1 | 4 | 6 | 0 | GES | VYIP | FTAVVG | T | KDKV | YLNGTP |
| Hyfl_L | cybase_cyclotide | 3 | 4 | 6 | 1 | 4 | 6 | 0 | AES | VYLP | FTGVIG | T | KDKV | YLNGTP |
| circulin_A | cybase_cyclotide | 3 | 4 | 6 | 1 | 4 | 6 | 0 | GES | VWIP | ISAALG | S | KNKV | YRNGIP |
| circulin_C | cybase_cyclotide | 3 | 4 | 6 | 1 | 4 | 6 | 0 | GES | VFIP | ITSVAG | S | KSKV | YRNGIP |
| circulin_D | cybase_cyclotide | 3 | 4 | 6 | 1 | 4 | 6 | 0 | GES | VWIP | VTSIFN | K | ENKV | YHDKIP |
| circulin_E | cybase_cyclotide | 3 | 4 | 6 | 1 | 4 | 6 | 0 | GES | VWIP | LTSVFN | K | ENKV | YHDKIP |
| cyclopsychotride_A | cybase_cyclotide | 3 | 4 | 7 | 1 | 4 | 6 | 0 | GES | VFIP | TVTALLG | S | KSKV | YKNSIP |
| cycloviolacin_B1 | cybase_cyclotide | 3 | 4 | 6 | 1 | 4 | 6 | 0 | GES | VYLP | FTAPLG | S | SSKV | YRNGIP |
| cycloviolacin_B10 | cybase_cyclotide | 3 | 4 | 6 | 1 | 4 | 6 | 0 | GES | VWIP | LTSAIG | S | KSSV | YRNGV P |
| cycloviolacin_B11 | cybase_cyclotide | 3 | 4 | 6 | 1 | 4 | 6 | 0 | GES | VLIP | ISSVIG | S | KSKV | YRNGIP |
| cycloviolacin_B13 | cybase_cyclotide | 3 | 4 | 6 | 1 | 4 | 6 | 0 | IET | YTFP | ISEMIN | S | KNSR | QKNGA G |
| cycloviolacin_B14 | cybase_cyclotide | 3 | 4 | 6 | 1 | 4 | 6 | 0 | GES | VWIP | ISSAIG | S | KNKV | YRKGIP |
| cycloviolacin_B15 | cybase_cyclotide | 3 | 4 | 6 | 1 | 4 | 6 | 0 | GES | VWIP | ISGAIG | S | KSKV | YRNGIP |
| cycloviolacin_H1 | cybase_cyclotide | 3 | 4 | 6 | 1 | 4 | 6 | 0 | GES | VWIP | LLATIG | S | KSKV | YRNGIP |
| cycloviolacin_O10 | cybase_cyclotide | 3 | 8 | 4 | 1 | 6 | 6 | 0 | GER | VIERTRAW | RTVG | I | SLHTLE | YRNGR L |
| cycloviolacin_O13 | cybase_cyclotide | 3 | 4 | 6 | 1 | 4 | 6 | 0 | GEG | VYLP | FTAPLG | S | SSKV | YRNGIP |
| cycloviolacin_O17 | cybase_cyclotide | 3 | 4 | 6 | 1 | 4 | 6 | 0 | GES | VWIP | LTAAIG | S | SSKV | YRNGIP |
| cycloviolacin_O2 | cybase_cyclotide | 3 | 4 | 6 | 1 | 4 | 6 | 0 | GES | VYIP | LTSAIG | S | KSKV | YRNGIP |
| cycloviolacin_O20 | cybase_cyclotide | 3 | 4 | 6 | 1 | 4 | 6 | 0 | GES | VYIP | LTSAVG | S | KNKV | YRNGIP |
| cycloviolacin_O25 | cybase_cyclotide | 3 | 4 | 6 | 1 | 4 | 6 | 0 | GES | VWIP | ISAAIG | S | KSKV | YRNGIP |
| cycloviolacin_O3 | cybase_cyclotide | 3 | 4 | 6 | 1 | 4 | 6 | 0 | GES | VWIP | ISSAIG | S | KSKV | YRDGIP |
| cycloviolacin_O4 | cybase_cyclotide | 3 | 4 | 7 | 1 | 4 | 6 | 0 | GET | AFIP | ITHVPGT | S | KSKV | YFNDIF |
| cycloviolacin_O5 | cybase_cyclotide | 3 | 4 | 6 | 1 | 4 | 6 | 0 | GES | VWIP | LTSAIG | S | KSKV | YRNGIP |
| cycloviolacin_O9 | cybase_cyclotide | 3 | 4 | 6 | 1 | 4 | 6 | 0 | GES | VWIP | ISSAIG | S | KNKV | YRNGIP |
| cycloviolacin_Y4 | cybase_cyclotide | 3 | 4 | 6 | 1 | 4 | 6 | 0 | GES | VWIP | ISSAVG | S | KNKV | YKNGT P |
| cycloviolin_B | cybase_cyclotide | 3 | 4 | 6 | 1 | 4 | 6 | 0 | GES | VWIP | LTSAVG | S | KSKV | YRNGV |
| cycloviolin_C | cybase_cyclotide | 3 | 4 | 4 | 1 | 4 | 6 | 0 | GES | VFIP | ITGVIG | S | SSNV | YLNGV P |
| cycloviolin_D | cybase_cyclotide | 3 | 4 | 4 | 1 | 4 | 6 | 0 | GES | YVLP | FTVG | T | TSSQ | FKNGT A |
| hcf-1 | cybase_cyclotide | 3 | 4 | 6 | 1 | 4 | 6 | 0 | GES | VFIP | LTTVAG | S | KNKV | YRNGIP |
| htf-1 | cybase_cyclotide | 3 | 4 | 6 | 1 | 4 | 6 | 0 | GES | VFIP | ISAAIG | S | KNKV | YRNGFP |
| kalata_B12 | cybase_cyclotide | 3 | 4 | 6 | 1 | 4 | 6 | 0 | GES | HYIP | VTSAIG | S | RNRS | MRNGIP |
| kalata_B18 | cybase_cyclotide | 3 | 4 | 4 | 1 | 4 | 6 | 0 | GDS | HYIP | VTSTIG | S | TNGS | MRNGIP |
| kalata_B5 | cybase_cyclotide | 3 | 4 | 4 | 1 | 4 | 6 | 0 | GDT | FVLG | NDSS | S | NYPI | VKDGS L |
| mram_2 | cybase_cyclotide | 3 | 4 | 6 | 1 | 4 | 6 | 0 | AES | VYIP | ISTVLG | S | SNQV | YRNGV P |
| | cybase_cyclotide | 3 | 4 | 6 | 1 | 4 | 6 | 0 | GES | VYIP | ISGVIG | S | TDKV | YLNGTP |
| | cybase_cyclotide | 3 | 4 | 6 | 1 | 4 | 6 | 0 | AES | VYIP | LTSAIG | S | KSKV | YRNGIP |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| mram_8 | cybase_cyclotide | 3 | 4 | 6 | 1 | 4 | 6 | 0 | GES | VFIP | LTSAIG | S | KSKV | YRNGIP |
| mram_9 | cybase_cyclotide | 3 | 4 | 6 | 1 | 4 | 6 | 0 | GES | VWIP | LTSIVG | S | KNNV | TLNGVP |
| vhl_1 | cybase_cyclotide | 3 | 5 | 6 | 1 | 4 | 6 | 1 | GES | AMISF | FTEVIG | S | KNKV | YLNSIS |
| vibi_I | cybase_cyclotide | 3 | 4 | 6 | 1 | 4 | 6 | 0 | GES | VWIP | LTSTVG | S | KSKV | YRNGIP |
| vibi_K | cybase_cyclotide | 3 | 4 | 6 | 1 | 4 | 6 | 0 | GES | VWIP | LTSAVG | P | KSKV | YRNGIP |
| vitri_A | cybase_cyclotide | 3 | 4 | 6 | 1 | 4 | 6 | 0 | GES | VWIP | ITSAIG | S | KSKV | YRNGIP |
| Hyfl_D | cybase_cyclotide | 3 | 4 | 6 | 1 | 4 | 7 | 0 | GES | VYIP | FTGIAG | S | KSKV | YYNGSVP |
| Hyfl_E | cybase_cyclotide | 3 | 4 | 4 | 1 | 4 | 7 | 0 | GES | VYLP | FLPN | Y | RNHV | YLNGEIP |
| Hyfl_M | cybase_cyclotide | 3 | 4 | 4 | 1 | 4 | 7 | 0 | GES | IFFP | FNPG | S | KDNL | YYNGNIP |
| PS-1 | cybase_cyclotide | 3 | 5 | 4 | 1 | 5 | 7 | 0 | GET | IWDKT | HAAG | S | SVANI | VRNGFIP |
| circulin_B | cybase_cyclotide | 3 | 4 | 6 | 1 | 4 | 7 | 0 | GES | VFIP | ISTLLG | S | KNKV | YRNGVIP |
| cycloviolacin_B12 | cybase_cyclotide | 3 | 4 | 6 | 1 | 4 | 7 | 0 | GES | VFIP | ISSVIG | S | KSKV | YRNGVIP |
| cycloviolacin_B17 | cybase_cyclotide | 3 | 4 | 4 | 1 | 4 | 7 | 0 | GET | TLGT | YTVG | T | SWPI | TRNGLPI |
| cycloviolacin_B6 | cybase_cyclotide | 3 | 4 | 4 | 1 | 4 | 7 | 0 | GET | VGGT | NTPG | G | SWPV | TRNGLPV |
| cycloviolacin_B7 | cybase_cyclotide | 3 | 4 | 4 | 1 | 4 | 7 | 0 | GET | VGGT | NTPG | A | SWPV | TRNGLPV |
| cycloviolacin_H2 | cybase_cyclotide | 3 | 4 | 4 | 1 | 4 | 7 | 0 | GES | VYIP | FIPG | S | RNRV | YLNSAIA |
| cycloviolacin_H3 | cybase_cyclotide | 3 | 4 | 4 | 1 | 5 | 7 | 0 | GET | FGGT | NTPG | I | DPWPV | TRNGLPV |
| cycloviolacin_O11 | cybase_cyclotide | 3 | 4 | 6 | 1 | 4 | 7 | 0 | GES | VWIP | ISAVVG | S | KSKV | YKNGTLP |
| cycloviolacin_O12 | cybase_cyclotide | 3 | 4 | 4 | 1 | 4 | 7 | 0 | GET | VGGT | NTPG | S | SWPV | TRNGLPI |
| cycloviolacin_O15 | cybase_cyclotide | 3 | 4 | 4 | 1 | 4 | 7 | 0 | GET | FTGK | YTPG | S | SYPI | KKNGLVP |
| cycloviolacin_O16 | cybase_cyclotide | 3 | 4 | 4 | 1 | 4 | 7 | 0 | GET | FTGK | YTPG | S | SYPI | KKINGLP |
| cycloviolacin_O19 | cybase_cyclotide | 3 | 4 | 6 | 1 | 4 | 7 | 0 | GES | VWIP | ISSWG | S | KSKV | YKDGTLP |
| cycloviolacin_O21 | cybase_cyclotide | 3 | 4 | 4 | 1 | 4 | 7 | 0 | GET | VTGS | YTPG | T | SWPV | TRNGLPV |
| cycloviolacin_O22 | cybase_cyclotide | 3 | 4 | 4 | 1 | 4 | 7 | 0 | GET | VGGT | NTPG | T | SWPV | TRNGLPI |
| cycloviolacin_O23 | cybase_cyclotide | 3 | 4 | 4 | 1 | 6 | 7 | 0 | GET | FGGT | NTPG | T | DSSWPI | THNGLPT |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| cycloviolacin_O24 | cybase_cyclotide | 3 | 4 | 4 | 1 | 5 | 7 | 0 | GET | FGGT | NTPG | T | DPWPV | THNGLPT |
| cycloviolacin_O6 | cybase_cyclotide | 3 | 4 | 6 | 1 | 4 | 7 | 0 | GES | VWIP | ISAAVG | S | KSKV | YKNGTLP |
| cycloviolacin_O8 | cybase_cyclotide | 3 | 4 | 6 | 1 | 4 | 7 | 0 | GES | VWIP | ISSVVG | S | KSKV | YKNGTLP |
| cycloviolin_A | cybase_cyclotide | 3 | 4 | 6 | 1 | 4 | 7 | 0 | GES | VFIP | ISAAIG | S | KNKV | YRNGVIP |
| kalata_B1 | cybase_cyclotide | 3 | 4 | 4 | 1 | 4 | 7 | 0 | GET | VGGT | NTPG | T | SWPV | TRNGLPV |
| kalata_B10 | cybase_cyclotide | 3 | 4 | 4 | 1 | 5 | 7 | 0 | GET | FGGT | NTPG | S | SSWPI | TRDGLPT |
| kalata_B10 linear | cybase_cyclotide | 3 | 4 | 4 | 1 | 5 | 7 | 0 | GET | FGGT | NTPG | S | SSWPI | TRDGLPT |
| kalata_B11 | cybase_cyclotide | 3 | 4 | 4 | 1 | 4 | 7 | 0 | GET | FGGT | NTPG | S | TDPI | TRDGLPV |
| kalata_B13 | cybase_cyclotide | 3 | 4 | 4 | 1 | 5 | 7 | 0 | GET | FGGT | NTPG | A | DPWPV | TRDGLPV |
| kalata_B14 | cybase_cyclotide | 3 | 4 | 4 | 1 | 5 | 7 | 0 | GES | FGGT | NTPG | A | DPWPV | TRDGLPV |
| kalata_B15 | cybase_cyclotide | 3 | 4 | 4 | 1 | 4 | 7 | 0 | GES | FGGS | YTPG | S | TWPI | TRDGLPV |
| kalata_B2 | cybase_cyclotide | 3 | 4 | 4 | 1 | 4 | 7 | 0 | GET | FGGT | NTPG | S | TWPI | TRDGLPV |
| kalata_B3 | cybase_cyclotide | 3 | 4 | 4 | 1 | 5 | 7 | 0 | GET | FGGT | NTPG | S | DPWPI | TRDGLPT |
| kalata_B4 | cybase_cyclotide | 3 | 4 | 4 | 1 | 4 | 7 | 0 | GET | VGGT | NTPG | T | SWPV | TRDGLPV |
| kalata_B6 | cybase_cyclotide | 3 | 4 | 4 | 1 | 5 | 7 | 0 | GET | FGGT | NTPG | S | SSWPI | TRNGLPT |
| kalata_B7 | cybase_cyclotide | 3 | 4 | 4 | 1 | 4 | 7 | 0 | GET | TLGT | YTQG | T | SWPI | KRNGLPV |
| kalata_S | cybase_cyclotide | 3 | 4 | 4 | 1 | 4 | 7 | 0 | GET | VGGT | NTPG | S | SWPV | TRNGLPV |
| mram_1 | cybase_cyclotide | 3 | 4 | 6 | 1 | 4 | 7 | 0 | GES | VYIP | ISSLLG | S | KSKV | YKNGSIP |
| mram_10 | cybase_cyclotide | 3 | 4 | 6 |   | 4 | 7 | 0 | GES | VFIP | ISSVLG | S | KNKV | YRNGVIP |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| mram_11 | cybase_cyclotide | 3 | 4 | 4 | 1 | 4 | 7 | 0 | GET | LLGT | YTPG | T | KRPV | YKNGHPT |
| mram_13 | cybase_cyclotide | 3 | 4 | 4 | 1 | 4 | 7 | 0 | GET | VGNK | YTPG | T | TWPV | YRNGHPI |
| mram_14 | cybase_cyclotide | 3 | 4 | 6 | 1 | 4 | 7 | 0 | GEG | VFIP | ISSIVG | S | KSKV | YKNGSIP |
| mram_4 | cybase_cyclotide | 3 | 4 | 6 | 1 | 4 | 7 | 0 | GES | VFIP | ISSVVG | S | KNKV | YKNGSIP |
| mram_5 | cybase_cyclotide | 3 | 4 | 6 | 1 | 4 | 7 | 0 | GES | VFIP | LTSAIG | S | KSKV | YKNGTIP |
| mram_6 | cybase_cyclotide | 3 | 4 | 6 | 1 | 4 | 7 | 0 | GES | VYIP | ISSLLG | S | ESKV | YKNGSIP |
| mram_7 | cybase_cyclotide | 3 | 4 | 4 | 1 | 4 | 7 | 0 | GES | VFIP | ISSIVG | S | KSKV | YKNGSIP |
| varv_peptide_A | cybase_cyclotide | 3 | 4 | 4 | 1 | 4 | 7 | 0 | GET | VGGT | NTPG | S | SWPV | TRNGLPV |
| varv_peptide_B | cybase_cyclotide | 3 | 4 | 4 | 1 | 5 | 7 | 0 | GET | FGGT | NTPG | S | DPWPM | SRNGLPV |
| varv_peptide_C | cybase_cyclotide | 3 | 4 | 4 | 1 | 4 | 7 | 0 | GET | VGGT | NTPG | S | SWPV | TRNGVPI |
| varv_peptide_D | cybase_cyclotide | 3 | 4 | 4 | 1 | 4 | 7 | 0 | GET | VGGS | NTPG | S | SWPV | TRNGLPI |
| varv_peptide_E | cybase_cyclotide | 3 | 4 | 4 | 1 | 4 | 7 | 0 | GET | VGGT | NTPG | S | SWPV | TRNGLPI |
| varv_peptide_F | cybase_cyclotide | 3 | 4 | 4 | 1 | 4 | 7 | 0 | GET | TLGT | YTAG | S | SWPV | TRNGVPI |
| varv_peptide_G | cybase_cyclotide | 3 | 4 | 4 | 1 | 5 | 7 | 0 | GET | FGGT | NTPG | S | DPWPV | SRNGVP |
| varv_peptide_H | cybase_cyclotide | 3 | 4 | 4 | 1 | 5 | 7 | 0 | GET | FGGT | NTPG | S | ETWPV | SRNGLPV |
| vhl_2 | cybase_cyclotide | 3 | 4 | 4 | 1 | 5 | 7 | 0 | GET | FTGT | YTNG | T | DPWPV | TRNGLPV |
| vibi_A | cybase_cyclotide | 3 | 4 | 4 | 1 | 4 | 7 | 0 | GET | FGGT | NTPG | S | SYPI | TRNGLPV |
| vibi_B | cybase_cyclotide | 3 | 4 | 4 | 1 | 4 | 7 | 0 | GET | FGGT | NTPG | T | SYPI | TRNGLPV |
| vibi_C | cybase_cyclotide | 3 | 4 | 4 | 1 | 4 | 7 | 0 | GET | AFGS | YTPG | S | SWPV | TRNGLPV |
| vibi_D | cybase_cyclotide | 3 | 4 | 4 | 1 | 4 | 7 | 0 | GET | FGGR | NTPG | T | SYPI | TRNGLPV |
| vibi_F | cybase_cyclotide | 3 | 4 | 6 | 1 | 4 | 7 | 0 | GES | VFIP | LTSALG | S | KSKV | YKNGTIP |
| vibi_G | cybase_cyclotide | 3 | 4 | 6 | 1 | 4 | 7 | 0 | GES | VFIP | LTSAIG | S | KSKV | YKNGTFP |
| vibi_H | cybase_cyclotide | 3 | 4 | 6 | 1 | 4 | 7 | 0 | AES | VYIP | LTTVIG | S | KSKV | YKNGLLP |
| vibi_J | cybase_cyclotide | 3 | 4 | 6 | 1 | 4 | 7 | 0 | GES | VWIP | ISKVIG | A | KSKV | YKNGTFP |
| vico_A | cybase_cyclotide | 3 | 4 | 6 | 1 | 4 | 7 | 0 | AES | VYIP | FTGIAG | S | KNKV | YYNGSIP |

TABLE 2-continued

| name | class | Loop 1 length | Loop 2 length | Loop 3 length | Loop 4 length | Loop 5 length | Loop 6 length | # 3D structures | Loop 1 | Loop 2 | Loop 3 | Loop 4 | Loop 5 | Loop 6 |
|---|---|---|---|---|---|---|---|---|---|---|---|---|---|---|
| vico_B | cybase_cyclotide | 3 | 4 | 6 | 1 | 4 | 7 | 0 | AES | VYIP | ITGIAG | S | KNKV | YYNGSIP |
| violapeptide_1 | cybase_cyclotide | 3 | 4 | 4 | 1 | 4 | 7 | 0 | GET | VGGT | NTPG | S | SRPV | TXNGLPV |
| vodo_M | cybase_cyclotide | 3 | 4 | 4 | 1 | 4 | 7 | 0 | GES | FTGK | YTVQ | S | SWPV | TRNGAPI |
| vodo_N | cybase_cyclotide | 3 | 4 | 4 | 1 | 4 | 7 | 0 | GET | TLGK | YTAG | S | SWPV | YRNGLPV |
| CD-1 | cybase_cyclotide | 3 | 4 | 6 | 1 | 6 | 8 | 0 | GES | YVIP | ISYLVG | S | DITEKV | KRNGADGF |
| Hyfl_B | cybase_cyclotide | 3 | 4 | 6 | 1 | 4 | 8 | 0 | AET | FIGK | YTEELG | T | TAFL | MKNGSPIQ |
| Hyfl_C | cybase_cyclotide | 3 | 4 | 6 | 1 | 4 | 8 | 0 | AET | FIGK | YTEELG | T | TAFL | MKNGSPRQ |
| cycloviolacin_O14 | cybase_cyclotide | 3 | 4 | 4 | 1 | 5 | 8 | 0 | GES | FKGK | YTPG | S | SKYPL | AKNGSIPA |
| kalata_B8 | cybase_cyclotide | 3 | 4 | 4 | 1 | 5 | 8 | 0 | GET | LLGT | YTTG | T | NKYRV | TKDGSVLN |
| kalata_B9 | cybase_cyclotide | 3 | 4 | 4 | 1 | 5 | 8 | 0 | GET | VLGT | YTPG | T | NTYRV | TKDGSVFN |
| kalata_B9_linear | cybase_cyclotide | 3 | 4 | 4 | 1 | 5 | 8 | 0 | GET | VLGT | YTPG | T | NTYRV | TKDGSVFN |
| mram_12 | cybase_cyclotide | 3 | 5 | 4 | 1 | 4 | 8 | 0 | GES | TLGE | YTPG | T | SWPI | TKNGSAIL |
| palicourein | cybase_cyclotide | 3 | 4 | 7 | 1 | 7 | 8 | 1 | GET | RVIPV | TYSAALG | T | DDRSDGL | KRNGDPTF |
| cycloviolacin_Y1 | cybase_cyclotide | 3 | 4 | 4 | 1 | 5 | 10 | 0 | GET | FLGT | YTPG | S | GNYGF | YGTNGGTIFD |
| cycloviolacin_Y2 | cybase_cyclotide | 3 | 4 | 4 | 1 | 5 | 10 | 0 | GES | FLGT | YTAG | S | GNWGL | YGTNGGTIFD |
| cycloviolacin_Y3 | cybase_cyclotide | 3 | 4 | 4 | 1 | 5 | 10 | 0 | GET | FLGT | YTAG | S | GNWGL | YGTNGGTIFD |
| tricyclon_A | cybase_cyclotide | 3 | 4 | 4 | 1 | 5 | 10 | 0 | GES | FLGT | YTKG | S | GEWKL | YGTNGGTIFD |
| tricyclon_B | cybase_cyclotide | 3 | 4 | 4 | 1 | 5 | 10 | 0 | GES | FLGT | YTKG | S | GEWKL | YGENGGTIFD |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09796764B2). An electronic copy of the "Sequence Listing" will also be available from the USPTO upon request and payment of the fee set forth in 37 CFR 1.19(b)(3).

We claim:

1. An isolated nucleic acid molecule encoding a proteinaceous molecule having a cystine knot backbone and a defined biological activity, comprising a sequence of nucleotides encoding a linear precursor form of a cyclic cystine knot polypeptide operably linked to a promoter, wherein said linear precursor form comprises an amino acid sequence comprising:

a signal peptide, a cystine knot polypeptide and a non-cystine knot polypeptide, wherein said cystine knot polypeptide in its mature form comprises the structure:

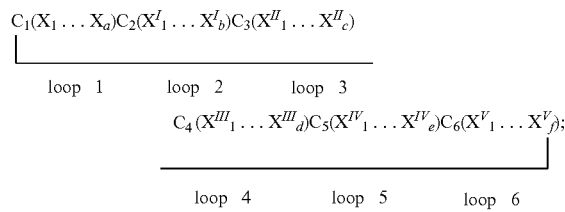

wherein $C_1$ to $C_6$ are cysteine residues;

wherein each of $C_1$ and $C_4$, $C_2$ and $C_5$, and $C_3$ and $C_6$ are connected by a disulfide bond to form a cystine knot;

wherein each X represents an amino acid residue in a loop, wherein said amino acid residues may be the same or different;

wherein a is any number from 3-10;

wherein d is 1-2;

wherein b, c, e, and f, may be the same or different, and may be any number from 1 to 20;

wherein one or two of loops 2, 3, 5 and 6 have an amino acid sequence comprising the sequence of a heterologous peptide comprising a plurality of contiguous amino acids and having a defined biological activity and wherein said heterologous peptide is about 2 to 30 amino acid residues, wherein the signal peptide has the amino acid sequence of SEQ ID NO:128, and wherein said non-cystine knot polypeptide comprises an albumin a-chain.

2. The isolated nucleic acid of claim 1, wherein said amino acid sequence of said heterologous peptide comprises a portion of an amino acid sequence of a larger protein, wherein said peptide confers said defined biological activity on said larger protein.

3. The isolated nucleic acid molecule of claim 1, wherein in said amino acid sequence of said precursor form, said signal peptide is adjacent to the N-terminal amino acid of the mature form of said cystine knot polypeptide.

4. A method for producing a cystine knot polypeptide, comprising: transforming a host cell with a vector comprising the nucleic acid molecule of claim 1, wherein said precursor form of said cystine knot polypeptide is expressed.

5. A method for producing a cyclic cystine knot polypeptide, comprising:

i) transforming a host cell with a vector comprising the isolated nucleic acid molecule according to claim 1, ii) expressing a linear precursor form of a cystine knot polypeptide; and iii) processing said linear precursor form to form a cyclic cystine knot polypeptide having the structure:

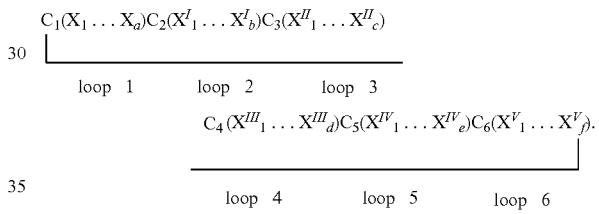

6. The method of claim 5, wherein said host cell is a plant cell.

7. The method of claim 6, wherein said plant cell is from the plant family Fabaceae.

8. The method of claim 4, wherein said host cell carries an enzyme for processing said precursor form of said cystine knot polypeptide to produce a cyclic cystine knot polypeptide.

9. The method of claim 5, wherein said host cell carries an enzyme for processing said precursor form of said cystine knot polypeptide to produce a cyclic cystine knot polypeptide.

10. A composition comprising a host cell comprising a heterologous nucleic acid comprising the isolated nucleic acid of claim 1.

11. The isolated nucleic acid of claim 1, wherein in the cyclic form of said cystine knot polypeptide, loop 6 has an amino acid sequence selected from the group consisting of YRNGVIP (SEQ ID NO: 110), YLNGVIP (SEQ ID NO: 111), YLDGVP (SEQ ID NO: 112), YLNGIP (SEQ ID NO: 113), YLDGIP (SEQ ID NO: 114), YLNGLP (SEQ ID NO: 115), YNNGLP (SEQ ID NO: 116), YNDGLP (SEQ ID NO: 117), YINGTVP (SEQ ID NO: 118), YIDGTVP (SEQ ID NO: 119), YNHEP (SEQ ID NO: 120), YDHEP (SEQ ID NO: 121), LKNGSAF (SEQ ID NO: 122), MKNGLP (SEQ ID NO: 123), YRNGIP (SEQ ID NO: 124), YKNGIP (SEQ ID NO: 125), and YRDGVIP (SEQ ID NO: 126).

* * * * *